(12) United States Patent
Gray et al.

(10) Patent No.: US 10,913,744 B2
(45) Date of Patent: Feb. 9, 2021

(54) LRRK2 INHIBITORS AND METHODS OF MAKING AND USING THE SAME

(71) Applicant: Dana-Farber Cancer Institute, Inc., Boston, MA (US)

(72) Inventors: Nathanael S. Gray, Boston, MA (US); John Hatcher, Marlborough, MA (US); Hwan Geun Choi, Seoul (KR)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 45 days.

(21) Appl. No.: 15/547,913

(22) PCT Filed: Feb. 12, 2016

(86) PCT No.: PCT/US2016/017754
§ 371 (c)(1),
(2) Date: Aug. 1, 2017

(87) PCT Pub. No.: WO2016/130920
PCT Pub. Date: Aug. 18, 2016

(65) Prior Publication Data
US 2018/0244676 A1     Aug. 30, 2018

Related U.S. Application Data

(60) Provisional application No. 62/116,038, filed on Feb. 13, 2015.

(51) Int. Cl.
C07D 487/04 (2006.01)
A61P 25/16 (2006.01)
A61P 25/28 (2006.01)
C07D 473/18 (2006.01)

(52) U.S. Cl.
CPC .......... C07D 487/04 (2013.01); A61P 25/28 (2018.01); C07D 473/18 (2013.01)

(58) Field of Classification Search
CPC ...... C07D 487/04; C07D 473/18; A61P 25/28
See application file for complete search history.

(56) References Cited

U.S. PATENT DOCUMENTS

| 2007/0060595 | A1 | 3/2007 | Yoshizawa et al. |
| 2009/0076037 | A1 | 3/2009 | Connolly et al. |
| 2011/0301141 | A1 | 12/2011 | Baker-Glenn et al. |
| 2013/0059847 | A1 | 3/2013 | Bearss et al. |
| 2014/0038940 | A1 | 2/2014 | Xu et al. |
| 2014/0200206 | A1 | 7/2014 | Calabrese et al. |
| 2018/0312508 | A1 | 11/2018 | Deng et al. |

FOREIGN PATENT DOCUMENTS

| CN | 1780840 A | 5/2006 |
| CN | 1784410 A | 6/2006 |
| CN | 102056925 A | 5/2011 |
| CN | 102264862 A | 11/2011 |
| CN | 103641816 A | 3/2014 |
| CN | 103889962 A | 6/2014 |
| WO | WO 01/09134 A1 | 2/2001 |
| WO | WO 2004/081013 A1 | 9/2004 |
| WO | 2005/035516 A1 | 4/2005 |
| WO | WO 2006/122003 A2 | 11/2006 |
| WO | WO 2007/042298 A1 | 4/2007 |
| WO | WO-2007042299 A1 * | 4/2007 | ........... C07D 487/04 |

(Continued)

OTHER PUBLICATIONS

Bae, J.R., "Function and dysfunction of leucine-rich repeat kinase 2 (LRRK2): Parkinson's disease and beyond." BMB reports 48.5 (2015): 243.*

Gilligan, P., "Inhibitors of leucine-rich repeat kinase 2 (LRRK2): progress and promise for the treatment of Parkinson's disease." Current topics in medicinal chemistry 15.10 (2015): 927-938.*

Li, B.-K. et al., "In silico prediction of spleen tyrosine kinase inhibitors using machine learning approaches and an optimized molecular descriptor subset generated by recursive feature elimination method," Computers in Biology and Medicine 43: 395-404 (2013).

(Continued)

*Primary Examiner* — John M Mauro
(74) *Attorney, Agent, or Firm* — Burns & Levinson, LLP; Daniel W. Clarke

(57) ABSTRACT

Compounds having the formula I, II, or III:

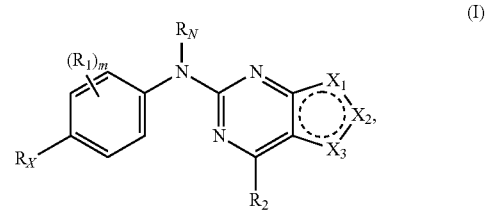

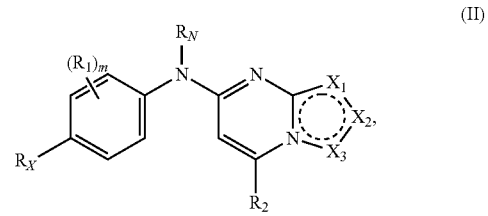

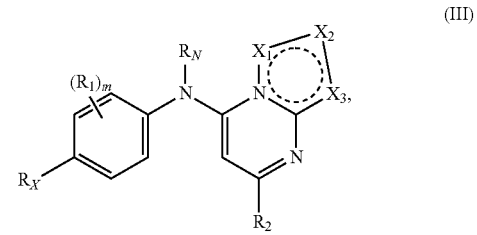

are provided. Compounds of the present disclosure are useful for the treatment of neurodegenerative diseases, such as Parkinson's Disease.

21 Claims, 5 Drawing Sheets

(56) References Cited

FOREIGN PATENT DOCUMENTS

| WO | WO 2007/071393 A2 | 6/2007 | |
| WO | WO-2007140222 A2 * | 12/2007 | ........... A61K 31/519 |
| WO | WO 2008/081928 A1 | 7/2008 | |
| WO | WO 2008/119792 A1 | 10/2008 | |
| WO | WO 2009/026107 A1 | 2/2009 | |
| WO | WO-2009020990 A1 * | 2/2009 | ............. A61P 35/00 |
| WO | WO 2009/032694 A1 | 3/2009 | |
| WO | WO 2009/032703 A1 | 3/2009 | |
| WO | WO 2009/079412 A2 | 6/2009 | |
| WO | WO-2009131687 A2 * | 10/2009 | ........... C07D 239/48 |
| WO | WO 2010/034740 A1 | 4/2010 | |
| WO | WO-2010045451 A1 * | 4/2010 | ........... C07D 487/04 |
| WO | WO 2010/051253 A1 | 5/2010 | |
| WO | WO 2010/090764 A1 | 8/2010 | |
| WO | 2010/111406 A2 | 9/2010 | |
| WO | WO 2010-100431 A1 | 9/2010 | |
| WO | WO 2010-129053 A2 | 11/2010 | |
| WO | WO 2011/032050 A2 | 3/2011 | |
| WO | WO 2011079231 A1 | 6/2011 | |
| WO | WO-2011130232 A1 * | 10/2011 | ........... A61K 31/436 |
| WO | WO-2012045195 A1 * | 4/2012 | ........... C07D 487/04 |
| WO | WO 2012-103297 A1 | 8/2012 | |
| WO | 2012143144 A1 | 10/2012 | |
| WO | 2012/170827 A1 | 12/2012 | |
| WO | WO 2012-170827 A2 | 12/2012 | |
| WO | WO 2013/126545 A1 | 8/2013 | |
| WO | WO 2014025486 A1 | 2/2014 | |
| WO | WO 2014/074580 A1 | 5/2014 | |
| WO | WO 2014-180524 A1 | 11/2014 | |
| WO | WO 2015/038417 A1 | 3/2015 | |
| WO | WO-2015113451 A1 * | 8/2015 | ........... A61K 31/437 |
| WO | 2015151006 A1 | 10/2015 | |
| WO | 2016173477 A1 | 11/2016 | |

OTHER PUBLICATIONS

STN search report, Columbus, Ohio, US Registry (Online), Jun. 4, 2014, 15 pages.

Tannous, B. A. et al., "Effects of the Selective MPS1 Inhibitor MPS1-IN-3 on Glioblastoma Sensitivity to Antimitotic Drugs," J Natl Cancer Inst, 105: 1322-1331 (2013).

Zhou, W. et al., "Discovery of selective irreversible inhibitors for EGFR-T790M," Bioorganic & Medicinal Chemistry Letters, 21:638-643 (2011).

STN search report, N7-cyclopropyl-N5[4-(4-morpholinyl)phenyl]-Pyrazolo[1,5-a]pyrimidine-5,7-diamine, Entered STN: Jan. 3, 2013; 1415887-59-0 Registry, 3 pages.

Perreira, M., et al., ""Reversine" and Its 2-Substituted Adenine Derivatives as Potent and Selective A3 Adenosine Receptor Antagonists," 2005, J. Med. Chem. 2005, 48:4910-4918.

Kumar, D., "Lead Optimization of Purine Based Orally Bioavailable Mps1 (TTK) Inhibitors," Bioorg. Med. Chem. Lett. 2012, 22:4377-4385.

* cited by examiner

Molecular model of Compound 18 with LRRK2.

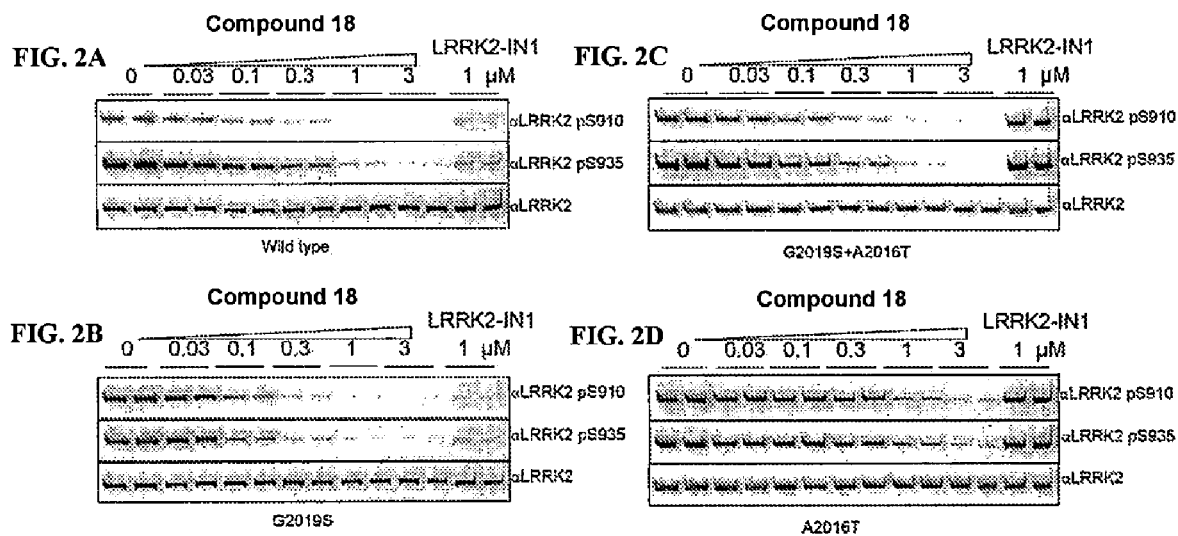

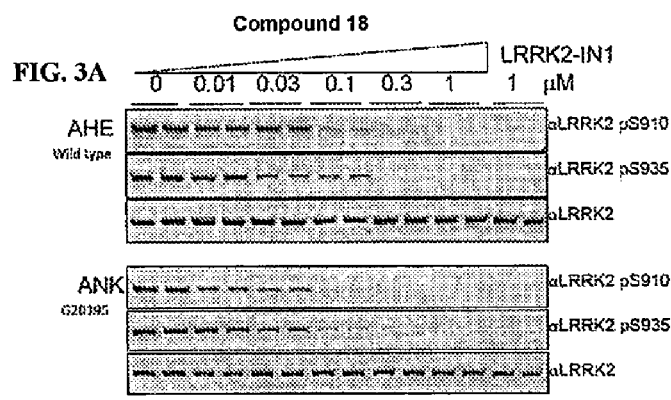
FIG. 3A
FIG. 3B
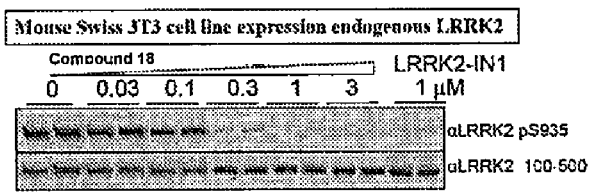
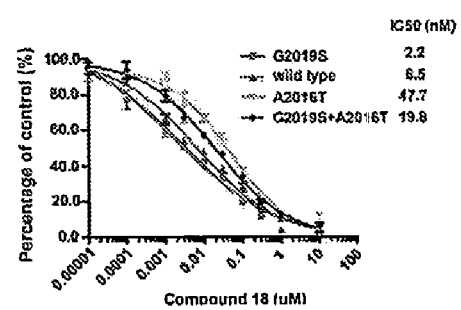
FIG. 3C

S-Score Table- Compound 18

| Compound Name | Selectivity Score Type | Number of Hits | Number of Non-Mutant Kinases | Screening Concentration (nM) | Selectivity Score |
|---|---|---|---|---|---|
| Compound 18 | S(35) | 4 | 392 | 1000 | 0.01 |
| Compound 18 | S(10) | 0 | 392 | 1000 | 0 |
| Compound 18 | S(1) | 0 | 392 | 1000 | 0 |

LRRK2 INHIBITORS AND METHODS OF MAKING AND USING THE SAME

RELATED APPLICATION

This application is a U.S. National Phase application, filed under 35 U.S.C. § 371, of International Application No. PCT/US2016/017754, filed on Feb. 12, 2016, which claims the benefit of and priority to U.S. provisional application No. 62/116,038, filed Feb. 13, 2015, the contents of each of which are incorporated herein by reference in their entireties.

GOVERNMENT SUPPORT

This invention was made with government support under grant number R01 CA136851 awarded by The National Institutes of Health. The government has certain rights in the invention.

FIELD OF THE DISCLOSURE

The present disclosure relates generally to molecularly targeted therapies for neurodegenerative diseases. More particularly, the disclosure relates to a family of compounds that are useful as therapeutic agents.

BACKGROUND

Neurodegenerative diseases are a class of disorders in which there is a gradual and progressive death of neurons. Though neurodegenerative diseases typically run a progressive course that may extend over several years, the diseases themselves develop spontaneously and without relation to external factors. Family history of degenerative nervous system diseases is a significant feature of this class of diseases, and the general group of diseases is frequently referred to as heterodegenerative, however a number of neurodegenerative diseases, not differing in any fundamental way from hereditary disorders, occur sporadically as isolated instances in a given family.

Neurodegenerative diseases include, but are not limited to, Parkinson's Disease, Alzheimer's Disease, Schizophrenia, progressive myoclonic epilepsy (Unver-Richt-Lundberg Lafora disease), Hallervorden-Spatz Disease, Retinitis Pigmentosa, Xeroderma Pigmentosum, and Melanin-related diseases.

Parkinson's Disease (PD), after Alzheimer's, is the second most common neurodegenerative disease in the world. It affects over one million Americans and more than 60,000 patients are newly diagnosed annually. PD is generally classified by somatic symptoms including tremors, rigidity, bradykinesis, and postural problems. In the early stages of the disease, there may be only slight disturbances of posture, locomotion, facial expressions, or speech. Symptoms may initially manifest as asymmetric, however as the disease progresses, the symptoms become bilateral and progressively debilitating. PD patients also commonly experience dementia, ataxia, dysphasia, and mood disorders, and the quality and life expectancy of patients with PD is substantially reduced.

Although tremendous effort has been made to find an effective treatment or cure for PD, most PD patients have experienced little relief from current treatment regimes, which may include medications, surgeries, and implants. Many of the benefits provided from standard treatments are relatively insignificant and are often accompanied by appreciable toxicity. The most common current therapy for Parkinsonism is oral administration of L-DOPA, 3-(3,4-dihydroxyphenil)-L-alanine:

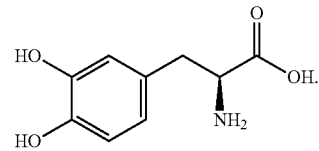 [SMILES: N[C@@H](Cc1ccc(O)c(O)c1)C(=O)O]

However, because L-DOPA is a precursor of epinephrine and melanin, there are certain contraindications associated with its use. L-DOPA may exacerbate malignant melanomas or other skin lesions, and may cause adverse side effects in patients with cardiovascular or pulmonary disease, asthma, or renal, hepatic, or endocrine disease.

There is an ongoing need for new treatments for degenerative neurological diseases, and more specifically, Parkinson's disease.

SUMMARY OF THE INTENTION

The present disclosure relates generally to the field of LRRK2 inhibiting compounds and to methods of making and using them. These compounds may be useful for treating Parkinson's disease.

The present disclosure provides compounds having formula I, IL, or III:

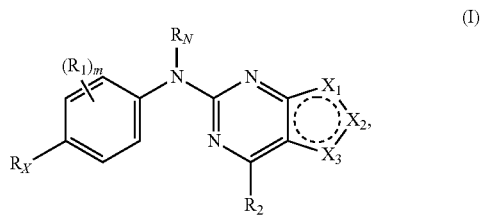

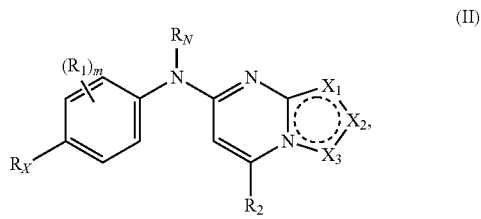

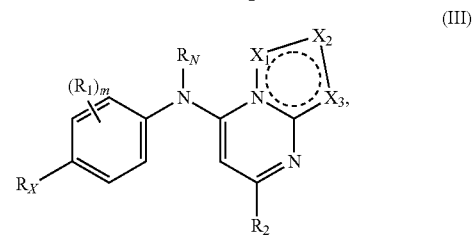

or a pharmaceutically acceptable salt thereof, wherein each of the variables in the above formulae is defined and exemplified in the following detailed description.

In one embodiment, a compound of the disclosure is a compound of formula Ia, IIa, IIIa, Ib1, Ib2, Ic1, Ic2, IIa1, IIa2, IIIa1, or IIIa2:

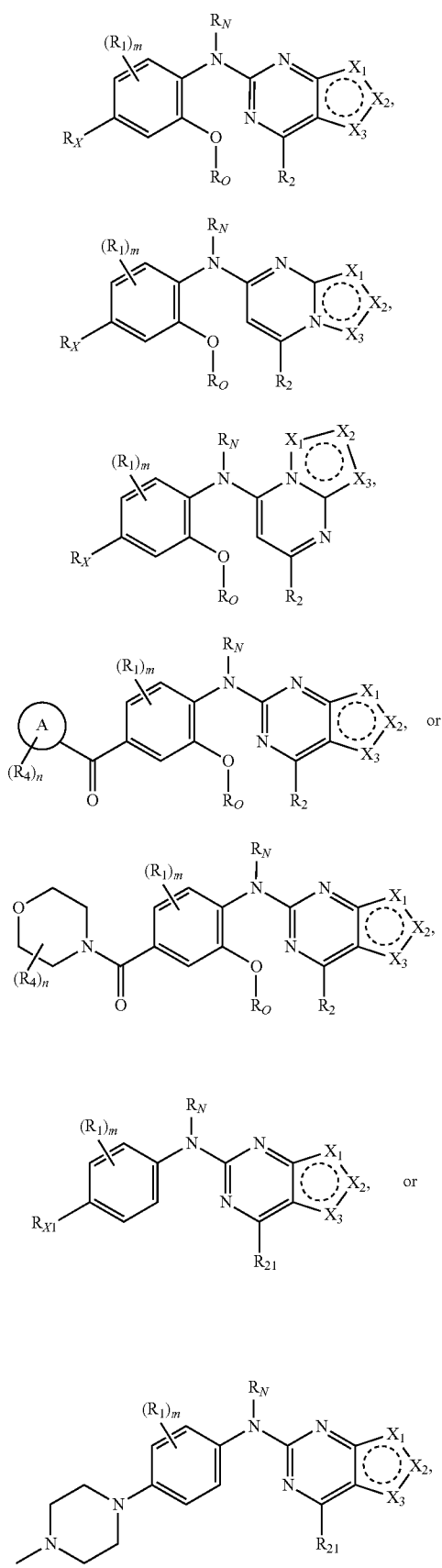
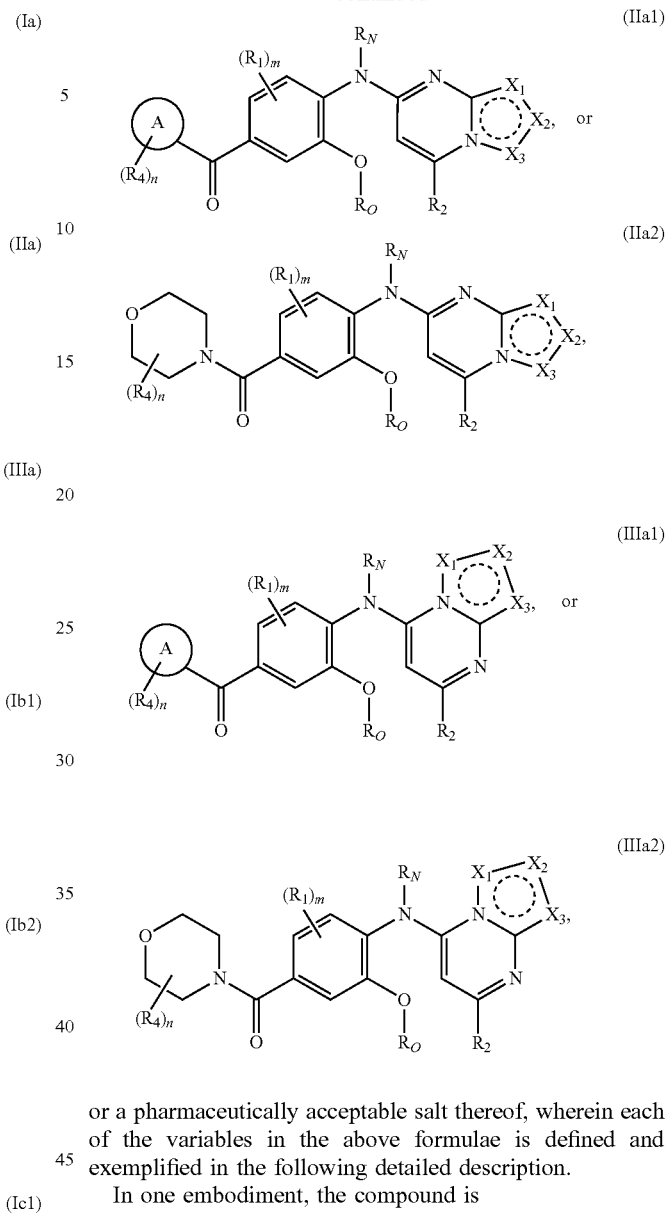

or a pharmaceutically acceptable salt thereof, wherein each of the variables in the above formulae is defined and exemplified in the following detailed description.

In one embodiment, the compound is

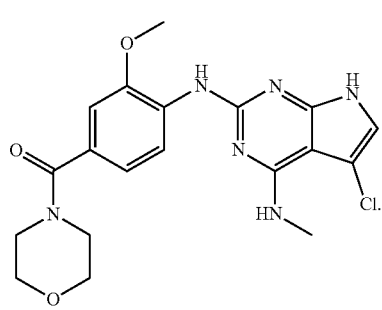 [SMILES: CNc1nc(Nc2ccc(C(=O)N3CCOCC3)cc2OC)nc2[nH]cc(Cl)c12]

In accordance with an aspect of the disclosure, a pharmaceutical composition is provided, the pharmaceutical composition comprising a compound of the present disclosure, or a pharmaceutically acceptable salt, ester, tautomer, or prodrug thereof, and a pharmaceutically acceptable carrier.

In one embodiment, the compound of the pharmaceutical composition is

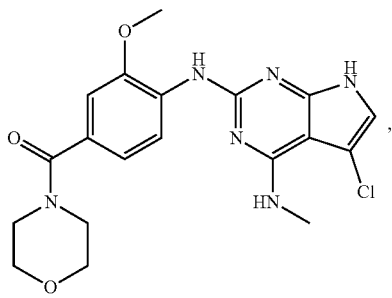 [SMILES: CNc1nc(Nc2ccc(C(=O)N3CCOCC3)cc2OC)nc2[nH]cc(Cl)c12]

or a pharmaceutically acceptable salt, ester, tautomer, or prodrug thereof.

Another aspect of the disclosure provides a method of treating or preventing a disease or disorder in which LRRK2 is involved (e.g., a neurodegenerative such as PD) in a subject, comprising administering to the subject an effective amount of a compound of the present disclosure, or a pharmaceutically acceptable salt, ester, tautomer, or prodrug thereof.

The method may further comprise administering the compound, or a pharmaceutically acceptable salt, ester, tautomer, or prodrug thereof orally, parenterally, or intravenously.

In one embodiment, the compound used in the methods of the present disclosure is

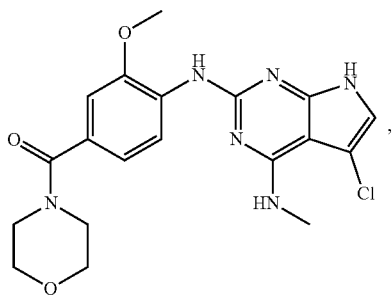 [SMILES: CNc1nc(Nc2ccc(C(=O)N3CCOCC3)cc2OC)nc2[nH]cc(Cl)c12]

or a pharmaceutically acceptable salt, ester, tautomer, or prodrug thereof.

In accordance with embodiments, the compounds of the present disclosure may be administered to a subject at a dose of about 1 mg/Kg to about 100 mg/Kg. In one embodiment, the compound is administered to a subject at a dose of about 30 mg/Kg.

Another aspect of the disclosure provides use of a compound of the disclosure, or a pharmaceutically acceptable salt, ester, tautomer, or prodrug thereof, in treating or preventing a disease or disorder in which LRRK2 is involved (e.g., a neurodegenerative such as PD).

Another aspect of the disclosure provides use of a compound of the disclosure, or a pharmaceutically acceptable salt, ester, tautomer, or prodrug thereof, in the manufacture of a medicament for the treatment or prevention of a disease or disorder in which LRRK2 is involved (e.g., a neurodegenerative such as PD).

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar to or equivalent to those described herein can be used in the practice and testing of the disclosure, suitable methods and materials are described below. All publications, patent applications, patents, and other references mentioned herein are incorporated by reference. The references cited herein are not admitted to be prior art to the claimed disclosure. In the case of conflict, the present specification, including definitions, will control. In addition, the materials, methods, and examples are illustrative only and not intended to be limiting.

Other features and advantages of the disclosure will be apparent from the following detailed description, examples, and claims.

BRIEF DESCRIPTION OF THE DRAWINGS

FIG. 2A-2D show inhibition of LRRK2 by Compound 18. HEK293 cells stably expressing FIG. 2A: wild-type GFP-LRRK2, FIG. 2B: GFP-LRRK2[G2019S], FIG. 2C: GFP-LRRK2[G2019S+A2016T], and FIG. 2D: GFP-LRRK2 [A2016T] were treated with dimethylsulfoxide (DMSO) or increasing concentrations of Compound 18 for 90 min (1 µM of LRRK2-IN-1 was used as a control). Cell lysates were subjected to immunoblotting for detection of LRRK2 phosphorylated at Ser910 and Ser935 and for total LRRK2.

FIG. 3A-3C show inhibition of endogenously expressed LRRK2 by Compound 18. FIG. 3A: Endogenous LRRK2 from EBV immortalized human lymphoblastoid cells from a control subject and a Parkinson's disease patient homozygous for the wild type GFP-LRRK2 and the LRRK2 [G2019S] mutation. After treatment of the cells with DMSO or the indicated concentration of 18 (or LRRK2-IN-1) for 90 min, cell lysates were subjected to immunoblot analysis with the indicated antibody for western analysis. Immunoblots were performed in duplicate, and results were representative of at least two independent experiments. FIG. 3B: As in FIG. 3A, except mouse Swiss 3T3 cells were used. FIG. 3C: Enzyme activity of Compound 18. GST-LRRK2(1326-2517), GST-LRRK2[G2019S](1326-2517), GST-LRRK2 [A2016T](1326-2517) and GST-LRRK2[G2019S+A2016T] (1326-2517) were assayed using 20 µM Nictide in the presence of 100 µM ATP. Results are average of duplicate experiments.

DETAILED DESCRIPTION OF THE DISCLOSURE

Figure 1:
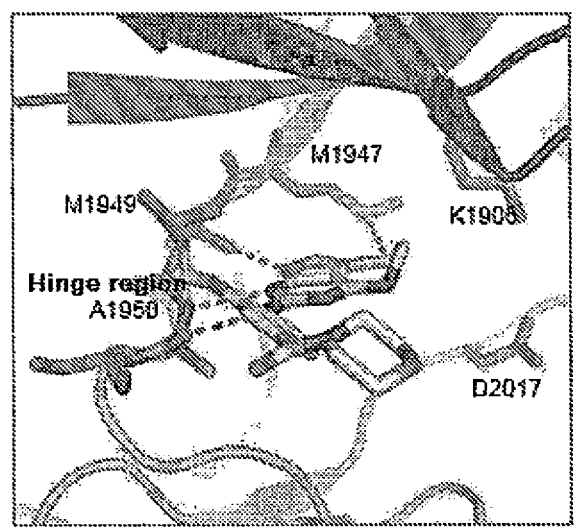
FIG. 1 is a molecular model of Compound 18 in complex with LRRK2.

Parkinson's Disease (PD) is defined clinically by the association of bradykinesia, resting tremor, muscular rigidity, and postural instability, and pathologically by the degeneration of dopaminergic neurons in the substantia nigra-pars compacta (SNpc) and other brain sites, with formation of ubiquitin containing inclusions (Lewy bodies) in the surviving neurons. The present disclosure provides a novel family of compounds that may be used in the treatment of PD.

Though the cause of PD remains unknown, a positive family history of PD is found in about 15% to about 25% of cases, and several chromosomal loci (termed PARK) genes and mutations have been linked to familial Parkinsonism through linkage mapping. Linkage mapping localizes mutant genes based on the coinheritance of genetic markers and phenotypes in families over several generations. By following families with dominantly inherited Parkinsonism, PARK loci can be mapped. Most recently, a novel PARK locus (PARK8) was mapped to chromosome 12q12. Pathogenic amino acid substitutions were subsequently identified in a novel gene; leucine-rich repeat kinase 2 (LRRK2). Activating mutations in LRRK2 are present in a subset of Parkinson's disease (PD) patients and may represent an attractive therapeutic target. For example, the G2019S missense mutation of LRRK2 increases kinase activity which may result in activation of the neuronal death signaling pathway, suggesting that small molecule LRRK2 kinase inhibitors may be able to serve as a new class of therapeutics for the treatment of PD. Kinase-dependent over expression of LRRK2 leads to cytotoxicity and neuron death. LRRK2 is phosphorylated at least at the Ser910 and Ser935 sites, which is critical LRRK2 kinase activity. The present disclosure provides novel compounds with potent LRRK2 inhibitor activity and favorable pharmacokinetic properties. The compounds of the present disclosure may advantageously reduce or inhibit LRRK2 phosphorylation at Ser910 and Ser935.

In addition, the present disclosure provides methods of synthesizing the foregoing compounds. Following synthesis, an effective amount of one or more of the compounds may be formulated with a pharmaceutically acceptable carrier for administration to a subject for use as a treatment for Parkinson's disease. The compounds or formulations may be administered, for example, via oral or parenteral routes, to provide an effective amount of the compound to the subject.

1. Definitions

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

Keto substituents are not present on aromatic moieties (i.e., phenyl, pyridinyl, etc.). Ring double bonds, as used herein, are double bonds that are formed between two adjacent ring atoms (e.g., C=C, C=N, or N=N).

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present disclosure containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present disclosure and intermediates made therein are considered to be part of the present disclosure. All tautomers of shown or described compounds are also considered to be part of the present disclosure.

When any variable (e.g., $R^1$) occurs more than one time in any constituent or formula for a compound, its definition at each occurrence is independent of its definition at every other occurrence. Thus, for example, if a group is shown to be substituted with 0-2 $R^1$ moieties, then the group may optionally be substituted with up to two $R^1$ moieties and $R^1$ at each occurrence is selected independently from the definition of $R^1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present disclosure that contain nitrogens can be converted to N-oxides by treatment with an oxidizing agent (e.g., MCPBA and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as MCPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, alkenyl, alkynyl, $C_{3-14}$ carbocycle, or 3-14-membered heterocycle) derivatives.

When an atom or chemical moiety is followed by a subscripted numeric range (e.g., $C_{1-6}$), the disclosure is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl.

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl. As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

As used herein, "halo" or "halogen" refers to fluoro, chloro, bromo, and iodo. "Counterion" is used to represent a small, negatively charged species such as chloride, bromide, hydroxide, acetate, and sulfate.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, but not limited to, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. Preferred bridges include, but are not limited to, one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present disclosure can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990).

Since prodrugs are known to enhance numerous desirable qualities of pharmaceuticals (e.g., solubility, bioavailability, manufacturing, etc.) the compounds of the present disclosure may be delivered in prodrug form. Thus, the present disclosure is intended to cover prodrugs of the presently claimed compounds, methods of delivering the same and compositions containing the same. "Prodrugs" are intended to include any covalently bonded carriers that release an active parent drug of the present disclosure in vivo when such prodrug is administered to a subject. Prodrugs the present disclosure are prepared by modifying functional groups present in the compound in such a way that the modifications are cleaved, either in routine manipulation or in vivo, to the parent compound. Prodrugs include compounds of the present disclosure wherein a hydroxy, amino, or sulfhydryl group is bonded to any group that, when the prodrug of the present disclosure is administered to a subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present disclosure.

"Stable compound" and "stable structure" are meant to indicate a compound that is sufficiently robust to survive isolation to a useful degree of purity from a reaction mixture, and formulation into an efficacious therapeutic agent.

As used herein, the term "treat," "treating," or "treatment" refers to decreasing the symptoms, markers, and/or any negative effect of a disease in any appreciable degree in a patient who currently has the disease. Treatment refers to a method of alleviating or abating a disease and/or its attendant symptoms.

As used herein, the term "prevent," "prevention," or "preventing" refers to any method to partially or completely prevent or delay the onset of one or more symptoms or features of a disease. Prevention may be administered to a subject who does not exhibit signs of a disease.

As used herein, the term "effective amount" refers to an amount of a compound, or a combination of compounds, of the present disclosure effective when administered alone or in combination as an anti-proliferative and/or anti-infective agent. The combination of compounds is preferably a synergistic combination. Synergy occurs when the effect of the compounds when administered in combination is greater than the additive effect of the compounds when administered alone as a single agent. In general, a synergistic effect is most clearly demonstrated at sub-optimal doses of the compounds. Synergy can be in terms of lower cytotoxicity, increased anti-proliferative and/or anti-infective effect, or some other beneficial effect of the combination compared with the individual components.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the disclosure remains operable.

Moreover, two or more steps or actions may be conducted simultaneously.

2. Compounds of the Disclosure

In one aspect, the disclosure provides a compound of formula I, II, or III:

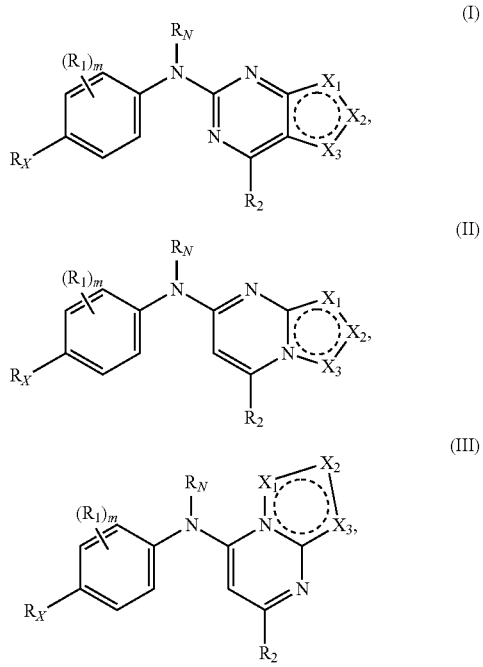

or a pharmaceutically acceptable salt thereof, wherein:
$R_X$ is $NR_A R_B$,

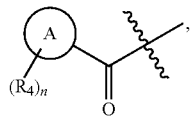

or a ring system comprising one or two 6-membered heterocycles selected from:

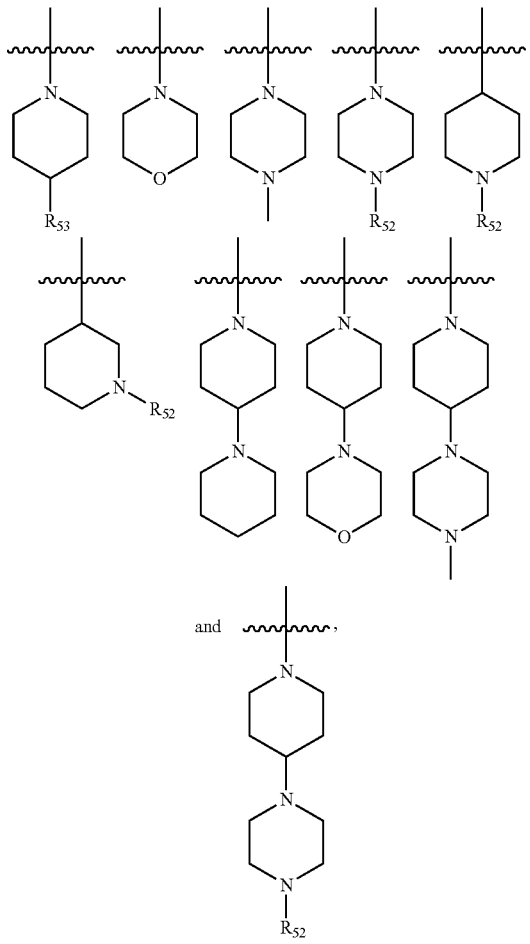

wherein each of the ring systems is optionally substituted with 1, 2, 3, 4, 5, or 6 $R_{51}$;
each $R_{51}$ is independently unsubstituted or substituted $C_1$-$C_6$ alkyl, $C(O)NR_{61}R_{62}$, $C(O)OR_{63}$, or $NR_{64}R_{65}$;
$R_{52}$ is H or $R_{51}$;
$R_{53}$ is H, OH, or $R_{51}$;
$R_{61}$, $R_{62}$, and $R_{63}$ are each independently H, unsubstituted or substituted $C_1$-$C_6$ alkyl, or unsubstituted or substituted $C_2$-$C_6$ alkenyl;
$R_{64}$ and $R_{65}$ are each independently H or unsubstituted or substituted $C_1$-$C_6$ alkyl;

is a ring system comprising one or two 6-membered heterocycles selected from:

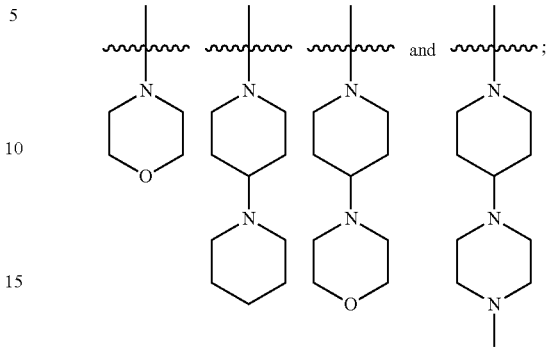

each $R_4$ is independently unsubstituted or substituted $C_1$-$C_6$ alkyl;
n is 0, 1, 2, 3, 4, 5, or 6;
$R_A$ and $R_B$ are each independently unsubstituted or substituted $C_1$-$C_6$ alkyl, or $C(O)R_7$;
$R_7$ is unsubstituted or substituted $C_1$-$C_6$ alkyl, unsubstituted or substituted $C_2$-$C_6$ alkenyl, or unsubstituted or substituted $C_2$-$C_6$ alkynyl;
$X_1$, $X_2$, and $X_3$ are each independently N, $NR_{31}$, or $CR_{32}$, wherein at least one of $X_1$, $X_2$, and $X_3$ is N or $NR_{31}$;
each $R_{31}$ is independently H or unsubstituted or substituted $C_1$-$C_6$ alkyl;
each $R_{32}$ is independently H, unsubstituted or substituted $C_1$-$C_6$ alkyl, halogen, or $NR_{81}R_{82}$;
$R_{81}$ is H or unsubstituted or substituted $C_1$-$C_6$ alkyl;
$R_{82}$ is $C(O)R_{83}$;
$R_{83}$ is unsubstituted or substituted $C_1$-$C_6$ alkyl, unsubstituted or substituted $C_2$-$C_6$ alkenyl, or unsubstituted or substituted $C_2$-$C_6$ alkynyl;
$R_N$ is H or unsubstituted or substituted $C_1$-$C_6$ alkyl;
each $R_1$ is independently unsubstituted or substituted $C_1$-$C_6$ alkyl, unsubstituted or substituted $C_1$-$C_6$ alkoxy, or halogen;
m is 0, 1, 2, or 3;
$R_2$ is H, unsubstituted or substituted $C_1$-$C_6$ alkyl, unsubstituted or substituted $C_1$-$C_6$ alkoxy, halogen, $NR_{N1}R_{N2}$, or $OR_{N3}$;
$R_{N1}$ and $R_{N2}$ are each independently H, unsubstituted or substituted $C_1$-$C_6$ alkyl, unsubstituted or substituted $C_2$-$C_6$ alkenyl, $(CH_2)_{1-3}$—O—$C_1$-$C_6$ alkyl, or $(CH_2)_{0-3}$—$R_{91}$, or $R_{N1}$ and $R_{N2}$, together with the nitrogen atom to which they are bonded, form a 5- or 6-membered heterocycle optionally comprising 1 or 2 additional heteroatoms selected from N and O;
$R_{N3}$ is $(CH_2)_{0-3}$—$R_{92}$;
$R_{91}$ is unsubstituted or substituted $C_3$-$C_8$ cycloalkyl, unsubstituted or substituted heterocycle comprising one 5- or 6-membered ring and 1-3 heteroatoms selected from N, O, and S, or phenyl substituted with $S(O)_2R_{10}$, $NHC(O)R_{11}$, $C(O)R_{12}$ or $C(O)NHR_{13}$;
$R_{92}$ is unsubstituted or substituted $C_3$-$C_8$ cycloalkyl, unsubstituted or substituted heterocycle comprising one 5- or 6-membered ring and 1-3 heteroatoms selected from N, O, and S, or phenyl substituted with $NO_2$, $S(O)_2R_{10}$, $NHC(O)R_{11}$, $C(O)R_{12}$, or $C(O)NHR_{13}$; and
$R_{10}$, $R_{11}$, $R_{12}$, and $R_{13}$ are each independently unsubstituted or substituted $C_1$-$C_6$ alkyl, unsubstituted or substituted $C_2$-$C_6$ alkenyl, NH—$C_1$-$C_6$ alkyl, unsubstituted or substi-

tuted heterocycle comprising one 5- or 6-membered ring and 1-3 heteroatoms selected from N, O, and S, unsubstituted or substituted phenyl, or unsubstituted or substituted heteroaryl comprising one 5- or 6-membered ring and 1-3 heteroatoms selected from N, O, and S.
In one embodiment,
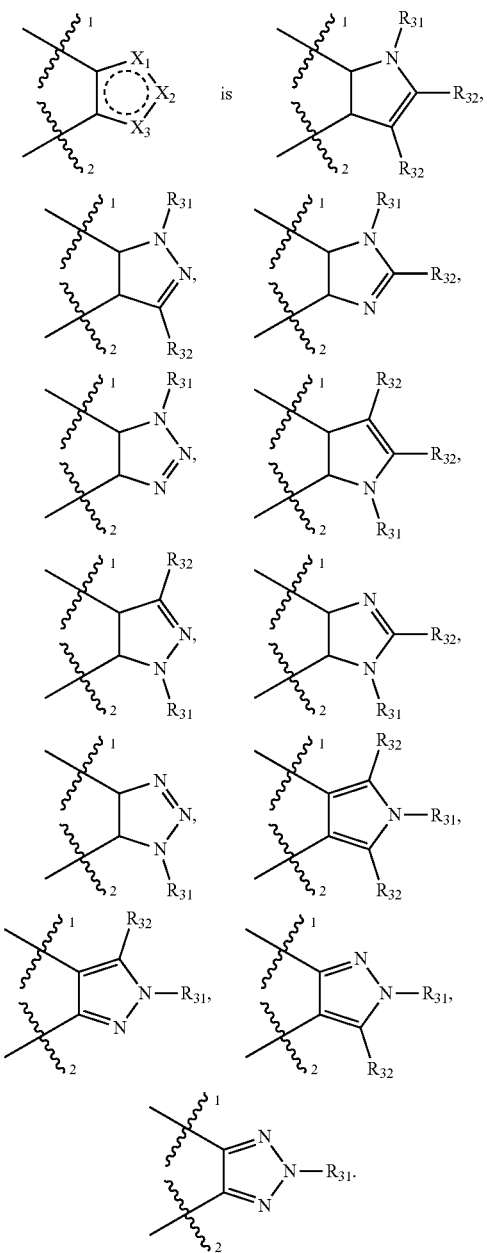
In a further embodiment,
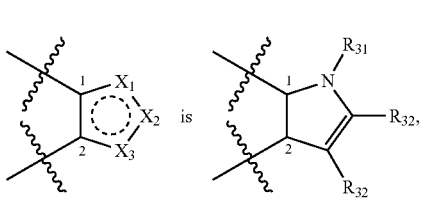
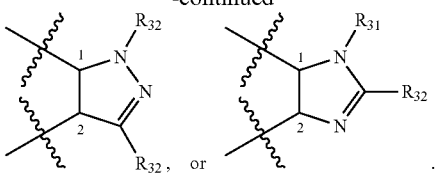
In one embodiment,
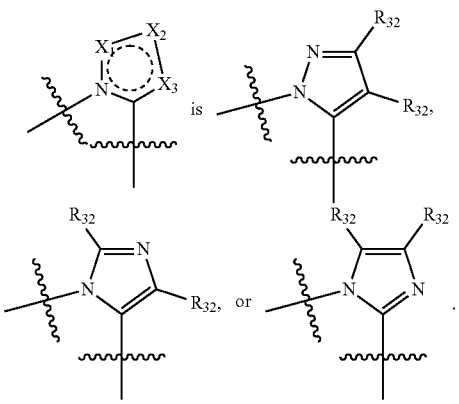
In a further embodiment,
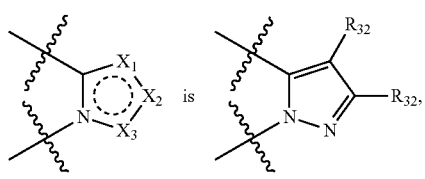
In one embodiment,
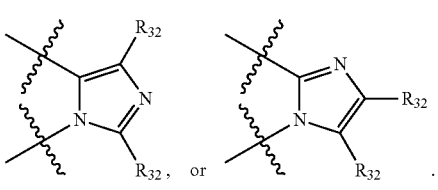

In a further embodiment,

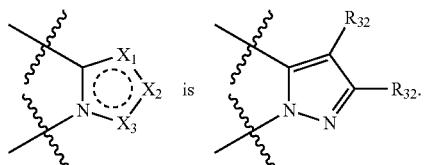 is

In one embodiment, each $R_{31}$ is H. In another embodiment, at least one $R_{31}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, at least one $R_{31}$ is $C_1$-$C_6$ alkyl substituted with one or more halogen (e.g., fluorine, chlorine, bromine, or iodine).

In one embodiment, each $R_{32}$ is H. In another embodiment, at least one $R_{32}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, at least one $R_{32}$ is $C_1$-$C_6$ alkyl substituted with one or more halogen (e.g., fluorine, chlorine, bromine, or iodine). In another embodiment, at least one $R_{32}$ is halogen (e.g., fluorine, chlorine, bromine, or iodine). In a further embodiment, at least one $R_{32}$ is fluorine or chlorine. In a further embodiment, at least one $R_{32}$ is chlorine. In another embodiment, at least one $R_{32}$ is $NR_{81}R_{82}$.

In one embodiment, each $R_{31}$ is H, and each $R_{32}$ is H. In another embodiment, each $R_{31}$ is H, and at least one $R_{32}$ is halogen (e.g., fluorine, chlorine, bromine, or iodine). In a further embodiment, each $R_{31}$ is H, and at least one $R_{32}$ is fluorine or chlorine. In another embodiment, each $R_{31}$ is H, and at least one $R_{32}$ is $NR_{81}R_{82}$.

In one embodiment, $R_{81}$ is H and $R_{82}$ is $C(O)R_{83}$. In another embodiment, $R_{81}$ is $C_1$-$C_6$ alkyl (e.g., methyl, ethyl, propyl, i-propyl, butyl, i-butyl, t-butyl, pentyl, or hexyl, each of which is optionally substituted) and $R_{82}$ is $C(O)R_{83}$.

In one embodiment, $R_{83}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_{83}$ is methyl or ethyl. In a further embodiment, $R_{83}$ is $C_1$-$C_6$ alkyl substituted with one or more halogen (e.g., F, Cl, Br, or I). In another embodiment, $R_{83}$ is $C_2$-$C_6$ alkenyl (e.g., ethenyl, propenyl, butenyl, pentenyl, or hexenyl, each of which is optionally substituted). In a further embodiment, $R_{83}$ is ethenyl. In another embodiment, $R_{83}$ is $C_2$-$C_6$ alkynyl (e.g., ethynyl, propynyl, butynyl, pentynyl, or hexynyl, each of which is optionally substituted).

In one embodiment, $R_X$ is

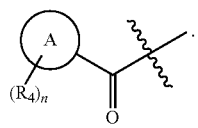

In one embodiment,

is

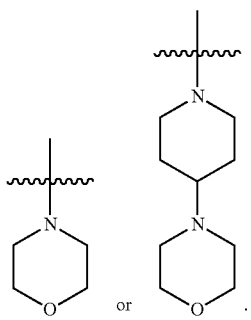 [SMILES: *N1CCOCC1 ; *N1CCC(N2CCOCC2)CC1]

In a further embodiment,

is

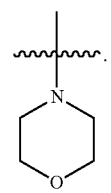 [SMILES: *N1CCOCC1]

In another further embodiment,

is

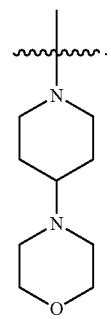

In another embodiment,

is

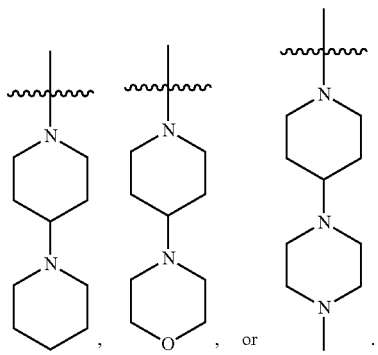

In one embodiment, n is 0. In one embodiment, n is 1. In one embodiment, n is 2. In one embodiment, n is 3. In one embodiment, n is 4. In one embodiment, n is 5. In one embodiment, n is 6.

In one embodiment, at least one $R_4$ is $C_1$-$C_6$ alkyl (e.g., methyl, ethyl, propyl, i-propyl, butyl, i-butyl, t-butyl, pentyl, or hexyl, each of which is optionally substituted). In a further embodiment, at least one $R_4$ is $C_1$-$C_6$ alkyl substituted with one or more halogen (e.g., fluorine, chlorine, bromine, or iodine).

In one embodiment, $R_X$ is a ring system selected from:

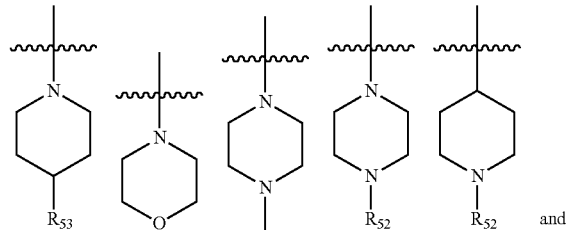

In a further embodiment, $R_X$ is

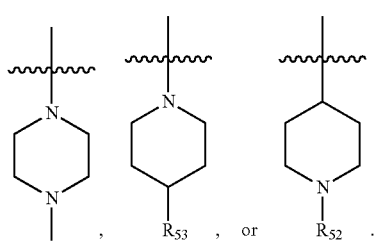

In a further embodiment, $R_X$ is

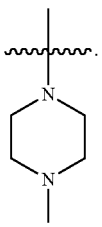 [SMILES: *N1CCN(C)CC1]

In another further embodiment, $R_X$ is

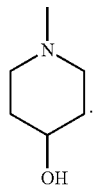

In another embodiment, $R_X$ is a ring system selected from:

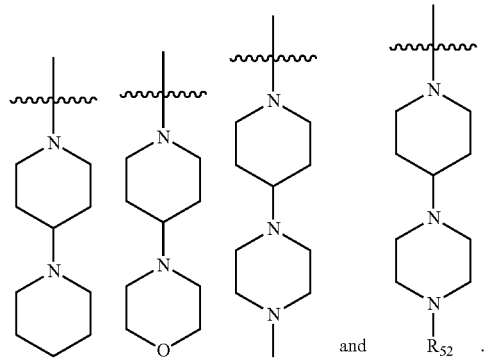

In a further embodiment, $R_X$ is

In one embodiment, at least one $R_{51}$ is $C_1$-$C_6$ alkyl (e.g., methyl, ethyl, propyl, i-propyl, butyl, i-butyl, t-butyl, pentyl, or hexyl, each of which is optionally substituted). In another embodiment, at least one $R_{51}$ is $C(O)NR_{61}R_{62}$ or $C(O)OR_{63}$. In another embodiment, at least one $R_{51}$ 1 S $NR_{64}R_{65}$.

In one embodiment, one of $R_{61}$ and $R_{62}$ is H, and the other is $C_1$-$C_6$ alkyl (e.g., methyl, ethyl, propyl, i-propyl, butyl, i-butyl, t-butyl, pentyl, or hexyl, each of which is optionally substituted), or $C_2$-$C_6$ alkenyl (e.g., ethenyl, propenyl, butenyl, pentenyl, or hexenyl, each of which is optionally substituted). In another embodiment, one of $R_{61}$ and $R_{62}$ is $C_1$-$C_6$ alkyl (e.g., methyl, ethyl, propyl, i-propyl, butyl, i-butyl, t-butyl, pentyl, or hexyl, each of which is optionally substituted), and the other is $C_1$-$C_6$ alkyl (e.g., methyl, ethyl, propyl, i-propyl, butyl, i-butyl, t-butyl, pentyl, or hexyl, each of which is optionally substituted), or $C_2$-$C_6$ alkenyl (e.g., ethenyl, propenyl, butenyl, pentenyl, or hexenyl, each of which is optionally substituted).

In one embodiment, $R_{63}$ is $C_1$-$C_6$ alkyl (e.g., methyl, ethyl, propyl, i-propyl, butyl, i-butyl, t-butyl, pentyl, or hexyl, each of which is optionally substituted). In another embodiment, $R_{63}$ is $C_2$-$C_6$ alkenyl (e.g., ethenyl, propenyl, butenyl, pentenyl, or hexenyl, each of which is optionally substituted).

In one embodiment, one of $R_{64}$ and $R_{65}$ is H, and the other is $C_1$-$C_6$ alkyl (e.g., methyl, ethyl, propyl, i-propyl, butyl, i-butyl, t-butyl, pentyl, or hexyl, each of which is optionally substituted). In another embodiment, $R_{64}$ and $R_{65}$ are each independently $C_1$-$C_6$ alkyl (e.g., methyl, ethyl, propyl, i-propyl, butyl, i-butyl, t-butyl, pentyl, or hexyl, each of which is optionally substituted).

In one embodiment, $R_{52}$ is H. In another embodiment, $R_{52}$ is $R_{51}$.

In one embodiment, $R_{53}$ is H. In another embodiment, $R_{53}$ is OH. In another embodiment, $R_{53}$ is $R_{51}$.

In one embodiment, $R_X$ is $NR_A R_B$.

In one embodiment, $R_A$ and $R_B$ are each independently $C_1$-$C_6$ alkyl (e.g., methyl, ethyl, propyl, i-propyl, butyl, i-butyl, t-butyl, pentyl, or hexyl, each of which is optionally substituted). In another embodiment, $R_A$ is $C_1$-$C_6$ alkyl (e.g., methyl, ethyl, propyl, i-propyl, butyl, i-butyl, t-butyl, pentyl, or hexyl, each of which is optionally substituted), and $R_B$ is $C(O)R_7$. In a further embodiment, $R_A$ is methyl, and $R_B$ is $C(O)R_7$.

In one embodiment, $R_7$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_7$ is methyl or ethyl. In another embodiment, $R_7$ is $C_2$-$C_6$ alkenyl (e.g., ethenyl, propenyl, butenyl, pentenyl, or hexenyl, each of which is optionally substituted). In another embodiment, $R_7$ is $C_2$-$C_6$ alkynyl (e.g., ethynyl, propynyl, butynyl, pentynyl, or hexynyl, each of which is optionally substituted).

In one embodiment, $R_N$ is H. In another embodiment, $R_N$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_N$ is $C_1$-$C_6$ alkyl substituted with one or more halogen (e.g., fluorine, chlorine, bromine, or iodine). In a further embodiment, $R_N$ is methyl, ethyl, or propyl, each of which is optionally substituted.

In one embodiment, m is 0. In one embodiment, m is 1. In one embodiment, m is 2. In one embodiment, m is 3.

In one embodiment, at least one $R_1$ is $C_1$-$C_6$ alkyl (e.g., methyl, ethyl, propyl, i-propyl, butyl, i-butyl, t-butyl, pentyl, or hexyl, each of which is optionally substituted). In a further embodiment, at least one $R_1$ is $C_1$-$C_6$ alkyl substituted with one or more halogen (e.g., fluorine, chlorine, bromine, or iodine).

In one embodiment, at least one $R_1$ is $C_1$-$C_6$ alkoxy (e.g., methoxy, ethoxy, propoxy, i-propoxy, butoxy, i-butoxy, t-butoxy, pentoxy, or hexyloxy, each of which is optionally substituted). In one embodiment, at least one $R_1$ is methoxy, ethoxy, or i-propoxy. In a further embodiment, at least one $R_1$ is methoxy or ethoxy. In a further embodiment, at least one $R_1$ is methoxy. In a further embodiment, at least one $R_1$ is $C_1$-$C_6$ alkoxy substituted with one or more halogen (e.g., fluorine, chlorine, bromine, or iodine).

In one embodiment, at least one $R_1$ is halogen (e.g., fluorine, chlorine, bromine, or iodine). In a further embodiment, at least one $R_1$ is fluorine or chlorine. In a further embodiment, at least one $R_1$ is fluorine.

In one embodiment, $R_2$ is H.

In one embodiment, $R_2$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_2$ is $C_1$-$C_6$ alkyl substituted with one or more halogen (e.g., fluorine, chlorine, bromine, or iodine).

In one embodiment, $R_2$ is halogen (e.g., fluorine, chlorine, bromine, or iodine). In a further embodiment, $R_2$ is fluorine or chlorine.

In one embodiment, $R_2$ is unsubstituted or substituted $C_1$-$C_6$ alkoxy, or $NR_{N1}R_{N2}$.

In one embodiment, $R_2$ is $C_1$-$C_6$ alkoxy (e.g., methoxy, ethoxy, propoxy, i-propoxy, butoxy, i-butoxy, t-butoxy, pentoxy, or hexyloxy, each of which is optionally substituted). In a further embodiment, $R_2$ is $C_1$-$C_6$ alkoxy substituted with one or more halogen (e.g., fluorine, chlorine, bromine, or iodine). In a further embodiment, $R_2$ is methoxy.

In one embodiment, $R_2$ is $NR_{N1}R_{N2}$.

In one embodiment, $R_{N1}$ and $R_{N2}$ are each H.

In one embodiment, one of $R_{N1}$ and $R_{N2}$ is H, and the other is unsubstituted or substituted $C_1$-$C_6$ alkyl, unsubstituted or substituted $C_2$-$C_6$ alkenyl, $(CH_2)_{1-3}$—O—$C_1$-$C_6$ alkyl, or $(CH_2)_{0-3}$—$R_{91}$.

In one embodiment, one of $R_{N1}$ and $R_{N2}$ is H, and the other is $C_1$-$C_6$ alkyl (e.g., methyl, ethyl, propyl, i-propyl, butyl, i-butyl, t-butyl, pentyl, or hexyl, each of which is optionally substituted). In a further embodiment, one of $R_{N1}$ and $R_{N2}$ is H, and the other is $C_1$-$C_6$ alkyl substituted with one or more substituents selected from halogen (e.g., fluorine, chlorine, bromine, or iodine), OH, and phenyl. In a further embodiment, one of $R_{N1}$ and $R_{N2}$ is H, and the other is methyl, ethyl, propyl, i-propyl, butyl, i-butyl, or t-butyl.

In one embodiment, one of $R_{N1}$ and $R_{N2}$ is H, and the other is $C_2$-$C_6$ alkenyl (e.g., ethenyl, propenyl, butenyl, pentenyl, or hexenyl, each of which is optionally substituted). In a further embodiment, one of $R_{N1}$ and $R_{N2}$ is H, and the other is ethenyl or propenyl.

In one embodiment, one of $R_{N1}$ and $R_{N2}$ is H, and the other is $(CH_2)$—O—$C_1$-$C_6$ alkyl. In another embodiment, one of $R_{N1}$ and $R_{N2}$ is H, and the other is $(CH_2)_2$—O—$C_1$-$C_6$ alkyl. In another embodiment, one of $R_{N1}$ and $R_{N2}$ is H, and the other is $(CH_2)_3$—O—$C_1$-$C_6$ alkyl. In a further embodiment, $C_1$-$C_6$ alkyl is selected from methyl, ethyl, propyl, i-propyl, butyl, i-butyl, t-butyl, pentyl, or hexyl, each of which is optionally substituted. In a further embodiment, one of $R_{N1}$ and $R_{N2}$ is H, and the other is $(CH_2)_2$—O-methyl, $(CH_2)_2$—O-ethyl, or $(CH_2)_2$—O-propyl. In a further embodiment, one of $R_{N1}$ and $R_{N2}$ is H, and the other is $(CH_2)_2$—O-methyl.

In one embodiment, one of $R_{N1}$ and $R_{N2}$ is H, and the other is $(CH_2)_{0-3}$—$R_{91}$. In a further embodiment, $(CH_2)_{0-3}$—$R_{91}$ is $R_{91}$. In another embodiment, $(CH_2)_{0-3}$—$R_{91}$ is $(CH_2)$—$R_{91}$. In another embodiment, $(CH_2)_{0-3}$—$R_{91}$ is $(CH_2)_2$—$R_{91}$. In another embodiment, $(CH_2)_{0-3}$—$R_{91}$ is $(CH_2)_3$—$R_{91}$.

In one embodiment, $R_{N1}$ and $R_{N2}$ are each independently $C_1$-$C_6$ alkyl (e.g., methyl, ethyl, propyl, i-propyl, butyl, i-butyl, t-butyl, pentyl, or hexyl, each of which is optionally substituted). In a further embodiment, $R_{N1}$ and $R_{N2}$ are each independently $C_1$-$C_6$ alkyl substituted with one or more halogen (e.g., fluorine, chlorine, bromine, or iodine).

In one embodiment, one of $R_{N1}$ and $R_{N2}$ is $C_1$-$C_6$ alkyl (e.g., methyl, ethyl, propyl, propyl, butyl, i-butyl, t-butyl, pentyl, or hexyl, each of which is optionally substituted), and the other is $(CH_2)_{1-3}$—O—$C_1$-$C_6$ alkyl. In a further embodiment, $(CH_2)_{1-3}$—O—$C_1$-$C_6$ alkyl is $(CH_2)$—O—$C_1$-$C_6$ alkyl. In another embodiment, $(CH_2)_{1-3}$—O—$C_1$-$C_6$ alkyl is $(CH_2)_2$—O—$C_1$-$C_6$ alkyl. In another embodiment, $(CH_2)_{1-3}$—O—$C_1$-$C_6$ alkyl is $(CH_2)_3$—O—$C_1$-$C_6$ alkyl. In a further embodiment, $C_1$-$C_6$ alkyl is selected from methyl, ethyl, propyl, i-propyl, butyl, i-butyl, t-butyl, pentyl, or hexyl, each of which is optionally substituted.

In one embodiment, one of $R_{N1}$ and $R_{N2}$ is $C_1$-$C_6$ alkyl (e.g., methyl, ethyl, propyl, propyl, butyl, i-butyl, t-butyl, pentyl, or hexyl, each of which is optionally substituted), and the other is $(CH_2)_{0-3}$—$R_{91}$. In a further embodiment, $(CH_2)_{0-3}$—$R_{91}$ is $R_{91}$. In another embodiment, $(CH_2)_{0-3}$—$R_{91}$ is $(CH_2)$—$R_{91}$. In another embodiment, $(CH_2)_{0-3}$—$R_{91}$ is $(CH_2)_2$—$R_{91}$. In another embodiment, $(CH_2)_{0-3}$—$R_{91}$ is $(CH_2)_3$—$R_{91}$.

In one embodiment, $R_{91}$ is $C_3$-$C_8$ cycloalkyl (e.g., cyclopropyl, cyclobutyl, cyclopentyl, cyclohexyl, cycloheptyl, or cyclooctyl, each of which is optionally substituted). In a further embodiment, $R_{91}$ is $C_3$-$C_8$ cycloalkyl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy). In a further embodiment, $R_{91}$ is cyclopropyl, cyclobutyl, cyclopentyl, or cyclohexyl.

In one embodiment, $R_{91}$ is heterocycle comprising one 5- or 6-membered ring and 1-3 heteroatoms selected from N, O, and S. In a further embodiment, $R_{91}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, hexahydropyridazine, and tetrahydrofuran. In a further embodiment, $R_{91}$ is a heterocycle selected from pyrrolidine, piperidine, piperazine, morpholine, and tetrahydrofuran. In a further embodiment, $R_{91}$ is pyrrolidine or tetrahydrofuran. In one embodiment, $R_{91}$ is heterocycle substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy). In one embodiment, $R_{91}$ is heterocycle substituted with $S(O)_2R_{10}$, $NHC(O)R_{11}$, $C(O)R_{12}$, or $C(O)NHR_{13}$.

In one embodiment, $R_{91}$ is phenyl substituted with $S(O)_2R_{10}$, $NHC(O)R_{11}$, $C(O)R_{12}$, or $C(O)NHR_{13}$.

In one embodiment, $R_2$ is $OR_{N3}$.

In one embodiment, $R_{N3}$ is $(CH_2)_{0-3}$—$R_{92}$. In a further embodiment, $(CH_2)_{0-3}$—$R_{92}$ is $R_{92}$. In another embodiment, $(CH_2)_{0-3}$—$R_{92}$ is $(CH_2)$—$R_{92}$. In another embodiment, $(CH_2)_{0-3}$—$R_{92}$ is $(CH_2)_2$—$R_{92}$. In another embodiment, $(CH_2)_{0-3}$—$R_{92}$ is $(CH_2)_3$—$R_{92}$.

In one embodiment, $R_{92}$ is $C_3$-$C_8$ cycloalkyl (e.g., cyclopropyl, cyclobutyl, cyclopentyl, cyclohexyl, cycloheptyl, or cyclooctyl, each of which is optionally substituted). In a further embodiment, $R_{92}$ is $C_3$-$C_8$ cycloalkyl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{92}$ is heterocycle comprising one 5- or 6-membered ring and 1-3 heteroatoms selected from N, O, and S. In a further embodiment, $R_{92}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, and hexahydropyridazine. In a further embodiment, $R_{92}$ is a heterocycle selected from pyrrolidine, piperidine, piperazine, and morpholine. In a further embodiment, $R_{92}$ is pyrrolidine. In one embodiment, $R_{92}$ is heterocycle substituted with one or more groups independently selected from halogen (e.g., fluorine, chlorine, bromine, or iodine), $C_1$-$C_6$ alkyl (e.g., methyl, ethyl, propyl, propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{92}$ is heterocycle substituted with $S(O)_2R_{10}$, $NHC(O)R_{11}$, $C(O)R_{12}$, or $C(O)NHR_{13}$.

In one embodiment, $R_{92}$ is phenyl substituted with $NO_2$, $S(O)_2R_{10}$, $NHC(O)R_{11}$, $C(O)R_{12}$, or $C(O)NHR_{13}$.

In one embodiment, $R_{10}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_{10}$ is methyl, ethyl, or i-propyl. In another embodiment, $R_{10}$ is $C_2$-$C_6$ alkenyl (e.g., ethenyl, propenyl, butenyl, pentenyl, or hexenyl, each of which is optionally substituted).

In one embodiment, $R_{10}$ is NH—$C_1$-$C_6$ alkyl (e.g., methyl, ethyl, propyl, i-propyl, butyl, i-butyl, t-butyl, pentyl, or hexyl, each of which is optionally substituted). In a further embodiment, $R_{10}$ is NH-t-butyl.

In one embodiment, $R_{10}$ is heterocycle comprising one 5- or 6-membered ring and 1-3 heteroatoms selected from N, O, and S. In a further embodiment, $R_{10}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, and hexahydropyridazine. In a further embodiment, $R_{10}$ is a heterocycle selected from pyrrolidine, piperidine, piperazine, and morpholine. In one embodiment, $R_{10}$ is heterocycle substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{10}$ is phenyl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{10}$ is heteroaryl comprising one 5- or 6-membered ring and 1-3 heteroatoms selected from N, O, and S. In a further embodiment, $R_{10}$ is a heteroaryl selected from the group consisting pyrrole, pyrazole, imidazole, triazole, oxazole, isoxazole, dioxazole, thiazole, isothiazole, pyridine, pyrazine, and pyrimidine. In a further embodiment, $R_{10}$ is a heteroaryl selected from pyrrole, pyridine, and pyrimidine. In one embodiment, $R_{10}$ is heteroaryl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{11}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_{11}$ is methyl or ethyl. In a further embodiment, $R_{11}$ is $C_1$-$C_6$ alkyl substituted with one or more halogen (e.g., F, Cl, Br, or I). In another embodiment, $R_{11}$ is $C_2$-$C_6$ alkenyl (e.g., ethenyl, propenyl, butenyl, pentenyl, or hexenyl, each of which is optionally substituted). In a further embodiment, $R_{11}$ is ethenyl.

In one embodiment, $R_{11}$ is NH—$C_1$-$C_6$ alkyl (e.g., methyl, ethyl, propyl, i-propyl, butyl, i-butyl, t-butyl, pentyl, or hexyl, each of which is optionally substituted).

In one embodiment, $R_{11}$ is heterocycle comprising one 5- or 6-membered ring and 1-3 heteroatoms selected from N, O, and S. In a further embodiment, $R_{11}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, and hexahydropyridazine. In a further embodiment, $R_{11}$ is a heterocycle selected from pyrrolidine, piperidine, piperazine, and morpholine. In one embodiment, $R_{11}$ is heterocycle substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{11}$ is phenyl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{11}$ is heteroaryl comprising one 5- or 6-membered ring and 1-3 heteroatoms selected from N, O, and S. In a further embodiment, $R_{11}$ is a heteroaryl selected from the group consisting pyrrole, pyrazole, imidazole, triazole, oxazole, isoxazole, dioxazole, thiazole, isothiazole, pyridine, pyrazine, and pyrimidine. In a further embodiment, $R_{11}$ is a heteroaryl selected from pyrrole, pyridine, and pyrimidine. In one embodiment, $R_{11}$ is heteroaryl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{12}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_{12}$ is methyl or ethyl. In a further embodiment, $R_{12}$ is $C_1$-$C_6$ alkyl substituted with one or more halogen (e.g., F, Cl, Br, or I). In another embodiment, $R_{12}$ is $C_2$-$C_6$ alkenyl (e.g., ethenyl, propenyl, butenyl, pentenyl, or hexenyl, each of which is optionally substituted). In a further embodiment, $R_{12}$ is ethenyl.

In one embodiment, $R_{12}$ is NH—$C_1$-$C_6$ alkyl (e.g., methyl, ethyl, propyl, i-propyl, butyl, i-butyl, t-butyl, pentyl, or hexyl, each of which is optionally substituted).

In one embodiment, $R_{12}$ is heterocycle comprising one 5- or 6-membered ring and 1-3 heteroatoms selected from N, O, and S. In a further embodiment, $R_{12}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, and hexahydropyridazine. In a further embodiment, $R_{12}$ is a heterocycle selected from pyrrolidine, piperidine, piperazine, and morpholine. In one embodiment, $R_{12}$ is heterocycle substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{12}$ is phenyl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{12}$ is heteroaryl comprising one 5- or 6-membered ring and 1-3 heteroatoms selected from N, O, and S. In a further embodiment, $R_{12}$ is a heteroaryl selected from the group consisting pyrrole, pyrazole, imidazole, triazole, oxazole, isoxazole, dioxazole, thiazole, isothiazole, pyridine, pyrazine, and pyrimidine. In a further embodiment, $R_{12}$ is a heteroaryl selected from pyrrole, pyridine, and pyrimidine. In one embodiment, $R_{12}$ is heteroaryl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{13}$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_{13}$ is methyl. In another embodiment, $R_{13}$ is $C_2$-$C_6$ alkenyl (e.g., ethenyl, propenyl, butenyl, pentenyl, or hexenyl, each of which is optionally substituted).

In one embodiment, $R_{13}$ is NH—$C_1$-$C_6$ alkyl (e.g., methyl, ethyl, propyl, i-propyl, butyl, i-butyl, t-butyl, pentyl, or hexyl, each of which is optionally substituted).

In one embodiment, $R_{13}$ is heterocycle comprising one 5- or 6-membered ring and 1-3 heteroatoms selected from N, O, and S. In a further embodiment, $R_{13}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, hexahydropyridazine, and tetrahydropyran. In a further embodiment, $R_{13}$ is a heterocycle selected from pyrrolidine, piperidine, piperazine, morpholine, and tetrahydropyran. In one embodiment, $R_{13}$ is heterocycle substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{13}$ is phenyl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{13}$ is heteroaryl comprising one 5- or 6-membered ring and 1-3 heteroatoms selected from N, O, and S. In a further embodiment, $R_{13}$ is a heteroaryl selected from the group consisting pyrrole, pyrazole, imidazole, triazole, oxazole, isoxazole, dioxazole, thiazole, isothiazole, pyridine, pyrazine, and pyrimidine. In a further embodiment, $R_{13}$ is a heteroaryl selected from pyrrole, pyridine, and pyrimidine. In one embodiment, $R_{13}$ is heteroaryl substituted with one or more groups independently selected from halogen (e.g., fluorine, chlorine, bromine, or iodine), $C_1$-$C_6$ alkyl (e.g., methyl, ethyl, propyl, i-propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy).

In one embodiment, $R_{N1}$ and $R_{N2}$, together with the nitrogen atom to which they are bonded, form a 5- or 6-membered heterocycle. In a further embodiment, the heterocycle is selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, hexahydropyridazine, and piperazinone. In a further embodiment, the heterocycle is piperazinone or piperidine. In a further embodiment, the heterocycle is substituted with one or more substituents independently selected from $C_1$-$C_6$ alkyl (e.g., methyl, ethyl, propyl, i-propyl, butyl, i-butyl, t-butyl, pentyl, or hexyl), halogen (e.g., fluorine, chlorine, bromine, or iodine), and NHC(O)—$C_1$-$C_6$ alkyl (e.g., methyl, ethyl, propyl, i-propyl, butyl, i-butyl, t-butyl, pentyl, or hexyl).

Any substituent group for any one, two, or more of

$R_X$, $R_A$, $R_B$, $X_1$, $X_2$, $X_3$, $R_1$, $R_2$, $R_{31}$, $R_{32}$, $R_4$, $R_{51}$, $R_{52}$, $R_{53}$, $R_{61}$, $R_{62}$, $R_{63}$, $R_{64}$, $R_{65}$, $R_7$, $R_{81}$, $R_{82}$, $R_{83}$, $R_{91}$, $R_{92}$, $R_{10}$, $R_{11}$, $R_{12}$, $R_{13}$, $R_N$, $R_{N1}$, $R_{N2}$, $R_{N3}$, m, and n as described in the various embodiments above can be combined with any substituent group for any one, two, or more of the reminder of

$R_X$, $R_A$, $R_B$, $X_1$, $X_2$, $X_3$, $R_2$, $R_{31}$, $R_{32}$, $R_4$, $R_{51}$, $R_{52}$, $R_{53}$, $R_{61}$, $R_{62}$, $R_{63}$, $R_{64}$, $R_{65}$, $R_7$, $R_{81}$, $R_{82}$, $R_{83}$, $R_{91}$, $R_{92}$, $R_{10}$, $R_{11}$, $R_{12}$, $R_{13}$, $R_N$, $R_{N1}$, $R_{N2}$, $R_{N3}$, m, and n as described in the various embodiments.

In one embodiment, a compound of formula I, II, or III is a compound of formula Ia, IIa, or IIIa:

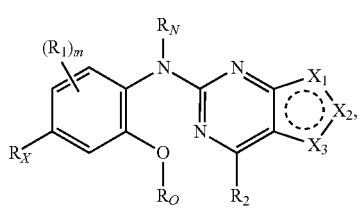

(Ia)

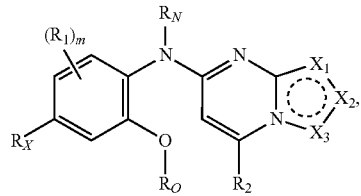

(IIa)

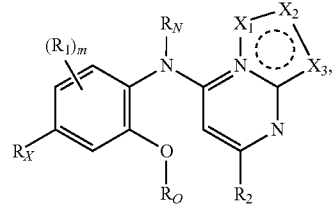

(IIIa)

or a pharmaceutically acceptable salt thereof, wherein $R_X$, $R_1$, $R_2$, $R_N$, $X_1$, $X_2$, $X_3$, and m are each as defined in formula I, II, or III, and $R_O$ is unsubstituted or substituted $C_1$-$C_6$ alkyl.

In one embodiment, each of $R_X$, $R_1$, $R_2$, $R_N$, $X_1$, $X_2$, $X_3$, and m can be selected from any of the substituent groups exemplified herein (e.g., for formula I, II, or III).

In one embodiment, $R_O$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_O$ is $C_1$-$C_6$ alkyl substituted with one or more halogen (e.g., fluorine, chlorine, bromine, or iodine). In a further embodiment, $R_O$ is methyl, ethyl, or i-propyl, each of which is optionally substituted. In a further embodiment, $R_O$ is methyl.

Any substituent group for any one, two, or more of $R_X$, $R_1$, $R_2$, $R_N$, $R_O$, $X_1$, $X_2$, $X_3$, and m as described in the various embodiments above can be combined with any substituent group for any one, two, or more of the reminder of $R_X$, $R_1$, $R_2$, $R_N$, $R_O$, $X_1$, $X_2$, $X_3$, and m as described in the various embodiments.

In one embodiment, a compound of formula I is a compound of formula Ib1 or Ib2:

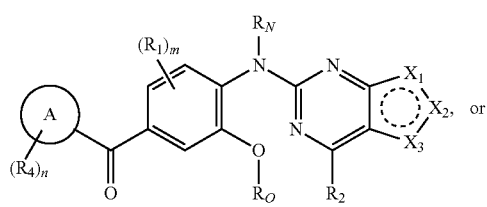

(Ib1)

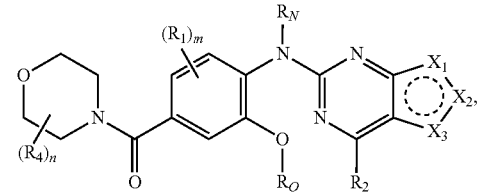

(Ib2)

or a pharmaceutically acceptable salt thereof, wherein $R_1$, $R_2$, $R_4$, $R_N$, $X_1$, $X_2$, $X_3$, m, n, and

are each as defined in formula I, and $R_O$ is unsubstituted or substituted $C_1$-$C_6$ alkyl.

In one embodiment, each of $R_1$, $R_2$, $R_4$, $R_N$, $X_1$, $X_2$, $X_3$, m, n, and

can be selected from any of the substituent groups exemplified herein (e.g., for formula I).

In one embodiment, $R_O$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_O$ is $C_1$-$C_6$ alkyl substituted with one or more halogen (e.g., fluorine, chlorine, bromine, or iodine). In a further embodiment, $R_O$ is methyl, ethyl, or i-propyl, each of which is optionally substituted. In a further embodiment, $R_O$ is methyl.

Any substituent group for any one, two, or more of $R_1$, $R_2$, $R_4$, $R_N$, $R_O$, $X_1$, $X_2$, $X_3$, m, n, and

as described in the various embodiments above can be combined with any substituent group for any one, two, or more of the reminder of $R_1$, $R_2$, $R_4$, $R_N$, $R_O$, $X_1$, $X_2$, $X_3$, m, n, and

as described in the various embodiments.

In one embodiment, a compound of formula I is a compound of formula Ic1 or Ic2:

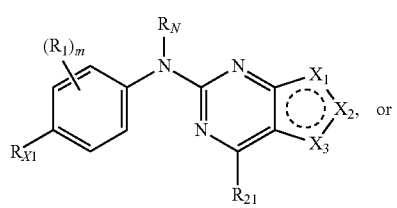

or a pharmaceutically acceptable salt thereof, wherein:

$R_{X1}$ is a ring system comprising one or two 6-membered heterocycles selected from:

wherein each of the ring systems is optionally substituted with 1, 2, 3, 4, 5, or 6 $R_{51}$;

$R_{21}$ is $NHR_{N4}$ or $OR_{N5}$;

$R_{N4}$ is heterocycle comprising one 5- or 6-membered ring and 1-3 heteroatoms selected from N, O, and S, or phenyl, wherein the heterocycle or phenyl is substituted with $S(O)_2R_{10}$, $NHC(O)R_{11}$, $C(O)R_{12}$, or $C(O)NHR_{13}$;

$R_{N5}$ is heterocycle comprising one 5- or 6-membered ring and 1-3 heteroatoms selected from N, O, and S, or phenyl, wherein the heterocycle or phenyl is substituted with $NO_2$, $S(O)_2R_{10}$, $NHC(O)R_{11}$, $C(O)R_{12}$, or $C(O)NHR_{13}$; and $R_1$, $R_N$, $X_1$, $X_2$, $X_3$, $R_{51}$, $R_{52}$, $R_{53}$, $R_{10}$, $R_{11}$, $R_{12}$, $R_{13}$, and m are each as defined in formula I.

In one embodiment, each of $R_1$, $R_N$, $X_1$, $X_2$, $X_3$, $R_{51}$, $R_{52}$, $R_{53}$, $R_{10}$, $R_{11}$, $R_{12}$, $R_{13}$, and m can be selected from any of the substituent groups exemplified herein (e.g., for formula I).

In one embodiment, $R_O$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_O$ is $C_1$-$C_6$ alkyl substituted with one or more halogen (e.g., fluorine, chlorine, bromine, or iodine). In a further embodiment, $R_O$ is methyl, ethyl, or propyl, each of which is optionally substituted. In a further embodiment, $R_O$ is methyl.

In one embodiment, $R_{21}$ is $NHR_{N4}$. In another embodiment, $R_{21}$ is $OR_{N5}$.

In one embodiment, $R_{N4}$ is heterocycle comprising one 5- or 6-membered ring and 1-3 heteroatoms selected from N, O, and S. In a further embodiment, $R_{N4}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, and hexahydropyridazine. In a further embodiment, $R_{N4}$ is a heterocycle selected from pyrrolidine, piperidine, piperazine, and morpholine. In a further embodiment, $R_{N4}$ is pyrrolidine. In one embodiment, $R_{N4}$ is heterocycle substituted with one or more groups independently selected from halogen (e.g., fluorine, chlorine, bromine, or iodine), $C_1$-$C_6$ alkyl (e.g., methyl, ethyl, propyl, propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy). In one embodiment, $R_{N4}$ is heterocycle substituted with $S(O)_2R_{10}$, $NHC(O)R_{11}$, $C(O)R_{12}$, or $C(O)NHR_{13}$.

In one embodiment, $R_{N4}$ is phenyl substituted with $S(O)_2R_{10}$, $NHC(O)R_{11}$, $C(O)R_{12}$, or $C(O)NHR_{13}$.

In one embodiment, $R_{N5}$ is heterocycle comprising one 5- or 6-membered ring and 1-3 heteroatoms selected from N, O, and S. In a further embodiment, $R_{N5}$ is a heterocycle selected from pyrrolidine, pyrazolidine, imidazolidine, triazolidine, oxazolidine, isoxazolidine, dioxazolidine, oxadiazolidine, thiazolidine, isothiazolidine, dithiazolidine, thiadiazolidine, piperidine, piperazine, morpholine, thiamorpholine, hexahydropyrimidine, and hexahydropyridazine. In a further embodiment, $R_{N5}$ is a heterocycle selected from pyrrolidine, piperidine, piperazine, and morpholine. In a further embodiment, $R_{N4}$ is pyrrolidine. In one embodiment, $R_{N5}$ is heterocycle substituted with one or more groups independently selected from halogen (e.g., fluorine, chlorine, bromine, or iodine), $C_1$-$C_6$ alkyl (e.g., methyl, ethyl, propyl, propyl, butyl, i-butyl, t-butyl, pentyl, or hexyl), and $C_1$-$C_6$ alkoxy (e.g., methoxy, ethoxy, propoxy, i-propoxy, butoxy, i-butoxy, t-butoxy, pentoxy, or hexyloxy). In one embodiment, $R_{N5}$ is heterocycle substituted with $S(O)_2R_{10}$, $NHC(O)R_{11}$, $C(O)R_{12}$, or $C(O)NHR_{13}$.

In one embodiment, $R_{N5}$ is phenyl substituted with $NO_2$, $S(O)_2R_{10}$, $NHC(O)R_{11}$, $C(O)R_{12}$, or $C(O)NHR_{13}$.

Any substituent group for any one, two, or more of $R_{X1}$, $R_1$, $R_{21}$, $R_N$, $X_1$, $X_2$, $X_3$, $R_{51}$, $R_{52}$, $R_{53}$, $R_{10}$, $R_{11}$, $R_{12}$, $R_{13}$, $R_{N4}$, $R_{N5}$, and m as described in the various embodiments above can be combined with any substituent group for any one, two, or more of the reminder of $R_{X1}$, $R_1$, $R_{21}$, $R_N$, $X_1$, $X_2$, $X_3$, $R_{51}$, $R_{52}$, $R_{53}$, $R_{10}$, $R_{11}$, $R_{12}$, $R_{13}$, $R_{N4}$, $R_{N5}$, and m as described in the various embodiments.

In one embodiment, $R_{21}$ is $NHR_{N4}$; $R_{N4}$ is phenyl substituted with $S(O)_2R_{10}$; and $R_{10}$ is methyl, ethyl, propyl, or i-propyl. In a further embodiment, $R_{10}$ is i-propyl.

In one embodiment, a compound of formula II is a compound of formula IIa1 or IIa2:

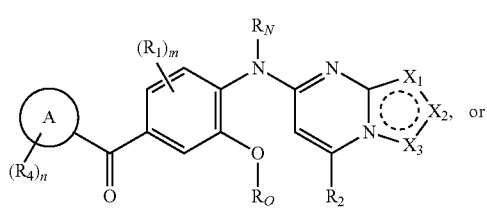

(IIa1)

(IIa2)

or a pharmaceutically acceptable salt thereof, wherein $R_1$, $R_2$, $R_4$, $R_N$, $X_1$, $X_2$, $X_3$, m, n, and (A)

are each as defined in formula II, and $R_O$ is unsubstituted or substituted $C_1$-$C_6$ alkyl.

In one embodiment, each of $R_1$, $R_2$, $R_4$, $R_N$, $X_1$, $X_2$, $X_3$, m, n, and (A)

can be selected from any of the substituent groups exemplified herein (e.g., for formula I, II, or III).

In one embodiment, $R_O$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_O$ is $C_1$-$C_6$ alkyl substituted with one or more halogen (e.g., fluorine, chlorine, bromine, or iodine). In a further embodiment, $R_O$ is methyl, ethyl, or i-propyl, each of which is optionally substituted. In a further embodiment, $R_O$ is methyl.

Any substituent group for any one, two, or more of $R_1$, $R_2$, $R_4$, $R_N$, $R_O$, $X_1$, $X_2$, $X_3$, m, n, and (A)

as described in the various embodiments above can be combined with any substituent group for any one, two, or more of the reminder of $R_1$, $R_2$, $R_4$, $R_N$, $R_O$, $X_1$, $X_2$, $X_3$, m, n, and (A)

as described in the various embodiments.

In one embodiment, a compound of formula III is a compound of formula IIIa1 or IIIa2:

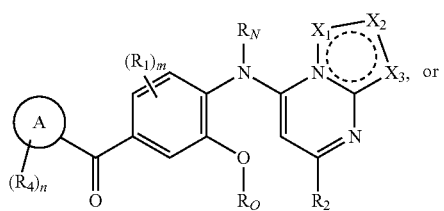

(IIIa1)

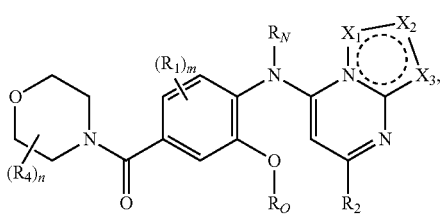

(IIIa2)

or a pharmaceutically acceptable salt thereof, wherein $R_1$, $R_2$, $R_4$, $R_N$, $X_1$, $X_2$, $X_3$, m, n, and (A)

are each as defined in formula III, and $R_O$ is unsubstituted or substituted $C_1$-$C_6$ alkyl.

In one embodiment, each of $R_1$, $R_2$, $R_4$, $R_N$, $X_1$, $X_2$, $X_3$, m, n, and (A)

can be selected from any of the substituent groups exemplified herein (e.g., for formula I, II, or III).

In one embodiment, $R_O$ is $C_1$-$C_6$ alkyl (e.g., methyl, ethyl, propyl, i-propyl, butyl, i-butyl, t-butyl, pentyl, or hexyl, each of which is optionally substituted). In a further embodiment, $R_O$ is $C_1$-$C_6$ alkyl substituted with one or more halogen (e.g., fluorine, chlorine, bromine, or iodine). In a further embodiment, $R_O$ is methyl, ethyl, or propyl, each of which is optionally substituted. In a further embodiment, $R_O$ is methyl.

Any substituent group for any one, two, or more of $R_1$, $R_2$, $R_4$, $R_N$, $R_O$, $X_1$, $X_2$, $X_3$, m, n, and (A)

as described in the various embodiments above can be combined with any substituent group for any one, two, or more of the reminder of $R_1$, $R_2$, $R_4$, $R_N$, $R_O$, $X_1$, $X_2$, $X_3$, m, n, and (A)

as described in the various embodiments.

Representative compounds of the disclosure are listed in Table A.

TABLE A

| Compound No. | Structure |
|---|---|
| 8 | 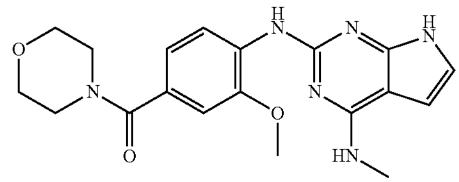 |
| 9 | 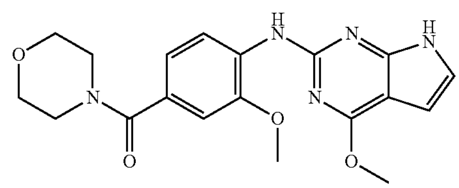 |
| 10 | 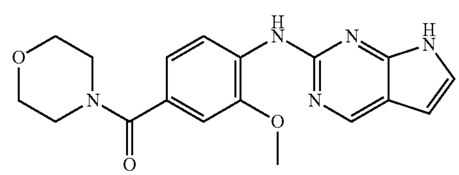 [SMILES: COc1cc(C(=O)N2CCOCC2)ccc1Nc1ncc2cc[nH]c2n1] |

TABLE A-continued
| Compound No. | Structure |
|---|---|
| 11 | 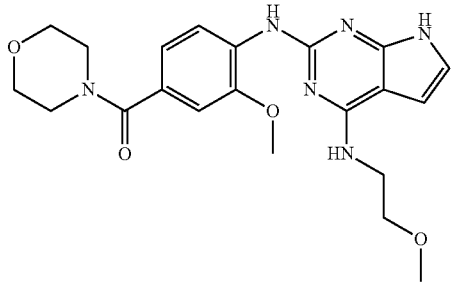 [SMILES: COCCNc1nc(Nc2ccc(C(=O)N3CCOCC3)cc2OC)nc2[nH]ccc12] |
| 12 | 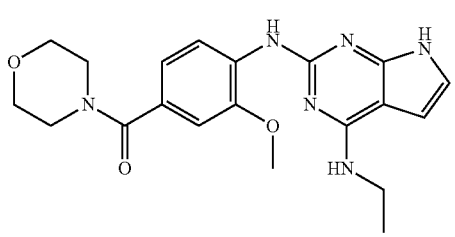 [SMILES: CCNc1nc(Nc2ccc(C(=O)N3CCOCC3)cc2OC)nc2[nH]ccc12] |
| 13 | 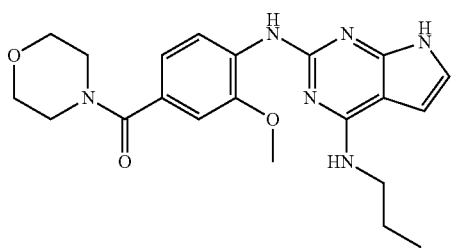 [SMILES: CCCNc1nc(Nc2ccc(C(=O)N3CCOCC3)cc2OC)nc2[nH]ccc12] |
| 14 | 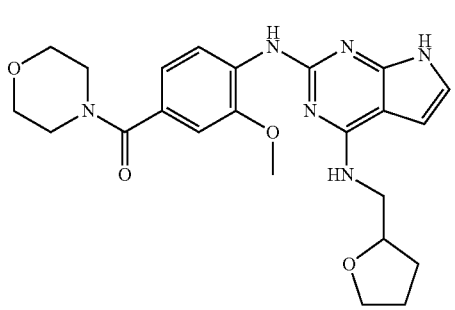 [SMILES: COc1cc(C(=O)N2CCOCC2)ccc1Nc1nc(NCC2CCCO2)c2cc[nH]c2n1] |
| 15 | 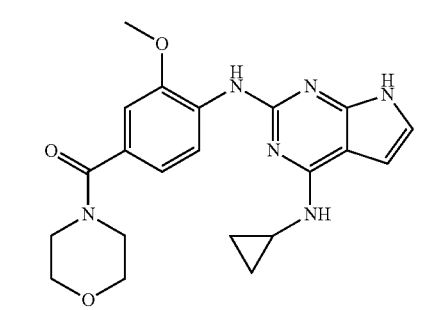 [SMILES: COc1cc(C(=O)N2CCOCC2)ccc1Nc1nc(NC2CC2)c2cc[nH]c2n1] |
| 16 | 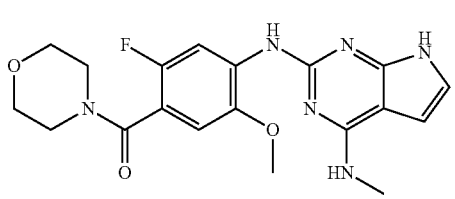 [SMILES: CNc1nc(Nc2cc(F)c(C(=O)N3CCOCC3)cc2OC)nc2[nH]ccc12] |

US 10,913,744 B2
37 38
TABLE A-continued
| Compound No. | Structure |
|---|---|
| 17 | 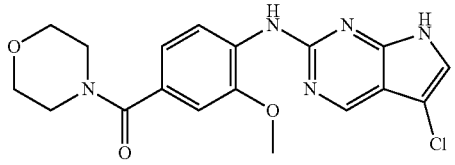 |
| 18 | 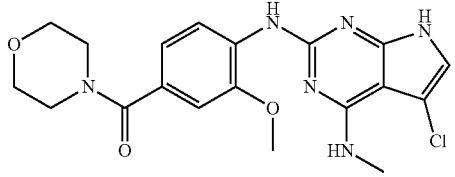 |
| 19 | 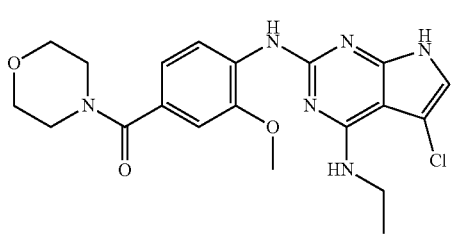 [SMILES: CCNc1nc(Nc2ccc(C(=O)N3CCOCC3)cc2OC)nc2[nH]cc(Cl)c12] |
| 20 | 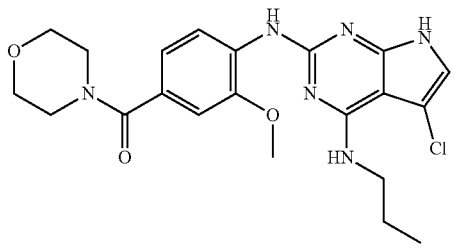 |
| 21 | 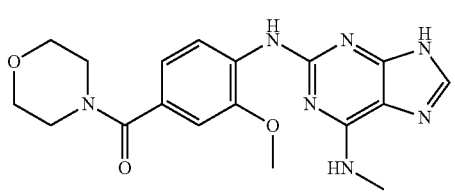 |
| 22 | 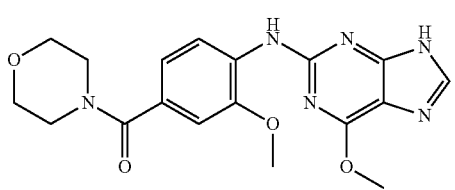 [SMILES: COc1cc(C(=O)N2CCOCC2)ccc1Nc1nc(OC)c2nc[nH]c2n1] |
| 23 | 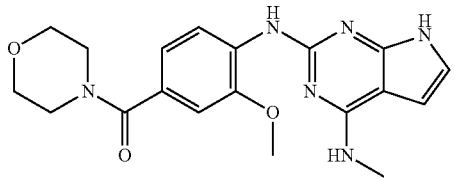 |
| 24 | 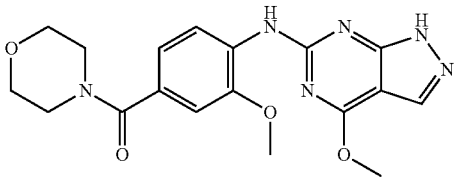 |

TABLE A-continued
| Compound No. | Structure |
|---|---|
| 25 | 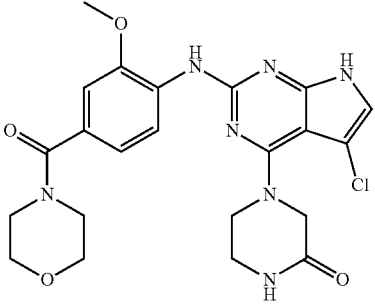 [SMILES: COc1cc(C(=O)N2CCOCC2)ccc1Nc1nc(N2CCNC(=O)C2)c2c(Cl)c[nH]c2n1] |
| 26 | 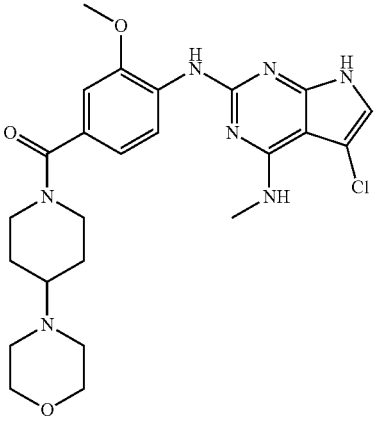 [SMILES: CNc1nc(Nc2ccc(C(=O)N3CCC(N4CCOCC4)CC3)cc2OC)nc2[nH]cc(Cl)c12] |
| 27 | 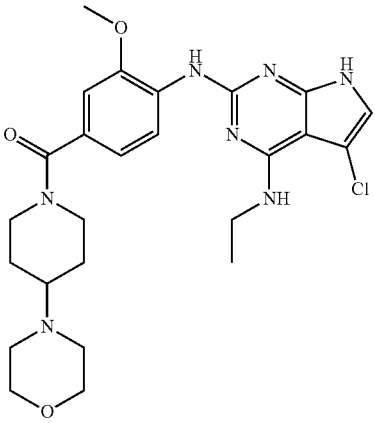 [SMILES: CCNc1nc(Nc2ccc(C(=O)N3CCC(N4CCOCC4)CC3)cc2OC)nc2[nH]cc(Cl)c12] |
| 28 | 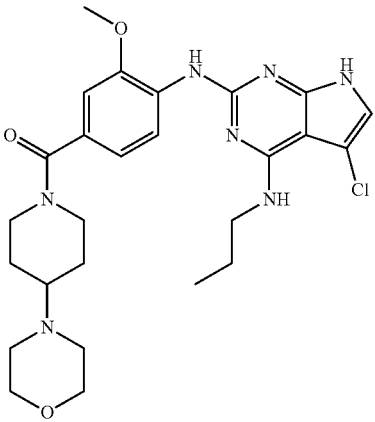 [SMILES: CCCNc1nc(Nc2ccc(C(=O)N3CCC(N4CCOCC4)CC3)cc2OC)nc2[nH]cc(Cl)c12] |

TABLE A-continued
| Compound No. | Structure |
|---|---|
| 29 | 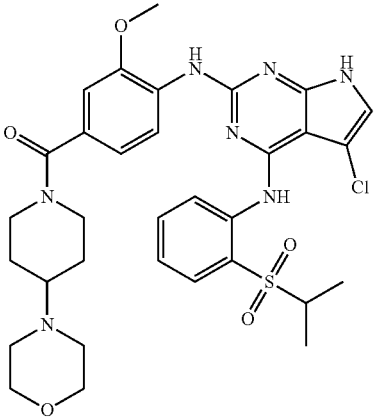 [SMILES: COc1cc(C(=O)N2CCC(N3CCOCC3)CC2)ccc1Nc1nc(Nc2ccccc2S(=O)(=O)C(C)C)c2c(Cl)c[nH]c2n1] |
| 30 | 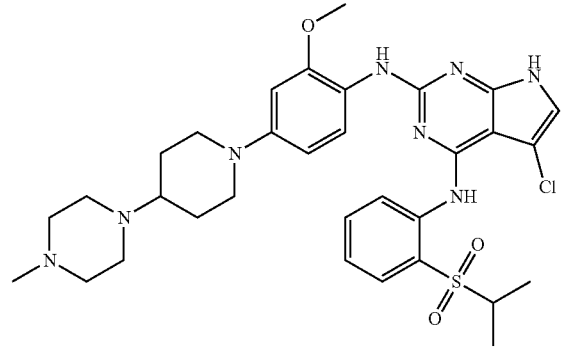 [SMILES: COc1cc(N2CCC(N3CCN(C)CC3)CC2)ccc1Nc1nc(Nc2ccccc2S(=O)(=O)C(C)C)c2c(Cl)c[nH]c2n1] |
| 31 | 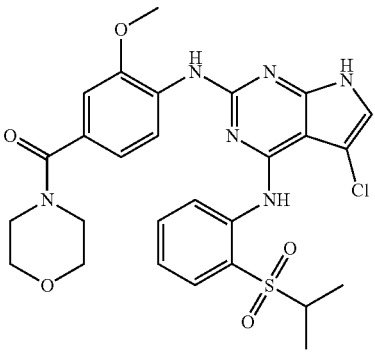 [SMILES: COc1cc(C(=O)N2CCOCC2)ccc1Nc1nc(Nc2ccccc2S(=O)(=O)C(C)C)c2c(Cl)c[nH]c2n1] |
| 32 | 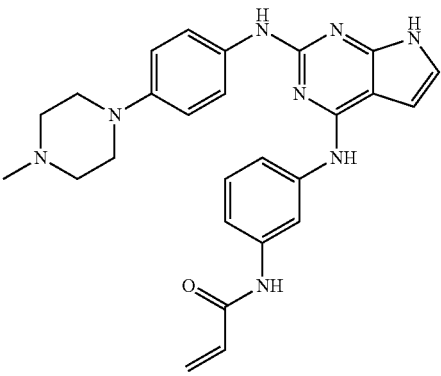 [SMILES: C=CC(=O)Nc1cccc(Nc2nc(Nc3ccc(N4CCN(C)CC4)cc3)nc3[nH]ccc23)c1] |

TABLE A-continued

| Compound No. | Structure |
|---|---|
| 33 | 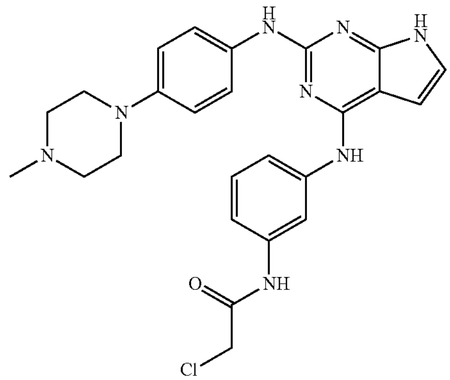 [SMILES: CN1CCN(c2ccc(Nc3nc(Nc4cccc(NC(=O)CCl)c4)c4cc[nH]c4n3)cc2)CC1] |
| 34 | 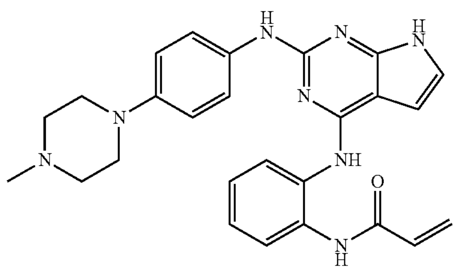 [SMILES: C=CC(=O)Nc1ccccc1Nc1nc(Nc2ccc(N3CCN(C)CC3)cc2)nc2[nH]ccc12] |
| 35 | 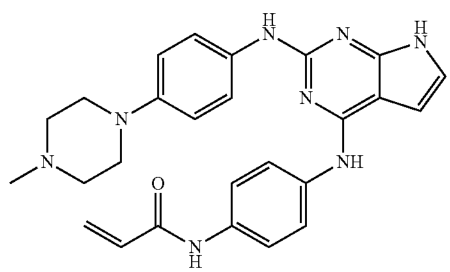 |
| 36 | 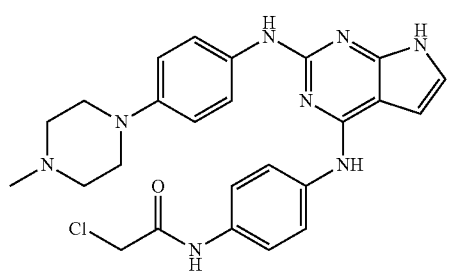 [SMILES: CN1CCN(c2ccc(Nc3nc(Nc4ccc(NC(=O)CCl)cc4)c4cc[nH]c4n3)cc2)CC1] |
| 37 | 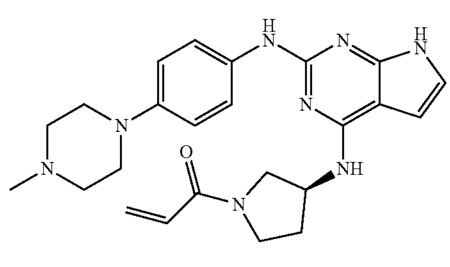 [SMILES: C=CC(=O)N1CC[C@H](Nc2nc(Nc3ccc(N4CCN(C)CC4)cc3)nc3[nH]ccc23)C1] |

TABLE A-continued

| Compound No. | Structure |
|---|---|
| 38 | 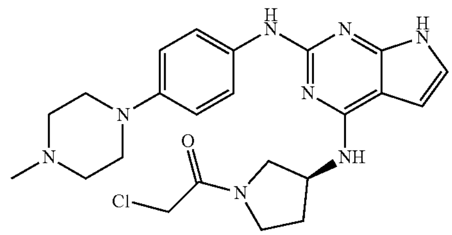 [SMILES: CN1CCN(c2ccc(Nc3nc(N[C@H]4CCN(C(=O)CCl)C4)c4cc[nH]c4n3)cc2)CC1] |
| 39 | 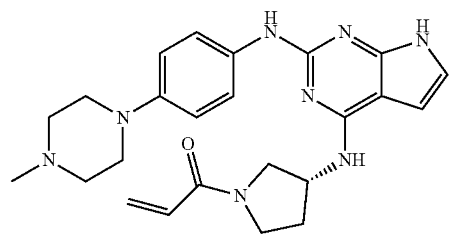 [SMILES: C=CC(=O)N1CC[C@@H](Nc2nc(Nc3ccc(N4CCN(C)CC4)cc3)nc3[nH]ccc23)C1] |
| 40 | 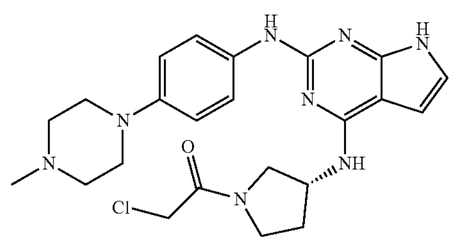 [SMILES: CN1CCN(c2ccc(Nc3nc(N[C@@H]4CCN(C(=O)CCl)C4)c4cc[nH]c4n3)cc2)CC1] |
| 41 | 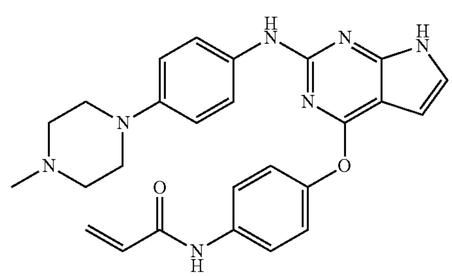 [SMILES: C=CC(=O)Nc1ccc(Oc2nc(Nc3ccc(N4CCN(C)CC4)cc3)nc3[nH]ccc23)cc1] |
| 42 | 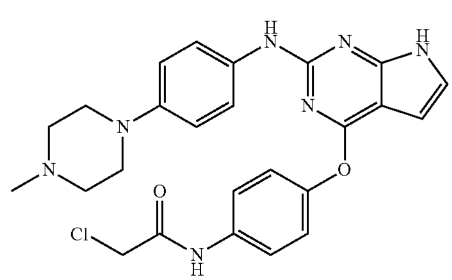 [SMILES: CN1CCN(c2ccc(Nc3nc(Oc4ccc(NC(=O)CCl)cc4)c4cc[nH]c4n3)cc2)CC1] |

TABLE A-continued
| Compound No. | Structure |
|---|---|
| 43 | 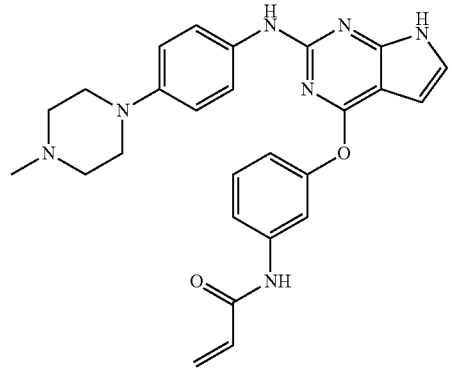 [SMILES: C=CC(=O)Nc1cccc(Oc2nc(Nc3ccc(N4CCN(C)CC4)cc3)nc3[nH]ccc23)c1] |
| 44 | 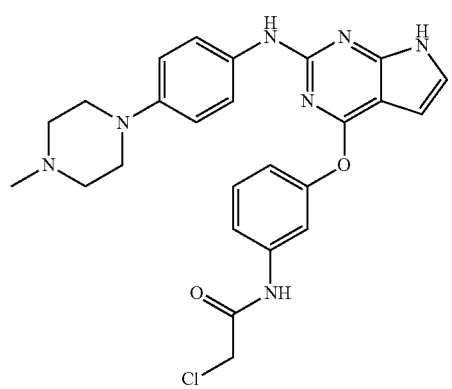 [SMILES: CN1CCN(c2ccc(Nc3nc(Oc4cccc(NC(=O)CCl)c4)c4cc[nH]c4n3)cc2)CC1] |
| 45 | 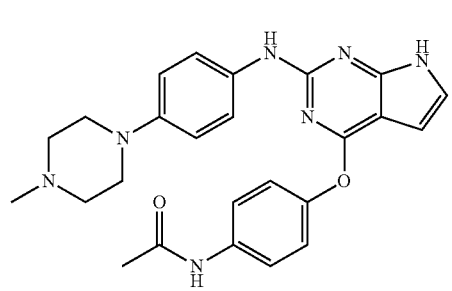 [SMILES: CC(=O)Nc1ccc(Oc2nc(Nc3ccc(N4CCN(C)CC4)cc3)nc3[nH]ccc23)cc1] |
| 46 | 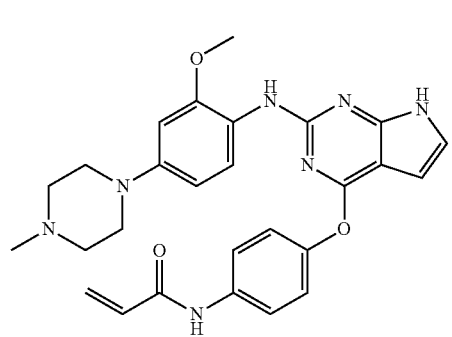 [SMILES: C=CC(=O)Nc1ccc(Oc2nc(Nc3ccc(N4CCN(C)CC4)cc3OC)nc3[nH]ccc23)cc1] |

TABLE A-continued

| Compound No. | Structure |
| --- | --- |
| 47 | 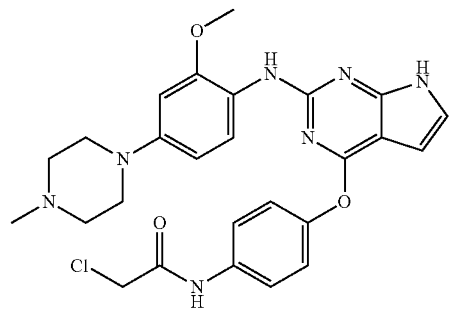 [SMILES: COc1cc(N2CCN(C)CC2)ccc1Nc1nc(Oc2ccc(NC(=O)CCl)cc2)c2cc[nH]c2n1] |
| 48 | 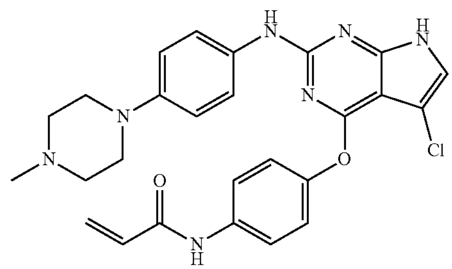 [SMILES: C=CC(=O)Nc1ccc(Oc2nc(Nc3ccc(N4CCN(C)CC4)cc3)nc3[nH]cc(Cl)c23)cc1] |
| 49 | 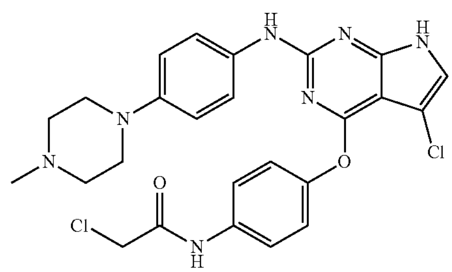 [SMILES: CN1CCN(c2ccc(Nc3nc(Oc4ccc(NC(=O)CCl)cc4)c4c(Cl)c[nH]c4n3)cc2)CC1] |
| 50 | 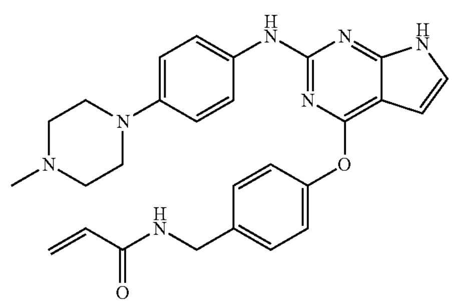 [SMILES: C=CC(=O)NCc1ccc(Oc2nc(Nc3ccc(N4CCN(C)CC4)cc3)nc3[nH]ccc23)cc1] |
| 51 | 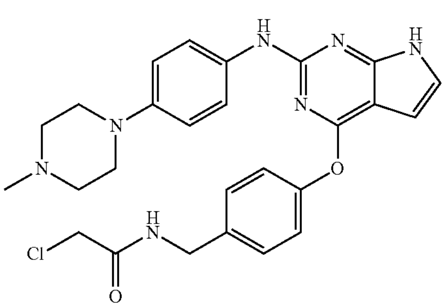 [SMILES: CN1CCN(c2ccc(Nc3nc(Oc4ccc(CNC(=O)CCl)cc4)c4cc[nH]c4n3)cc2)CC1] |

TABLE A-continued
| Compound No. | Structure |
|---|---|
| 52 | 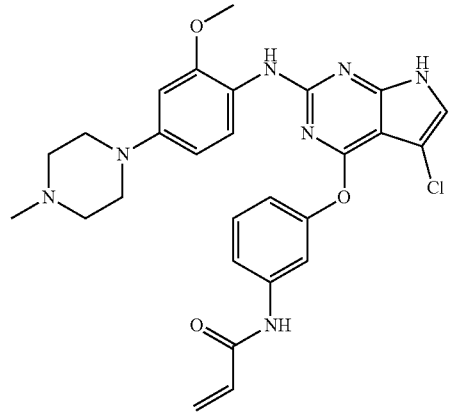 [SMILES: C=CC(=O)Nc1cccc(Oc2nc(Nc3ccc(N4CCN(C)CC4)cc3OC)nc3[nH]cc(Cl)c23)c1] |
| 53 | 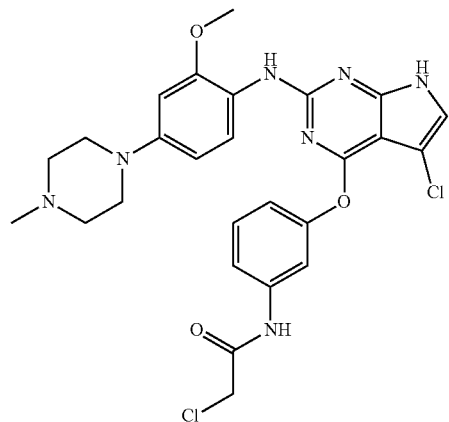 [SMILES: COc1cc(N2CCN(C)CC2)ccc1Nc1nc(Oc2cccc(NC(=O)CCl)c2)c2c(Cl)c[nH]c2n1] |
| 54 | 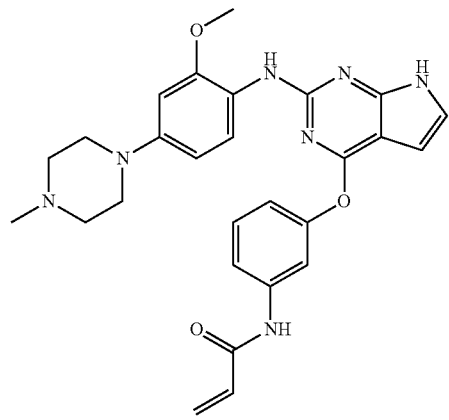 [SMILES: C=CC(=O)Nc1cccc(Oc2nc(Nc3ccc(N4CCN(C)CC4)cc3OC)nc3[nH]ccc23)c1] |

TABLE A-continued
| Compound No. | Structure |
|---|---|
| 55 | 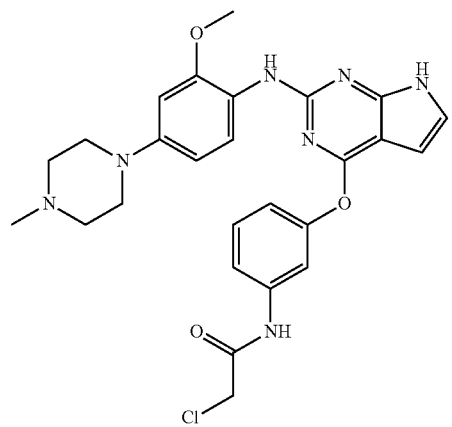 [SMILES: COc1cc(N2CCN(C)CC2)ccc1Nc1nc(Oc2cccc(NC(=O)CCl)c2)c2cc[nH]c2n1] |
| 56 | 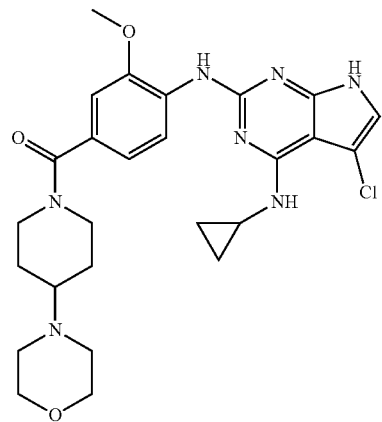 [SMILES: COc1cc(C(=O)N2CCC(N3CCOCC3)CC2)ccc1Nc1nc(NC2CC2)c2c(Cl)c[nH]c2n1] |
| 57 | 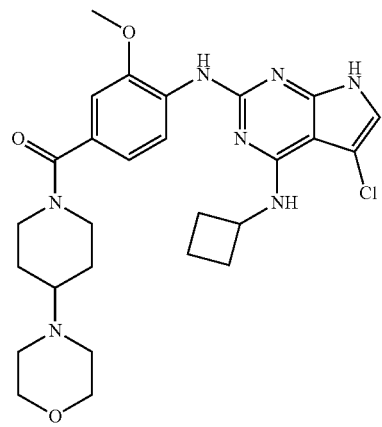 [SMILES: COc1cc(C(=O)N2CCC(N3CCOCC3)CC2)ccc1Nc1nc(NC2CCC2)c2c(Cl)c[nH]c2n1] |

TABLE A-continued
| Compound No. | Structure |
|---|---|
| 58 | 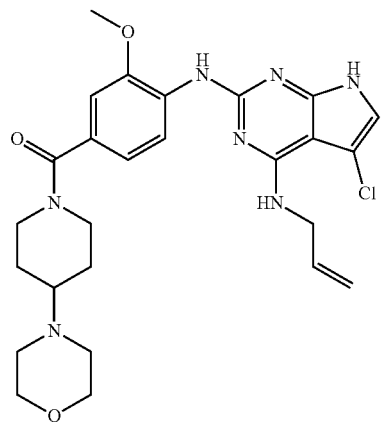 [SMILES: C=CCNc1nc(Nc2ccc(C(=O)N3CCC(N4CCOCC4)CC3)cc2OC)nc2[nH]cc(Cl)c12] |
| 59 | 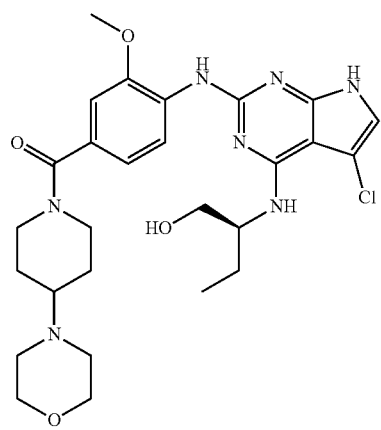 [SMILES: CC[C@@H](CO)Nc1nc(Nc2ccc(C(=O)N3CCC(N4CCOCC4)CC3)cc2OC)nc2[nH]cc(Cl)c12] |
| 60 | 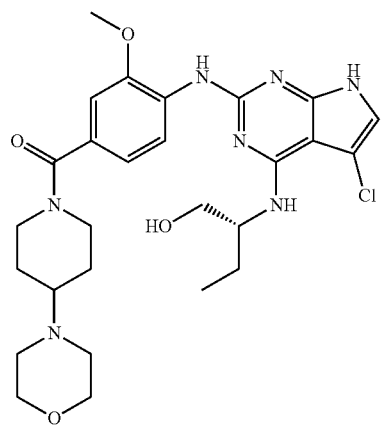 [SMILES: CC[C@H](CO)Nc1nc(Nc2ccc(C(=O)N3CCC(N4CCOCC4)CC3)cc2OC)nc2[nH]cc(Cl)c12] |

TABLE A-continued
| Compound No. | Structure |
|---|---|
| 61 | 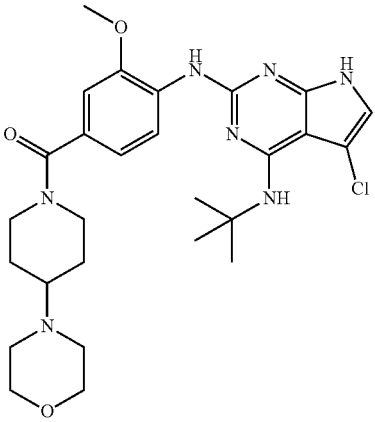 [SMILES: COc1cc(C(=O)N2CCC(N3CCOCC3)CC2)ccc1Nc1nc(NC(C)(C)C)c2c(Cl)c[nH]c2n1] |
| 62 | 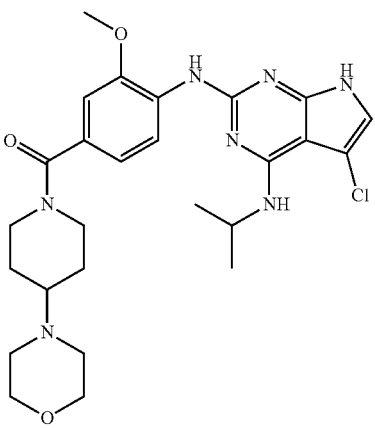 [SMILES: COc1cc(C(=O)N2CCC(N3CCOCC3)CC2)ccc1Nc1nc(NC(C)C)c2c(Cl)c[nH]c2n1] |
| 63 | 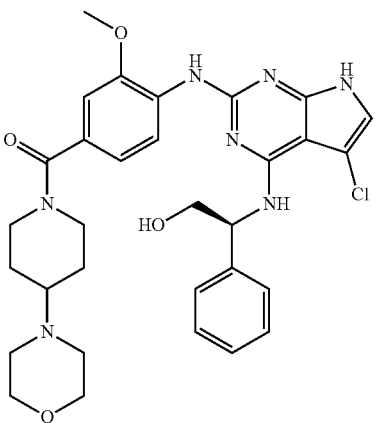 [SMILES: COc1cc(C(=O)N2CCC(N3CCOCC3)CC2)ccc1Nc1nc(N[C@H](CO)c2ccccc2)c2c(Cl)c[nH]c2n1] |

TABLE A-continued
| Compound No. | Structure |
|---|---|
| 64 | 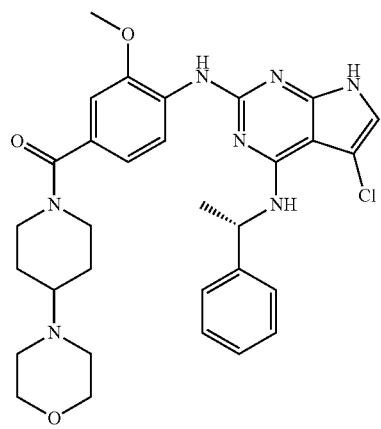 [SMILES: COc1cc(C(=O)N2CCC(N3CCOCC3)CC2)ccc1Nc1nc(N[C@@H](C)c2ccccc2)c2c(Cl)c[nH]c2n1] |
| 65 | 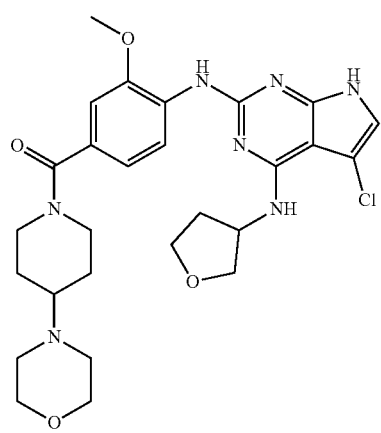 |
| 66 | 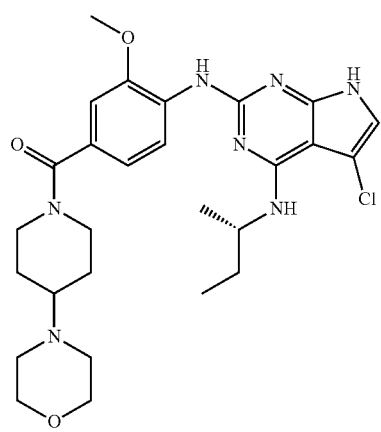 [SMILES: CC[C@H](C)Nc1nc(Nc2ccc(C(=O)N3CCC(N4CCOCC4)CC3)cc2OC)nc2[nH]cc(Cl)c12] |

TABLE A-continued
| Compound No. | Structure |
|---|---|
| 67 | 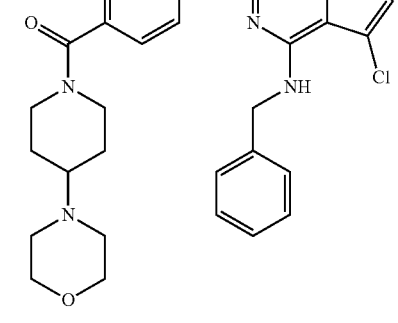 |
| 68 | 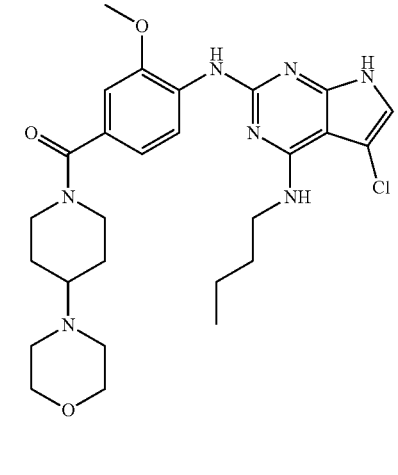 [SMILES: CCCCNc1nc(Nc2ccc(C(=O)N3CCC(N4CCOCC4)CC3)cc2OC)nc2[nH]cc(Cl)c12] |
| 69 | 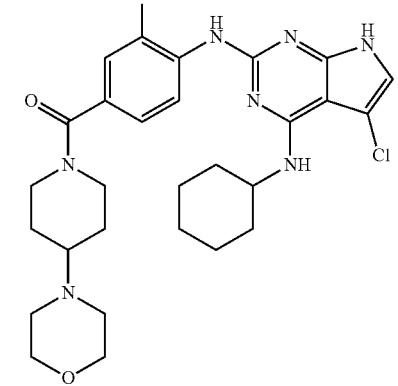 |

TABLE A-continued
| Compound No. | Structure |
|---|---|
| 70 | 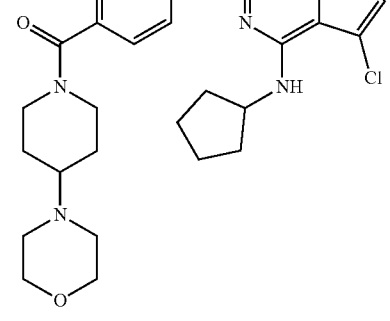 |
| 71 | 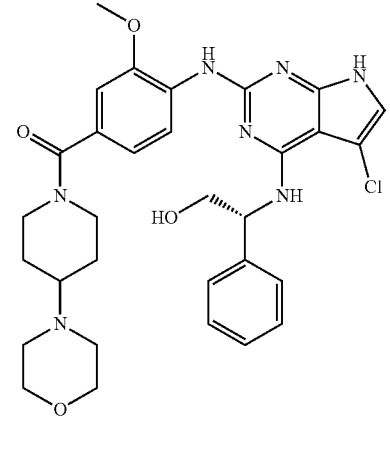 [SMILES: COc1cc(C(=O)N2CCC(N3CCOCC3)CC2)ccc1Nc1nc(N[C@@H](CO)c2ccccc2)c2c(Cl)c[nH]c2n1] |
| 72 | 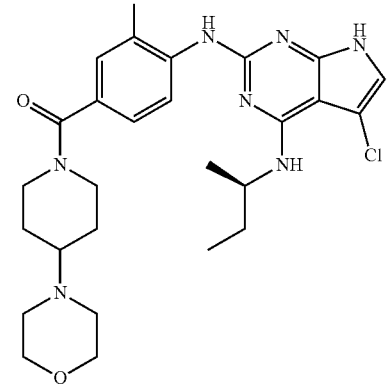 |

TABLE A-continued

| Compound No. | Structure |
|---|---|
| 73 | 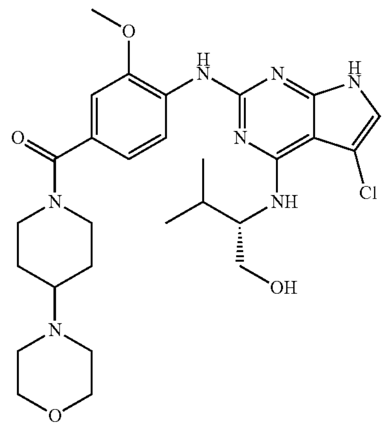 [SMILES: COc1cc(C(=O)N2CCC(N3CCOCC3)CC2)ccc1Nc1nc(N[C@H](CO)C(C)C)c2c(Cl)c[nH]c2n1] |
| 74 | 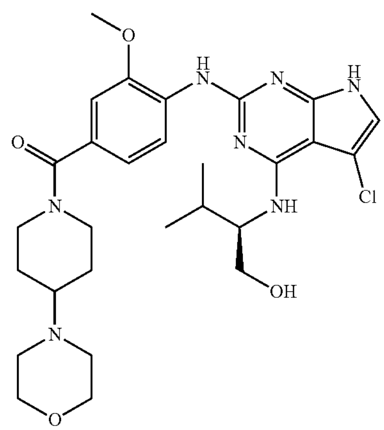 [SMILES: COc1cc(C(=O)N2CCC(N3CCOCC3)CC2)ccc1Nc1nc(N[C@@H](CO)C(C)C)c2c(Cl)c[nH]c2n1] |
| 75 | 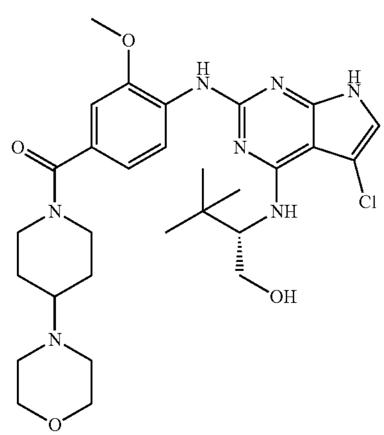 [SMILES: COc1cc(C(=O)N2CCC(N3CCOCC3)CC2)ccc1Nc1nc(N[C@H](CO)C(C)(C)C)c2c(Cl)c[nH]c2n1] |

TABLE A-continued

| Compound No. | Structure |
| --- | --- |
| 76 | 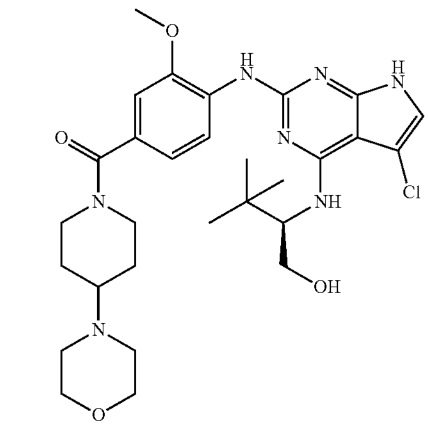 [SMILES: COc1cc(C(=O)N2CCC(N3CCOCC3)CC2)ccc1Nc1nc(N[C@@H](CO)C(C)(C)C)c2c(Cl)c[nH]c2n1] |
| 77 | 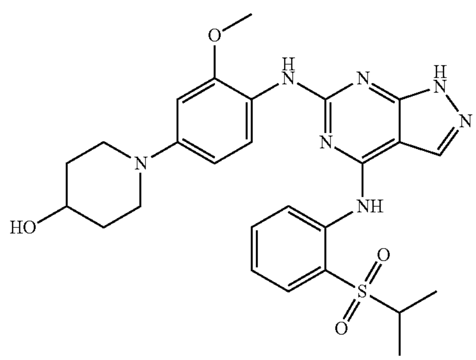 [SMILES: COc1cc(N2CCC(O)CC2)ccc1Nc1nc(Nc2ccccc2S(=O)(=O)C(C)C)c2cn[nH]c2n1] |
| 78 | 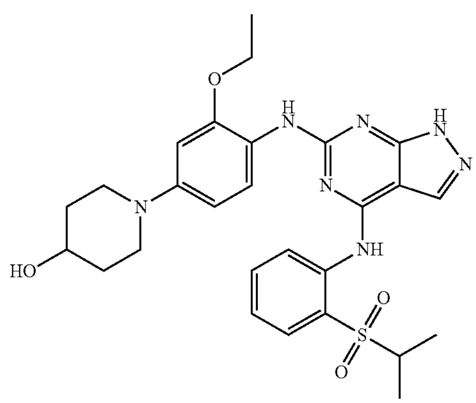 [SMILES: CCOc1cc(N2CCC(O)CC2)ccc1Nc1nc(Nc2ccccc2S(=O)(=O)C(C)C)c2cn[nH]c2n1] |
| 79 | 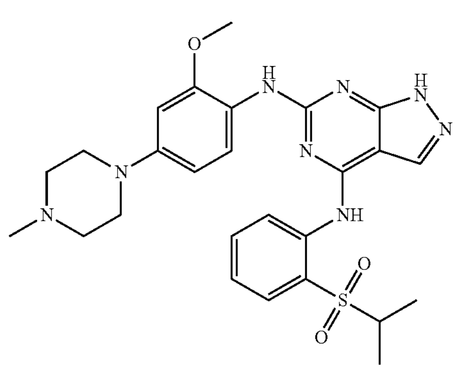 [SMILES: COc1cc(N2CCN(C)CC2)ccc1Nc1nc(Nc2ccccc2S(=O)(=O)C(C)C)c2cn[nH]c2n1] |

TABLE A-continued
| Compound No. | Structure |
|---|---|
| 80 | 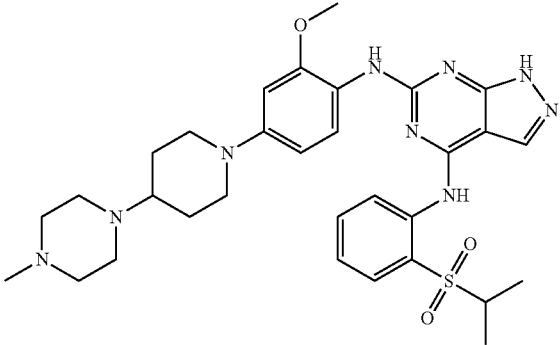 [SMILES: COc1cc(N2CCC(N3CCN(C)CC3)CC2)ccc1Nc1nc(Nc2ccccc2S(=O)(=O)C(C)C)c2cn[nH]c2n1] |
| 81 | 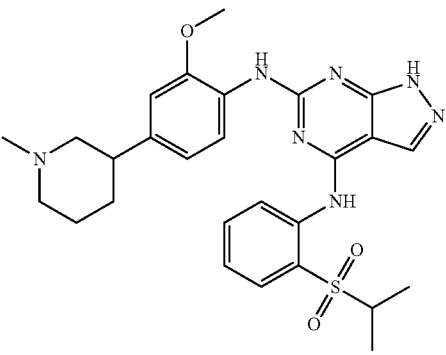 [SMILES: COc1cc(C2CCCN(C)C2)ccc1Nc1nc(Nc2ccccc2S(=O)(=O)C(C)C)c2cn[nH]c2n1] |
| 82 | 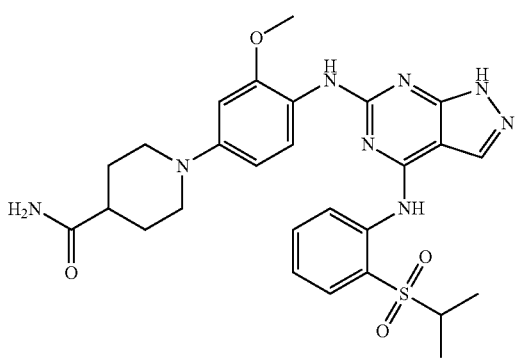 [SMILES: COc1cc(N2CCC(C(N)=O)CC2)ccc1Nc1nc(Nc2ccccc2S(=O)(=O)C(C)C)c2cn[nH]c2n1] |
| 83 | 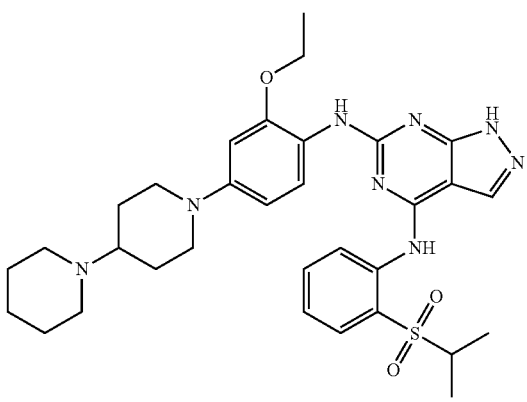 [SMILES: CCOc1cc(N2CCC(N3CCCCC3)CC2)ccc1Nc1nc(Nc2ccccc2S(=O)(=O)C(C)C)c2cn[nH]c2n1] |

TABLE A-continued

| Compound No. | Structure |
| --- | --- |
| 84 | 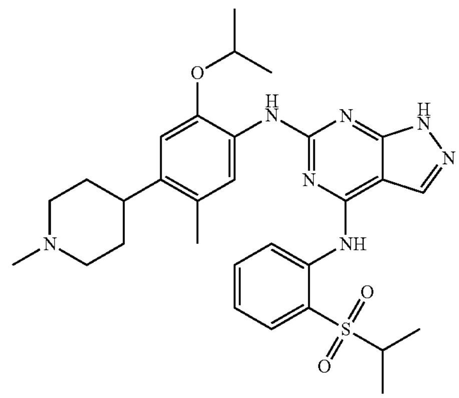 [SMILES: Cc1cc(Nc2nc(Nc3ccccc3S(=O)(=O)C(C)C)c3cn[nH]c3n2)c(OC(C)C)cc1C1CCN(C)CC1] |
| 85 | 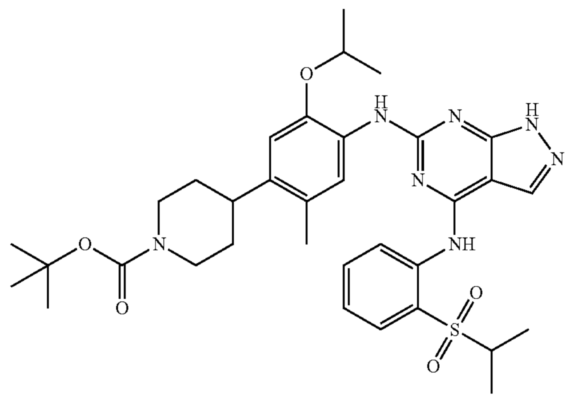 [SMILES: Cc1cc(Nc2nc(Nc3ccccc3S(=O)(=O)C(C)C)c3cn[nH]c3n2)c(OC(C)C)cc1C1CCN(C(=O)OC(C)(C)C)CC1] |
| 86 | 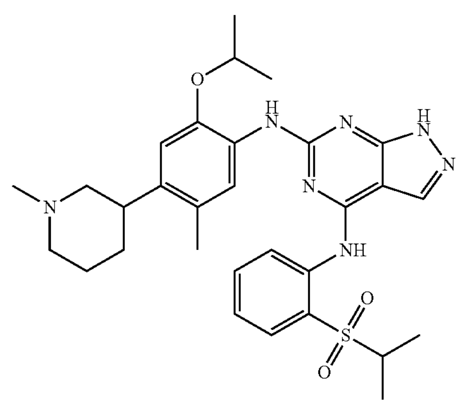 [SMILES: Cc1cc(Nc2nc(Nc3ccccc3S(=O)(=O)C(C)C)c3cn[nH]c3n2)c(OC(C)C)cc1C1CCCN(C)C1] |
| 87 | 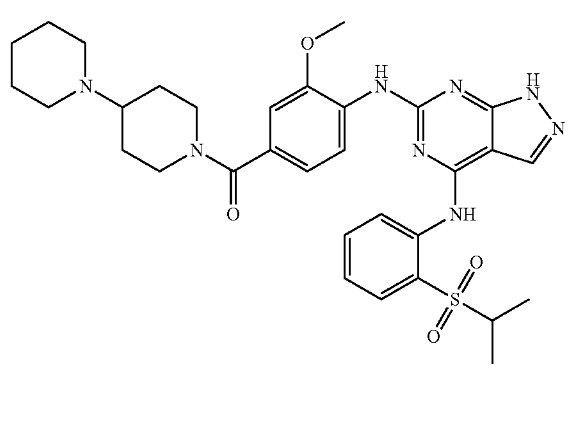 [SMILES: COc1cc(C(=O)N2CCC(N3CCCCC3)CC2)ccc1Nc1nc(Nc2ccccc2S(=O)(=O)C(C)C)c2cn[nH]c2n1] |

TABLE A-continued
| Compound No. | Structure |
|---|---|
| 88 | 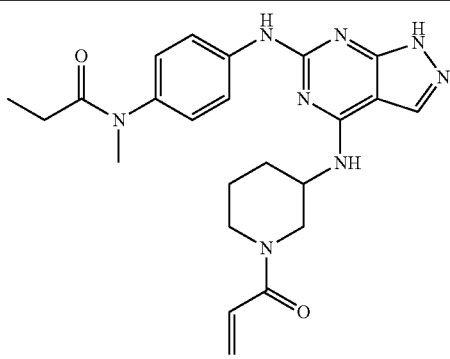 |
| 89 | 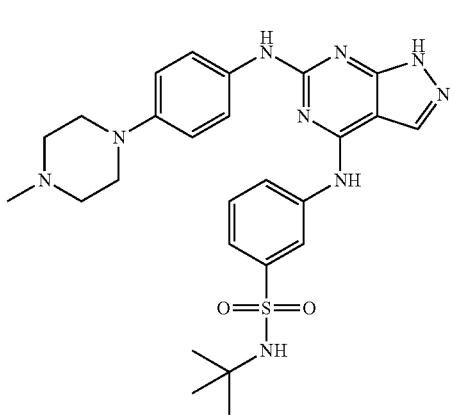 [SMILES: CN1CCN(c2ccc(Nc3nc(Nc4cccc(S(=O)(=O)NC(C)(C)C)c4)c4cn[nH]c4n3)cc2)CC1] |
| 90 | 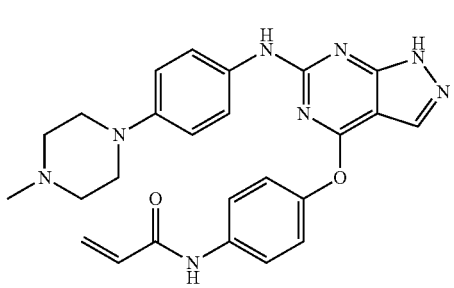 [SMILES: C=CC(=O)Nc1ccc(Oc2nc(Nc3ccc(N4CCN(C)CC4)cc3)nc3[nH]ncc23)cc1] |
| 91 | 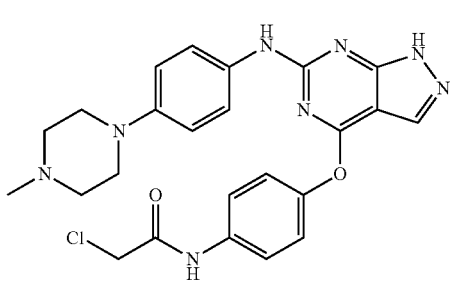 |
| 92 | 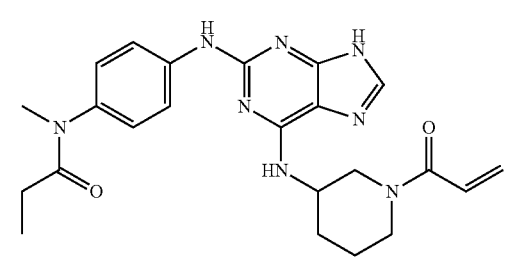 [SMILES: C=CC(=O)N1CCCC(Nc2nc(Nc3ccc(N(C)C(=O)CC)cc3)nc3[nH]cnc23)C1] |

TABLE A-continued
| Compound No. | Structure |
|---|---|
| 93 | 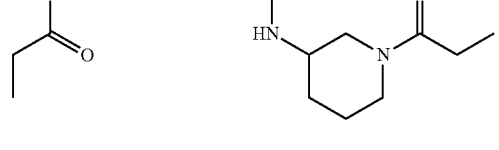 |
| 94 | 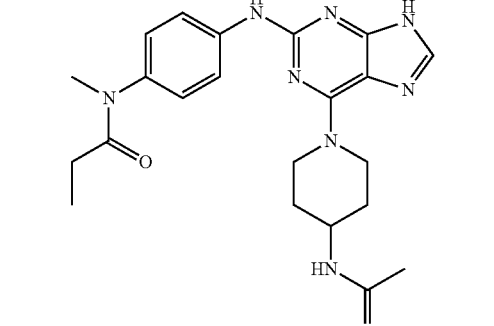 |
| 95 | 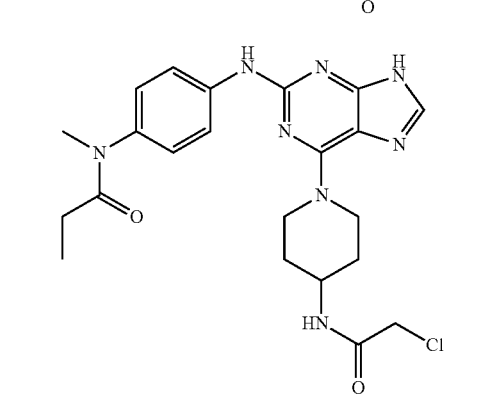 |
| 96 | 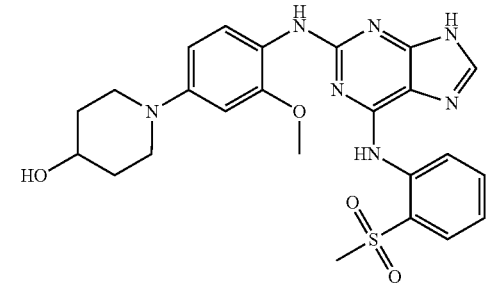 [SMILES: COc1cc(N2CCC(O)CC2)ccc1Nc1nc(Nc2ccccc2S(C)(=O)=O)c2nc[nH]c2n1] |
| 97 | 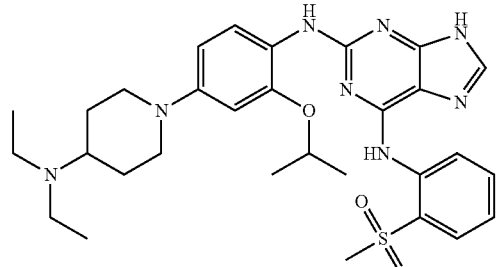 |

TABLE A-continued
| Compound No. | Structure |
|---|---|
| 98 | 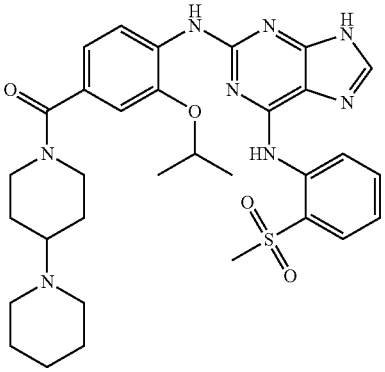 [SMILES: CC(C)Oc1cc(C(=O)N2CCC(N3CCCCC3)CC2)ccc1Nc1nc(Nc2ccccc2S(C)(=O)=O)c2nc[nH]c2n1] |
| 99 | 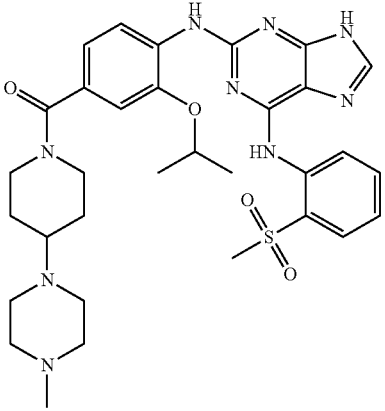 [SMILES: CC(C)Oc1cc(C(=O)N2CCC(N3CCN(C)CC3)CC2)ccc1Nc1nc(Nc2ccccc2S(C)(=O)=O)c2nc[nH]c2n1] |
| 100 | 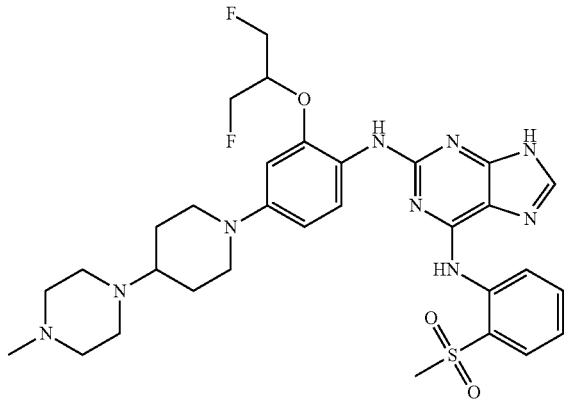 [SMILES: CN1CCN(C2CCN(c3ccc(Nc4nc(Nc5ccccc5S(C)(=O)=O)c5nc[nH]c5n4)c(OC(CF)CF)c3)CC2)CC1] |
| 101 | 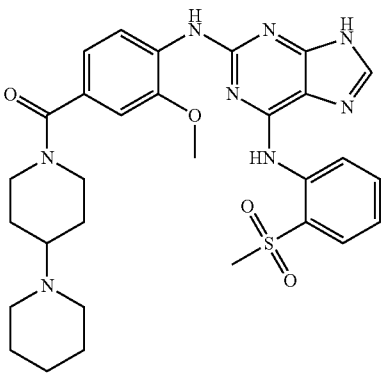 [SMILES: COc1cc(C(=O)N2CCC(N3CCCCC3)CC2)ccc1Nc1nc(Nc2ccccc2S(C)(=O)=O)c2nc[nH]c2n1] |

TABLE A-continued

| Compound No. | Structure |
| --- | --- |
| 102 | 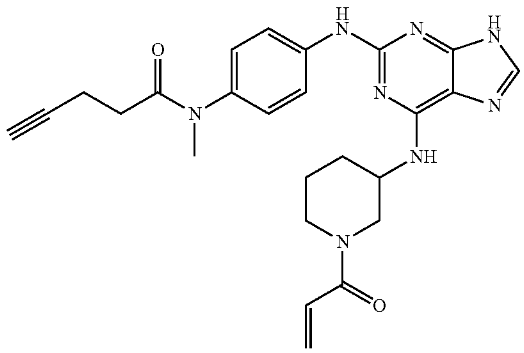 [SMILES: C#CCCC(=O)N(C)c1ccc(Nc2nc(NC3CCCN(C(=O)C=C)C3)c3nc[nH]c3n2)cc1] |
| 103 | 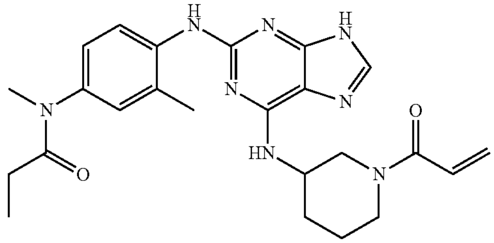 [SMILES: C=CC(=O)N1CCCC(Nc2nc(Nc3ccc(N(C)C(=O)CC)cc3C)nc3[nH]cnc23)C1] |
| 104 | 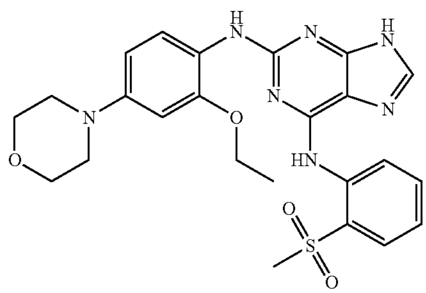 [SMILES: CCOc1cc(N2CCOCC2)ccc1Nc1nc(Nc2ccccc2S(C)(=O)=O)c2nc[nH]c2n1] |
| 105 | 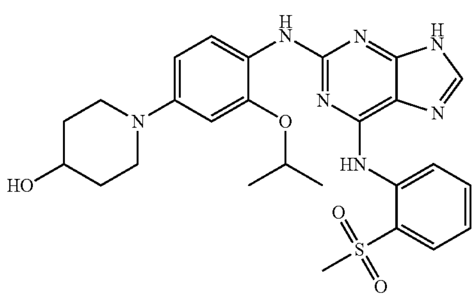 [SMILES: CC(C)Oc1cc(N2CCC(O)CC2)ccc1Nc1nc(Nc2ccccc2S(C)(=O)=O)c2nc[nH]c2n1] |
| 106 | 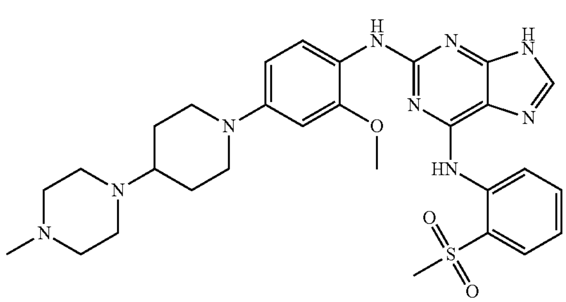 [SMILES: COc1cc(N2CCC(N3CCN(C)CC3)CC2)ccc1Nc1nc(Nc2ccccc2S(C)(=O)=O)c2nc[nH]c2n1] |

TABLE A-continued

| Compound No. | Structure |
| --- | --- |
| 107 | 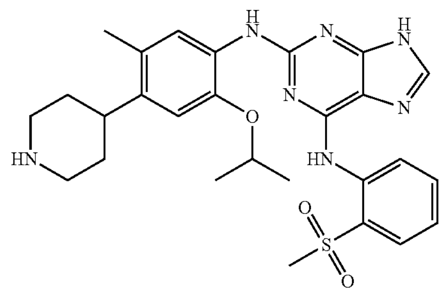 [SMILES: Cc1cc(Nc2nc(Nc3ccccc3S(C)(=O)=O)c3nc[nH]c3n2)c(OC(C)C)cc1C1CCNCC1] |
| 108 | 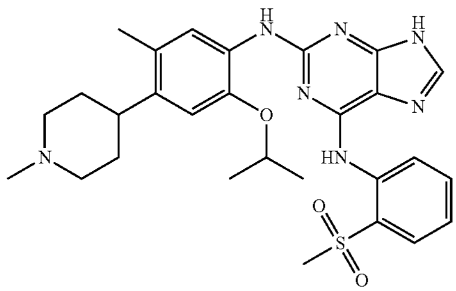 [SMILES: Cc1cc(Nc2nc(Nc3ccccc3S(C)(=O)=O)c3nc[nH]c3n2)c(OC(C)C)cc1C1CCN(C)CC1] |
| 109 | 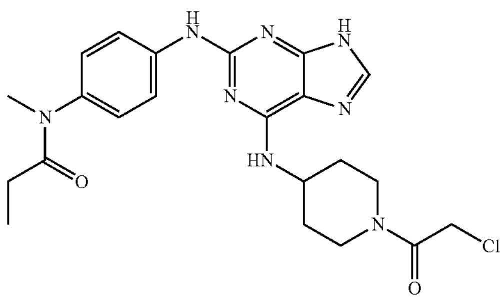 [SMILES: CCC(=O)N(C)c1ccc(Nc2nc(NC3CCN(C(=O)CCl)CC3)c3nc[nH]c3n2)cc1] |
| 110 | 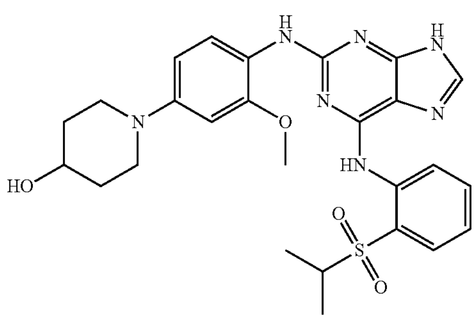 [SMILES: COc1cc(N2CCC(O)CC2)ccc1Nc1nc(Nc2ccccc2S(=O)(=O)C(C)C)c2nc[nH]c2n1] |
| 111 | 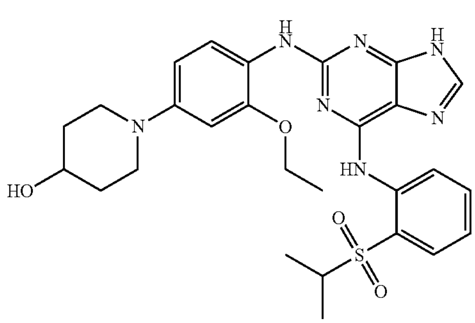 [SMILES: CCOc1cc(N2CCC(O)CC2)ccc1Nc1nc(Nc2ccccc2S(=O)(=O)C(C)C)c2nc[nH]c2n1] |

TABLE A-continued

| Compound No. | Structure |
| --- | --- |
| 112 | 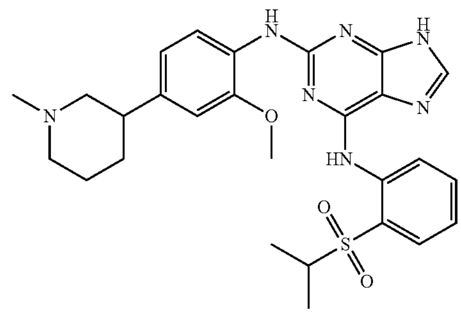 [SMILES: COc1cc(C2CCCN(C)C2)ccc1Nc1nc(Nc2ccccc2S(=O)(=O)C(C)C)c2nc[nH]c2n1] |
| 113 | 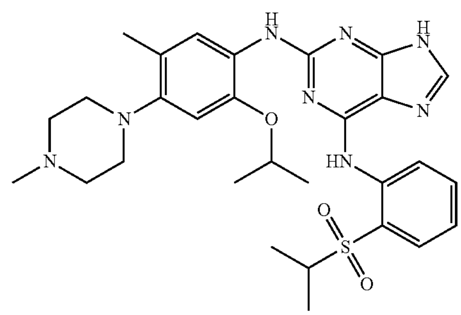 [SMILES: Cc1cc(Nc2nc(Nc3ccccc3S(=O)(=O)C(C)C)c3nc[nH]c3n2)c(OC(C)C)cc1N1CCN(C)CC1] |
| 114 | 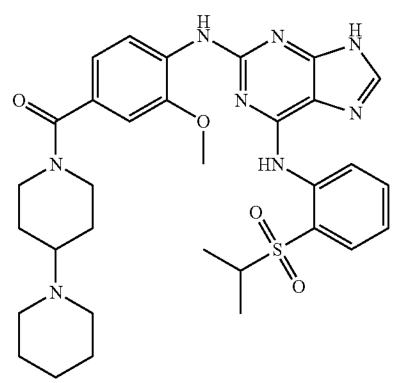 [SMILES: COc1cc(C(=O)N2CCC(N3CCCCC3)CC2)ccc1Nc1nc(Nc2ccccc2S(=O)(=O)C(C)C)c2nc[nH]c2n1] |
| 115 | 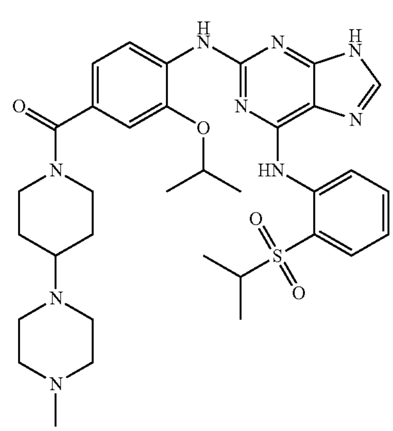 [SMILES: CC(C)Oc1cc(C(=O)N2CCC(N3CCN(C)CC3)CC2)ccc1Nc1nc(Nc2ccccc2S(=O)(=O)C(C)C)c2nc[nH]c2n1] |

TABLE A-continued

| Compound No. | Structure |
|---|---|
| 116 | 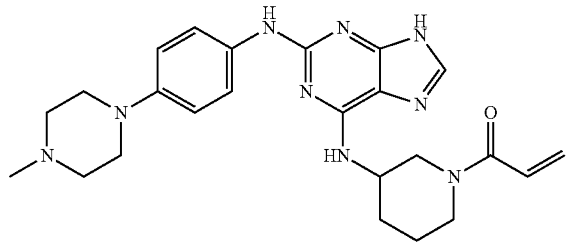 [SMILES: C=CC(=O)N1CCCC(Nc2nc(Nc3ccc(N4CCN(C)CC4)cc3)nc3[nH]cnc23)C1] |
| 117 | 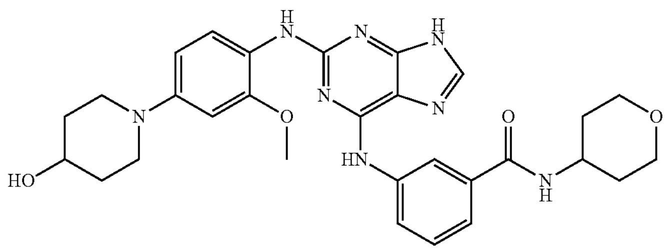 [SMILES: COc1cc(N2CCC(O)CC2)ccc1Nc1nc(Nc2cccc(C(=O)NC3CCOCC3)c2)c2nc[nH]c2n1] |
| 118 | 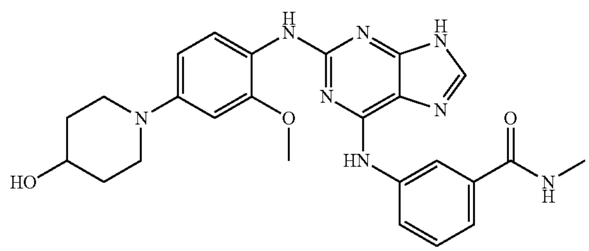 [SMILES: CNC(=O)c1cccc(Nc2nc(Nc3ccc(N4CCC(O)CC4)cc3OC)nc3[nH]cnc23)c1] |
| 119 | 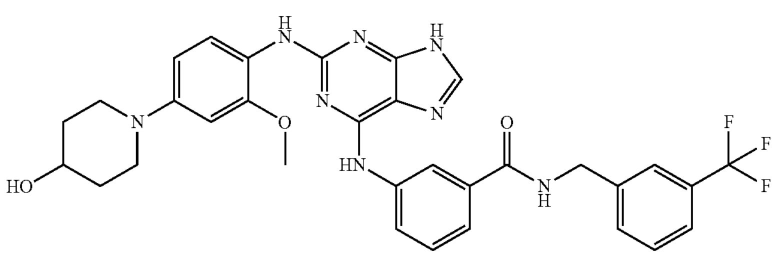 [SMILES: COc1cc(N2CCC(O)CC2)ccc1Nc1nc(Nc2cccc(C(=O)NCc3cccc(C(F)(F)F)c3)c2)c2nc[nH]c2n1] |
| 120 | 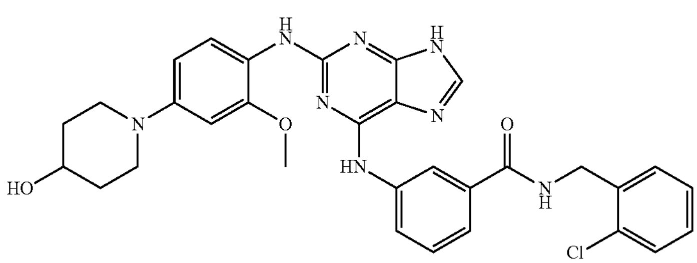 [SMILES: COc1cc(N2CCC(O)CC2)ccc1Nc1nc(Nc2cccc(C(=O)NCc3ccccc3Cl)c2)c2nc[nH]c2n1] |
| 121 | 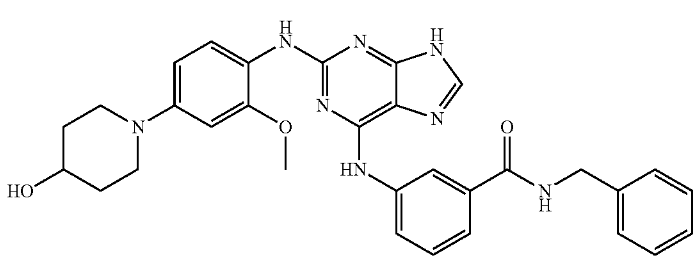 [SMILES: COc1cc(N2CCC(O)CC2)ccc1Nc1nc(Nc2cccc(C(=O)NCc3ccccc3)c2)c2nc[nH]c2n1] |

TABLE A-continued
| Compound No. | Structure |
|---|---|
| 122 | 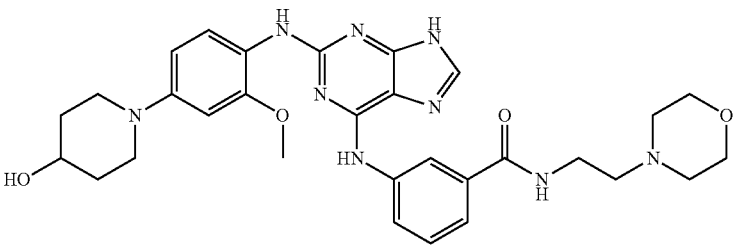 [SMILES: COc1cc(N2CCC(O)CC2)ccc1Nc1nc(Nc2cccc(C(=O)NCCN3CCOCC3)c2)c2nc[nH]c2n1] |
| 123 | 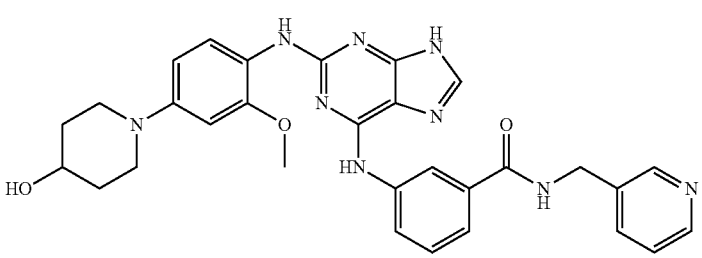 [SMILES: COc1cc(N2CCC(O)CC2)ccc1Nc1nc(Nc2cccc(C(=O)NCc3cccnc3)c2)c2nc[nH]c2n1] |
| 124 | 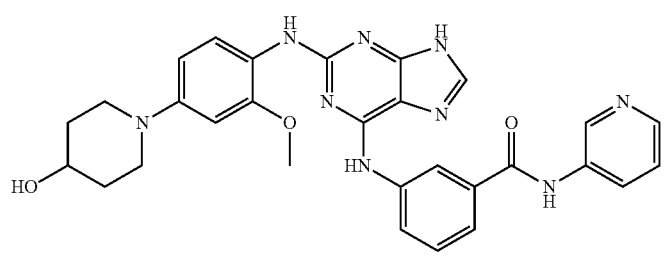 [SMILES: COc1cc(N2CCC(O)CC2)ccc1Nc1nc(Nc2cccc(C(=O)Nc3cccnc3)c2)c2nc[nH]c2n1] |
| 125 | 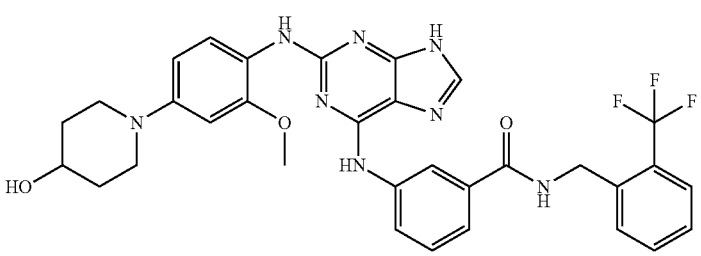 [SMILES: COc1cc(N2CCC(O)CC2)ccc1Nc1nc(Nc2cccc(C(=O)NCc3ccccc3C(F)(F)F)c2)c2nc[nH]c2n1] |
| 126 | 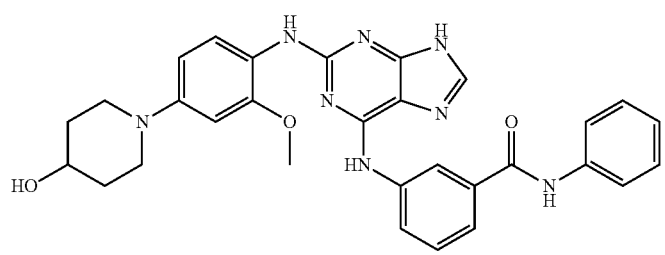 [SMILES: COc1cc(N2CCC(O)CC2)ccc1Nc1nc(Nc2cccc(C(=O)Nc3ccccc3)c2)c2nc[nH]c2n1] |
| 127 | 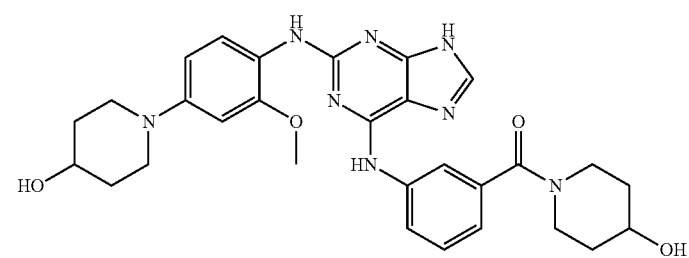 [SMILES: COc1cc(N2CCC(O)CC2)ccc1Nc1nc(Nc2cccc(C(=O)N3CCC(O)CC3)c2)c2nc[nH]c2n1] |

TABLE A-continued
| Compound No. | Structure |
|---|---|
| 128 | 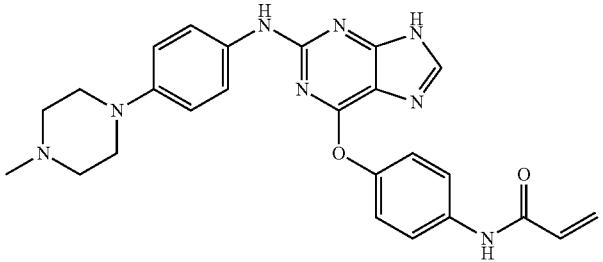 [SMILES: C=CC(=O)Nc1ccc(Oc2nc(Nc3ccc(N4CCN(C)CC4)cc3)nc3[nH]cnc23)cc1] |
| 129 | 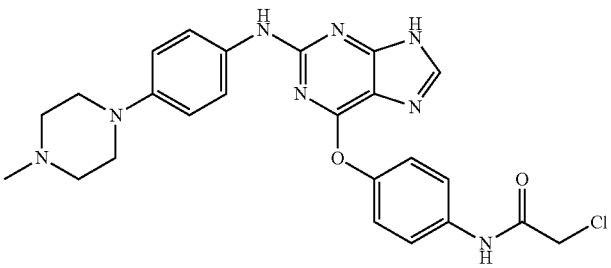 [SMILES: CN1CCN(c2ccc(Nc3nc(Oc4ccc(NC(=O)CCl)cc4)c4nc[nH]c4n3)cc2)CC1] |
| 130 | 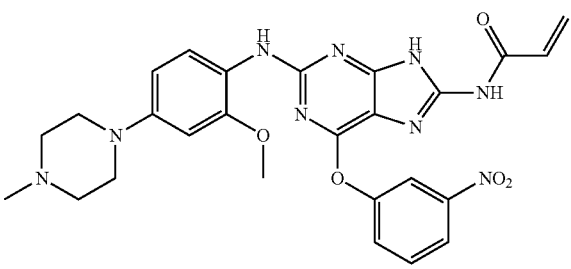 [SMILES: C=CC(=O)Nc1nc2c(Oc3cccc([N+](=O)[O-])c3)nc(Nc3ccc(N4CCN(C)CC4)cc3OC)nc2[nH]1] |
| 131 | 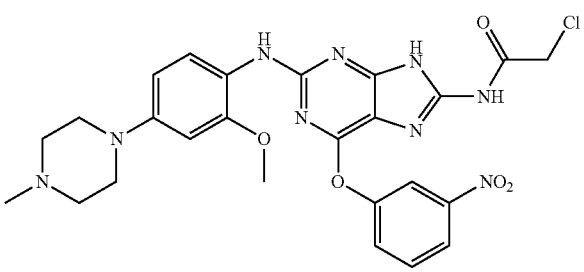 [SMILES: COc1cc(N2CCN(C)CC2)ccc1Nc1nc(Oc2cccc([N+](=O)[O-])c2)c2nc(NC(=O)CCl)[nH]c2n1] |
| 132 | 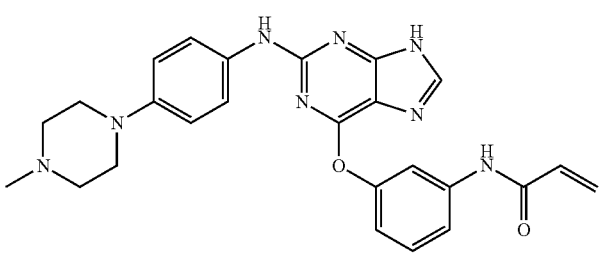 [SMILES: C=CC(=O)Nc1cccc(Oc2nc(Nc3ccc(N4CCN(C)CC4)cc3)nc3[nH]cnc23)c1] |

TABLE A-continued
| Compound No. | Structure |
|---|---|
| 133 | 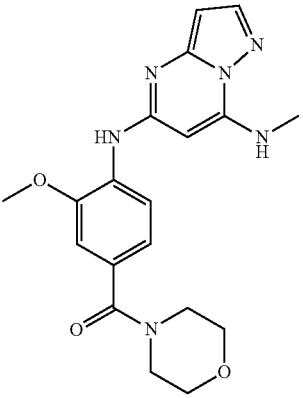 |
| 134 | 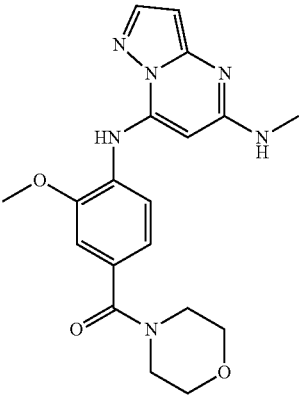 |
| 135 | 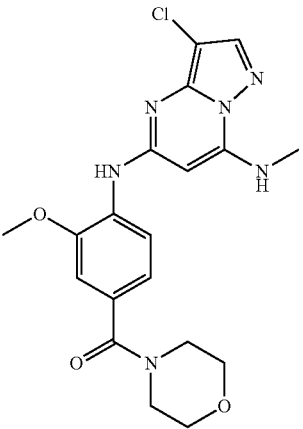 |

TABLE A-continued

| Compound No. | Structure |
|---|---|
| 136 | 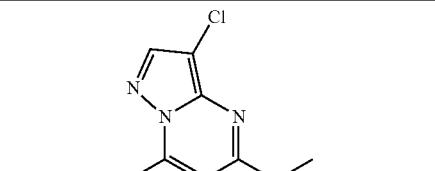 |

Compounds of the present disclosure are highly potent, selective and brain penetrant LRRK2 inhibitors. Particularly, compounds of the present disclosure potently inhibit both the wild-type and the G2019S mutant and/or the A20161T mutant of LRRK2.

In one embodiment, compounds of the present disclosure inhibit wild-type LRRK2 at an $IC_{50}$ below 200 nM, 190 nM, 180 nM, 170 nM, 160 nM, 150 nM, 100 nM, 90 nM, 80 nM, 70 nM, 60 nM, 50 nM, 40 nM, 30 nM, 20 nM, 10 nM, or 5 nM. In a further embodiment, compounds of the present disclosure inhibit wild-type LRRK2 at an $IC_{50}$ below 50 nM, 40 nM, 30 nM, 20 nM, 10 nM, or 5 nM. In a further embodiment, compounds of the present disclosure inhibit wild-type LRRK2 at an $IC_{50}$ below 20 nM, 10 nM, or 5 nM. In a further embodiment, compounds of the present disclosure inhibit wild-type LRRK2 at an $IC_{50}$ below 20 nM. In a further embodiment, compounds of the present disclosure inhibit wild-type LRRK2 at an $IC_{50}$ below 10 nM or 5 nM. In a further embodiment, compounds of the present disclosure inhibit wild-type LRRK2 at an $IC_{50}$ below 10 nM. In a further embodiment, compounds of the present disclosure inhibit wild-type LRRK2 at an $IC_{50}$ below 5 nM.

In one embodiment, compounds of the present disclosure inhibit G2019S mutant LRRK2 at an $IC_{50}$ below 150 nM, 100 nM, 90 nM, 80 nM, 70 nM, 60 nM, 50 nM, 40 nM, 30 nM, 20 nM, 10 nM, or 5 nM. In a further embodiment, compounds of the present disclosure inhibit G2019S mutant LRRK2 at an $IC_{50}$ below 50 nM, 40 nM, 30 nM, 20 nM, 10 nM, or 5 nM. In a further embodiment, compounds of the present disclosure inhibit G2019S mutant LRRK2 at an $IC_{50}$ below 20 nM, 10 nM, or 5 nM. In a further embodiment, compounds of the present disclosure inhibit G2019S mutant LRRK2 at an $IC_{50}$ below 20 nM. In a further embodiment, compounds of the present disclosure inhibit G2019S mutant LRRK2 at an $IC_{50}$ below 10 nM or 5 nM. In a further embodiment, compounds of the present disclosure inhibit G2019S mutant LRRK2 at an $IC_{50}$ below 10 nM. In a further embodiment, compounds of the present disclosure inhibit G2019S mutant LRRK2 at an $IC_{50}$ below 5 nM.

In one embodiment, compounds of the present disclosure inhibit A2016T mutant LRRK2 at an $IC_{50}$ below 200 nM, 190 nM, 180 nM, 170 nM, 160 nM, 150 nM, 100 nM, 90 nM, 80 nM, 70 nM, 60 nM, 50 nM, 40 nM, 30 nM, 20 nM, 10 nM, or 5 nM. In a further embodiment, compounds of the present disclosure inhibit A2016T mutant LRRK2 at an $IC_{50}$ below 150 nM, 100 nM, 90 nM, 80 nM, 70 nM, 60 nM, 50 nM, 40 nM, 30 nM, 20 nM, 10 nM, or 5 nM. In a further embodiment, compounds of the present disclosure inhibit A2016T mutant LRRK2 at an $IC_{50}$ below 100 nM, 90 nM, 80 nM, 70 nM, 60 nM, 50 nM, 40 nM, 30 nM, 20 nM, 10 nM, or 5 nM. In a further embodiment, compounds of the present disclosure inhibit A2016T mutant LRRK2 at an $IC_{50}$ below 50 nM, 40 nM, 30 nM, 20 nM, 10 nM, or 5 nM. In a further embodiment, compounds of the present disclosure inhibit A2016T mutant LRRK2 at an $IC_{50}$ below 50 nM.

In one embodiment, compounds of the present disclosure inhibit both the wild-type and G2019S mutant LRRK2 at an $IC_{50}$ below 150 nM, 100 nM, 90 nM, 80 nM, 70 nM, 60 nM, 50 nM, 40 nM, 30 nM, 20 nM, 10 nM, or 5 nM. In a further embodiment, compounds of the present disclosure inhibit both the wild-type and G2019S mutant LRRK2 at an $IC_{50}$ below 100 nM, 90 nM, 80 nM, 70 nM, 60 nM, 50 nM, 40 nM, 30 nM, 20 nM, 10 nM, or 5 nM. In a further embodiment, compounds of the present disclosure inhibit both the wild-type and G2019S mutant LRRK2 at an $IC_{50}$ below 50 nM, 40 nM, 30 nM, 20 nM, 10 nM, or 5 nM. In a further embodiment, compounds of the present disclosure inhibit both the wild-type and G2019S mutant LRRK2 at an $IC_{50}$ below 20 nM, 10 nM, or 5 nM. In a further embodiment, compounds of the present disclosure inhibit both the wild-type and G2019S mutant LRRK2 at an $IC_{50}$ below 20 nM. In a further embodiment, compounds of the present disclosure inhibit both the wild-type and G2019S mutant LRRK2 at an $IC_{50}$ below 10 nM or 5 nM. In a further embodiment, compounds of the present disclosure inhibit both the wild-type and G2019S mutant LRRK2 at an $IC_{50}$ below 10 nM. In a further embodiment, compounds of the present disclosure inhibit both the wild-type and G2019S mutant LRRK2 at an $IC_{50}$ below 5 nM.

In one embodiment, compounds of the present disclosure inhibit both the wild-type LRRK2 at an $IC_{50}$ below 150 nM, 100 nM, 90 nM, 80 nM, 70 nM, 60 nM, 50 nM, 40 nM, 30 nM, 20 nM, 10 nM, or 5 nM, and A2016T mutant LRRK2 at an $IC_{50}$ below 200 nM, 190 nM, 180 nM, 170 nM, 160 nM, 150 nM, 100 nM, 90 nM, 80 nM, 70 nM, 60 nM, 50 nM, 40 nM, 30 nM, 20 nM, 10 nM, or 5 nM. In a further embodiment compounds of the present disclosure inhibit both the wild-type LRRK2 at an $IC_{50}$ below 50 nM, 40 nM, 30 nM, 20 nM, 10 nM, or 5 nM, and A2016T mutant LRRK2 at an IC$_{50}$ below 150 nM, 100 nM, 90 nM, 80 nM, 70 nM, 60 nM, 50 nM, 40 nM, 30 nM, 20 nM, 10 nM, or 5 nM. In a further embodiment, compounds of the present disclosure inhibit both the wild-type LRRK2 at an IC$_{50}$ below 50 nM, 40 nM, 30 nM, 20 nM, 10 nM, or 5 nM, and A2016T mutant LRRK2 at an IC$_{50}$ below 100 nM, 90 nM, 80 nM, 70 nM, 60 nM, 50 nM, 40 nM, 30 nM, 20 nM, 10 nM, or 5 nM. In a further embodiment, compounds of the present disclosure inhibit both the wild-type LRRK2 at an IC$_{50}$ below 50 nM, and A2016T mutant LRRK2 at an IC$_{50}$ below 50 nM. In a further embodiment, compounds of the present disclosure inhibit both the wild-type LRRK2 at an IC$_{50}$ below 20 nM, and A2016T mutant LRRK2 at an IC$_{50}$ below 50 nM. In a further embodiment, compounds of the present disclosure inhibit both the wild-type LRRK2 at an IC$_{50}$ below 10 nM, and A2016T mutant LRRK2 at an IC$_{50}$ below 50 nM. In a further embodiment, compounds of the present disclosure inhibit both the wild-type LRRK2 at an IC$_{50}$ below 5 nM, and A2016T mutant LRRK2 at an IC$_{50}$ below 50 nM.

In one embodiment, compounds of the present disclosure inhibit both the wild-type and the G2019S mutant of LRRK2 at a concentration below 1 µM, 0.9 M, 0.8 µM, 0.7 µM, 0.6 µM, 0.5 µM, 0.4 µM, 0.3 µM, or 0.2 µM. For example compounds of the present disclosure inhibit both the wild-type and the G2019S mutant of LRRK2 at a concentration between 0.1-0.3 µM.

In another aspect, the present disclosure provides a pharmaceutical composition comprising an effective amount of one or more of the compounds of the disclosure and a pharmaceutically acceptable carrier. Suitable formulating agents are described in detail in Section 5 herein.

In accordance with an aspect of the disclosure, a method of treating or preventing a disease or disorder in which LRRK2 is involved, comprising administering to the subject an effective amount of a compound according to the present disclosure, or a pharmaceutically acceptable salt, ester, tautomer, or prodrug thereof.

In another aspect, the disclosure provides a method for treating or preventing a neurodegenerative disorder, for example, PD, in a subject. The method comprises administering an effective amount of one or more compounds or pharmaceutical compositions of the disclosure, for example, via oral or parenteral routes.

The disclosure further provides a method of treating a disorder in a subject comprising the step of administering to the subject an effective amount of one or more compounds of the disclosure thereby to ameliorate a symptom of a particular disorder. Such a disorder may be a neurodegenerative disorder, and may, for example, be Parkinson's disease.

3. Synthesis and Analysis of Compounds of the Disclosure

Compounds of the present disclosure can be conveniently prepared by a variety of methods familiar to those skilled in the art. The compounds of each of the formulae described herein may be prepared according to the following procedures from commercially available starting materials or starting materials which can be prepared using literature procedures. These procedures show the preparation of representative compounds of this disclosure. It is understood that compounds of the present disclosure other than those illustrated in the following schemes can be made using these schemes with modifications commonly known in the art (e.g., using different starting material, changing reaction solvents, or adjusting reaction duration or temperature).

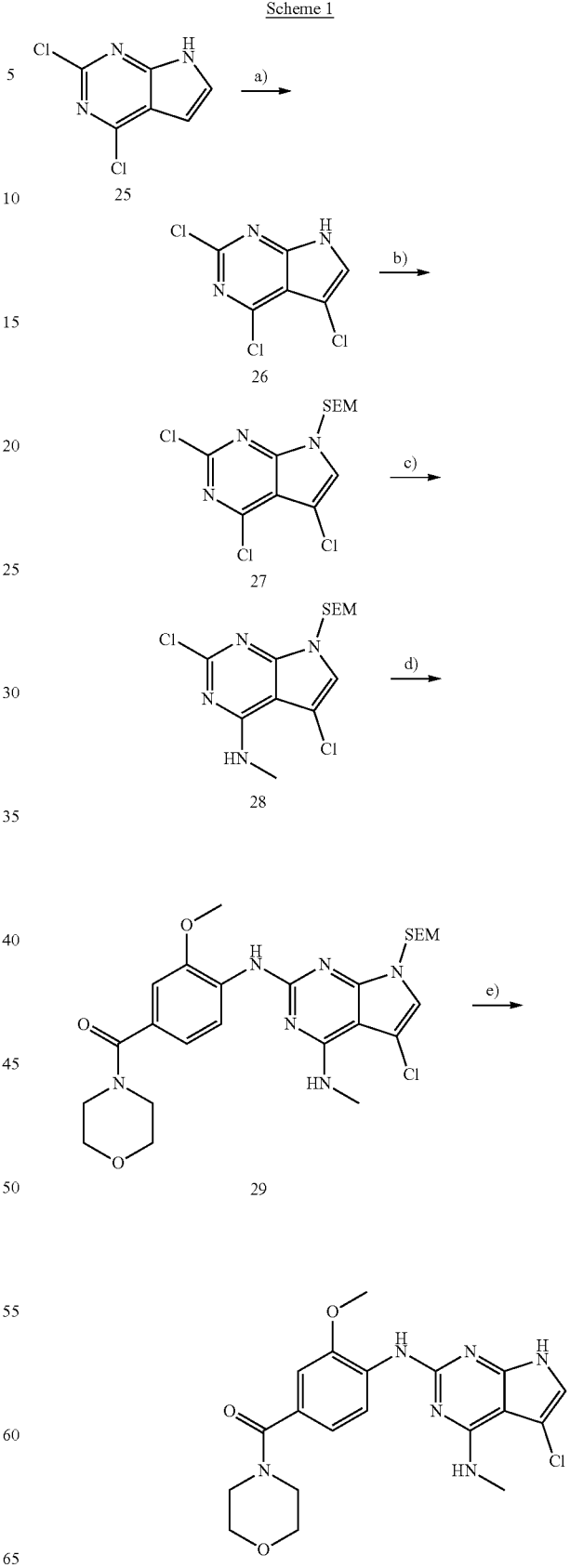

Scheme 1

-continued
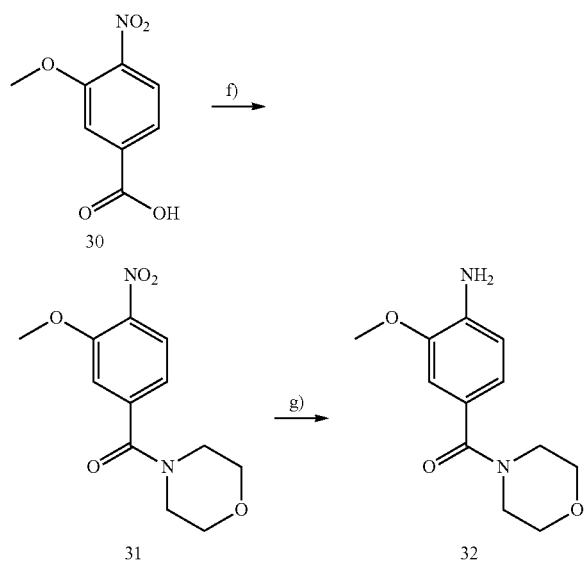
Scheme 1. Reagents and conditions: a) NCS, THF/DCM, 90° C., 2.5 h, 93%, b) NaH, SEMCl, 0° C. to RT 3 h, 90%, c) 33% MeNH₂ in EtOH, EtOH, 70° C. 1 h, 93%, d) 32, Pd₂(dba)₃, XPhos, K₂CO₃, sec-BuOH 90° C., 6 h, e) (i) TFA, DCM RT, 2 h, (ii) NaHCO₃, THF, H₂O, 12 h, 58%, f) (i) toluene, thionyl chloride, 120° C., 2 h (ii) DIEA, morpholine, THF, 0° C. to RT, 1 h, 92%, g) 10% Pd/C, MeOH, RT, 12 h, 98%.
Scheme 1-1
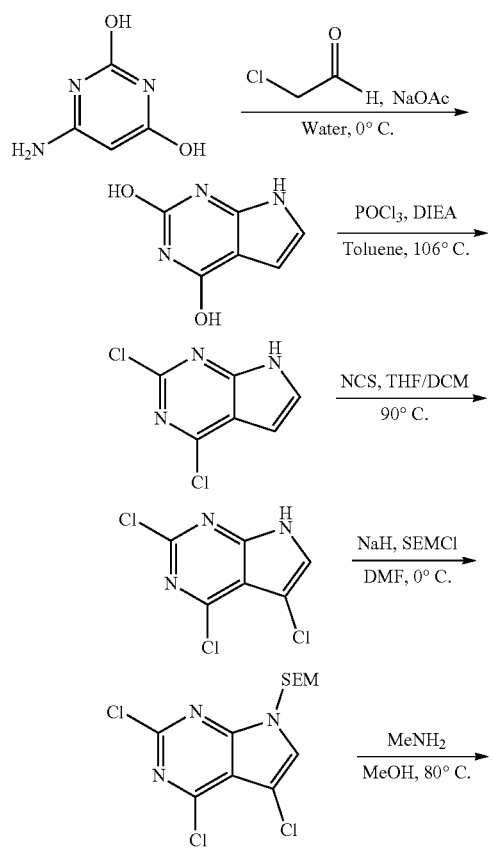
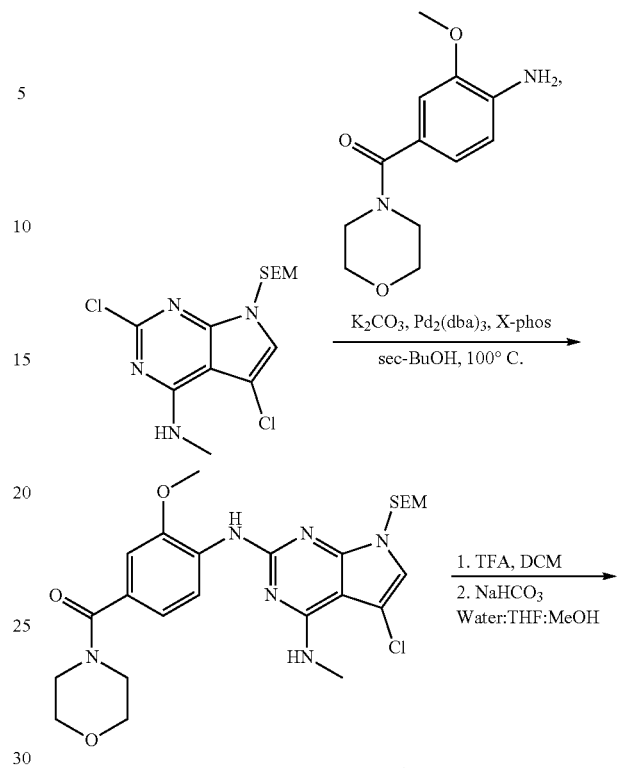
Scheme 2
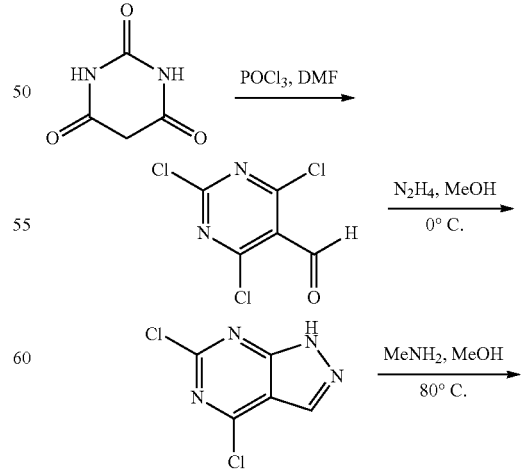

99
-continued
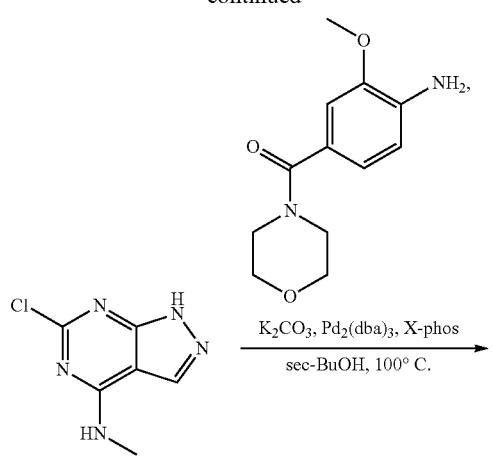
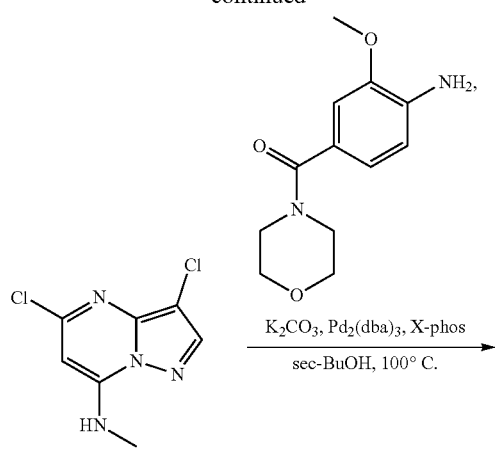
100
-continued
Scheme 3
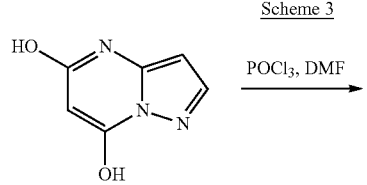
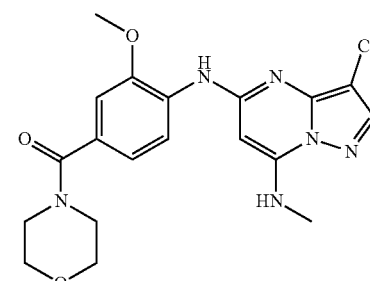
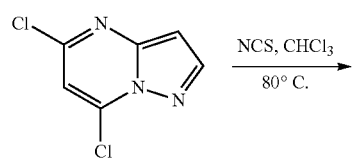
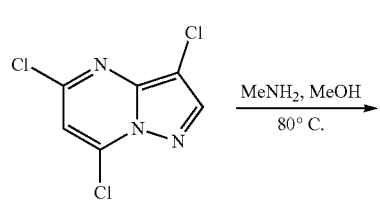
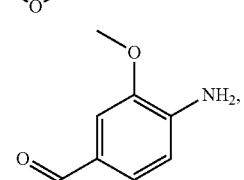
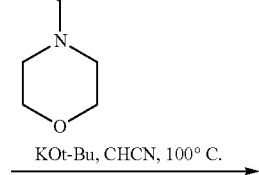
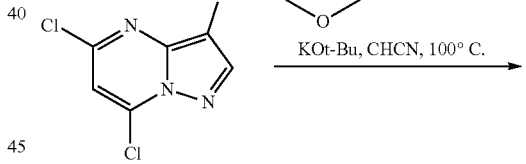
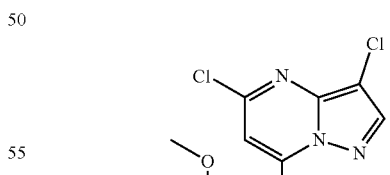
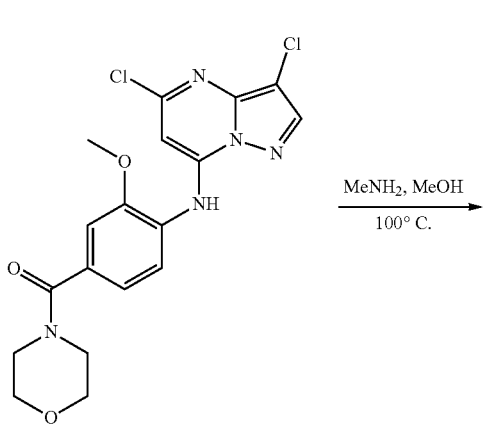

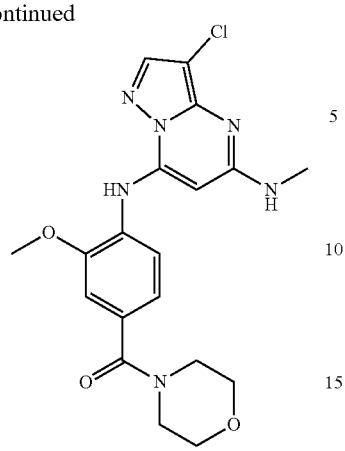

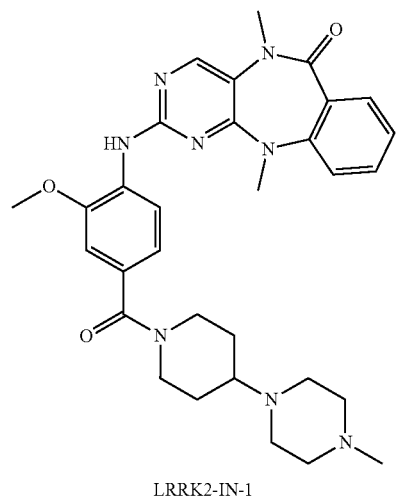

LRRK2-IN-1

Among the genes associated with PD, LRRK2 is unique because a missense mutation, G2019S, is frequently found in both familial and sporadic Parkinson's disease cases. The G2019S mutation leads to a two- or three-fold increase in kinase activity, which may result in activation of the neuronal death signaling pathway. For example, transgenic G2019S LRRK2 mice aged 12 to 16 months display progressive degeneration of SNpc dopaminergic neurons and Parkinson's phenotypes of motor dysfunction, demonstrating that the G2109S mutation may be functionally relevant to the disease. Furthermore, other mutations, for example, A2016T may also play a role in the disease. This suggests that small molecule LRRK2 kinase inhibitors may be able to serve as a new class of therapeutics for the treatment of PD.

Several 2,4-diaminopyrimidine based inhibitors of LRRK2 have been reported, including LRRK2-IN-1, CSC-25146, and TAE684. Additionally, GSK2578215A, a benzamide ATP-site directed scaffold, was found to be a potent and selective inhibitor of LRRK2.

None of the above compounds however is capable of effectively inhibiting phosphorylation of the Ser910 and Ser935 of LRRK2 in mouse brain at intraperitoneal doses of up to 100 mg/Kg, which limits their use as tools in murine PD models.

Additional 2,4-diaminopyrimidines have been developed, including HG-10-102-01 and GNE7915 that are potent and selective LRRK2 inhibitors that can traverse the blood-brain barrier. These diaminopyrimidines were shown to significantly reduce LRRK2 activity in the brain of G2019S LRRK2 transgenic mice after oral dosing, judged through their ability to reduce LRRK2 phosphorylation at Ser935 that is dependent on LRRK2 catalytic activity. The pyrrolopyrimidine PF-06447474 was recently reported to also be a potent and selective LRRK2 inhibitor capable of reducing LRRK2 activity in the brain of G2019S LRRK3 mice after oral dosing. Additional ATP-competitive LRRK2 inhibitors that have been reported include cinnolines, triazolopyridazines, and 3-cyanquinazolines, as well as others. The above-referenced LRRK2 inhibitors are shown below.

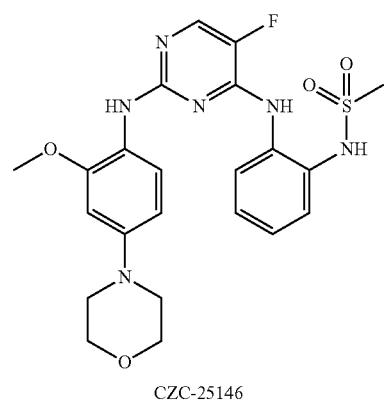

CZC-25146

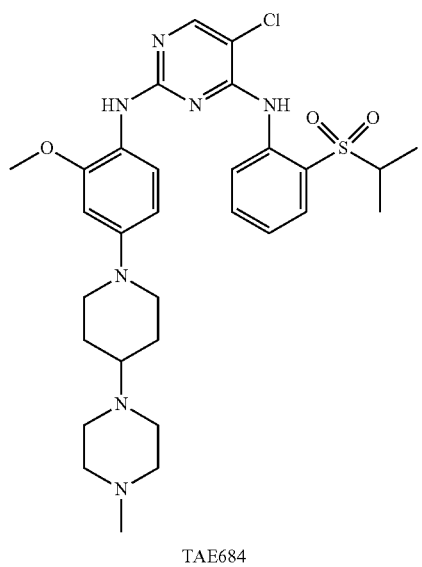

TAE684

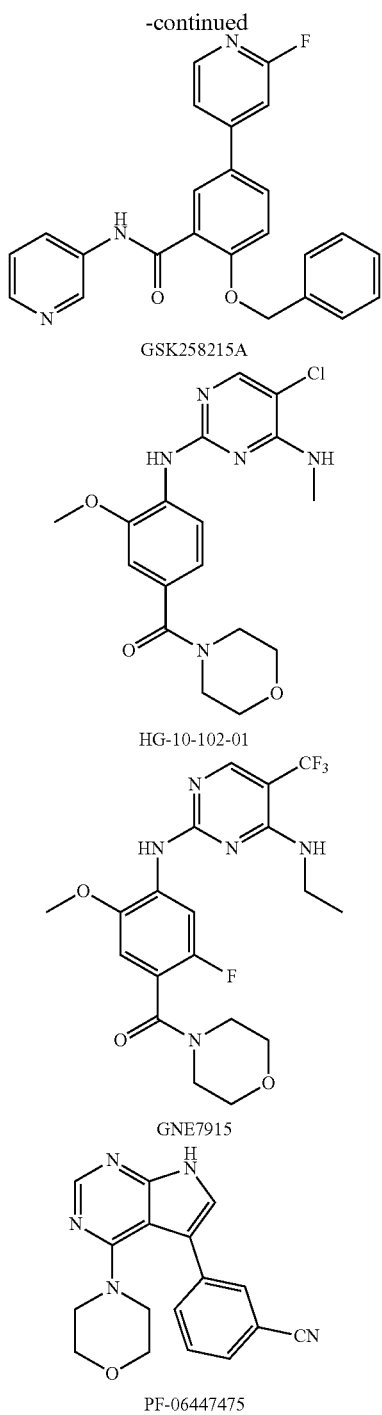

GSK258215A

HG-10-102-01

GNE7915

PF-06447475

LRRK2 kinase activity is thought to be dependent on phosphorylation of the activation segment of the protein. In catalytic domains of protein kinases, a small N terminal lobe and a larger C terminal lobe are connected to form a cleft in which adenosine triphosphate (ATP) and the protein substrate may react, which is known as the activation segment. The activation segment of LRRK2 is thought to be a ribbon of protein from 2017 to 2042 amino acids of the large C terminal lobe. A region defined by conserved tripeptide "hinges" may serve to block substrate access to the catalytic site. Without wishing to be bound to a single theory, molecules capable of binding with LRRK2, more specifically, binding to the activation site and interacting with the hinge regions of the kinase, may inhibit LRRK2 kinase activity.

Because GNE7915 has the ability to inhibit phosphorylation, the compound is a candidate for further study. Based on a structural analysis of GNE7915, intramolecular hydrogen bonding is likely to exist between the C-5 trifluoromethyl group and the C-6 hydrogen to give a pseudobicycle. In accordance with embodiments, binding affinity to the LLRK2 activation site may be increased relative to standard GNE7915 by modification of the compound to present a fused bicyclic analogue of GNE7915. Binding affinity may be increased with a fused bicyclic analogue due to the additional hydrogen bond donor at the 7-position. This modification may advantageously enhance binding affinity without a large increase in molecular weight. Without wishing to be bound to a single theory, a fused bicyclic compound may also better fill the hydrophobic area around the hinge region, leading to an increase in binding affinity and thus better LRRK2 inhibition. Furthermore, a chlorine at the 5-position of a pyrimidine may advantageously increase binding affinity by interacting with the gatekeeper Met790 of EGFR and the Met1947 residue.

The present disclosure thus provides compounds with enhanced binding affinity that may reduce or inhibit phosphorylation and thus kinase activity of LRRK2, and may, for example, be useful in treating Parkinsonism. In accordance with embodiments, a ring-closed version of GNE7915 was constructed using a series of 6.5-fused ring analogues. A pyrrolopyrimidine was selected to allow for the installation of a chlorine heteroatom at the C-5 position.

Pyrrolopyrimidine analogues were synthesized with a variety of substitutions at the C-4 position and used to make compounds of the present disclosure. Amine substituents exhibited excellent potency in both wild type LRRK2 and LRRK2[G2019S] enzymatic assays, while compounds with a methoxy group or no substituent at the C-4 position showed reduced activity. Compounds with a chlorine at the C-5 position and various amine substituents at the C-4 position also showed excellent potency in both wild type and LRRK2[G2019S] kinase assays. Table 1 shows non-limiting examples of compounds of the present disclosure having substituted pyrrolopyrimidines and their ability to inhibit LRRK2.

TABLE 1

Pyrrolopyrimidine SAR with enzyme IC50s

| compd | $R_1$ | $R_2$ | $R_3$ | Enzyme IC50 wt (nM) | Enzyme IC50 G2019S (nM) |
|---|---|---|---|---|---|
| 8 | H | NHMe | H | 2.6 | 5.1 |
| 9 | H | OMe | H | 13.6 | 95.7 |
| 10 | H | H | H | 34 | 40 |
| 11 | H | HN~~~O~ | H | 4 | 3 |
| 12 | H | HN~~ | H | 1.1 | 2.5 |

TABLE 1-continued

Pyrrolopyrimidine SAR with enzyme IC50s

| compd | R$_1$ | R$_2$ | R$_3$ | Enzyme IC50 wt (nM) | Enzyme IC50 G2019S (nM) |
|---|---|---|---|---|---|
| 13 | H | HN-propyl | H | 1.6 | 2.4 |
| 14 | H | HN-CH$_2$-tetrahydrofuran | H | 3.3 | 4.4 |
| 15 | H | HN-cyclopropyl | H | 2.4 | 4.7 |
| 16 | F | NHMe | H | 2.1 | 7.1 |
| 17 | H | H | Cl | 159 | 108 |
| 18 | H | NHMe | Cl | 6.5 | 2.2 |
| 19 | H | HN-propyl | Cl | 1.4 | 4.4 |
| 20 | H | HN-butyl | Cl | 7.7 | 12.4 |

The amount of ATP used for the above kinase assay was based on the Km value for ATP wild type and LRRK[G2019S], which was 36 μm and 112 μm, respectively.

Known LRRK2 inhibitors and Compound 18, also referred to herein as (18), were assayed using 20 μM Nictide in the presence of 100 μm ATP to compare each compound's effectiveness at inhibiting wild type LRRK2, LRRK2 [G2019S], LRRK2[A2016T] and LRRK2[G20192+ A20161], as shown in Table 2. Assay procedures are further discussed in Section 4 herein.

TABLE 2

Known LRRK2 inhibitors compared to Compound 18

| | IC50 (nM)$^a$ | | | |
|---|---|---|---|---|
| Compound ID | wild-type LRRK2 | LRRK2-G2019S | LRRK2-A2016T | LRRK2-G2019S + A2016T |
| LRRK2-IN-1 | 13 | 6 | 2450 | 3080 |
| TAE684 | 7.8 | 6.1 | 93.3 | 21.9 |
| GSK2578215A | 10.9 | 8.9 | 81.1 | 61.3 |
| HG-10-102-01 | 20.3 | 3.2 | 153.7 | 95.9 |
| Compound 18 | 6.6 | 2.2 | 47.7 | 19.8 |

Table 2: Known LRRK2 inhibitors compared to Compound 18. GST-LRRK2(1,326-2,517), GST-LRRK2[G2019S](1,326-2,527), GST-LRRKT[A2016T](1,326-2,517) and GST-LRRK2[G2019S + A2016T](1,326-2,517) were assayed using 20 mM Nictide in the presence of 100 μM ATP.
Results are the average of duplicate experiments.

The biochemical potency of (18) for inhibition of wild-type LRRK2 and LRRK2[G2019S] is superior to each of the known inhibitors assayed. Notably, the potency of (18) for inhibition of LRRK2 and LRRK2[G2019S] is similar to that observed for LRRK2-IN-1, however (18) maintains inhibition of the A2016T mutation, whereas A2016T mutation induces dramatic resistance to LRRK2-IN-1.

The present disclosure further provides methods and intermediates for making the compounds of the present disclosure. The following schemes depict some exemplary chemistries available for synthesizing the compounds of the disclosure. It will be appreciated, however, that the desired compounds may be synthesized using alternative chemistries known in the art.

Scheme 1 shows a non-limiting synthesis of compounds prepared from analogues having a substituted pyrrolopyrimidine, for example, Compound 18.

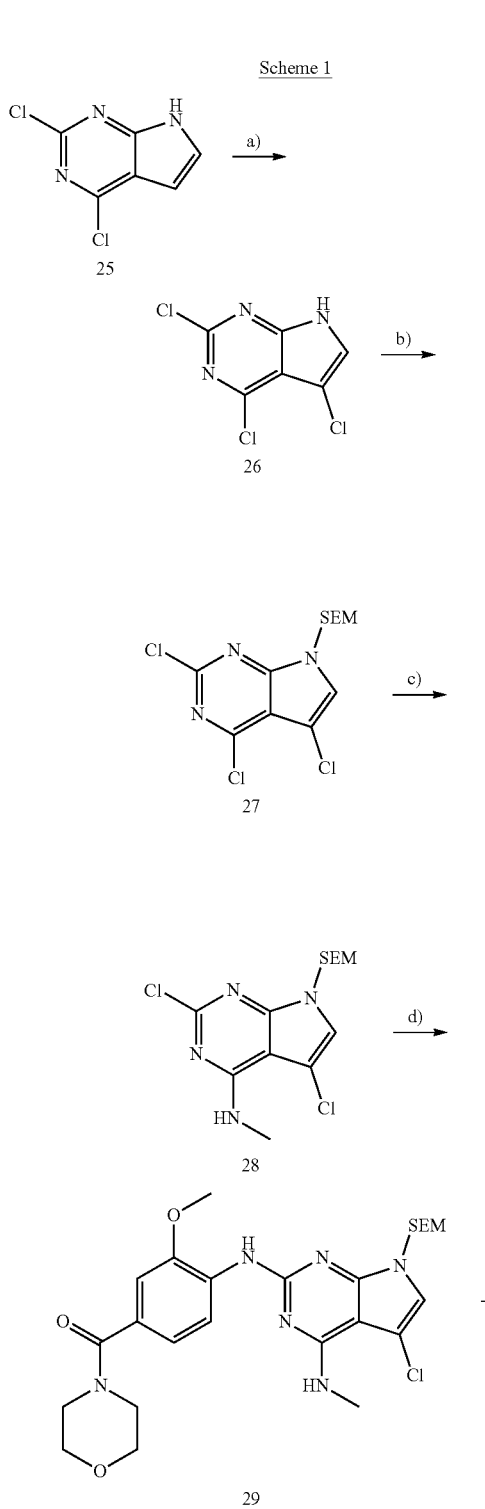

Scheme 1

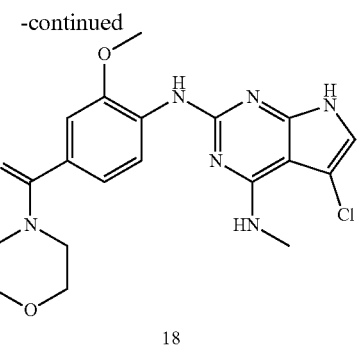

18

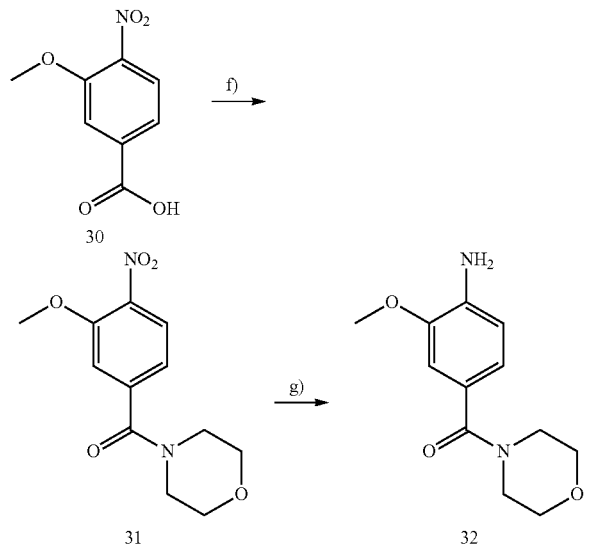

Scheme 1. Reagents and conditions: a) NCS, THF/DCM, 90° C., 2.5 h, 93%, b) NaH, SEMCl, 0° C. to RT 3 h, 90%, c) 33% MeNH₂ in EtOH, EtOH, 70° C. 1 h, 93%, d) 32, Pd₂(dba)₃, XPhos, K₂CO₃, sec-BuOH 90° C., 6 h, e) (i) TFA, DCM RT, 2 h, (ii) NaHCO₃, THF, H₂O, 12 h, 58%, f) (i) toluene, thionyl chloride, 120° C., 2 h (ii) DIEA, morpholine, THF, 0° C. to RT, 1 h, 92%, g) 10% Pd/C, MeOH, RT, 12 h, 98%.

As shown in Scheme 1, compounds prepared from a pyrrolopyrimidine analogue, for example Compound 18, can be prepared from commercially available 2,4-dichloropyrrolopyrimidine and 3-methoxy-4-nitrobenzoic acid. In accordance with Scheme 1, 3-methoxy-4-nitrobenzoic acid (30) was subjected to chlorination with thionyl chloride (SOCl₂), followed by reaction with morpholine (C₄H₉NO) to generate amide (31) which was reduced by hydrogenation to yield aniline. 2,4-dichloropyrrolopyrimidine (25) was chlorinated using thyocynate (NCS) followed by SEM ([2-(Trimethylsilyl)ethoxy]methyl) protection to give the SEM-protected trichloropyrrolopyrimidine (27). Compound 27 was regioselectively aminated with methylamine to afford 2,5-dichloro-N-methylpyrrolopyrimidine-4-amine (28). Compound 28 was aminated with an aniline using Buchwald coupling conditions followed by removal of the SEM group to furnish the desired compound, in this non-limiting embodiment, Compound 18.

An evaluation of pyrazolopyrimidines and purine analogues was also conducted. In accordance with embodiments, the additional nitrogens of the pyrazole compound of the purine rings may enhance potency by introducing an additional hydrogen bond acceptor. Compounds were synthesized with pyrazolopyrimidines having an N-methyl (21) and an O-methyl (22) substitution at the C-4 position, respectively (Table 3). Surprisingly, a compound having a pyrazolopyrimidine with a methoxy substituent at the C-4 position (22) showed greater potency in both wild type LRRK2 and G2019S enzymatic assays than the corresponding N-methyl substituted compound (21), which was the opposite of what was observed in the pyrrolopyrimidine series (Table 2).

Purine analogues having N-methyl and O-methyl substitution at the C-4 position were then made using the synthesis of similarly substituted compounds (23 and 24, respectively). In this instance, a compound having a purine with an N-methyl substituent was more potent than the corresponding purine compound with the methoxy substituent. Table 3 shows non-limiting examples of compounds having substituted pyrrolopyrimidines and purines and their ability to inhibit LRRK2.

TABLE 3

Pyrazolopyrimidine and Purine SAR with enzyme IC50s

| compd | R | R1 | R2 | X | Y | Enzyme IC50 WT nM | Enzyme IC50 G2019S nM |
|---|---|---|---|---|---|---|---|
| 21 | H | NHMe | — | N | CH | 35 | 44 |
| 22 | H | OMe | — | N | CH | 3 | 3 |
| 23 | H | NHMe | H | CH | N | 11.5 | 4 |
| 24 | H | OMe | H | CH | N | 19.4 | 18.5 |

Scheme 2 shows a non-limiting synthesis of compounds, for example compound 23, prepared from purine analogies.

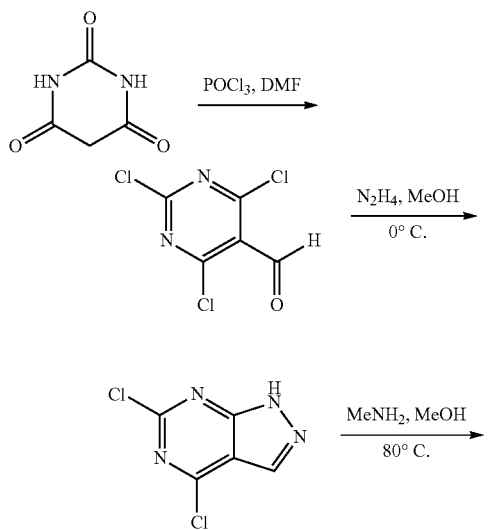

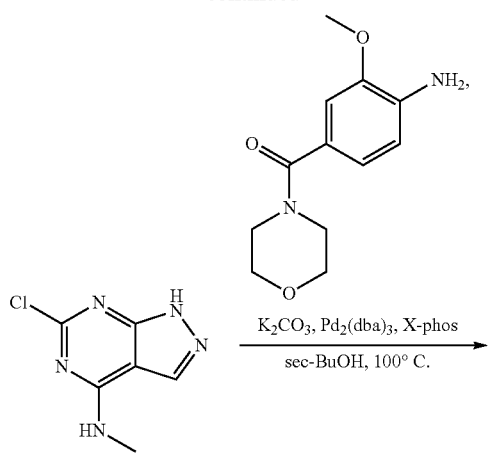
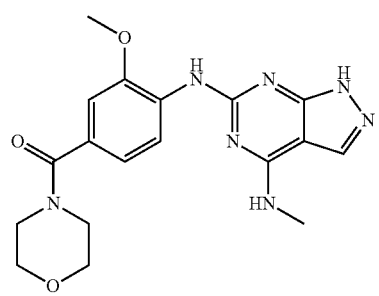
Scheme 3 shows a further non-limiting synthesis of compounds of the present disclosure.
Scheme 3
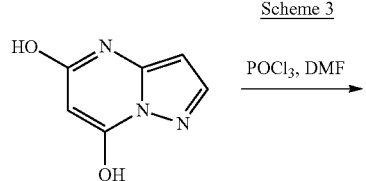
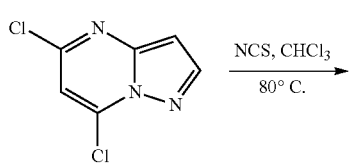
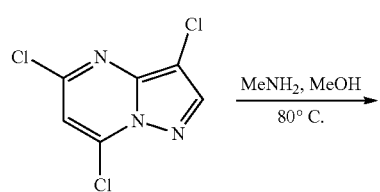
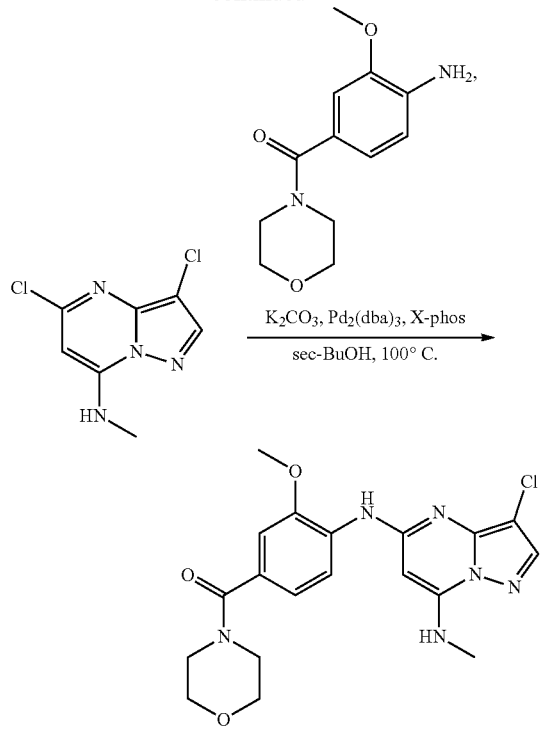
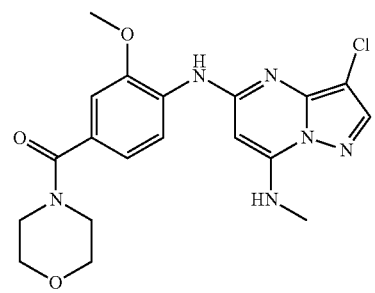
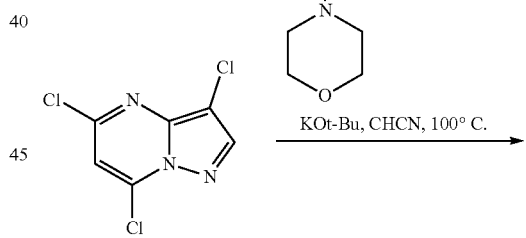
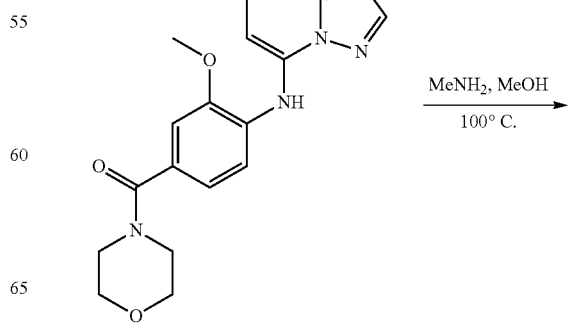

-continued

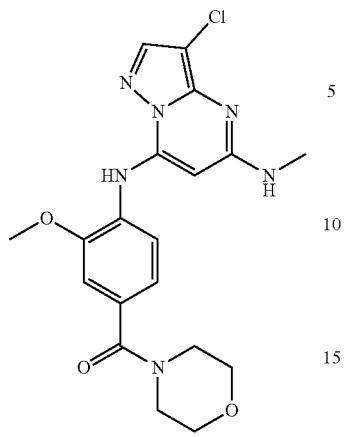

Exemplary compounds of the present disclosure synthesized in accordance with the methods disclosed herein are shown in Table 4.

TABLE 4

| Compound No. | Structure | Physical Data $^1$H NMR 400 MHz and/or MS (m/z) |
|---|---|---|
| 8 | 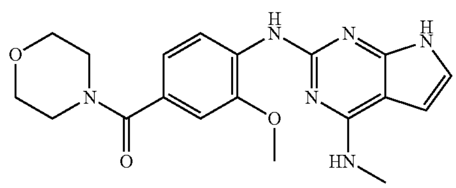 [SMILES: CNc1nc(Nc2ccc(C(=O)N3CCOCC3)cc2OC)nc2[nH]ccc12] | $^1$H NMR (400 MHz, DMSO-d$_6$) δ 11.96 (br, 1H), 8.48 (d, J = 4 Hz, 1H), 7.04 (s, 1H), 6.96 (m, 1H), 6.54 (s, 1H), 3.95 (s, 3H), 2.48 (s, 3H) 2.44-2.39 (m, 8H); MS m/z: 383.74 [M + 1]. |
| 9 | 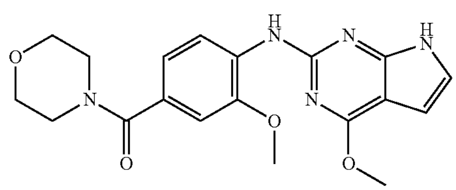 [SMILES: COc1cc(C(=O)N2CCOCC2)ccc1Nc1nc(OC)c2cc[nH]c2n1] | $^1$H NMR (400 MHz, DMSO-d$_6$) δ 11.58 (br, 1H), 8.58 (d, J = 7 Hz, 1H), 7.67 (m, 1H), 7.07-6.99 (m, 2H), 6.34-6.31 (m, 1H), 4.01 (s, 1H), 3.92 (s, 3H), 2.52 (s, 1H), 2.51-2.46 (m, 8H); MS m/z: 384.58 [M + 1]. |
| 10 | 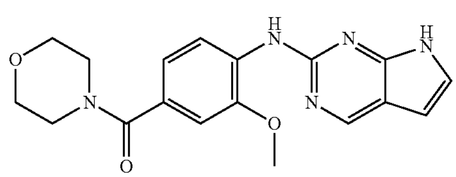 [SMILES: COc1cc(C(=O)N2CCOCC2)ccc1Nc1ncc2cc[nH]c2n1] | $^1$H NMR 400 MHz (DMSO-d$_6$) δ 12.05 (br, 1H), 8.81 (s, 1H), 8.56 (br, 1H), 8.38 (d, J = 7 Hz, 1H), 7.37 (m, 2H), 7.22 (m, 1H), 7.01 (m, 1H), 3.90 (s, 3H), 2.51-2.46 (m, 8H); MS m/z: 354.58 [M + 1]. |
| 11 | 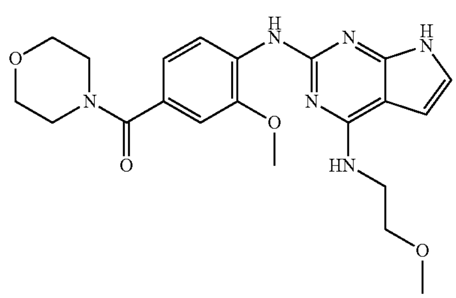 [SMILES: COCCNc1nc(Nc2ccc(C(=O)N3CCOCC3)cc2OC)nc2[nH]ccc12] | $^1$H NMR (400 MHz, DMSO-d$_6$) δ 11.87 (br, 1H), 8.40 (d, J = 9 Hz, 1H), 7.23 (s, 1H), 7.10 (m, 1H), 7.03-6.98 (m, 1H), 3.92 (s, 3H), 3.27 (s, 3H), 2.48 (m, 8H); MS m/z: 427.19 [M + 1]. |

татьe 4-continued

| Compound No. | Structure | Physical Data ¹H NMR 400 MHz and/or MS (m/z) |
|---|---|---|
| 12 | 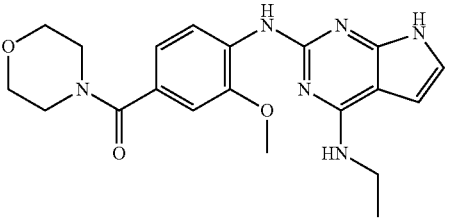 [SMILES: CCNc1nc(Nc2ccc(C(=O)N3CCOCC3)cc2OC)nc2[nH]ccc12] | ¹H NMR (400 MHz, DMSO-d₆) δ 11.98 (br, 1H), 9.01 (m, 1H), 8.4 (m, 1H), 7.13 (s, 1H), 7.02 (m, 1H), 6.84 (m, 1H), 6.64 (s, 1H), 3.95 (s, 3H), 2.45-2.41 (m, 8H), 1.68 (q, J = 7 Hz, 2H), 0.88 (t, J = 7 Hz, 3H); MS m/z: 397.09 [M + 1]. |
| 13 | 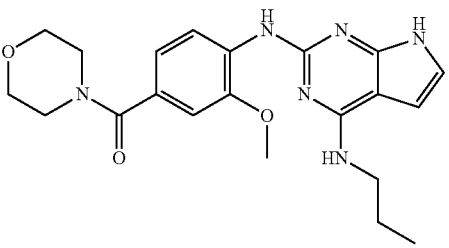 [SMILES: CCCNc1nc(Nc2ccc(C(=O)N3CCOCC3)cc2OC)nc2[nH]ccc12] | ¹H NMR (400 MHz, DMSO-d₆) δ 11.91 (br, 1H), 8.43 (d, J = 4 Hz, 1H), 7.81 (m, 1H), 7.10 (s, 1H), 7.0 (m, 1H), 6.61 (s, 1H), 6.48 (m, 1H), 3.98 (s, 3H), 2.47 (s, 1H), 2.45-2.41 (m, 8H), 1.38-1.01 (m, 4H), 0.88 (t, J = 7 Hz, 3H); MS m/z: 411.33 [M + 1]. |
| 14 | 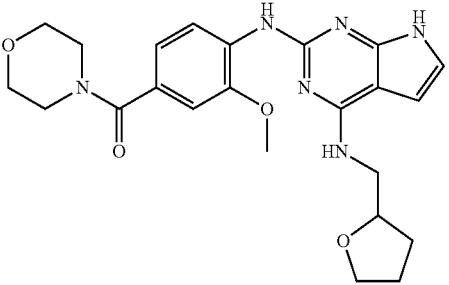 [SMILES: COc1cc(C(=O)N2CCOCC2)ccc1Nc1nc(NCC2CCCO2)c2cc[nH]c2n1] | ¹H NMR (400 MHz, DMSO-d₆) δ 7.22 (s, 1H), 7.16 (d, J = 9 Hz, 1H), 7.23 (s, 1H), 4.01 (s, 3H), 3.14 (d, J = 4 Hz 3H), 2.61-2.58 (m, 8H); MS m/z: 453.07 [M + 1]. |
| 15 | 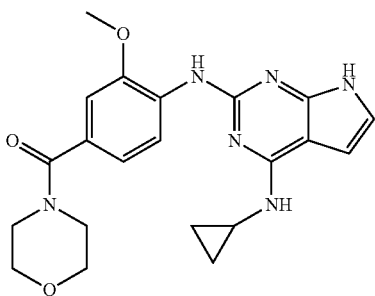 [SMILES: COc1cc(C(=O)N2CCOCC2)ccc1Nc1nc(NC2CC2)c2cc[nH]c2n1] | ¹H NMR (400 MHz, DMSO-d₆) δ 12.06 (br, 1H), 8.56 (d, J = 4 Hz, 1H), 7.98 (m, 1H), 7.08 (s, 1H), 6.64 (s, 1H), 4.01 (s, 3H), 2.56 (s, 3H) 2.48 (m, 8H), 0.99 (m, 1H), 0.81-0.55 (m, 4H); MS m/z: 409.21 [M + 1]. |
| 16 | 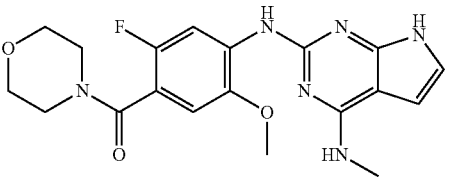 [SMILES: CNc1nc(Nc2cc(F)c(C(=O)N3CCOCC3)cc2OC)nc2[nH]ccc12] | ¹H NMR (400 MHz, DMSO-d₆) δ 11.94 (br, 1H), 8.26 (s, 1H), 7.64 (s, 1H), 6.96 (m, 1H), 6.54 (s, 1H), 3.95 (s, 3H), 2.48 (s, 3H) 2.44-2.39 (m, 8H); MS m/z: 401.36 [M + 1]. |
| 17 | 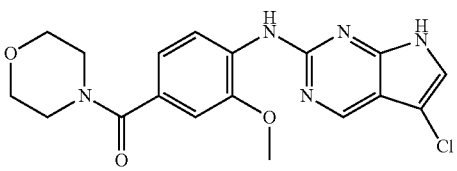 [SMILES: COc1cc(C(=O)N2CCOCC2)ccc1Nc1ncc2c(Cl)c[nH]c2n1] | ¹H NMR 400 MHz (DMSO-d₆) δ 12.05 (br, 1H), 8.81 (s, 1H), 8.56 (br, 1H), 8.38 (d, J = 7 Hz, 1H), 7.37 (m, 2H), 7.22 (m, 1H), 6.88 (s, 1H), 3.92 (s, 3H), 2.50-2.48 (m, 8H); MS m/z: 388.27 [M + 1]. |

TABLE 4-continued

| Compound No. | Structure | Physical Data ¹H NMR 400 MHz and/or MS (m/z) |
|---|---|---|
| 18 | 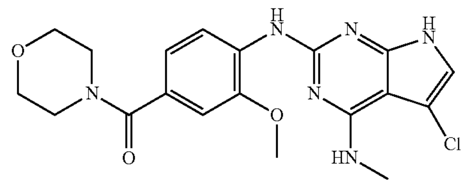 [SMILES: CNc1nc(Nc2ccc(C(=O)N3CCOCC3)cc2OC)nc2[nH]cc(Cl)c12] | ¹H NMR 400 MHz (DMSO-d$_6$) δ 11.43 (br, 1H), 8.62 (d, J = 4 Hz, 1H), 7.44 (s, 1H), 7.03 (m, 1H), 6.6 (m, 1H), 3.95 (s, 3H), 3.62-3.5 (m, 8H), 2.48 (s, 3H); ¹³C NMR 100 MHz (DMSO-d$_6$) δ 169.65, 156.91, 150.37, 146.98, 131.83, 127.29, 120.39, 116.70, 116.43, 110.00, 102.03, 95.63, 66.59, 56.42, 28.17; MS m/z: 417.34 [M + 1]. |
| 19 | 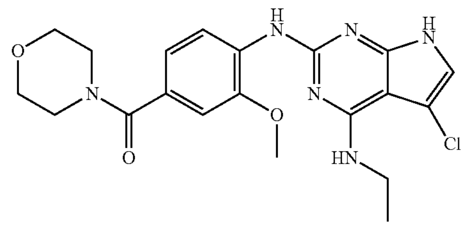 [SMILES: CCNc1nc(Nc2ccc(C(=O)N3CCOCC3)cc2OC)nc2[nH]cc(Cl)c12] | ¹H NMR 400 MHz (DMSO-d$_6$) δ 12.01 (br, 1H), 8.62 (d, J = 4 Hz, 1H), 7.68 (br, 1H), 7.42 (s, 1H), 6.98 (m, 1H), 6.6 (m, 1H), 4.01 (q, J = 7 Hz, 2H), 3.91 (s, 3H), 2.50-2.46 (m, 8H), 1.2 (m, 3H); MS m/z: 431.17 [M + 1]. |
| 20 | 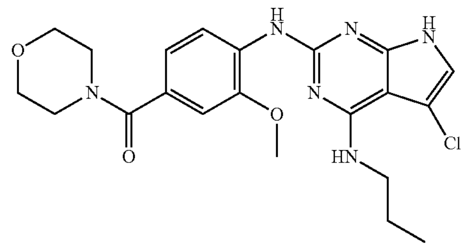 [SMILES: CCCNc1nc(Nc2ccc(C(=O)N3CCOCC3)cc2OC)nc2[nH]cc(Cl)c12] | ¹H NMR 400 MHz (DMSO-d$_6$) δ 11.48 (br, 1H), 8.59 (m, 1H), 7.0 (m, 2H), 3.91 (s, 3H), 2.50-2.46 (m, 8H), 1.65 (m, 5H), 0.95 (m, 2H); MS m/z: 445.25 [M + 1]. |
| 21 | 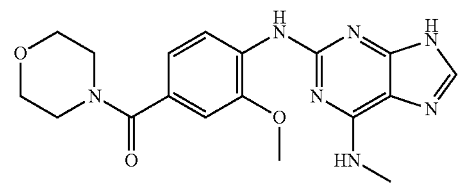 [SMILES: CNc1nc(Nc2ccc(C(=O)N3CCOCC3)cc2OC)nc2[nH]cnc12] | ¹H NMR (400 MHz, DMSO-d$_6$) δ 8.39 (d, J = 9 Hz, 1H), 8.06 (s, 1H), 7.06-7.02 (m, 1H), 6.98 (d, J = 3 Hz, 1H), 3.85 (s, 1H), 2.47 (s, 3H), 2.45-2.51 (m, 8H); MS m/z 384.19 [M + 1]. |
| 22 | 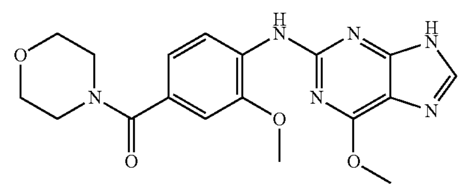 [SMILES: COc1cc(C(=O)N2CCOCC2)ccc1Nc1nc(OC)c2nc[nH]c2n1] | ¹H NMR (400 MHz, DMSO-d$_6$) δ 8.46 (d, J = 9 Hz, 1H), 8.01 (s, 1H), 7.89 (s, 1H), 7.04 (m, 1H), 4.03 (s, 3H), 3.96 (s, 3H), 2.48-2.40 (m, 8H); MS m/z 385.62 [M + 1]. |
| 23 | 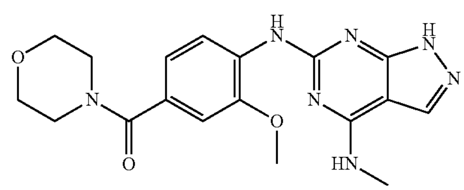 [SMILES: CNc1nc(Nc2ccc(C(=O)N3CCOCC3)cc2OC)nc2[nH]ncc12] | ¹H NMR 400 MHz (CD$_3$OD-d$_6$) δ 8.18 (m, 1H), 8.10 (br, 1H), 8.02 (m, 1H), 7.83 (m, 1H), 7.58 (m, 1H), 7.20 (m, 1H), 6.86 (m, 1H), 4.05 (m, 1H), 3.97 (s, 3H), 3.80 (m, 2H), 3.50 (m, 2H), 2.20 (m, 2H), 1.98 (m, 2H), 1.18 (d, J = 6.6 Hz, 6H); MS m/z: 384.63 [M + 1]. |
| 24 | 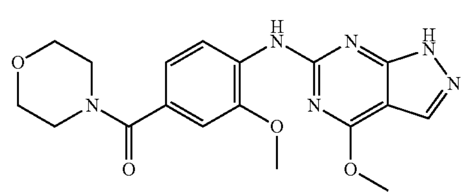 [SMILES: COc1cc(C(=O)N2CCOCC2)ccc1Nc1nc(OC)c2cn[nH]c2n1] | ¹H NMR 400 MHz (DMSO-d$_6$) δ 13.31 (br, 1H), 8.39 (d, J = 4 Hz, 1H), 7.98 (d, J = 8 Hz, 1H), 7.01 (m, 2H), 4.05 (s, 3H), 3.98 (s, 3H), 2.46 (m, 8H); MS m/z: 385.23 [M + 1]. |

TABLE 4-continued

| Compound No. | Structure | Physical Data ¹H NMR 400 MHz and/or MS (m/z) |
|---|---|---|
| 25 | 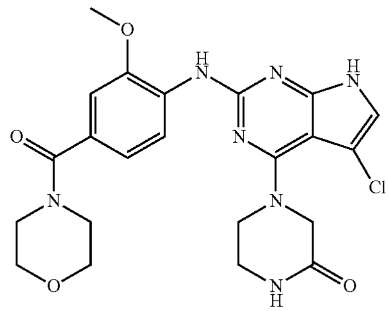 [SMILES: COc1cc(C(=O)N2CCOCC2)ccc1Nc1nc(N2CCNC(=O)C2)c2c(Cl)c[nH]c2n1] | MS m/z: 486.23 [M + 1]. |
| 26 | 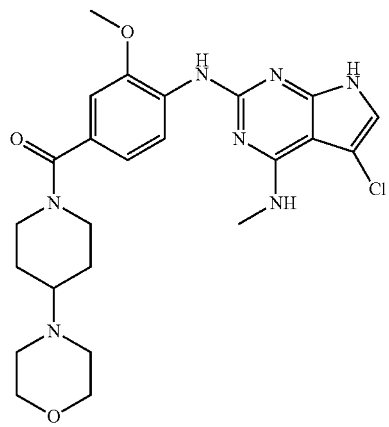 [SMILES: CNc1nc(Nc2ccc(C(=O)N3CCC(N4CCOCC4)CC3)cc2OC)nc2[nH]cc(Cl)c12] | MS m/z: 501.27 [M + 1]. |
| 27 | 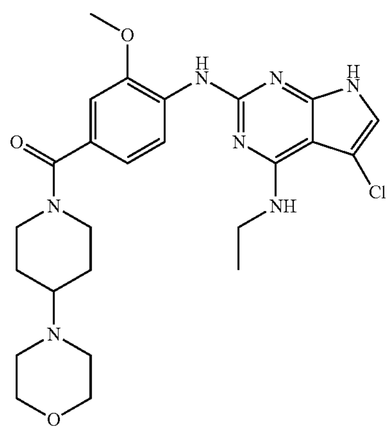 [SMILES: CCNc1nc(Nc2ccc(C(=O)N3CCC(N4CCOCC4)CC3)cc2OC)nc2[nH]cc(Cl)c12] | MS m/z: 515.15 [M + 1]. |
| 28 | 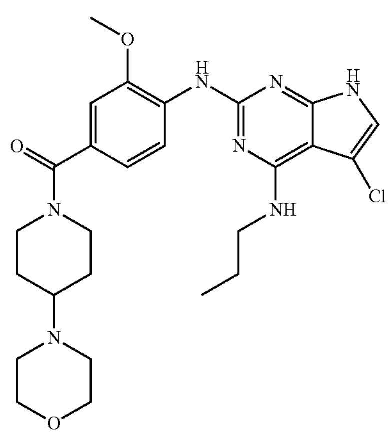 [SMILES: CCCNc1nc(Nc2ccc(C(=O)N3CCC(N4CCOCC4)CC3)cc2OC)nc2[nH]cc(Cl)c12] | MS m/z: 529.03 [M + 1]. |

TABLE 4-continued

| Compound No. | Structure | Physical Data ¹H NMR 400 MHz and/or MS (m/z) |
|---|---|---|
| 29 | 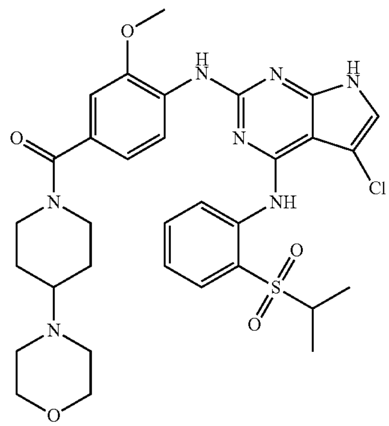 [SMILES: COc1cc(C(=O)N2CCC(N3CCOCC3)CC2)ccc1Nc1nc(Nc2ccccc2S(=O)(=O)C(C)C)c2c(Cl)c[nH]c2n1] | MS m/z: 669.25 [M + 1]. |
| 30 | 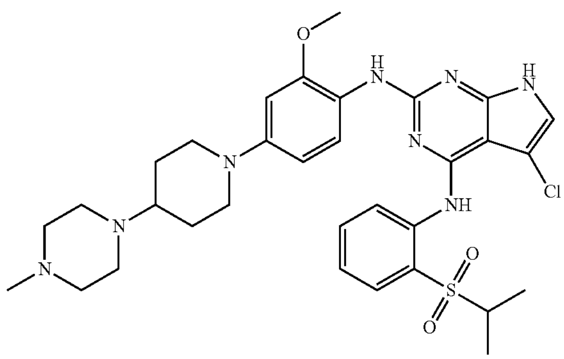 [SMILES: COc1cc(N2CCC(N3CCN(C)CC3)CC2)ccc1Nc1nc(Nc2ccccc2S(=O)(=O)C(C)C)c2c(Cl)c[nH]c2n1] | MS m/z: 654.27 [M + 1]. |
| 31 | 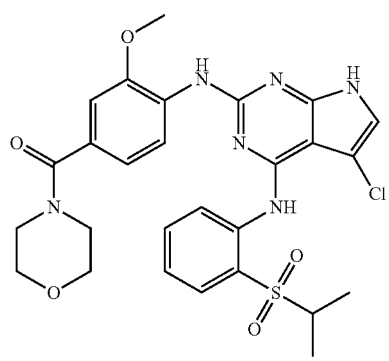 [SMILES: COc1cc(C(=O)N2CCOCC2)ccc1Nc1nc(Nc2ccccc2S(=O)(=O)C(C)C)c2c(Cl)c[nH]c2n1] | MS m/z: 586.23 [M + 1]. |
| 32 | 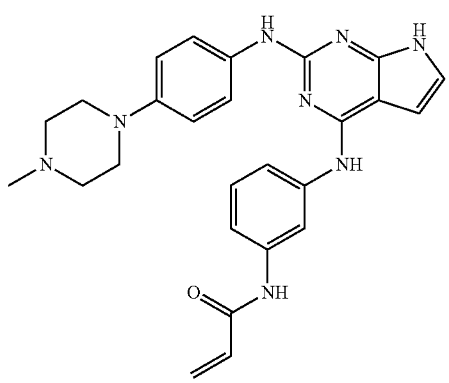 | MS m/z: 469.57 [M + 1]. |

TABLE 4-continued

| Compound No. | Structure | Physical Data ¹H NMR 400 MHz and/or MS (m/z) |
|---|---|---|
| 33 | 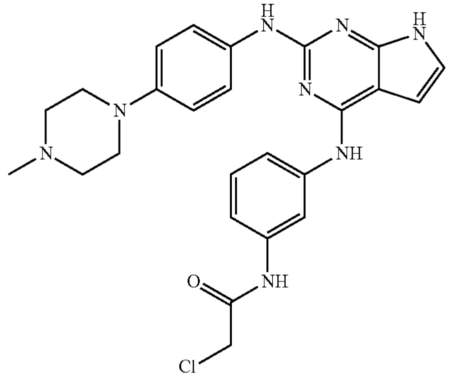 [SMILES: CN1CCN(c2ccc(Nc3nc(Nc4cccc(NC(=O)CCl)c4)c4cc[nH]c4n3)cc2)CC1] | MS m/z: 492.21 [M + 1]. |
| 34 | 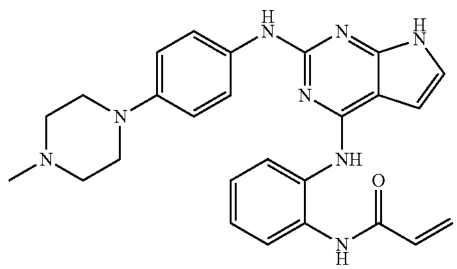 [SMILES: C=CC(=O)Nc1ccccc1Nc1nc(Nc2ccc(N3CCN(C)CC3)cc2)nc2[nH]ccc12] | MS m/z: 469.35 [M + 1]. |
| 35 | 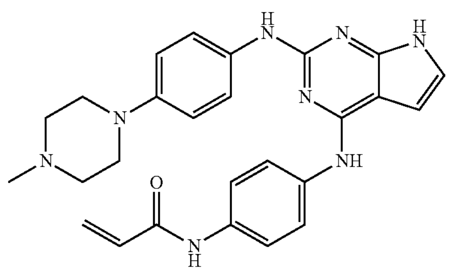 [SMILES: C=CC(=O)Nc1ccc(Nc2nc(Nc3ccc(N4CCN(C)CC4)cc3)nc3[nH]ccc23)cc1] | MS m/z: 469.70 [M + 1]. |
| 36 | 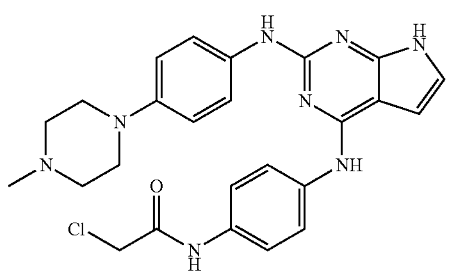 | MS m/z: 492.03 [M + 1]. |
| 37 | 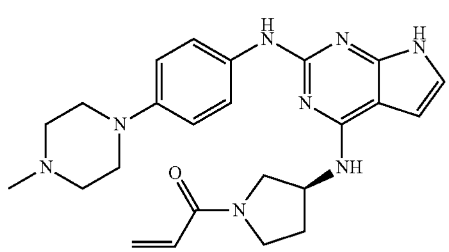 [SMILES: C=CC(=O)N1CC[C@H](Nc2nc(Nc3ccc(N4CCN(C)CC4)cc3)nc3[nH]ccc23)C1] | MS m/z: 447.57 [M + 1]. |

TABLE 4-continued
| Compound No. | Structure | Physical Data ¹H NMR 400 MHz and/or MS (m/z) |
|---|---|---|
| 38 | 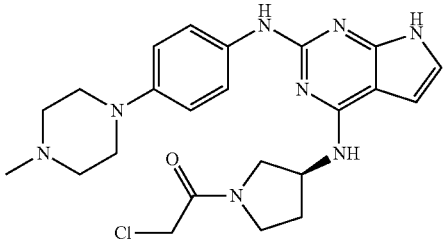 [SMILES: CN1CCN(c2ccc(Nc3nc(N[C@H]4CCN(C(=O)CCl)C4)c4cc[nH]c4n3)cc2)CC1] | MS m/z: 469.55 [M + 1]. |
| 39 | 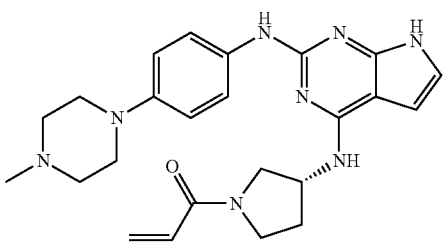 [SMILES: C=CC(=O)N1CC[C@@H](Nc2nc(Nc3ccc(N4CCN(C)CC4)cc3)nc3[nH]ccc23)C1] | MS m/z: 447.37 [M + 1]. |
| 40 | 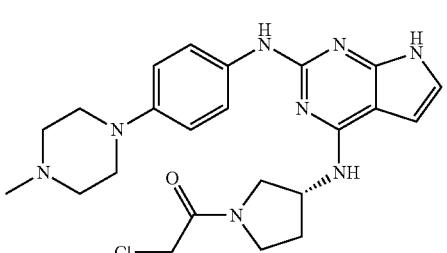 | MS m/z: 470.36 [M + 1]. |
| 41 | 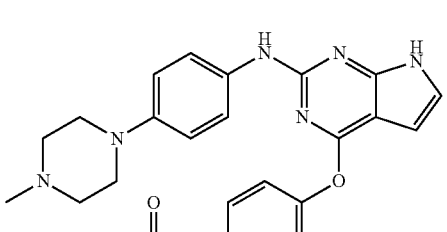 | MS m/z: 586.23 [M + 1]. |
| 42 | 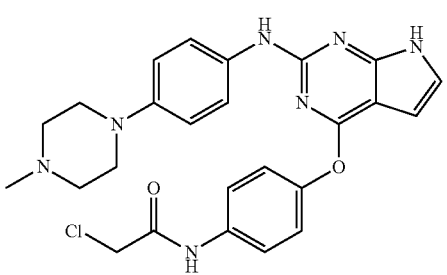 [SMILES: CN1CCN(c2ccc(Nc3nc(Oc4ccc(NC(=O)CCl)cc4)c4cc[nH]c4n3)cc2)CC1] | MS m/z: 492.47 [M + 1]. |

TABLE 4-continued

| Compound No. | Structure | Physical Data ¹H NMR 400 MHz and/or MS (m/z) |
|---|---|---|
| 43 | 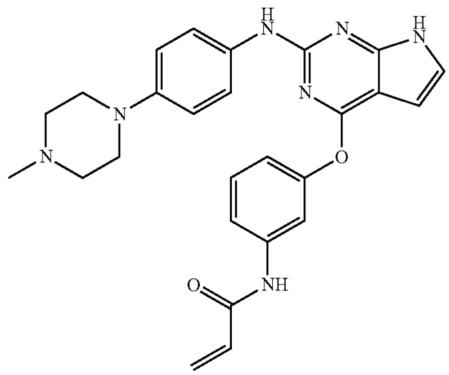 [SMILES: C=CC(=O)Nc1cccc(Oc2nc(Nc3ccc(N4CCN(C)CC4)cc3)nc3[nH]ccc23)c1] | MS m/z: 470.09 [M + 1]. |
| 44 | 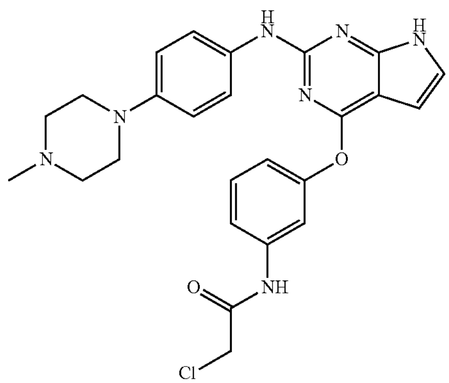 [SMILES: CN1CCN(c2ccc(Nc3nc(Oc4cccc(NC(=O)CCl)c4)c4cc[nH]c4n3)cc2)CC1] | MS m/z: 492.77 [M + 1]. |
| 45 | 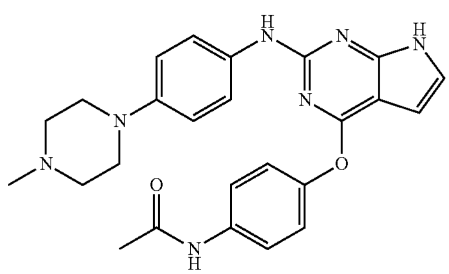 [SMILES: CC(=O)Nc1ccc(Oc2nc(Nc3ccc(N4CCN(C)CC4)cc3)nc3[nH]ccc23)cc1] | MS m/z: 458.98 [M + 1]. |
| 46 | 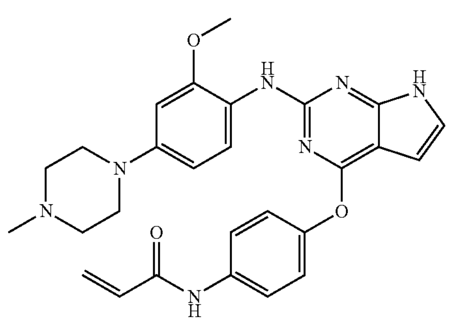 [SMILES: C=CC(=O)Nc1ccc(Oc2nc(Nc3ccc(N4CCN(C)CC4)cc3OC)nc3[nH]ccc23)cc1] | MS m/z: 500.75 [M + 1]. |

TABLE 4-continued

| Compound No. | Structure | Physical Data ¹H NMR 400 MHz and/or MS (m/z) |
|---|---|---|
| 47 | 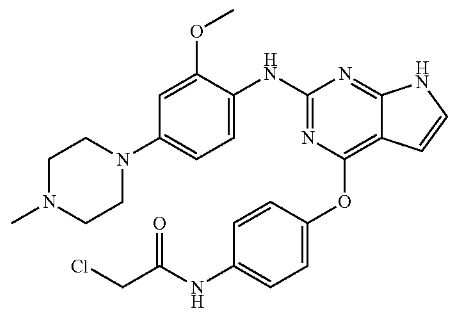 [SMILES: COc1cc(N2CCN(C)CC2)ccc1Nc1nc(Oc2ccc(NC(=O)CCl)cc2)c2cc[nH]c2n1] | MS m/z: 504.60 [M + 1]. |
| 48 | 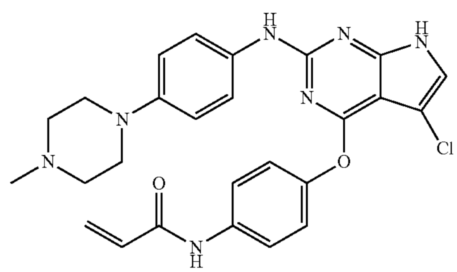 | MS m/z: 586.23 [M + 1]. |
| 49 | 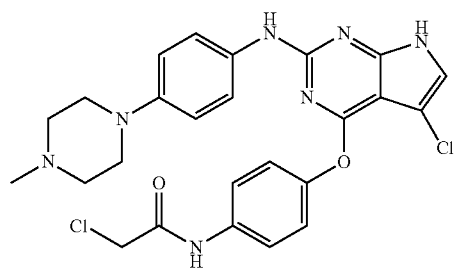 [SMILES: CN1CCN(c2ccc(Nc3nc(Oc4ccc(NC(=O)CCl)cc4)c4c(Cl)c[nH]c4n3)cc2)CC1] | MS m/z: 527.79 [M + 1]. |
| 50 | 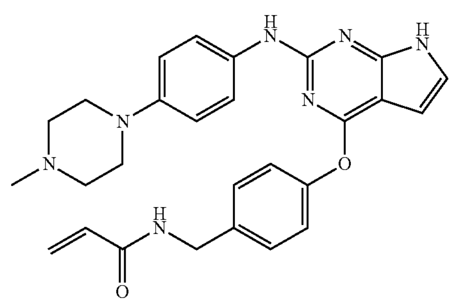 [SMILES: C=CC(=O)NCc1ccc(Oc2nc(Nc3ccc(N4CCN(C)CC4)cc3)nc3[nH]ccc23)cc1] | MS m/z: 484.22 [M + 1]. |
| 51 | 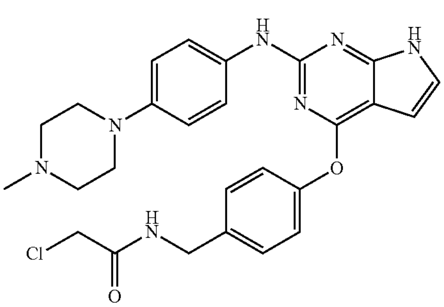 [SMILES: CN1CCN(c2ccc(Nc3nc(Oc4ccc(CNC(=O)CCl)cc4)c4cc[nH]c4n3)cc2)CC1] | MS m/z: 507.13 [M + 1]. |

TABLE 4-continued
| Compound No. | Structure | Physical Data ¹H NMR 400 MHz and/or MS (m/z) |
|---|---|---|
| 52 | 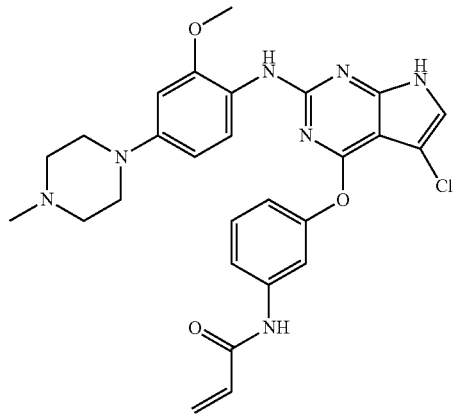 [SMILES: C=CC(=O)Nc1cccc(Oc2nc(Nc3ccc(N4CCN(C)CC4)cc3OC)nc3[nH]cc(Cl)c23)c1] | MS m/z: 535.03 [M + 1]. |
| 53 | 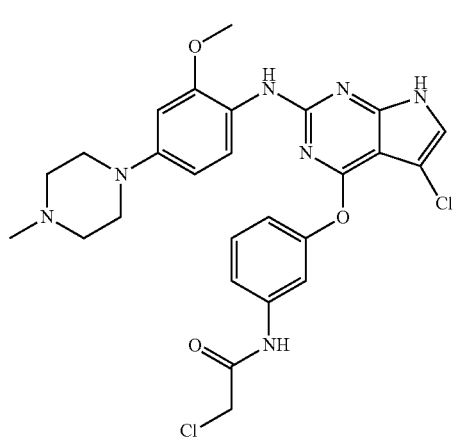 [SMILES: COc1cc(N2CCN(C)CC2)ccc1Nc1nc(Oc2cccc(NC(=O)CCl)c2)c2c(Cl)c[nH]c2n1] | MS m/z: 557.22 [M + 1]. |
| 54 | 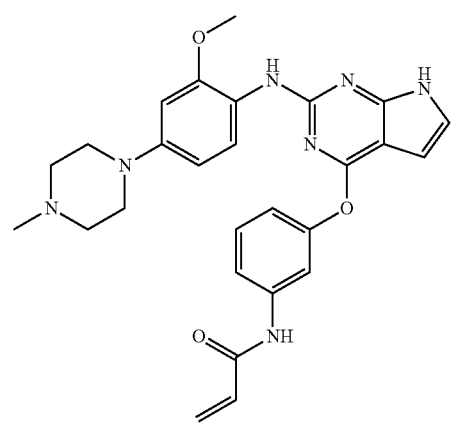 [SMILES: C=CC(=O)Nc1cccc(Oc2nc(Nc3ccc(N4CCN(C)CC4)cc3OC)nc3[nH]ccc23)c1] | MS m/z: 500.82 [M + 1]. |

TABLE 4-continued
| Compound No. | Structure | Physical Data $^1$H NMR 400 MHz and/or MS (m/z) |
|---|---|---|
| 55 | 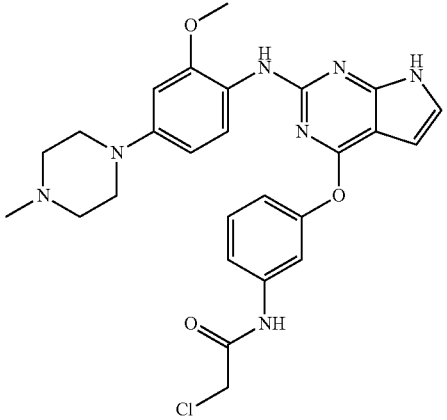 [SMILES: COc1cc(N2CCN(C)CC2)ccc1Nc1nc(Oc2cccc(NC(=O)CCl)c2)c2cc[nH]c2n1] | MS m/z: 523.08 [M + 1]. |
| 56 | 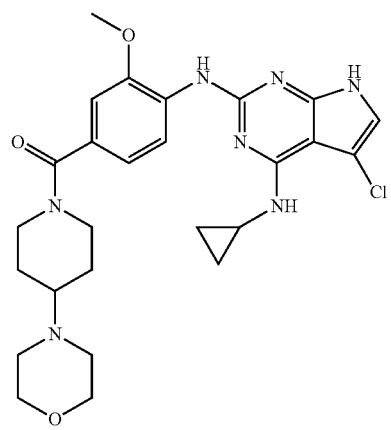 [SMILES: COc1cc(C(=O)N2CCC(N3CCOCC3)CC2)ccc1Nc1nc(NC2CC2)c2c(Cl)c[nH]c2n1] | MS m/z: 527.55 [M + 1]. |
| 57 | 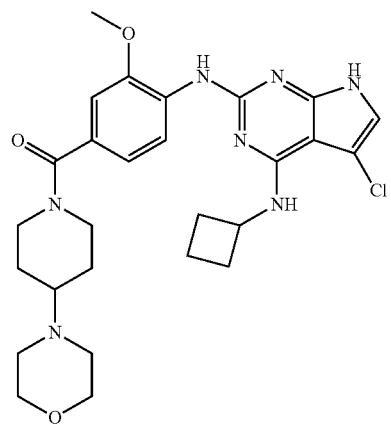 [SMILES: COc1cc(C(=O)N2CCC(N3CCOCC3)CC2)ccc1Nc1nc(NC2CCC2)c2c(Cl)c[nH]c2n1] | MS m/z: 541.36 [M + 1]. |

TABLE 4-continued
| Compound No. | Structure | Physical Data ¹H NMR 400 MHz and/or MS (m/z) |
|---|---|---|
| 58 | 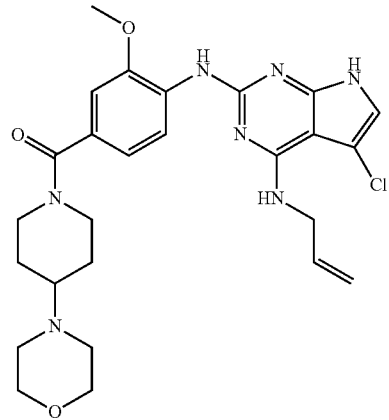 [SMILES: C=CCNc1nc(Nc2ccc(C(=O)N3CCC(N4CCOCC4)CC3)cc2OC)nc2[nH]cc(Cl)c12] | MS m/z: 527.88 [M + 1]. |
| 59 | 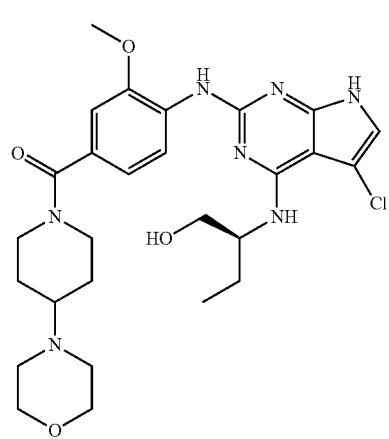 | MS m/z: 526.71 [M + 1]. |
| 60 | 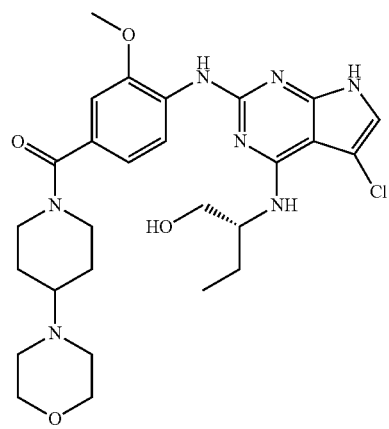 | MS m/z: 541.19 [M + 1]. |

TABLE 4-continued
| Compound No. | Structure | Physical Data ¹H NMR 400 MHz and/or MS (m/z) |
|---|---|---|
| 61 | 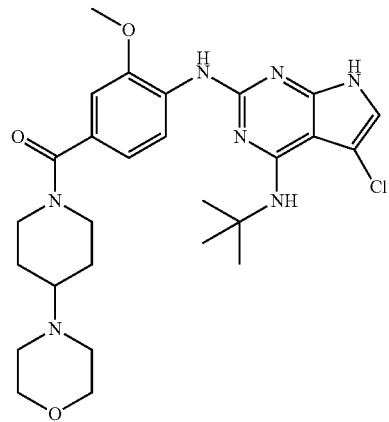 | MS m/z: 527.08 [M + 1]. |
| 62 | 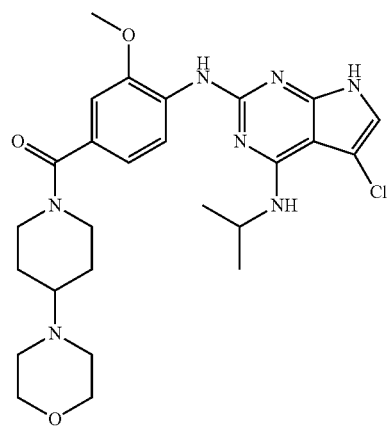 | MS m/z: 559.47 [M + 1]. |
| 63 | 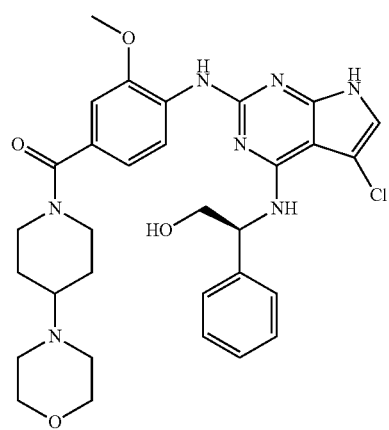 | MS m/z: 559.23 [M + 1]. |

TABLE 4-continued
| Compound No. | Structure | Physical Data $^1$H NMR 400 MHz and/or MS (m/z) |
|---|---|---|
| 64 | 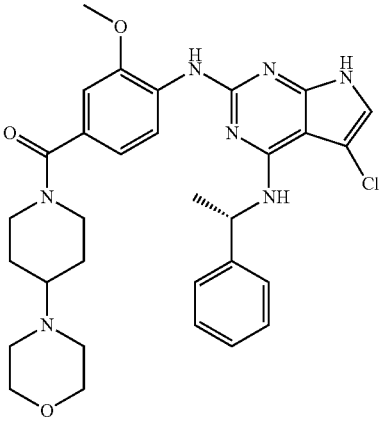 | MS m/z: 543.08 [M + 1]. |
| 65 | 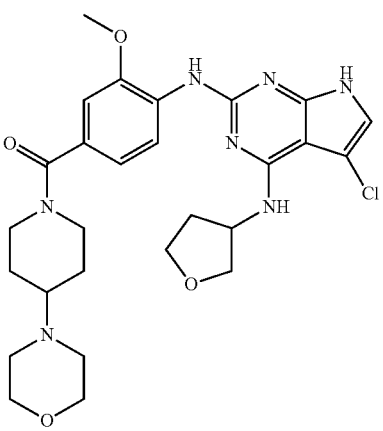 | MS m/z: 529.05 [M + 1]. |
| 66 | 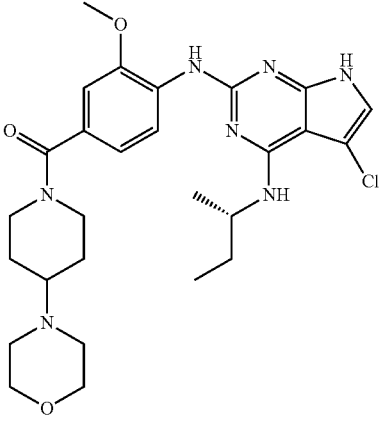 | MS m/z: 607.35 [M + 1]. |

TABLE 4-continued
| Compound No. | Structure | Physical Data ¹H NMR 400 MHz and/or MS (m/z) |
|---|---|---|
| 67 | 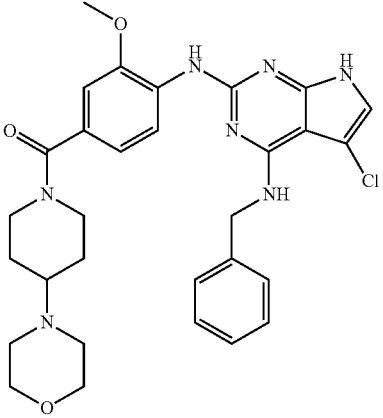 | MS m/z: 591.82 [M + 1]. |
| 68 | 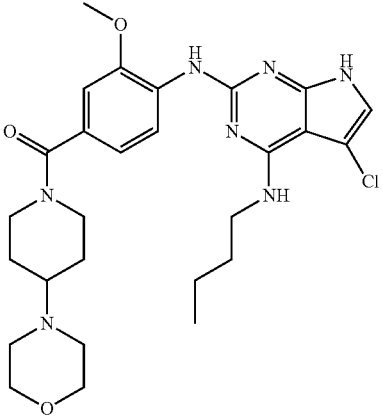 | MS m/z: 557.52 [M + 1]. |
| 69 | 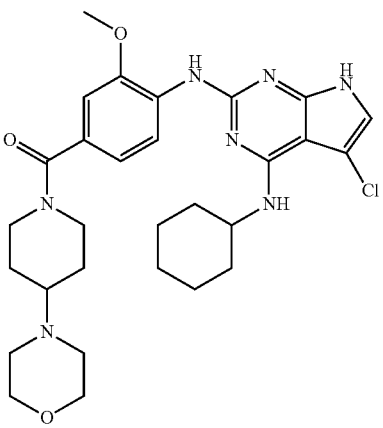 | MS m/z: 543.71 [M + 1]. |

TABLE 4-continued
| Compound No. | Structure | Physical Data ¹H NMR 400 MHz and/or MS (m/z) |
|---|---|---|
| 70 | 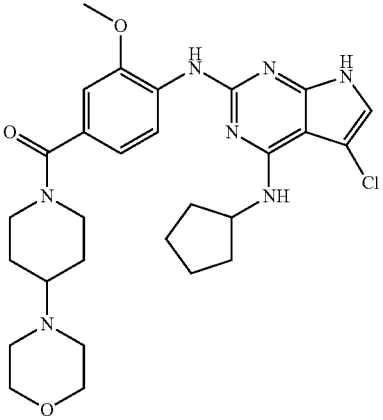 | MS m/z: 577.49 [M + 1]. |
| 71 | 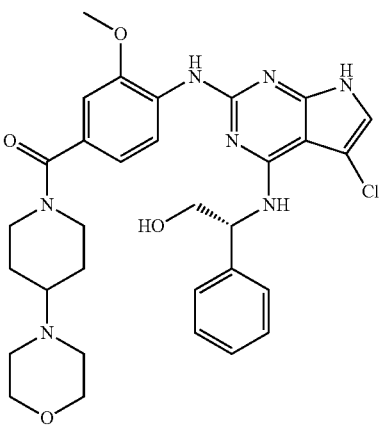 [SMILES: COc1cc(C(=O)N2CCC(N3CCOCC3)CC2)ccc1Nc1nc(N[C@@H](CO)c2ccccc2)c2c(Cl)c[nH]c2n1] | MS m/z: 607.35 [M + 1]. |
| 72 | 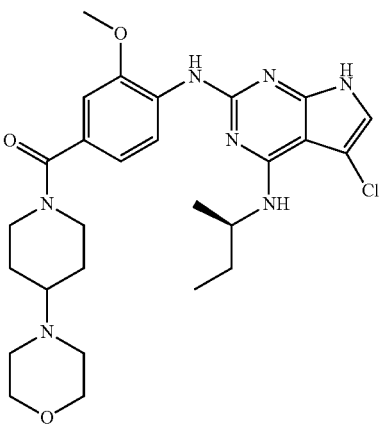 [SMILES: CC[C@@H](C)Nc1nc(Nc2ccc(C(=O)N3CCC(N4CCOCC4)CC3)cc2OC)nc2[nH]cc(Cl)c12] | MS m/z: 543.86 [M + 1]. |

TABLE 4-continued
| Compound No. | Structure | Physical Data ¹H NMR 400 MHz and/or MS (m/z) |
|---|---|---|
| 73 | 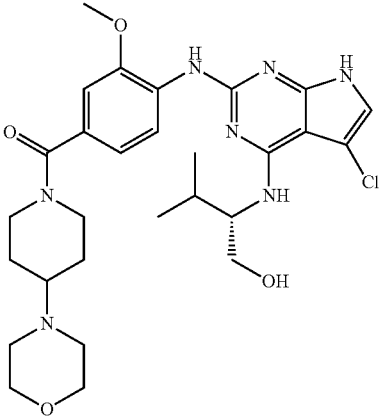 [SMILES: COc1cc(C(=O)N2CCC(N3CCOCC3)CC2)ccc1Nc1nc(N[C@H](CO)C(C)C)c2c(Cl)c[nH]c2n1] | MS m/z: 573.72 [M + 1]. |
| 74 | 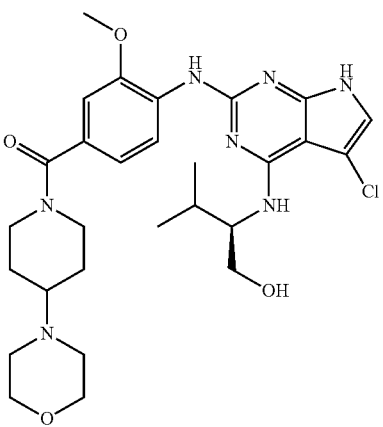 [SMILES: COc1cc(C(=O)N2CCC(N3CCOCC3)CC2)ccc1Nc1nc(N[C@@H](CO)C(C)C)c2c(Cl)c[nH]c2n1] | MS m/z: 573.52 [M + 1]. |
| 75 | 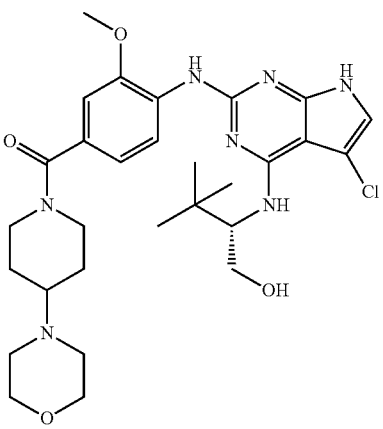 [SMILES: COc1cc(C(=O)N2CCC(N3CCOCC3)CC2)ccc1Nc1nc(N[C@H](CO)C(C)(C)C)c2c(Cl)c[nH]c2n1] | MS m/z: 587.21 [M + 1]. |

TABLE 4-continued

| Compound No. | Structure | Physical Data ¹H NMR 400 MHz and/or MS (m/z) |
| --- | --- | --- |
| 76 | 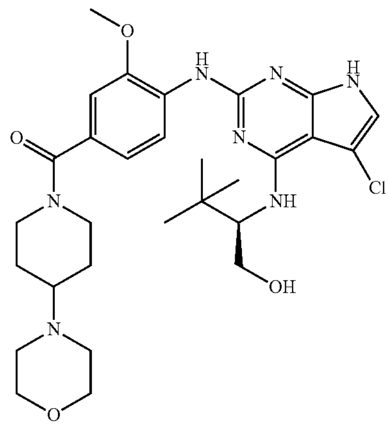 [SMILES: COc1cc(C(=O)N2CCC(N3CCOCC3)CC2)ccc1Nc1nc(N[C@@H](CO)C(C)(C)C)c2c(Cl)c[nH]c2n1] | MS m/z: 587.02 [M + 1][M + 1]. |
| 77 | 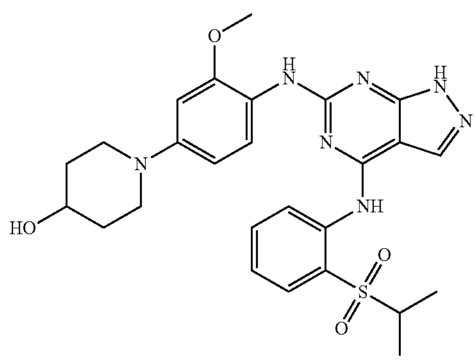 [SMILES: COc1cc(N2CCC(O)CC2)ccc1Nc1nc(Nc2ccccc2S(=O)(=O)C(C)C)c2cn[nH]c2n1] | MS m/z: 538.65 [M + 1]. |
| 78 | 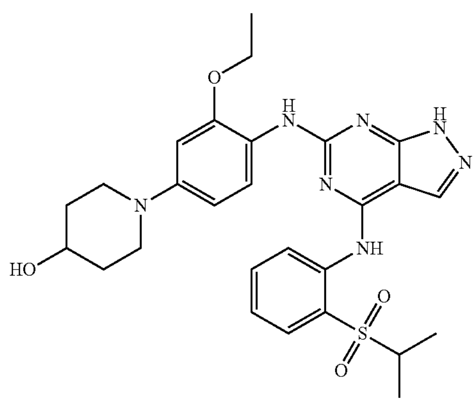 [SMILES: CCOc1cc(N2CCC(O)CC2)ccc1Nc1nc(Nc2ccccc2S(=O)(=O)C(C)C)c2cn[nH]c2n1] | MS m/z: 552.18 [M + 1]. |
| 79 | 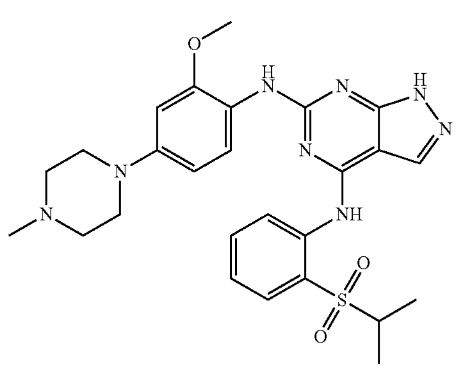 [SMILES: COc1cc(N2CCN(C)CC2)ccc1Nc1nc(Nc2ccccc2S(=O)(=O)C(C)C)c2cn[nH]c2n1] | MS m/z: 537.81 [M + 1]. |

TABLE 4-continued
| Compound No. | Structure | Physical Data $^1$H NMR 400 MHz and/or MS (m/z) |
|---|---|---|
| 80 | 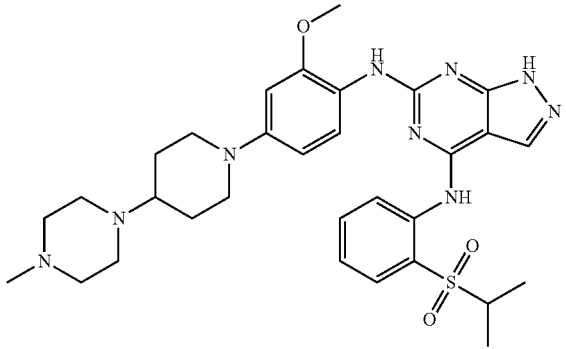 [SMILES: COc1cc(N2CCC(N3CCN(C)CC3)CC2)ccc1Nc1nc(Nc2ccccc2S(=O)(=O)C(C)C)c2cn[nH]c2n1] | MS m/z: 620.79 [M + 1]. |
| 81 | 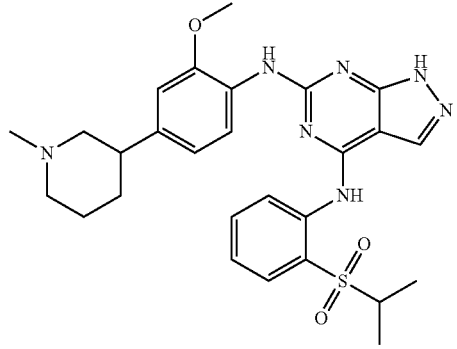 [SMILES: COc1cc(C2CCCN(C)C2)ccc1Nc1nc(Nc2ccccc2S(=O)(=O)C(C)C)c2cn[nH]c2n1] | MS m/z: 536.24 [M + 1]. |
| 82 | 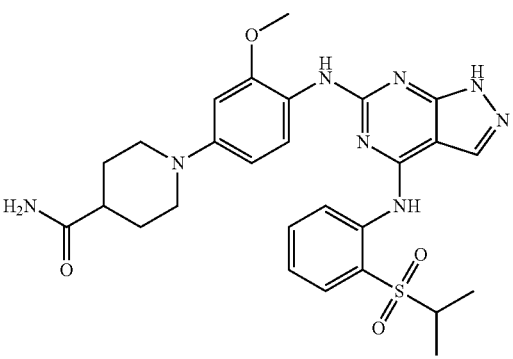 [SMILES: COc1cc(N2CCC(C(N)=O)CC2)ccc1Nc1nc(Nc2ccccc2S(=O)(=O)C(C)C)c2cn[nH]c2n1] | MS m/z: 565.03 [M + 1]. |
| 83 | 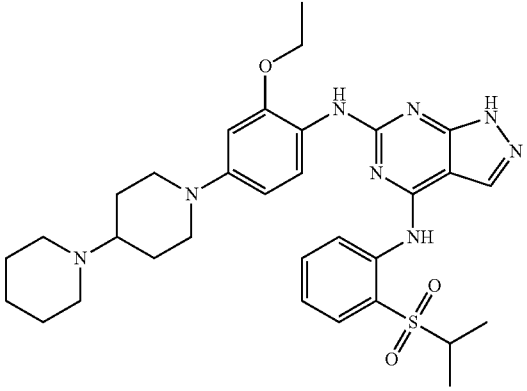 [SMILES: CCOc1cc(N2CCC(N3CCCCC3)CC2)ccc1Nc1nc(Nc2ccccc2S(=O)(=O)C(C)C)c2cn[nH]c2n1] | MS m/z: 619.50 [M + 1]. |

TABLE 4-continued

| Compound No. | Structure | Physical Data ¹H NMR 400 MHz and/or MS (m/z) |
|---|---|---|
| 84 | 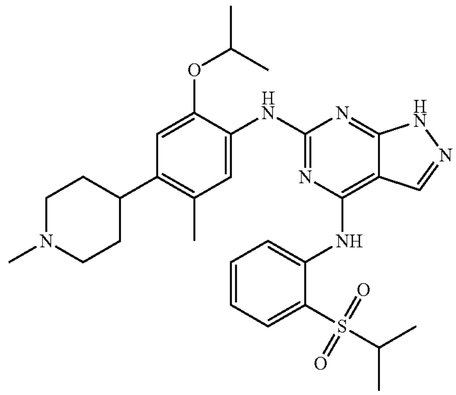 [SMILES: Cc1cc(Nc2nc(Nc3ccccc3S(=O)(=O)C(C)C)c3cn[nH]c3n2)c(OC(C)C)cc1C1CCN(C)CC1] | MS m/z: 578.28 [M + 1]. |
| 85 | 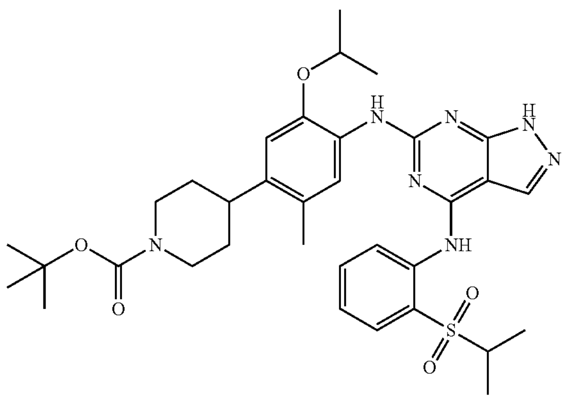 [SMILES: Cc1cc(Nc2nc(Nc3ccccc3S(=O)(=O)C(C)C)c3cn[nH]c3n2)c(OC(C)C)cc1C1CCN(C(=O)OC(C)(C)C)CC1] | MS m/z: 664.92 [M + 1]. |
| 86 | 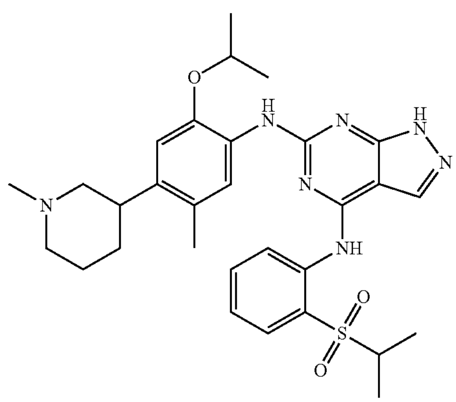 [SMILES: Cc1cc(Nc2nc(Nc3ccccc3S(=O)(=O)C(C)C)c3cn[nH]c3n2)c(OC(C)C)cc1C1CCCN(C)C1] | MS m/z: 578.01 [M + 1]. |
| 87 | 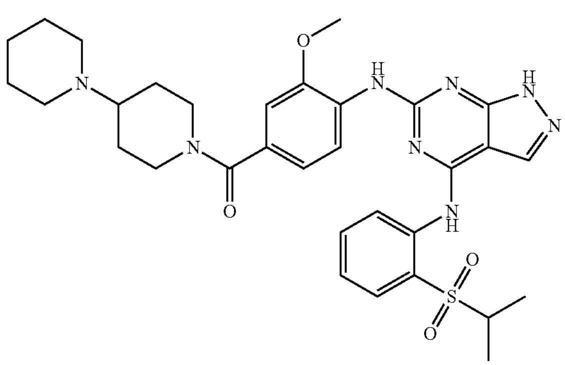 [SMILES: COc1cc(C(=O)N2CCC(N3CCCCC3)CC2)ccc1Nc1nc(Nc2ccccc2S(=O)(=O)C(C)C)c2cn[nH]c2n1] | MS m/z: 633.42 [M + 1]. |

TABLE 4-continued
| Compound No. | Structure | Physical Data ¹H NMR 400 MHz and/or MS (m/z) |
|---|---|---|
| 88 | 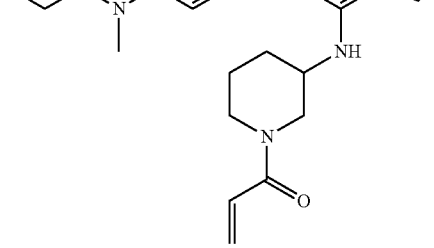 | MS m/z: 449.38 [M + 1]. |
| 89 | 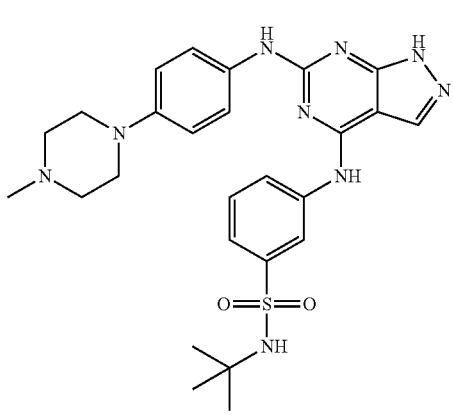 [SMILES: CN1CCN(c2ccc(Nc3nc(Nc4cccc(S(=O)(=O)NC(C)(C)C)c4)c4cn[nH]c4n3)cc2)CC1] | MS m/z: 536.95 [M + 1]. |
| 90 | 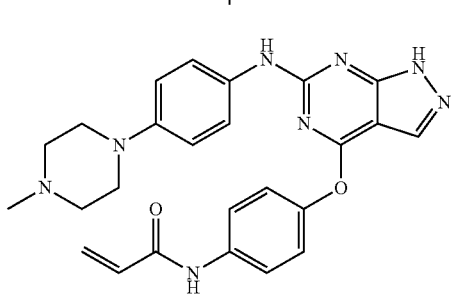 | MS m/z: 471.68 [M + 1]. |
| 91 | 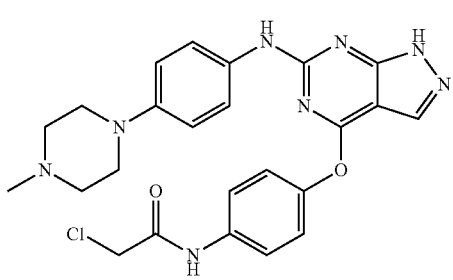 [SMILES: CN1CCN(c2ccc(Nc3nc(Oc4ccc(NC(=O)CCl)cc4)c4cn[nH]c4n3)cc2)CC1] | MS m/z: 493.09 [M + 1]. |
| 92 | 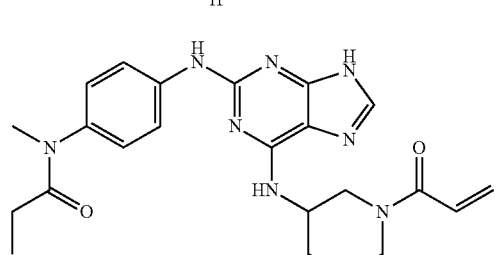 | MS m/z: 449.03 [M + 1]. |

TABLE 4-continued

| Compound No. | Structure | Physical Data ¹H NMR 400 MHz and/or MS (m/z) |
|---|---|---|
| 93 | 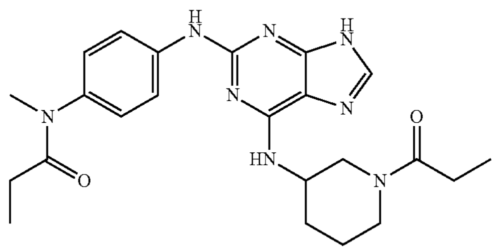 [SMILES: CCC(=O)N1CCCC(Nc2nc(Nc3ccc(N(C)C(=O)CC)cc3)nc3[nH]cnc23)C1] | MS m/z: 451.27 [M + 1]. |
| 94 | 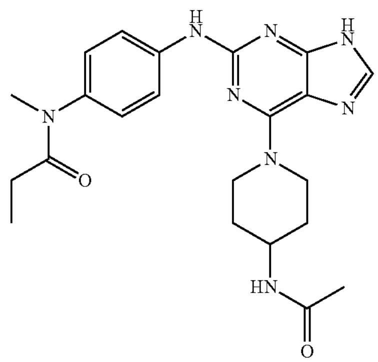 | MS m/z: 493.09 [M + 1]. |
| 95 | 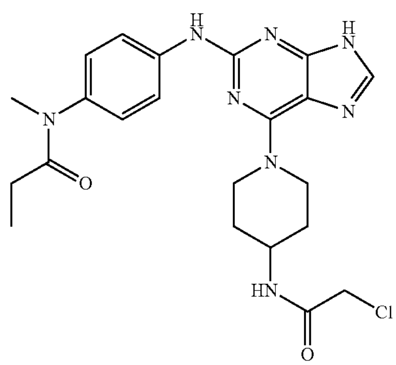 | MS m/z: 437.87 [M + 1]. |
| 96 | 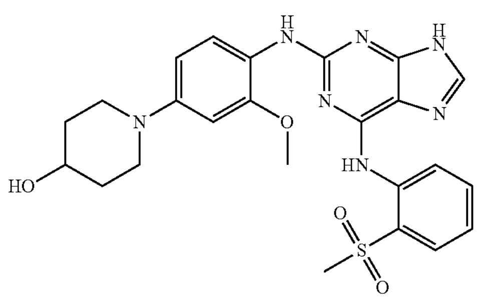 [SMILES: COc1cc(N2CCC(O)CC2)ccc1Nc1nc(Nc2ccccc2S(C)(=O)=O)c2nc[nH]c2n1] | MS m/z: 510.20 [M + 1]. |
| 97 | 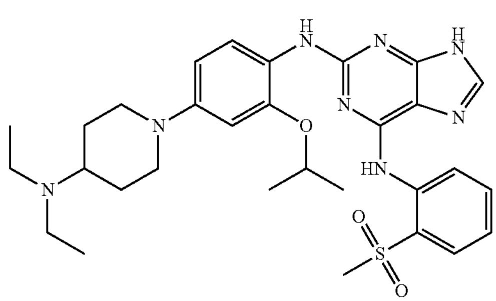 [SMILES: CCN(CC)C1CCN(c2ccc(Nc3nc(Nc4ccccc4S(C)(=O)=O)c4nc[nH]c4n3)c(OC(C)C)c2)CC1] | MS m/z: 593.11 [M + 1]. |

TABLE 4-continued

| Compound No. | Structure | Physical Data $^1$H NMR 400 MHz and/or MS (m/z) |
|---|---|---|
| 98 | 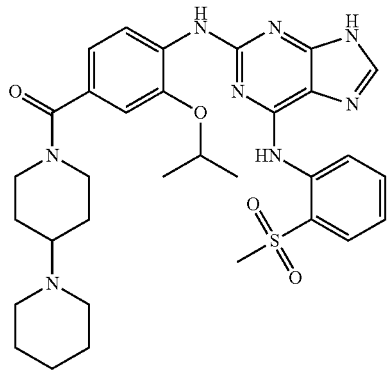 [SMILES: CC(C)Oc1cc(C(=O)N2CCC(N3CCCCC3)CC2)ccc1Nc1nc(Nc2ccccc2S(C)(=O)=O)c2nc[nH]c2n1] | MS m/z: 633.80 [M + 1]. |
| 99 | 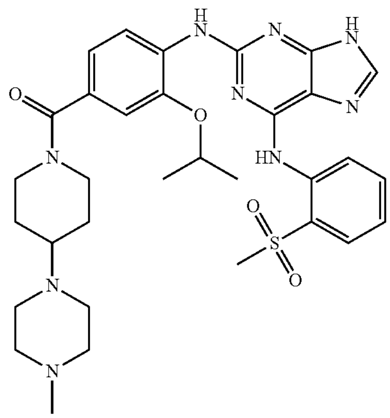 [SMILES: CC(C)Oc1cc(C(=O)N2CCC(N3CCN(C)CC3)CC2)ccc1Nc1nc(Nc2ccccc2S(C)(=O)=O)c2nc[nH]c2n1] | MS m/z: 649.41 [M + 1]. |
| 100 | 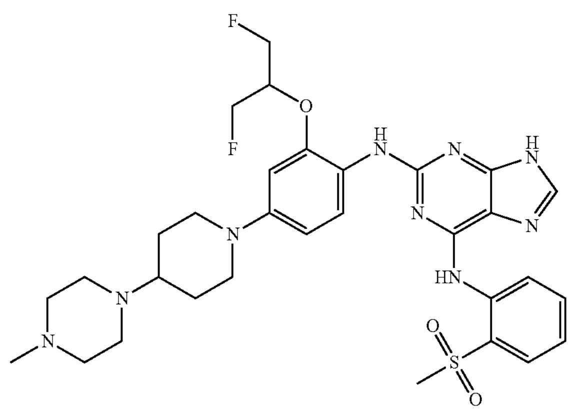 [SMILES: CN1CCN(C2CCN(c3ccc(Nc4nc(Nc5ccccc5S(C)(=O)=O)c5nc[nH]c5n4)c(OC(CF)CF)c3)CC2)CC1] | MS m/z: 656.04 [M + 1]. |
| 101 | 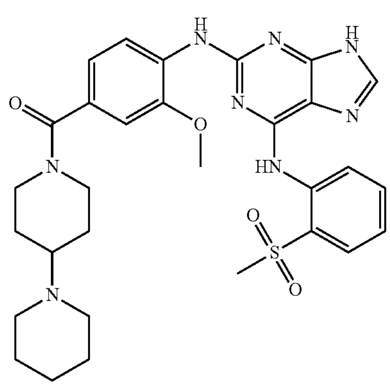 [SMILES: COc1cc(C(=O)N2CCC(N3CCCCC3)CC2)ccc1Nc1nc(Nc2ccccc2S(C)(=O)=O)c2nc[nH]c2n1] | MS m/z: 605.90 [M + 1]. |

TABLE 4-continued

| Compound No. | Structure | Physical Data ¹H NMR 400 MHz and/or MS (m/z) |
|---|---|---|
| 102 | 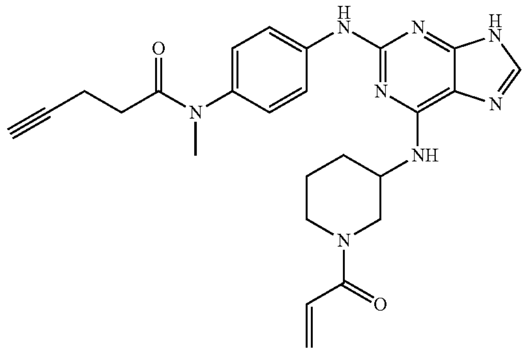 [SMILES: C#CCCC(=O)N(C)c1ccc(Nc2nc(NC3CCCN(C(=O)C=C)C3)c3nc[nH]c3n2)cc1] | MS m/z: 473.50 [M + 1]. |
| 103 | 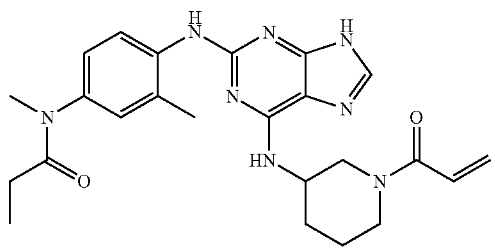 [SMILES: C=CC(=O)N1CCCC(Nc2nc(Nc3ccc(N(C)C(=O)CC)cc3C)nc3[nH]cnc23)C1] | MS m/z: 463.23 [M + 1]. |
| 104 | 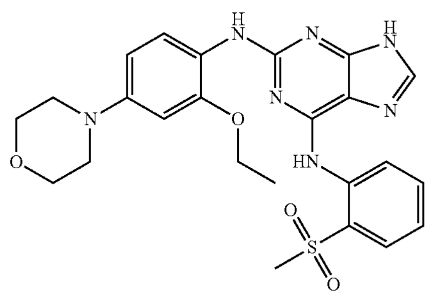 [SMILES: CCOc1cc(N2CCOCC2)ccc1Nc1nc(Nc2ccccc2S(C)(=O)=O)c2nc[nH]c2n1] | MS m/z: 510.17 [M + 1]. |
| 105 | 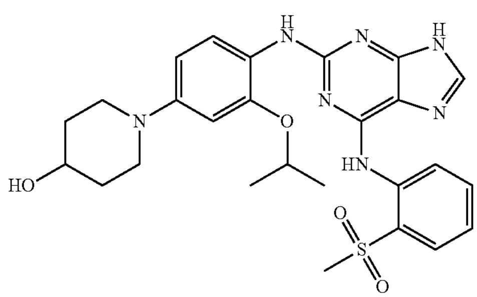 [SMILES: CC(C)Oc1cc(N2CCC(O)CC2)ccc1Nc1nc(Nc2ccccc2S(C)(=O)=O)c2nc[nH]c2n1] | MS m/z: 538.98 [M + 1]. |
| 106 | 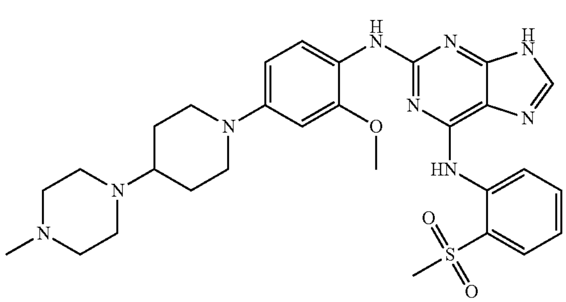 [SMILES: COc1cc(N2CCC(N3CCN(C)CC3)CC2)ccc1Nc1nc(Nc2ccccc2S(C)(=O)=O)c2nc[nH]c2n1] | MS m/z: 592.72 [M + 1]. |

TABLE 4-continued

| Compound No. | Structure | Physical Data ¹H NMR 400 MHz and/or MS (m/z) |
|---|---|---|
| 107 | 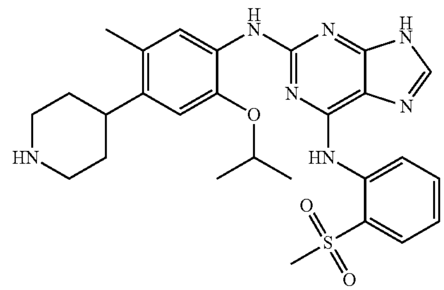 [SMILES: Cc1cc(Nc2nc(Nc3ccccc3S(C)(=O)=O)c3nc[nH]c3n2)c(OC(C)C)cc1C1CCNCC1] | MS m/z: 536.75 [M + 1]. |
| 108 | 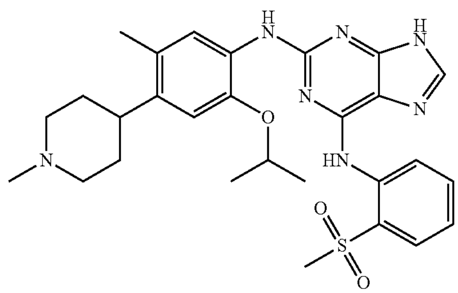 [SMILES: Cc1cc(Nc2nc(Nc3ccccc3S(C)(=O)=O)c3nc[nH]c3n2)c(OC(C)C)cc1C1CCN(C)CC1] | MS m/z: 550.10 [M + 1]. |
| 109 | 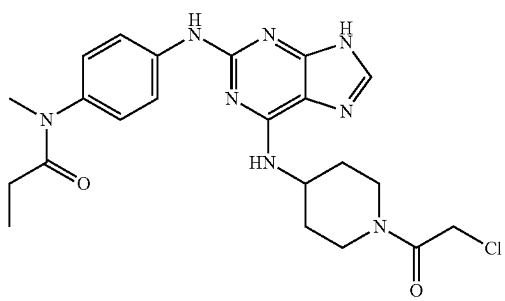 [SMILES: CCC(=O)N(C)c1ccc(Nc2nc(NC3CCN(C(=O)CCl)CC3)c3nc[nH]c3n2)cc1] | MS m/z: 471.23 [M + 1]. |
| 110 | 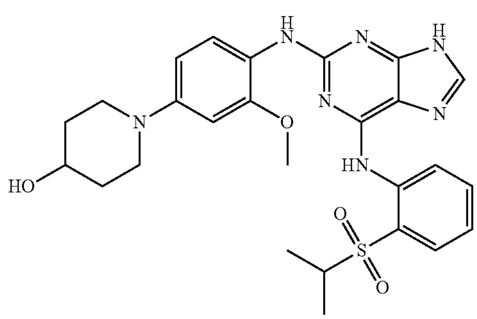 [SMILES: COc1cc(N2CCC(O)CC2)ccc1Nc1nc(Nc2ccccc2S(=O)(=O)C(C)C)c2nc[nH]c2n1] | MS m/z: 538.69 [M + 1]. |
| 111 | 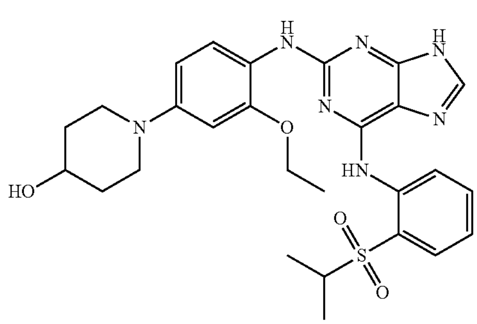 [SMILES: CCOc1cc(N2CCC(O)CC2)ccc1Nc1nc(Nc2ccccc2S(=O)(=O)C(C)C)c2nc[nH]c2n1] | MS m/z: 552.15 [M + 1]. |

TABLE 4-continued

| Compound No. | Structure | Physical Data ¹H NMR 400 MHz and/or MS (m/z) |
|---|---|---|
| 112 | 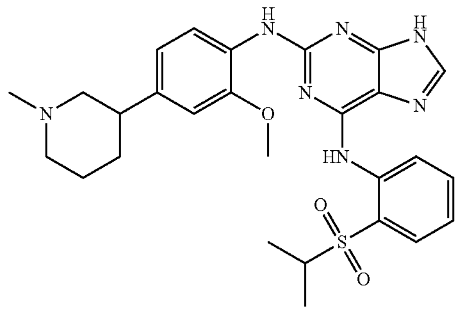 [SMILES: COc1cc(C2CCCN(C)C2)ccc1Nc1nc(Nc2ccccc2S(=O)(=O)C(C)C)c2nc[nH]c2n1] | MS m/z: 536.61 [M + 1]. |
| 113 | 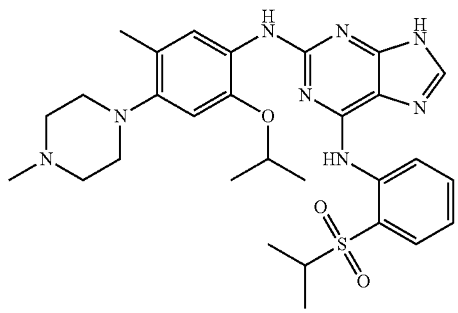 [SMILES: Cc1cc(Nc2nc(Nc3ccccc3S(=O)(=O)C(C)C)c3nc[nH]c3n2)c(OC(C)C)cc1N1CCN(C)CC1] | MS m/z: 579.14 [M + 1]. |
| 114 | 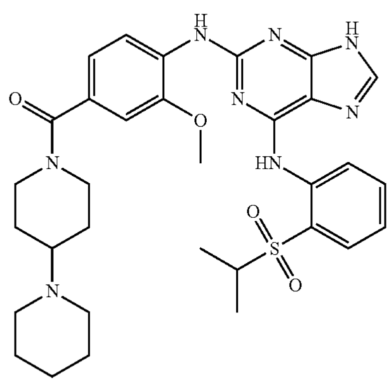 [SMILES: COc1cc(C(=O)N2CCC(N3CCCCC3)CC2)ccc1Nc1nc(Nc2ccccc2S(=O)(=O)C(C)C)c2nc[nH]c2n1] | MS m/z: 633.95 [M + 1]. |
| 115 | 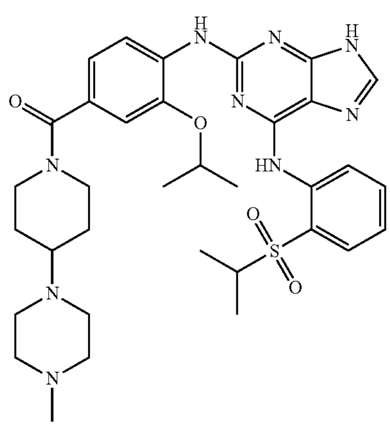 [SMILES: CC(C)Oc1cc(C(=O)N2CCC(N3CCN(C)CC3)CC2)ccc1Nc1nc(Nc2ccccc2S(=O)(=O)C(C)C)c2nc[nH]c2n1] | MS m/z: 676.40 [M + 1]. |

TABLE 4-continued

| Compound No. | Structure | Physical Data ¹H NMR 400 MHz and/or MS (m/z) |
|---|---|---|
| 116 | 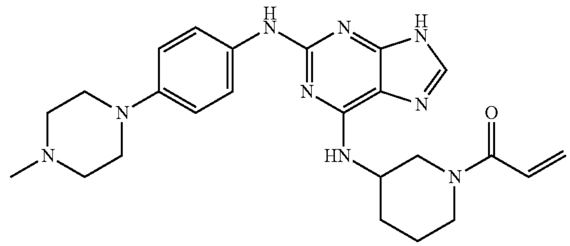 [SMILES: C=CC(=O)N1CCCC(Nc2nc(Nc3ccc(N4CCN(C)CC4)cc3)nc3[nH]cnc23)C1] | MS m/z: 462.07 [M + 1]. |
| 117 | 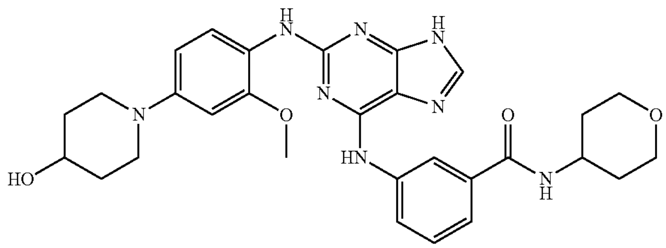 [SMILES: COc1cc(N2CCC(O)CC2)ccc1Nc1nc(Nc2cccc(C(=O)NC3CCOCC3)c2)c2nc[nH]c2n1] | MS m/z: 559.51 [M + 1]. |
| 118 | 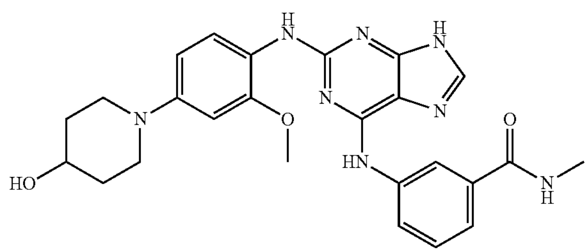 [SMILES: CNC(=O)c1cccc(Nc2nc(Nc3ccc(N4CCC(O)CC4)cc3OC)nc3[nH]cnc23)c1] | MS m/z: 489.27 [M + 1]. |
| 119 | 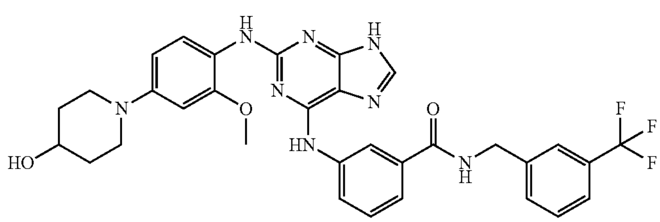 [SMILES: COc1cc(N2CCC(O)CC2)ccc1Nc1nc(Nc2cccc(C(=O)NCc3cccc(C(F)(F)F)c3)c2)c2nc[nH]c2n1] | MS m/z: 633.04 [M + 1]. |
| 120 | 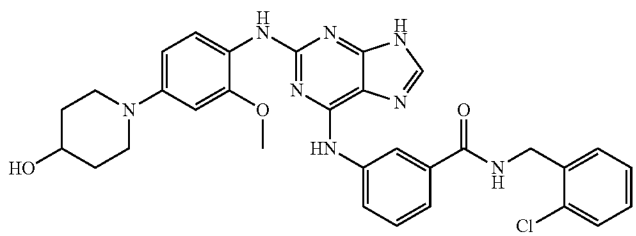 [SMILES: COc1cc(N2CCC(O)CC2)ccc1Nc1nc(Nc2cccc(C(=O)NCc3ccccc3Cl)c2)c2nc[nH]c2n1] | MS m/z: 600.35 [M + 1]. |
| 121 | 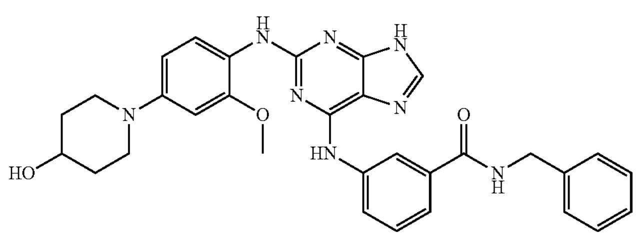 [SMILES: COc1cc(N2CCC(O)CC2)ccc1Nc1nc(Nc2cccc(C(=O)NCc3ccccc3)c2)c2nc[nH]c2n1] | MS m/z: 565.92 [M + 1]. |

TABLE 4-continued

| Compound No. | Structure | Physical Data ¹H NMR 400 MHz and/or MS (m/z) |
|---|---|---|
| 122 | 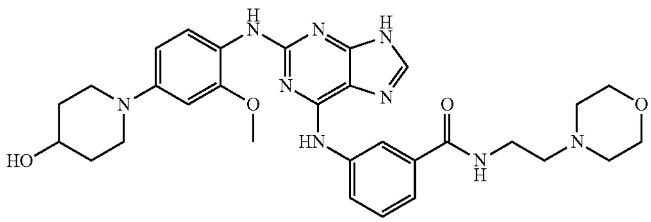 [SMILES: COc1cc(N2CCC(O)CC2)ccc1Nc1nc(Nc2cccc(C(=O)NCCN3CCOCC3)c2)c2nc[nH]c2n1] | MS m/z: 588.81 [M + 1]. |
| 123 | 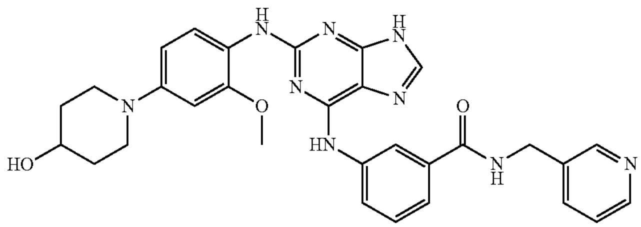 [SMILES: COc1cc(N2CCC(O)CC2)ccc1Nc1nc(Nc2cccc(C(=O)NCc3cccnc3)c2)c2nc[nH]c2n1] | MS m/z: 566.33 [M + 1]. |
| 124 | 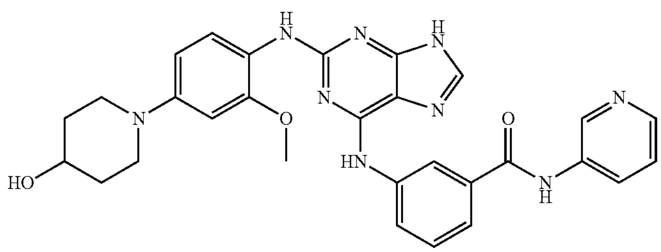 [SMILES: COc1cc(N2CCC(O)CC2)ccc1Nc1nc(Nc2cccc(C(=O)Nc3cccnc3)c2)c2nc[nH]c2n1] | MS m/z: 552.41 [M + 1]. |
| 125 | 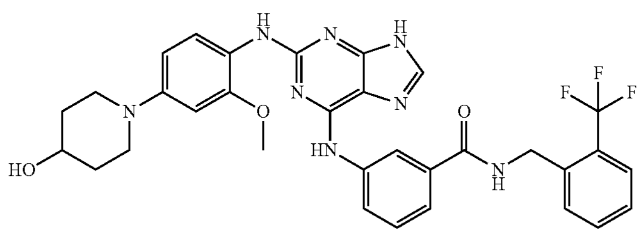 [SMILES: COc1cc(N2CCC(O)CC2)ccc1Nc1nc(Nc2cccc(C(=O)NCc3ccccc3C(F)(F)F)c2)c2nc[nH]c2n1] | MS m/z: 633.20 [M + 1]. |
| 126 | 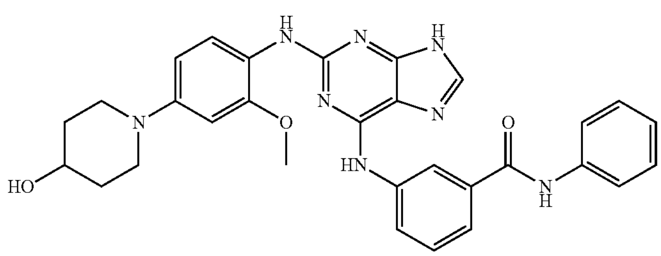 [SMILES: COc1cc(N2CCC(O)CC2)ccc1Nc1nc(Nc2cccc(C(=O)Nc3ccccc3)c2)c2nc[nH]c2n1] | MS m/z: 551.19 [M + 1]. |
| 127 | 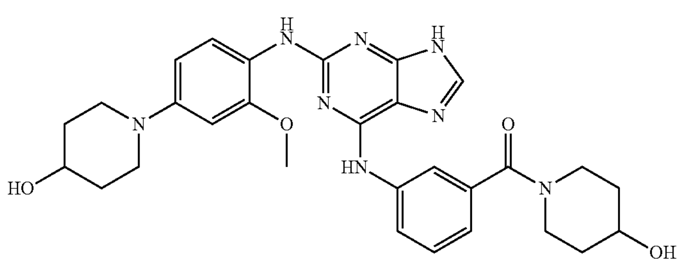 [SMILES: COc1cc(N2CCC(O)CC2)ccc1Nc1nc(Nc2cccc(C(=O)N3CCC(O)CC3)c2)c2nc[nH]c2n1] | MS m/z: 559.98 [M + 1]. |

TABLE 4-continued

| Compound No. | Structure | Physical Data $^1$H NMR 400 MHz and/or MS (m/z) |
|---|---|---|
| 128 | 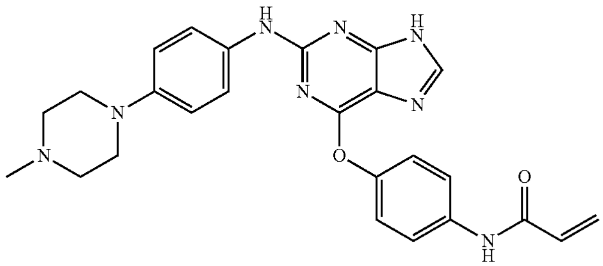 [SMILES: C=CC(=O)Nc1ccc(Oc2nc(Nc3ccc(N4CCN(C)CC4)cc3)nc3[nH]cnc23)cc1] | MS m/z: 471.18 [M + 1]. |
| 129 | 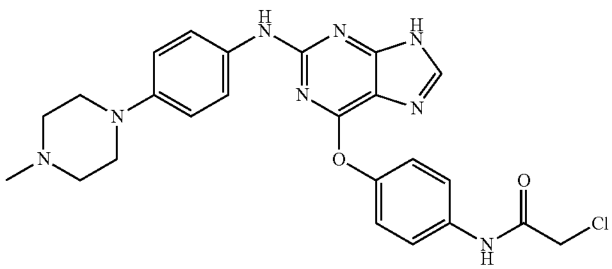 [SMILES: CN1CCN(c2ccc(Nc3nc(Oc4ccc(NC(=O)CCl)cc4)c4nc[nH]c4n3)cc2)CC1] | MS m/z: 493.39 [M + 1]. |
| 130 | 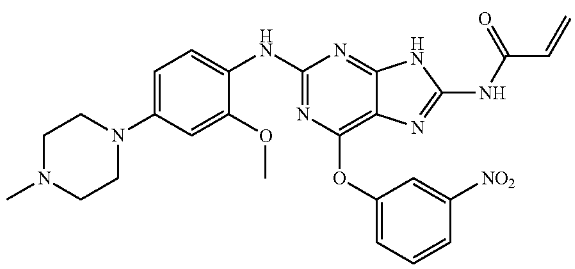 [SMILES: C=CC(=O)Nc1nc2c(Oc3cccc([N+](=O)[O-])c3)nc(Nc3ccc(N4CCN(C)CC4)cc3OC)nc2[nH]1] | MS m/z: 546.76 [M + 1]. |
| 131 | 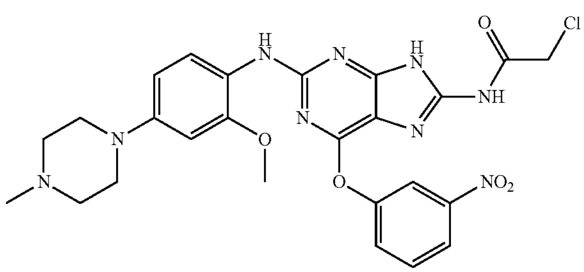 [SMILES: COc1cc(N2CCN(C)CC2)ccc1Nc1nc(Oc2cccc([N+](=O)[O-])c2)c2nc(NC(=O)CCl)[nH]c2n1] | MS m/z: 568.98 [M + 1]. |
| 132 | 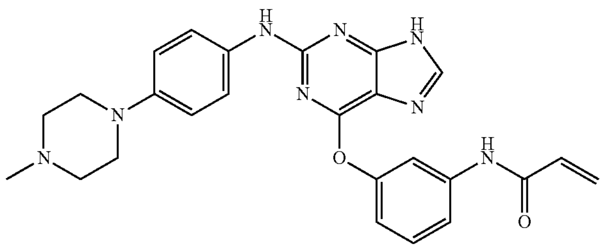 [SMILES: C=CC(=O)Nc1cccc(Oc2nc(Nc3ccc(N4CCN(C)CC4)cc3)nc3[nH]cnc23)c1] | MS m/z: 471.20 [M + 1]. |

TABLE 4-continued

| Compound No. | Structure | Physical Data $^1$H NMR 400 MHz and/or MS (m/z) |
|---|---|---|
| 133 | 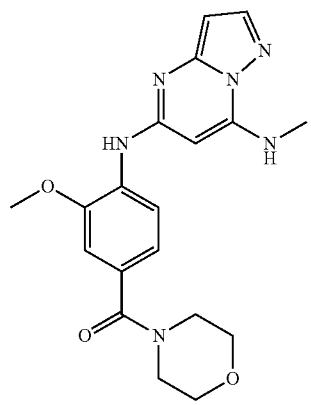 | MS m/z: 383.71 [M + 1]. |
| 134 | 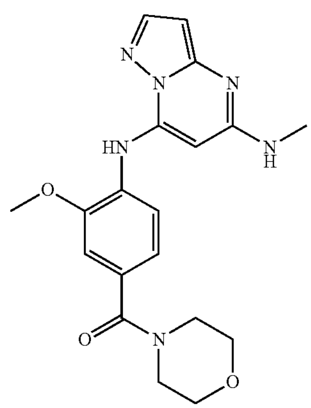 | MS m/z: 383.18 [M + 1]. |
| 135 | 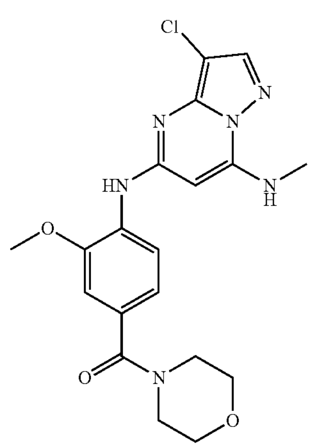 | MS m/z: 417.61 [M + 1]. |

TABLE 4-continued

| Compound No. | Structure | Physical Data ¹H NMR 400 MHz and/or MS (m/z) |
|---|---|---|
| 136 | 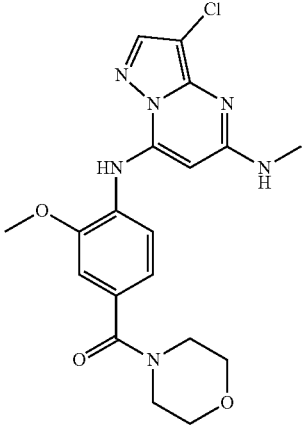 | MS m/z: 417.43 [M + 1]. |

4. Characterization of Compounds of the Disclosure

The compounds described herein, once produced, can be characterized using a variety of assays known to those skilled in the art to determine whether the compounds have the desired biological activity. For example, the molecules can be characterized by conventional assays, including but not limited to those assays described h (e.g., treating cells of interest, such as HEK293 cells, Swiss 3T3 cells, and human lymphoblastoid cells from a Parkinson's disease patient homozygous for the LRRK2[G2019S] mutation, with a test compound and then performing immunoblotting against the indicated proteins such as wild type LRRK2 and LRRK2 [G2019S], or treating certain cells of interest with a test compound and then measuring LRRK2 phosphorylation at Ser910, LRRK2 phosphorylation at Ser935 and total LRRK2), to determine whether they have a predicted activity, binding activity, and/or binding specificity.

The pharmacokinetic profile of the compounds of the present disclosure may be evaluated by intraperitoneal injection into mice, using a known compound as a control. After treatment, mice may be sacrificed and certain tissue, for example, kidney, spleen, and brain tissue, may be dissected to determine bioavailability, half-life, and plasma exposure.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3rd edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the disclosure.

5. Formulation and Administration

The compounds of the disclosure may be useful in the prevention or treatment of Parkinson's Disease. It is contemplated that, once identified, the active molecules of the disclosure may be incorporated into any suitable carrier prior to use. The dose of active molecule, mode of administration, and use of suitable carrier will depend upon the intended recipient. The formulations of compounds according to the present disclosure typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the disclosure and/or known in the art) also can be incorporated into the compositions. The formulations may conveniently be presented in dosage unit form and may be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the disclosure should be formulated to be compatible with its intended route of administration. Examples of routes of administration include oral or parenteral, for example, intravenous, intradermal, inhalation, and transmucosal, and administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example; in *Remington's Pharmaceutical Sciences,* 18th ed. (Mack Publishing Company, 1990). The parenteral preparation can be enclosed in ampoules, disposable syringes or multiple dose vials made of glass or plastic. Formulations also can include, for example, polyalkylene glycols such as polyethylene glycol, oils of vegetable origin, and hydrogenated naphthalenes. Other potentially useful parenteral carriers for these drugs include ethylene-vinyl acetate copolymer particles, osmotic pumps, implantable infusion systems, and liposomes.

Formulations of the present disclosure suitable for oral administration may be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug may also be administered in the form of a bolus, electuary or paste. A tablet may be made by compressing or molding the drug optionally with one or more accessory ingredients. Compressed tablets may be prepared by compressing, in a suitable machine, the drug in a free-flowing form such as a powder or granules, optionally mixed by a binder, lubricant, inert diluent, surface active or dispersing agent. Molded tablets may be made by molding; in a suitable machine; a mixture of the powdered drug and suitable carrier moistened with an inert liquid diluent.

Oral compositions generally include an inert diluent or an edible carrier. For the purpose of oral therapeutic administration, the active compound can be incorporated with excipients. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water; ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions; methods of preparation include vacuum drying and freeze-drying which yields a powder of the active ingredient plus any additional desired ingredient from a previously sterile-filtered solution thereof.

Formulations suitable for intra-articular administration may be in the form of a sterile aqueous preparation of the drug that may be in microcrystal line form, for example, in the form of an aqueous microcrystalline suspension. Liposomal formulations or biodegradable polymer systems may also be used to present the drug for both intra-articular and ophthalmic administration.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds may be prepared with carriers that will protect the compound against rapid elimination from the body, such as a controlled release formulation, including implants and microencapsulated delivery systems. Biodegradable, biocompatible polymers can be used; such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

Active compounds as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

In therapeutic use for treating, preventing, or combating, neurodegeneration in subjects, the compounds or pharmaceutical compositions thereof will be administered orally or parenterally at a dosage to obtain and maintain a concentration, that is, an amount, or blood-level or tissue level of active component in the animal undergoing treatment which will be effective. The term "effective amount" is understood to mean that the compound of the disclosure is present in or on the recipient in an amount sufficient to elicit biological activity, for example, inhibit LRRK2 kinase activity. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue level, or the initial dosage may be smaller than the optimum and the daily dosage may be progressively increased during the course of treatment depending on the particular situation. If desired, the daily dose may also be divided into multiple doses for administration, for example, two to four times per day.

EXAMPLES

General Methods of Synthesis

All reactions were monitored by thin layer chromatography (TLC) with 0.25 mm E. Merck pre-coated silica gel plates (60 F$_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 µm particle size): solvent gradient=100% A at 0 min, 1% A at 5 min; solvent A=0.035% TFA in Water; solvent B=0.035% TFA in MeOH; flow rate: 2.5 mL/min. Purification of reaction products was carried out by flash chromatography using CombiFlash® Rf with Teledyne Isco RediSep® Rf High Performance Gold or Silicycle SiliaSep™ High Performance columns (4 g, 12 g, 24 g, 40 g or 80 g). The purity of all compounds was over 95% and was analyzed with Waters LCMS system. $^1$H NMR and $^{13}$C NMR spectra were obtained using a Varian Inova-400 (400 MHz for $^1$H, and 75 MHz for $^{13}$C) spectrometer. Chemical shifts are reported relative to chloroform ($\delta$=7.24) for $^1$H NMR or dimethyl sulfoxide ($\delta$=2.50) for $^1$H NMR and dimethyl sulfoxide ($\delta$=39.51) for $^{13}$C NMR. Data are reported as (br=broad, s=singlet, d=doublet, t=triplet, q=quartet, m=multiplet). The compounds of Table 5 are synthesized in accordance with the methods described above.

Example 1

Synthesis of (4-((5-chloro-4-(methylamino)-7H-pyrrolo[2,3-d]pyrimidin-2-yl) amino)-3-methoxyphenyl)(morpholino)methanone (18)

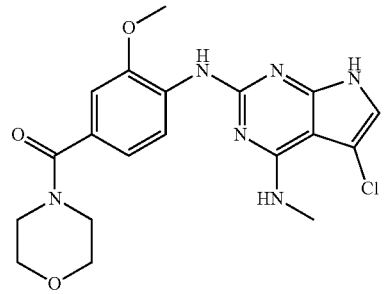 [SMILES: CNc1nc(Nc2ccc(C(=O)N3CCOCC3)cc2OC)nc2[nH]cc(Cl)c12]

Compound 18 was synthesized in accordance with Scheme 1 and as detailed below.

Example 1.1: 7H-pyrrolo[2,3-d]pyrimidine-2,4-diol

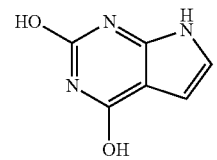 [SMILES: Oc1nc(O)c2cc[nH]c2n1]

To a suspended solution of 6-aminouracil (12.7 g, 100 mmol) and sodium acetate (8.2 g, 100 mmol) in H$_2$O (100 mL) at a temperature of 70-75° C. was added a solution of chloroacetaldehyde (50% in water, 23.6 g, 150 mmol). The resulting reaction mixture was stirred at 80° C. for 20 min and then cooled to room temperature. The resulting solid was collected by filtration, washed with water and acetone, and dried in vacuo to give the title compound as a light-brown solid (14.74 g, 98% yield). $^1$H NMR (DMSO-d$_6$, 400 MHz) $\delta$ 11.38 (br, 1H), 11.10 (br, 1H), 10.46 (s, 1H), 6.53 (s, 1H), 6.18 (s, 1H), MS m/z 152.43 [M+1].

Example 1.2: 2,4-dichloro-7H-pyrrolo[2,3-d]pyrimidine

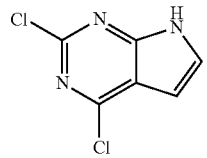 [SMILES: Clc1nc(Cl)c2cc[nH]c2n1]

POCl$_3$ (229 mmol) was slowly added at room temperature to a suspension of 7H-pyrrolo[2,3-d]pyrimidine-2,4-diol 11.5 g (76 mmol) in toluene (60 mL). The reaction mixture was heated to 70° C. and 26.5 mL of N,N-diisopropylethylamine (DIPEA) (153 mmol) was added drop-wise over a period of 2 hours (hr), at which time the reaction temperature was increased to 106° C. and the mixture stirred overnight. After cooling to room temperature, the reaction mixture was poured into a mixture of 200 mL EtOAc and 300 mL ice-water and then filtered through celite. The aqueous layer was extracted with EtOAc (3×200 mL) and the combined organic layers were washed with brine, decolored with activated carbon, filtered through celite and concentrated to give the title compound. MS m/z 189.64 [M+1].

Example 1.3: 2,4,5-trichloro-7H-pyrrolo[2,3-d]pyrimidine

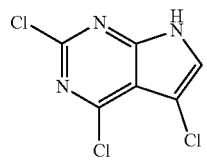 [SMILES: Clc1nc(Cl)c2c(Cl)c[nH]c2n1]

To a solution of 2,4-dichloro-7H-pyrrolo[2,3-d]pyrimidine (2.0 g, 10.64 mmol) in dichloromethane/tetrahydrofuran (DCM/THF) (15 mL/6 mL) was added NCS (1.70 g, 12.76 mmol). The mixture was heated to 90° C. under microwave irradiation for 2.5 hr. The solvent was removed in vacuo and the crude product was purified by flash column chromatography using a 9:1 v/v Hexane:Ethyl acetate to afford the title compound (2.2 g, 93% yield) as a white crystalline solid. MS m/z 223.48 [M+1].

Example 1.4: 2,4,5-trichloro-7-((2-(trimethylsilyl)ethoxy)methyl)-7H-pyrrolo[2,3-d]pyrimidine

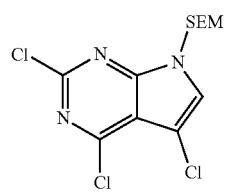 [SMILES: C[Si](C)(C)CCOCn1cc(Cl)c2c(Cl)nc(Cl)nc21]

To a solution of 2,4,5-trichloro-7H-pyrrolo[2,3-d]pyrimidine (2.0 g, 8.99 mmol) in N,N-dimethylformamide (30 mL) was added sodium hydride (60%, 432 mg, 10.78 mmol) at 0° C. The reaction mixture was allowed to stir for 30 min. after which time 2-(trimethylsilyl)ethoxymethyl chloride (1.91 mL, 10.78 mmol) was added. The reaction mixture was further stirred at room temperature for a period of 3 hr after which time water was added and the resulting mixture was stirred for 20 minutes. The resulting precipitate was filtered and dried to yield the title compound (2.85 g, 90% yield) as a brown solid. MS m/z 353.84 [M+1].

Example 1.5: 2,5-dichloro-N-methyl-7-((2-(trimethylsilyl)ethoxy)methyl)-7H-pyrrolo[2,3-d]pyrimidin-4-amine

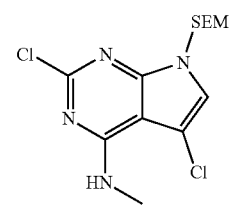 [SMILES: CNc1nc(Cl)nc2c1c(Cl)cn2COCC[Si](C)(C)C]

To a solution 2,4,5-trichloro-7-((2-(trimethylsilyl)ethoxy)methyl)-7H-pyrrolo[2,3-d]pyrimidine (1 g, 2.8 mmol) in MeOH (15 mL) was added a solution of methylamine 33% in MeOH (0.29 mL, 3.11 mmol). The mixture was heated to 70° C. for 1 hour followed by cooling to room temperature at which time the solvent was removed in vacuo and the crude product was purified by flash column chromatography using a 9:1 v/v Hexane:Ethyl acetate to afford the title compound (916 mg, 93% yield) as a white solid. MS m/z 348.08 [M+1].

Example 1.6: (4-((5-chloro-4-(methylamino)-7H-pyrrolo[2,3-d]pyrimidin-2-yl)amino)-3-methoxyphenyl)(morpholino)methanone (18)

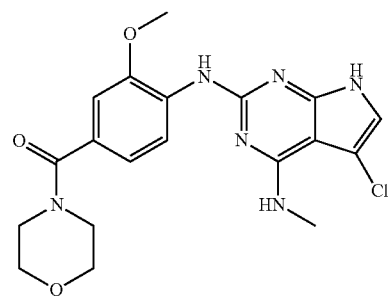 [SMILES: CNc1nc(Nc2ccc(C(=O)N3CCOCC3)cc2OC)nc2[nH]cc(Cl)c12]

To a solution of 2,5-dichloro-N-methyl-7-((2-(trimethylsilyl)ethoxy)methyl)-7H-pyrrolo[2,3-d]pyrimidin-4-amine (100 mg, 0.28 mmol) in sec-BuOH (5 mL) was added (4-amino-3-methoxyphenyl)(morpholino)methanone (82 mg, 0.35 mmol) and K$_2$CO$_3$ (77.4 mg, 0.56 mmol). The reaction mixture was degassed for 5 min and then Pd$_2$(dba)$_3$ (Tris(dibenzylideneacetone)dipalladium(0)) (15.4 mg, 0.017 mmol) and 2-dicyclohexylphosphino-2',4',6'-triisopropylbiphenyl (12 mg, 0.025 mmol) were added. The reaction flask was stirred at 90° C. for 6 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over MgSO$_4$, filtered, and concentrated. The crude product was dissolved in DCM (10 mL) and TFA (2 mL) was added. The resulting mixture was stirred at 50° C. for 3 hr and then the solvent was removed in vacuo. The crude material was dissolved in THF (10 mL) and a saturated solution of NaHCO$_3$ (10 mL) was added and the resulting mixture was stirred for 6 hr. The mixture was extracted with ethyl acetate and the combined organic extracts were washed with brine, dried over MgSO$_4$, filtered, and concentrated. Purification by HPLC gave the title compound (68 mg, 58% yield) as a brown solid. $^1$H NMR 400 MHz (DMSO-d$_6$) δ 11.43 (br, 1H), 8.62 (d, J=4 Hz, 1H), 7.44 (s, 1H), 7.03 (m, 1H), 6.6 (m, 1H), 3.95 (s, 3H), 3.62-3.5 (m, 8H), 2.48 (s, 3H); $^{13}$C NMR 100 MHz (DMSO-d$_6$) δ 169.65, 156.91, 150.37, 146.98, 131.83, 127.29, 120.39, 116.70, 116.43, 110.00, 102.03, 95.63, 66.59, 56.42, 28.17; MS m/z: 417.34 [M+1].

Example 2

Synthesis of (3-methoxy-4-((4-methoxy-7H-pyrrolo[2,3-d]pyrimidin-2-yl)amino)phenyl) (morpholino)methanone (9)

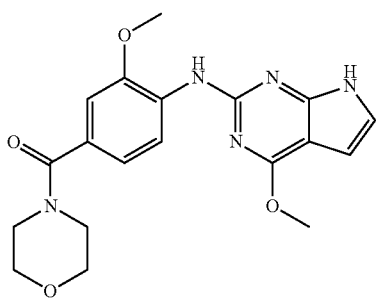 [SMILES: COc1cc(C(=O)N2CCOCC2)ccc1Nc1nc(OC)c2cc[nH]c2n1]

Example 2.1: 2-chloro-4-methoxy-7H-pyrrolo[2,3-d]pyrimidine

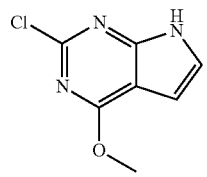

To a solution of 2-chloro-4-methoxy-7H-pyrrolo[2,3-d]pyrimidine (1 g, 5.4 mmol) in MeOH (15 mL) was added a solution of methylamine 33% in MeOH (0.56 mL, 5.9 mmol). The mixture was heated to 70° C. for 1 hour followed by cooling to room temperature at which time the solvent was removed in vacuo and the crude product was purified by flash column chromatography using a 9:1 v/v Hexane:Ethyl acetate as solvent to afford the title compound 965 mg (95% yield) as a white solid. MS m/z 184.08 [M+1]

Example 2.2: (4-((5-chloro-4-methoxy-7H-pyrrolo[2,3-d]pyrimidin-2-yl)amino)-3-methoxyphenyl)(morpholino)methanone (9)

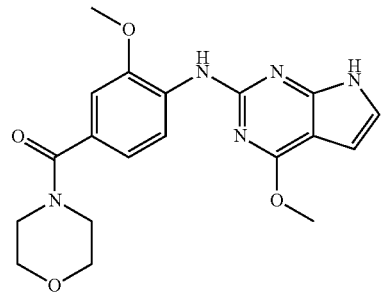

To a solution of 2-chloro-4-methoxy-7H-pyrrolo[2,3-d]pyrimidine (100 mg, 0.54 mmol) in sec-BuOH (5 mL) was added (4-amino-3-methoxyphenyl)(morpholino)methanone (154 mg, 0.65 mmol) and K$_2$CO$_3$ (150 mg, 1.08 mmol). The reaction mixture was degassed for 5 min and then Pd$_2$(dba)$_3$ (30 mg, 0.032 mmol) and 2-dicyclohexylphosphino-2',4',6'-triisopropylbiphenyl (23 mg, 0.049 mmol) were added. The reaction flask was stirred at 110° C. for 8 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over MgSO$_4$, filtered, and concentrated. Purification by HPLC gave the title compound (64 mg, 31% yield) as a brown solid. $^1$H NMR 400 MHz (DMSO-d$_6$) δ 11.58 (br, 1H), 8.58 (d, J=7 Hz, 1H), 7.67 (m, 1H), 7.07-6.99 (m, 2H), 6.34-6.31 (m, 1H), 4.01 (s, 1H), 3.92 (s, 3H), 2.52 (s, 1H), 2.51-2.46 (m, 8H) MS m/z: 384.58 [M+1].

Example 3

Synthesis of (3-methoxy-4-((4-(methylamino)-1H-pyrazolo[3,4-d]pyrimidin-6-yl)amino)phenyl)(morpholino)methanone (23)

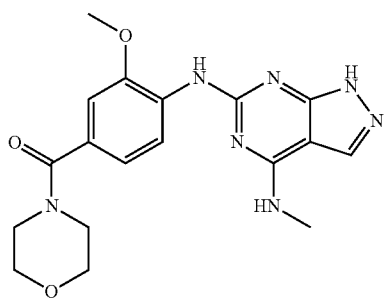 [SMILES: CNc1nc(Nc2ccc(C(=O)N3CCOCC3)cc2OC)nc2[nH]ncc12]

Compound 23 was synthesized in accordance with Scheme 2 and as further detailed below.

Example 3.1: 2,4,6-trichloropyrimidine-5-carbaldehyde

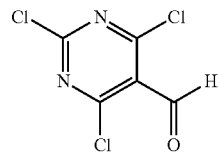 [SMILES: O=Cc1c(Cl)nc(Cl)nc1Cl]

DMF (12 mL) was added drop-wise to POCl₃ (75 mL, 800 mmol) at 0° C., followed by the portion-wise addition of barbituric acid (15 g, 118 mmol) to the mixture. The resulting mixture was stirred at 120° C. for 16 hr. Excess POCl₃ was removed in vacuo and the resulting residue was gradually poured into ice water. The mixture was extracted with DCM and the organic layer was washed with sat. NaHCO₃ solution, dried, and concentrated to give the title compound as a yellow solid (19.0 g, 77% yield). $^1$H NMR (CDCl₃, 400 MHz): δ 10.45 (s, 1H). MS m/z 212.81 [M+1].

Example 3.2: 4,6-dichloro-1H-pyrazolo[3,4-d]pyrimidine

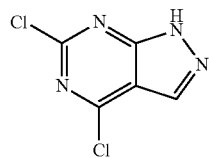 [SMILES: Clc1nc(Cl)c2cn[nH]c2n1]

To a solution of 2,4,6-trichloropyrimidine-5-carbaldehyde (19.0 g, 990 mmol) in methanol (300 mL) was added drop-wise a solution of hydrazine monohydrate (4.8 mL) in methanol (80 mL) at 0° C. followed by drop-wise addition of triethylamine (13 mL) in methanol (80 mL) at 0° C. The mixture was stirred at the same temperature for 30 min. The solvent was removed and the residue was purified by flash chromatography to afford the title compound (10.3 g, 62% yield) as a yellow solid. $^1$H NMR (CDCl₃, 400 MHz): δ 11.56 (br, 1H), 8.43 (s, 1H). MS m/z 190.68 [M+1].

Example 3.3: 6-chloro-N-methyl-1H-pyrazolo[3,4-d]pyrimidin-4-amine

To a solution of 4,6-dichloro-1H-pyrazolo[3,4-d]pyrimidine (1 g, 5.29 mmol) in MeOH (15 mL) was added a solution of methylamine 33% in MeOH (0.55 mL, 5.89 mmol). The mixture was heated to 70° C. for 1 hour followed by cooling to room temperature. The resulting precipitate was filtered, washed with ice-cold MeOH and dried to afford the title compound (874 mg, 90% yield) as a white solid. MS m/z 184.73 [M+1].

Example 3.4: 3-methoxy-4-((4-(methylamino)-1H-pyrazolo[3,4-d]pyrimidin-6-yl)amino)phenyl)(morpholino)methanone (23)

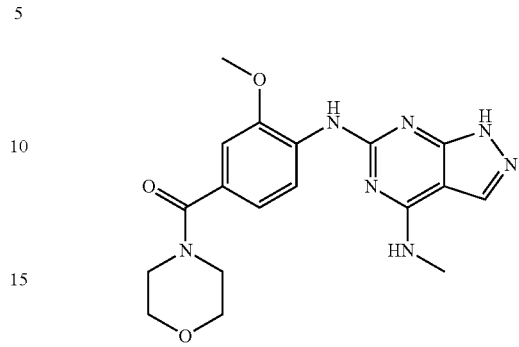

To a solution of 6-chloro-N-methyl-1H-pyrazolo[3,4-d]pyrimidin-4-amine (100 mg, 0.54 mmol) in sec-BuOH (5 mL) was added (4-amino-3-methoxyphenyl)(morpholino)methanone (154 mg, 0.65 mmol) and K₂CO₃ (150 mg, 1.08 mmol). The reaction mixture was degassed for 5 min and then Pd₂(dba)₃ (30 mg, 0.032 mmol) and 2-dicyclohexylphosphino-2',4',6'-triisopropylbiphenyl (23 mg, 0.049 mmol) were added. The reaction flask was stirred at 110° C. for 8 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over MgSO₄, filtered, and concentrated. Purification by HPLC gave the title compound (64 mg, 31% yield) as a brown solid. $^1$H NMR 400 MHz (CD₃OD) δ 8.18 (m, 1H), 8.10 (br, 1H), 8.02 (m, 1H), 7.83 (m, 1H), 7.58 (m, 1H), 7.20 (m, 1H), 6.86 (m, 1H), 4.05 (m, 1H), 3.97 (s, 3H), 3.80 (m, 2H), 3.50 (m, 2H), 2.20 (m, 2H), 1.98 (m, 2H), 1.18 (d, J=6.6 Hz, 6H), MS m/z: 384.63 [M+1].

Example 4

Synthesis of (3-methoxy-4-((4-methoxy-1H-pyrazolo[3,4-d]pyrimidin-6-yl)amino)phenyl) (morpholino)methanone (24)

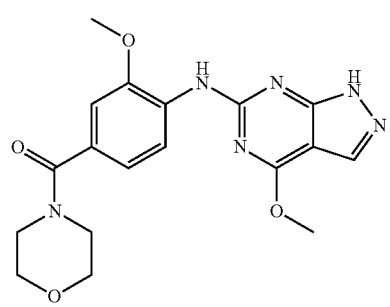 [SMILES: COc1cc(C(=O)N2CCOCC2)ccc1Nc1nc(OC)c2cn[nH]c2n1]

Example 4.1: 6-chloro-4-methoxy-1H-pyrazolo[3,4-d]pyrimidine

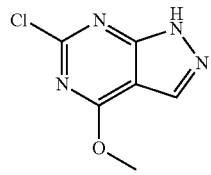

To a solution of 6-chloro-4-methoxy-1H-pyrazolo[3,4-d]pyrimidine (1 g, 5.29 mmol) in MeOH (15 mL) was added a solution of NaOMe 25% in MeOH (1.26 mL, 5.89 mmol). The mixture was heated to 80° C. for 1 hour followed by cooling to room temperature. The resulting precipitate was filtered, washed with ice-cold MeOH and dried to afford the title compound (910 mg, 92% yield) as a white solid. MS m/z 185.46 [M+1].

Example 4.2: (3-methoxy-4-((4-methoxy-1H-pyrazolo[3,4-d]pyrimidin-6-yl)amino)phenyl) (morpholino)methanone (24)

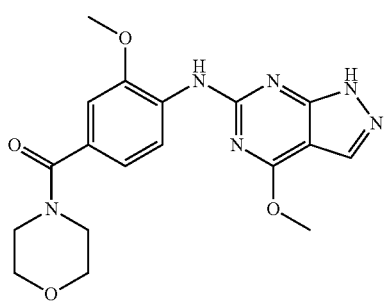 [SMILES: COc1cc(C(=O)N2CCOCC2)ccc1Nc1nc(OC)c2cn[nH]c2n1]

To a solution of 6-chloro-4-methoxy-1H-pyrazolo[3,4-d]pyrimidine (100 mg, 0.54 mmol) in sec-BuOH (5 mL) was added (4-amino-3-methoxyphenyl)(morpholino)methanone (154 mg, 0.65 mmol) and $K_2CO_3$ (150 mg, 1.08 mmol). The reaction mixture was degassed for 5 min and then $Pd_2(dba)_3$ (30 mg, 0.032 mmol) and 2-dicyclohexylphosphino-2',4',6'-triisopropylbiphenyl (23 mg, 0.049 mmol) were added. The reaction flask was stirred at 110° C. for 8 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over $MgSO_4$, filtered, and concentrated. Purification by HPLC gave the title compound 58 mg (28% yield) as a light-brown solid. $^1$H NMR 400 MHz (DMSO-$d_6$) δ 13.31 (br, 1H), 8.39 (d, J=4 Hz, 1H), 7.98 (d, J=8 Hz, 1H), 7.01 (m, 2H), 4.05 (s, 3H), 3.98 (s, 3H), 2.46 (m, 8H), MS m/z: 385.23 [M+1].

Example 5

Synthesis of (3-methoxy-4-((6-(methylamino)-9H-purin-2-yl)amino)phenyl)(morpholino) methanone (21)

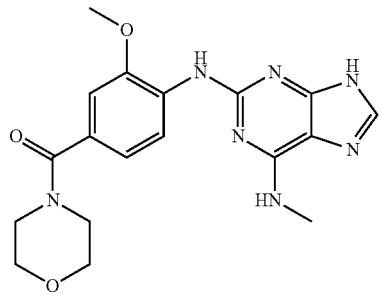

Compound 21 was synthesized in accordance with Scheme 2 and as detailed below.

Example 5.1: 2-chloro-N-methyl-9H-purin-6-amine

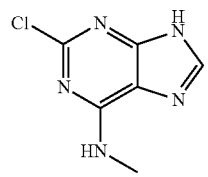

To a solution of 2,6-dichloro-9H-purine (1 g, 5.29 mmol) in MeOH (15 mL) was added a solution of methylamine 33% in MeOH (0.55 mL, 5.89 mmol). The mixture was heated to 70° C. for 1 hour followed by cooling to room temperature. The resulting precipitate was filtered, washed with ice-cold MeOH, and dried to afford the title compound 880 mg (92% yield) as a white solid. MS m/z 184.73 [M+1].

Example 5.2: (3-methoxy-4-((6-(methylamino)-9H-purin-2-yl)amino)phenyl)(morpholino) methanone (21)

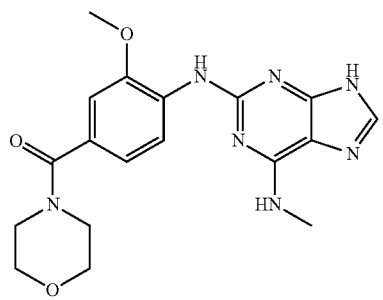 [SMILES: CNc1nc(Nc2ccc(C(=O)N3CCOCC3)cc2OC)nc2[nH]cnc12]

To a solution of 2-chloro-N-methyl-9H-purin-6-amine (100 mg, 0.54 mmol) in sec-BuOH (5 mL) was added (4-amino-3-methoxyphenyl)(morpholino)methanone (154 mg, 0.65 mmol) and $K_2CO_3$ (150 mg, 1.08 mmol). The reaction mixture was degassed for 5 min and then $Pd_2(dba)_3$ (30 mg, 0.032 mmol) and 2-dicyclohexylphosphino-2',4',6'-triisopropylbiphenyl (23 mg, 0.049 mmol) were added. The reaction flask was stirred at 110° C. for 8 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over MgSO$_4$, filtered, and concentrated. Purification by HPLC gave the title compound 70 mg (35% yield) as a light-brown solid. $^1$H NMR (400 MHz, DMSO-d$_6$) δ 8.39 (d, J=9 Hz, 1H), 8.06 (s, 1H), 7.06-7.02 (m, 1H), 6.98 (d, J=3 Hz, 1H), 3.85 (s, 1H), 2.47 (s, 3H), 2.45-2.51 (m, 8H), MS m/z 384.19 [M+1].

Example 6

Synthesis of (3-methoxy-4-((6-methoxy-9H-purin-2-yl)amino)phenyl)(morpholino)methanone (22)

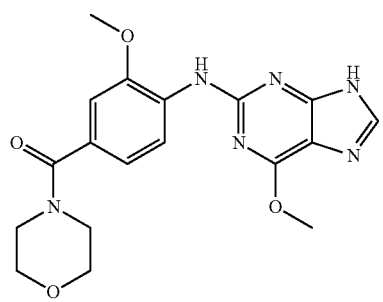 [SMILES: COc1cc(C(=O)N2CCOCC2)ccc1Nc1nc(OC)c2nc[nH]c2n1]

Example 6.1: 2-chloro-6-methoxy-9H-purine

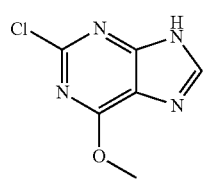

To a solution of 2,6-dichloro-9H-purine (1 g, 5.29 mmol) in MeOH (15 mL) was added a solution of NaOMe 25% in MeOH (1.26 mL, 5.89 mmol). The mixture was heated to 80° C. for 1 hour followed by cooling to room temperature. The resulting precipitate was filtered, washed with ice-cold MeOH and dried to afford the title compound 920 mg (94% yield) as a white solid. MS m/z 185.36 [M+1].

Example 6.2: (3-methoxy-4-((6-methoxy-9H-purin-2-yl)amino)phenyl) (morpholino)methanone (22)

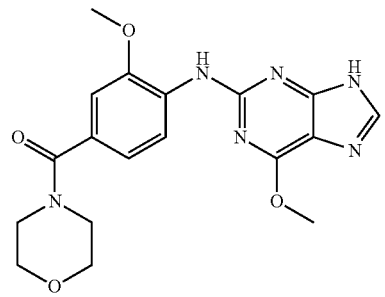 [SMILES: COc1cc(C(=O)N2CCOCC2)ccc1Nc1nc(OC)c2nc[nH]c2n1]

To a solution of 2-chloro-6-methoxy-9H-purine (100 mg, 0.54 mmol) in sec-BuOH (5 mL) was added (4-amino-3-methoxyphenyl)(morpholino)methanone (154 mg, 0.65 mmol) and K$_2$CO$_3$ (150 mg, 1.08 mmol). The reaction mixture was degassed for 5 min and then Pd$_2$(dba)$_3$ (30 mg, 0.032 mmol) and 2-dicyclohexylphosphino-2',4',6'-triisopropylbiphenyl (23 mg, 0.049 mmol) were added. The reaction flask was stirred at 110° C. for 8 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over MgSO$_4$, filtered, and concentrated. Purification by HPLC gave the title compound (50 mg, 24% yield) as a light-brown solid. $^1$H NMR (400 MHz, DMSO-d$_6$) δ 8.46 (d, J=9 Hz, 1H), 8.01 (s, 1H), 7.89 (s, 1H), 7.04 (m, 1H), 4.03 (s, 3H), 3.96 (s, 3H), 2.48-2.40 (m, 8H), MS m/z 385.62 [M+1].

Example 7

The following exemplary compound was synthesized in accordance with scheme 3 and as detailed below.

Synthesis of (4-((3-chloro-7-(methylamino)pyrazolo[1,5-a]pyrimidin-5-yl)amino)-3-methoxyphenyl)(morpholino)methanone

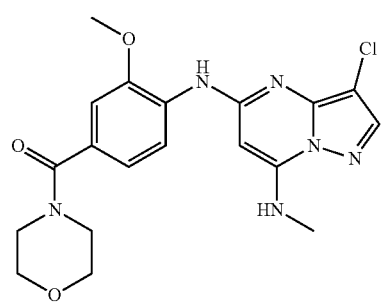 [SMILES: CNc1cc(Nc2ccc(C(=O)N3CCOCC3)cc2OC)nc2c(Cl)cnn12]

Example 7.1: 5,7-dichloropyrazole[1,5-a]pyrimidine

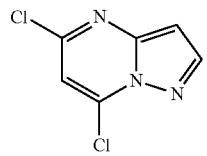 [SMILES: Clc1cc(Cl)n2nccc2n1]

POCl$_3$ (130 mL) was added to pyrazolo[1,5-a]pyrimidine-5,7-diol (10 g, 66 mmol). The suspension was cooled to 0° C. and N,N-dimethylaniline (23 mL, 179 mmol) was slowly added. After warming to room temperature, the reaction was heated at 60° C. under N$_2$ for 16 hr. Upon cooling, the reaction mixture was concentrated in vacuo to give a brown viscous liquid, which was slowly poured onto ice and allowed to warm to room temperature. The pH was adjusted to pH~8 with saturated NaHCO$_3$. The organic layer was then extracted with CH$_2$Cl$_2$ (4×50 mL), dried (MgSO$_4$), and concentrated in vacuo to give a brown liquid. Purification by flash column chromatography using 1:1 v/v DCM:hexanes to 2:1 v/v DCM:hexanes afforded the title compound (10.7 g, 86% yield) as a white crystalline solid. MS m/z 189.36 [M+1].

Example 7.2: 3,5,7-trichloropyrazolo[1,5-a]pyrimidine

To a solution of 5,7-dichloropyrazolo[1,5-a]pyrimidine (2.0 g, 10.64 mmol) in CHCl$_3$ (15 mL) was added NCS (1.70 bg, 12.76 mmol). The mixture was heated to 90° C. under microwave irradiation for 2.5 hr. The solvent was removed in vacuo and the crude product was purified by flash column chromatography using a 9:1 v/v Hexanes:Ethyl acetate to afford the title compound (2.0 g, 90% yield) as a white crystalline solid. MS m/z 223.76 [M+1].

Example 7.3: 3,5-dichloro-N-methylpyrazolo[1,5-a]pyrimidin-7-amine

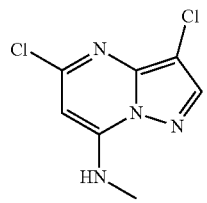

To a solution of 3,5,7-trichloropyrazolo[1,5-a]pyrimidine (1 g, 4.5 mmol) in MeOH (15 mL) was added a solution of methylamine 33% in MeOH (0.47 mL, 4.95 mmol). The mixture was heated to 70° C. for 1 hour followed by cooling to room temperature. The resulting precipitate was filtered, washed with ice-cold MeOH and dried to afford the title compound (859 mg, 88% yield) as a white solid. MS m/z 218.43 [M+1].

Example 7.4: (4-((3-chloro-7-(methylamino)pyrazolo[1,5-a]pyrimidin-5-yl)amino)-3-methoxyphenyl)(morpholino)methanone

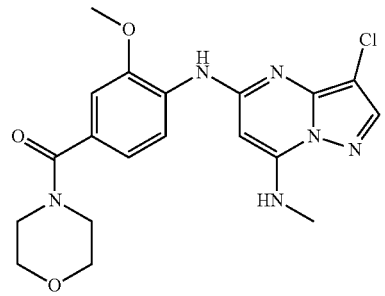 [SMILES: CNc1cc(Nc2ccc(C(=O)N3CCOCC3)cc2OC)nc2c(Cl)cnn12]

To a solution of 3,5-dichloro-N-methylpyrazolo[1,5-a]pyrimidin-7-amine (100 mg, 0.46 mmol) in sec-BuOH (5 mL) was added (4-amino-3-methoxyphenyl)(morpholino)methanone (130 mg, 0.55 mmol) and K$_2$CO$_3$ (127 mg, 0.92 mmol). The reaction mixture was degassed for 5 min and then Pd$_2$(dba)$_3$ (25 mg, 0.028 mmol) and 2-dicyclohexylphosphino-2',4',6'-triisopropylbiphenyl (20 mg, 0.0414 mmol) were added. The reaction flask was stirred at 100° C. for 6 hr. After cooling to room temperature, the reaction mixture was filtered through a pad of celite and partitioned between ethyl acetate and water. The organic layer was separated and the aqueous layer was extracted with ethyl acetate. The combined organic extracts were washed with brine, dried over MgSO$_4$, filtered, and concentrated. Purification by HPLC gave the title compound (84 mg, 44% yield) as a light-brown solid.

Example 7.5: (4-((3,5-dichloropyrazolo[1,5-a]pyrimidin-7-yl)amino)-3-methoxyphenyl) morpholino)methanone

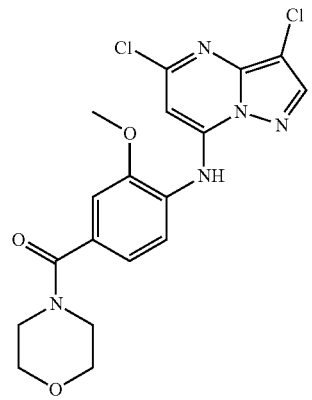 [SMILES: COc1cc(C(=O)N2CCOCC2)ccc1Nc1cc(Cl)nc2c(Cl)cnn12]

To a solution of 3,5,7-trichloropyrazolo[1,5-a]pyrimidine (0.5 g, 2.3 mmol) in THF (15 mL) was added (4-amino-3-methoxyphenyl)(morpholino) methanone (637 mg, 2.7 mmol) followed by KOt-Bu (2.7 mL, 2.7 mmol) The mixture was heated to 70° C. for 1 hour followed by cooling to room temperature. The reaction was quenched with water, extracted with Ethyl Acetate, dried over (MgSO$_4$), and concentrated to give a light brown solid, which was used without further purification. MS m/z 423.23 [M+1].

Example 7.6: (4-((3-chloro-5-(methylamino)pyrazolo[1,5-a]pyrimidin-7-yl)amino)-3-methoxyphenyl)(morpholino)methanone

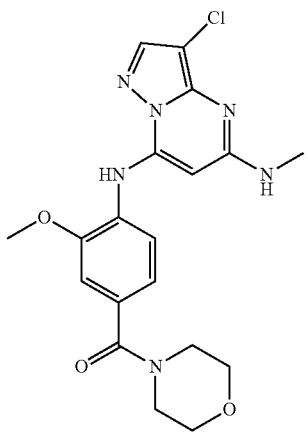

To a solution of (4-((3,5-dichloropyrazolo[1,5-a]pyrimidin-7-yl)amino)-3-methoxyphenyl) morpholino) methanone (100 mg, 0.23 mmol) in MeOH (5 mL) was added a solution of methylamine 33% in MeOH (0.11 mL, 1.15 mmol). The mixture was heated to 90° C. for 1 hour followed by cooling to room temperature. The solvent was removed in vacuo and the crude material was purified by column chromatography using DCM/MeOH 10:1 to give the title compound as a white solid (71 mg, 74% yield) as a white solid. MS m/z 417.43 [M+1].

Example 8: Characterization of Compounds of the Present Disclosure

Reagents, Biological Materials, and General Methods

Tissue-culture reagents were from Life Technologies. P81 phosphocellulose paper was from Whatman and [γ-32P]-ATP was from Perkin Elmer. Nictide and LRRKtide were synthesized by Pepceuticals. Protein G sepharose was from Amersham. DNA constructs used for transfection were purified from *Escherichia coli* DH5α using Qiagen or Invitrogen plasmid Maxi kits according to the manufacturer's protocol. All DNA constructs were verified by DNA sequencing, which was performed by The Sequencing Service, School of Life Sciences, University of Dundee, Scotland, U.K., using DYEnamic ET terminator chemistry (Amersham Biosciences) on Applied Biosystems automated DNA sequencers.

Cell Culture, Treatments and Cell Lysis

HEK293 and Swiss 3T3 cells were cultured in DMEM (Dulbecco's Modified Eagle's medium) supplemented with 10% FBS (fetal bovine serum), 2 mM glutamine and 1× penicillin/streptomycin solution. HEK-293 T-Rex cell lines were cultured in DMEM supplemented with 10% (v/v) FBS and 2 mM glutamine, 1× penicillin/streptomycin solution, 15 μg/ml blasticidin and 100 μg/ml hygromycin. T-Rex cultures were induced to express the indicated protein by inclusion of 0.1 μg/ml doxycycline in the culture medium for 24-48 hr. Human lymphoblastoid cells were maintained in RPMI 1640 with 10% FBS, 2 mM glutamine, 1× penicillin/streptomycin solution and were maintained at cell density of $0.3 \times 10^6$-$2 \times 10^6$ cells per ml. Epstein-Barr virus immortalized primary human lymphoblastoid cells from one control subject and one Parkinson's disease patient homozygous for the LRRK2[G2019S] mutation were kindly provided by Alastair Reith (GSK) and have been described previously. For inhibitor experiments, Compound 18 and/or LRRK2-IN-1 was dissolved in DMSO and utilized at the indicated concentrations. The concentration of DMSO in the culture media did not exceed 1%. Following treatment, cells were washed once with PBS and lysed with buffer containing 50 mM Tris/HCl, pH 7.5, 1 mM EGTA, 1 mM EDTA, 1 mM sodium orthovanadate, 10 mM sodium β-glycerophosphate, 50 mM NaF, 5 mM sodium pyrophosphate, 0.27 M sucrose, 1 mM benzamidine, 2 mM phenylmethanesulphonylfluoride (PMSF) and 1% Triton X-100. When not used immediately, all lysate supernatants were snap-frozen in liquid nitrogen and stored at −80° C. until use. Protein concentrations were determined following centrifugation of the lysate at 16,000×g at 4° C. for 20 minutes using the Bradford method with BSA as the standard. Transient transfection of HEK293 cells was performed using the PEI method.

IC$_{50}$ Determination

Active GST-LRRK2 (1326-2527), GST-LRRK2 [G2019S] (1326-2527), GST-LRRK2[A2016T] (1326-2527) and GST-LRRK2[A2016T+G2019S] (1326-2527) enzyme was purified with glutathione sepharose from HEK293 cell lysate 36 h following transient transfection of the appropriate cDNA constructs. Peptide kinase assays, performed in triplicate, were set up in a total volume of 40 μl containing 0.5 μg LRRK2 kinase (which at approximately 10% purity gives a final concentration of 8 nM) in 50 mM Tris/HCl, pH 7.5, 0.1 mM EGTA, 10 mM MgCl$_2$, 20 μM Nictide, 0.1 μM [γ-32P]ATP (~500 cpm/pmol) and the indicated concentrations of inhibitor dissolved in DMSO. After incubation for 15 min at 30° C., reactions were terminated by spotting 35 μl of the reaction mix onto P81 phosphocellulose paper and immersion in 50 mM phosphoric acid. Samples were washed extensively and the incorporation of [γ-32P]ATP into Nictide was quantified by Cerenkov counting. IC$_{50}$ values were calculated with GraphPad Prism using non-linear regression analysis.

Immunoblot Procedures

Cell lysates from Swiss 3T3 cells, human lymphoblastoid cells, GFP-LRRK2 expressing stable cell lines and mouse tissues were eluted in 65 μl 2×LDS sample buffer (Invitrogen) with final concentration of 1 μg/μl. Following heating at 70° C. for 10 min, 15 μl aliquots were resolved on 8% SDS polyacrylamide gels and transferred to nitrocellulose membranes for detection of LRRK2 phosphorylated at Ser910, LRRK2 phosphorylated at Ser935 and total LRRK2, using purified rabbit monoclonal antibodies (LRRK2 phospho-serine 910 clone, LRRK2 phospho-serine 935 clone and LRRK2 100-500 clone) in PBS with 0.1% sodium azide (Epitomics). Immunoblot film were scanned on an Epson 4990 scanner, and images were managed with Adobe Photoshop.

Example 9: Molecular Docking Study of (18)

A molecular docking study of Compound 18 was pursued based on a crystal structure of Roco kinase (PDB accession code: 4F1T), which revealed three hydrogen bonds to the hinge region between backbone M1949, A1950 and the pyrrolopyrimidine. Additionally, the docking study confirmed a halogen interaction with M1947 and the chlorine at the 5-position of the pyrrolopyrimidine, as shown in FIG. 1.

Example 10: Further Evaluation of Compounds Compared to LRRK2-IN-1

Bicyclic compounds that showed the greatest potency in enzymatic assay to inhibit LRRK2 in a cellular context in comparison to LRRK2-IN-1 were further evaluated. As there are no validated direct phosphorylation substrates of LRRK2, phosphorylation of Ser910 and Ser935, two residues whose phosphorylation is known to be dependent upon LRRK2 kinase activity, was monitored. Compound 18 emerged as the most potent compound and induced a dose-dependent inhibition of Ser910 and Ser935 phosphorylation in both wild-type LRRK2 and LRRK2[G2019S] stably transfected into HEK293 cells, as shown in FIG. 2A and FIG. 2B. Substantial dephosphorylation of Ser910 and Ser935 was observed at approximately 0.3 concentrations of Compound 18 for wild-type LRRK2 and LRRK2[G2019S], which is a similar potency to that observed for LRRK2-IN-1. Consistent with the biochemical results, Compound 18 also induced dephosphorylation of Ser910 and Ser935 at a concentration of about 0.3 µM to about 1 µM in the drug-resistant LRRK2[A2016T+G2019S] and LRRK2[A2016T] mutants, revealing that the A2016T mutation is not an effective way to induce resistance to Compound 18.

The effect of Compound 18 on endogenously expressed LRRK2 in human lymphoblastoid cells derived from a control and Parkinson's patient homozygous for the LRRK2 [G2019S] mutation was then examined. The results are shown in FIG. 3A. As shown by a comparison of FIG. 2A and FIG. 2B to FIG. 3A, increasing doses of (18) led to similar dephosphorylation of endogenous LRRK2 at Ser910 and Ser935, as was observed in HEK293 cells stably expressing wild-type LRRK2 or LRRK2[G2019S]. Consistent with the trend observed in HEK293 cells, endogenous LRRK2 was also more sensitive to Compound 18 than LRRK2-IN-1. Compound 18 induced similar dose-dependent Ser935 dephosphorylation of endogenous LRRK2 in mouse Swiss 3T3 cells, as shown in FIG. 3B. IC50s were calculated for (18) against wild-type LRRK2, G2019S, A2016T and G2019S+A2016T mutants, which showed compound 18 had an increase in potency against all of the mutants as compared to known compounds (FIG. 3C).

Example 11: Pharmacokinetic Study of (18) in Mice

Compound 18 was dissolved in 5% 1-methyl-2-pyrrolidinone (NMP)/95% PEG 300 (Sigma) solution and administered by intraperitoneal injection into wild type male C57BL/6 mice at doses of 0, 3, 10, 30, 50 and 100 mg/kg and at 100 mg/kg LRRK2-IN-1 as a comparative control. Control mice were treated with an equal volume of NMP/PEG solution. One hour after administration, mice were sacrificed by cervical dislocation and, kidney, spleen and brain tissues were rapidly dissected and snap-frozen in liquid nitrogen. Animal experiments were approved by the University of Dundee Ethics Committee and performed under a U.K. Home office project license As shown in Table 5, The mouse pharmacokinetic profile of Compound 18 demonstrated good oral bioavailability (116% F), a half-life of 0.66 hours and a plasma exposure of 3094.58 (hr*ng/mL, $AUC_{last}$) following 10 mg/kg p.o. dosing. Additionally, following 2 mg/kg i.v. dosing, Compound 18 showed a plasma exposure of 532.67 (hr*ng/mL, $AUC_{last}$), and a brain exposure of 239.31 (hr*ng/mL, $AUC_{last}$), which equates to a brain/plasma concentration ratio of 0.45.

Figure 4:
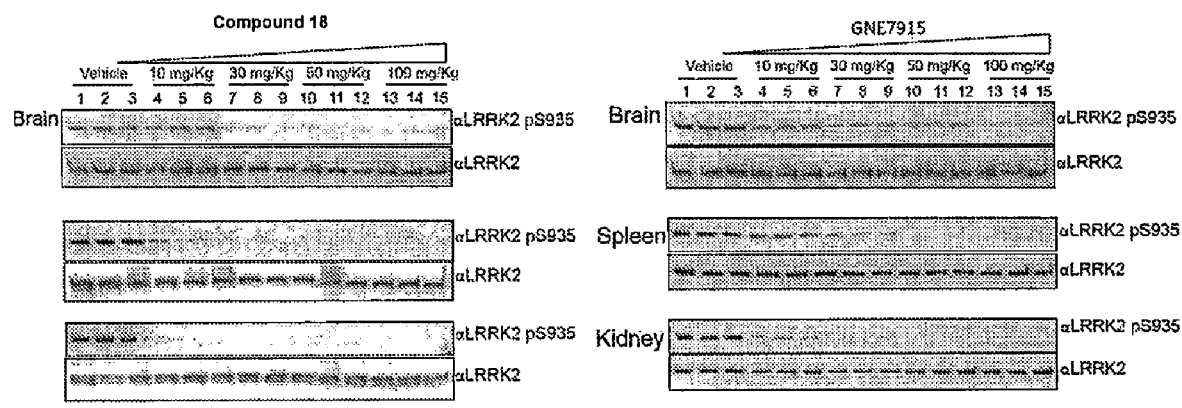
FIG. 4 shows pharmacodynamic analysis for Compound 18 and GNE7915. Pharmacodynamic study of Compound 18 and GNE7915 for brain, spleen and kidney following oral gavage administration at the indicated doses. Tissues were collected and endogenous LRRK2 was resolved by SDS-PAGE and blotted with a phospho-specific antibody directed against Ser935 and total LRRK2.

As shown in FIG. 4, the pharmacodynamic properties of Compound 18 were compared with those of GNE7915 by monitoring inhibition of LRRK2 Ser910/Ser935 phosphorylation in mouse kidney, spleen and brain following intraperitoneal delivery of 100 mg/kg of Compound 18 and GNE7915. A near complete dephosphorylation of Ser935 of LRRK2 was observed in in all tissues including brain at this dose for both compounds. The study was then repeated at lower doses of 50, 30 and 10 mg/kg of (18) and GNE7915. With Compound 18, near complete inhibition in all tissues was observed at 30 mg/kg but only partial inhibition in brain at the 10 mg/kg dose. However, with GNE7915, complete inhibition in brain was only observed at the 100 mg/kg. Without wishing to be bound by the theory, these results indicate that (18) is a promising chemo-type for achieving dephosphorylation of Ser935 in the brain.

TABLE 5

Pharmacokinetic parameters for Compound 18

| Matrix | Route | Dose (mg/kg) | $T_{max}$ (hr) | $^aC_0/C_{max}$ (ng/mL) | $AUC_{last}$ (hr * ng/mL) | $AUC_{INF}$ (hr * ng/mL) | $T_{1/2}$ (hr) | CL (mL/min/kg) | $V_{ss}$ (L/kg) | % $F^b$ |
|---|---|---|---|---|---|---|---|---|---|---|
| Plasma | i.v. | 2 | — | 1604.47 | 532.67 | 535.57 | 0.66 | 62.24 | 1.73 | 116 |
|  | p.o. | 10 | 1 | 802.72 | 3094.58 | 3867.07 | — | — | — |  |
| Brain | i.v. | 2 | — | 1343.6 | 239.31 | 246.47 | 0.23 | 135.24 | 1.7 |  |
|  | p.o. | 10 | 1 | 247.35 | 688.21 | 762.38 | — | — | — |  |

$^aC_0$, back extrapolated conc. for i.v. group.
$^bAUC_{last}$ was considered for calculating bioavailability.

Example 12: Dundee Profiling

The kinase selectivity of (18) was further assessed using standard radioactivity-base enzymatic assays against a panel of 138 kinases (Dundee profiling). At a concentration of 1 µM, Compound 18 only inhibited the kinase activities of SmMLCK and CHK2 to greater than 90% of the DMSO control. Dose-response analysis revealed inhibition of SmMLCK with an $IC_{50}$ of 81.3 nM and CHK2 with an $IC_{50}$ of 27.6 nM. Without wishing to be bound by the theory, the results, shown in Table 6, show percent remaining enzymatic activity relative to the DMSO control, and suggest that Compound 18 is a highly selective LRRK2 inhibitor.

TABLE 6

| K | I1 | K | I10 |
|---|---|---|---|
| TGEBR1 | 128 | BTK | 126 |
| Aurora A | 124 | EPH-B1 | 126 |

TABLE 6-continued

| K | I1 | K | I10 |
|---|---|---|---|
| MARK3 | 120 | TGFBR1 | 119 |
| EPH-B1 | 119 | WNK1 | 115 |
| PKBb | 118 | Aurora A | 112 |
| MELK | 118 | Lck | 111 |
| RSK2 | 117 | PKCγ | 109 |
| p38g MAPK | 116 | MPSK1 | 106 |
| BTK | 116 | PKBa | 105 |
| IKKe | 114 | PAK6 | 105 |
| PKCγ | 113 | TLK1 | 105 |
| TAO1 | 113 | p38a MAPK | 104 |
| MPSK1 | 113 | AMPK | 103 |
| ROCK2 | 113 | ABL | 103 |
| AMPK | 112 | PKBb | 103 |
| MAP4K5 | 110 | NEK2a | 103 |
| ULK2 | 110 | FGF-R1 | 102 |
| Src | 110 | PAK2 | 102 |
| PAK2 | 110 | S6K1 | 102 |
| CHK1 | 110 | EF2K | 102 |
| BRSK2 | 110 | p38d MAPK | 102 |
| SIK2 | 109 | Src | 102 |
| MARK4 | 109 | EPH-A4 | 102 |
| MSK1 | 109 | ROCK 2 | 101 |
| IRAK1 | 109 | EPH-A2 | 101 |
| PDGFRA | 109 | PKA | 101 |
| WNK1 | 108 | PKCa | 100 |
| ERK8 | 108 | TAO1 | 100 |
| p38b MAPK | 108 | VEG-FR | 100 |
| p38d MAPK | 107 | MSK1 | 99 |
| EPH-A4 | 107 | BRSK2 | 98 |
| ERK1 | 107 | BRSK1 | 98 |
| SIK3 | 107 | MARK4 | 98 |
| TLK1 | 106 | IKKe | 98 |
| ABL | 106 | TTBK1 | 98 |
| S6K1 | 106 | MST4 | 97 |
| HIPK3 | 106 | JAK2 | 97 |
| CDK9-Cyclin T1 | 105 | GSK3b | 97 |
| PINK | 105 | SIK3 | 96 |
| EF2K | 105 | p38g MAPK | 96 |
| TTBK2 | 105 | LKB1 | 96 |
| VEG-FR | 104 | IKKb | 95 |
| TIE2 | 104 | MST3 | 95 |
| AMPK (hum) | 104 | TESK1 | 95 |
| EPH-A2 | 104 | ULK1 | 95 |
| TTBK1 | 103 | ULK2 | 95 |
| PRK2 | 103 | RSK2 | 94 |
| ULK1 | 103 | PKCz | 94 |
| LKB1 | 103 | TIE2 | 94 |
| MST4 | 103 | PRK2 | 93 |
| MST3 | 102 | CHK1 | 93 |
| PKCa | 102 | HIPK3 | 93 |
| EIF2AK3 | 102 | DDR2 | 93 |
| MNK1 | 102 | MAP4K5 | 92 |
| PAK4 | 102 | EPH-B3 | 92 |
| RIPK2 | 102 | AMPK (hum) | 92 |
| PAK6 | 102 | CSK | 92 |
| CDK2-Cyclin A | 102 | PAK4 | 92 |
| NEK6 | 101 | IRAK1 | 92 |
| PKBa | 101 | MARK3 | 92 |
| ZAP70 | 101 | SIK2 | 92 |
| MKK2 | 101 | CDK9-Cyclin T1 | 91 |
| MARK2 | 101 | Aurora B | 90 |
| CK1γ2 | 100 | TTBK2 | 90 |
| IKKb | 100 | PDGFRA | 89 |
| JAK2 | 99 | PINK | 89 |
| PKA | 99 | PDK1 | 88 |
| DDR2 | 98 | PIM1 | 88 |
| MAP4K3 | 98 | EPH-B4 | 86 |
| MAPKAP-K3 | 97 | YES1 | 85 |
| Aurora B | 97 | MEKK1 | 85 |
| NEK2a | 97 | ZAP70 | 85 |
| Lck | 97 | MAPKAP-K3 | 84 |
| TESK1 | 97 | TrkA | 84 |
| PIM3 | 96 | RIPK2 | 83 |
| RSK1 | 96 | NEK6 | 83 |
| TAK1 | 96 | MST2 | 82 |
| IRAK4 | 95 | IRAK4 | 82 |
| MINK1 | 95 | PIM2 | 82 |
| HIPK1 | 95 | MARK2 | 82 |
| PIM2 | 95 | SYK | 81 |
| PIM1 | 95 | p38b MAPK | 79 |
| MEKK1 | 94 | EIF2AK3 | 79 |
| ERK2 | 94 | MELK | 79 |
| HER4 | 94 | MNK1 | 78 |
| BRSK1 | 94 | MARK1 | 77 |
| CK2 | 94 | SGK1 | 76 |
| FGF-R1 | 94 | PIM3 | 75 |
| EPH-B3 | 92 | MKK2 | 72 |
| PDK1 | 91 | ERK2 | 71 |
| MKK1 | 91 | ERK8 | 71 |
| SYK | 91 | HER4 | 71 |
| MST2 | 90 | CK2 | 70 |
| p38a MAPK | 90 | PAK5 | 70 |
| MARK1 | 89 | ERK1 | 68 |
| CSK | 89 | MINK1 | 68 |
| PAK5 | 89 | TBK1 | 67 |
| SRPK1 | 89 | CDK2 -Cyclin A | 67 |
| TBK1 | 88 | RSK1 | 60 |
| GCK | 86 | EPH-B2 | 58 |
| SGK1 | 86 | MKK1 | 56 |
| MAPKAP-K2 | 86 | ERK5 | 52 |
| YES1 | 85 | CK1γ2 | 45 |
| TrkA | 85 | HIPK1 | 44 |
| HIPK2 | 84 | HIPK2 | 43 |
| GSK3b | 82 | TAK1 | 42 |
| MLKI | 81 | MAP4K3 | 41 |
| EPH-B4 | 80 | GCK | 41 |
| CAMK1 | 80 | MAPKAP-K2 | 40 |
| MLK3 | 78 | MLK1 | 38 |
| ERK5 | 76 | MLK3 | 35 |
| PKCz | 76 | CAMK1 | 34 |
| MNK2 | 75 | CK1δ | 33 |
| NUAK1 | 75 | SRPK1 | 31 |
| CK1δ | 74 | DYRK3 | 30 |
| DYRK3 | 74 | MNK2 | 25 |
| TTK | 69 | BRK | 19 |
| DYRK2 | 67 | DYRK2 | 18 |
| BRK | 62 | NUAK1 | 17 |
| PLK1 | 62 | CAMKKb | 16 |
| OSR1 | 61 | STK33 | 15 |
| EPH-B2 | 60 | PLK1 | 13 |
| ASK1 | 56 | TTK | 12 |
| CAMKKb | 50 | OSR1 | 12 |
| DYRK1A | 49 | MKK6 | 11 |
| PKD1 | 47 | IRR | 10 |
| PRAK | 43 | IR | 10 |
| JNK1 | 38 | ASK1 | 10 |
| MKK6 | 37 | IGF-1R | 9 |
| IRR | 31 | JNK3 | 9 |
| JNK3 | 29 | DYRK1A | 8 |
| JNK2 | 27 | PKD1 | 7 |
| STK33 | 22 | TSSK1 | 7 |
| DAPK1 | 21 | PRAK | 6 |
| IR | 21 | JNK1 | 6 |
| TSSK1 | 14 | DAPK1 | 5 |
| CLK2 | 13 | JNK2 | 4 |
| PHK | 13 | CLK2 | 2 |
| IGF-1R | 13 | PHK | 1 |
| SmMLCK | 9 | CHK2 | 1 |
| CHK2 | 5 | SmMLCK | 1 |

Example 13: Further Evaluation of Kinase Selectivity of Compound 18

Figure 5:
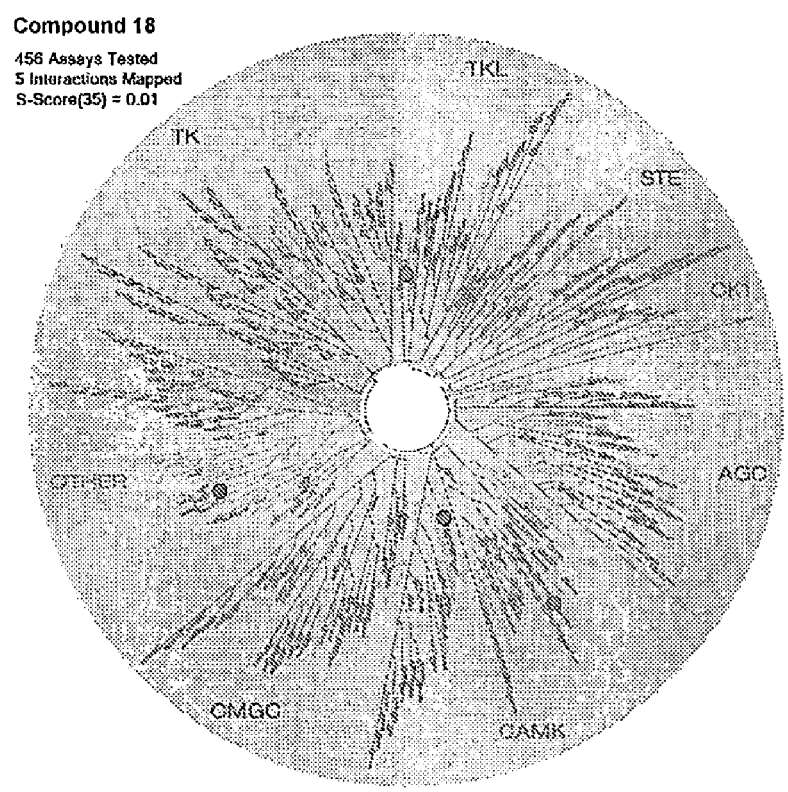
FIG. 5 shows the KinomeScan analysis of Compound 18.

The kinase selectivity of Compound 18 was further evaluated by KinomeScan. KinomeScan analysis against a near comprehensive panel of 451 kinases at a concentration of 1 μM resulted in no interactions detected with kinases other than LRRK2[G2019S] with the exception of TTK and RPS6KA4, demonstrating the outstanding selectivity of this inhibitor. These results, shown in Table 7 and FIG. 5, demonstrate that (18) is a highly selective LRRK2 inhibitor.

TABLE 7

| Compound ID | Compound 18 |
|---|---|
| Compound Concentration (uM) | 1 |
| AAK1 | 88 |
| ABL1 (E255K)-phosphorylated | 95 |
| ABL1 (F317I)-nonphosphorylated | 96 |
| ABL1 (F317I)-phosphorylated | 100 |
| ABL1 (F317L)-nonphosphorylated | 93 |
| ABL1 (F317L)-phosphorylated | 100 |
| ABL1 (H396P)-nonphosphorylated | 100 |
| ABL1 (H396P)-phosphorylated | 95 |
| ABL1 (M351T)-phosphorylated | 80 |
| ABL1 (Q252H)-nonphosphorylated | 88 |
| ABL1 (Q252H)-phosphorylated | 94 |
| ABL1 (T315I)-nonphosphorylated | 91 |
| ABL1 (T315I)-phosphorylated | 96 |
| ABL1 (Y253F)-phosphorylated | 97 |
| ABL1-nonphosphorylated | 100 |
| ABL1-phosphorylated | 100 |
| ABL2 | 96 |
| ACVR1 | 91 |
| ACVR1B | 82 |
| ACVR2A | 100 |
| ACVR2B | 100 |
| ACVRL1 | 85 |
| ADCK3 | 100 |
| ADCK4 | 100 |
| AKT1 | 97 |
| AKT2 | 93 |
| AKT3 | 93 |
| ALK | 70 |
| ALK (C1156Y) | 68 |
| ALK (L1196M) | 74 |
| AMPK-alpha1 | 97 |
| AMPK-alpha2 | 98 |
| ANKK1 | 95 |
| ARK5 | 89 |
| ASK1 | 84 |
| ASK2 | 100 |
| AURKA | 100 |
| AURKB | 80 |
| AURKC | 100 |
| AXL | 97 |
| BIKE | 97 |
| BLK | 100 |
| BMPR1A | 91 |
| BMPR1B | 98 |
| BMPR2 | 100 |
| BMX | 100 |
| BRAF | 100 |
| BRAF (V600E) | 100 |
| BRK | 97 |
| BRSK1 | 100 |
| BRSK2 | 100 |
| BTK | 100 |
| BUB1 | 100 |
| CAMK1 | 100 |
| CAMK1D | 100 |
| CAMK1G | 85 |
| CAMK2A | 92 |
| CAMK2B | 86 |
| CAMK2D | 99 |
| CAMK2G | 95 |
| CAMK4 | 100 |
| CAMKK1 | 96 |
| CAMKK2 | 100 |
| CASK | 88 |
| CDC2L1 | 85 |
| CDC2L2 | 100 |
| CDC2L5 | 100 |
| CDK11 | 63 |
| CDK2 | 95 |
| CDK3 | 96 |
| CDK4-cyclinD1 | 95 |
| CDK4-cyclinD3 | 92 |
| CDK5 | 100 |
| CDK7 | 95 |
| CDK8 | 74 |
| CDK9 | 92 |
| CDKL1 | 87 |
| CDKL2 | 86 |
| CDKL3 | 86 |
| CDKL5 | 100 |
| CHEK1 | 100 |
| CHEK2 | 31 |
| CIT | 92 |
| CLK1 | 87 |
| CLK2 | 56 |
| CLK3 | 99 |
| CLK4 | 63 |
| CSF1R | 79 |
| CSF1R-autoinhibited | 47 |
| CSK | 100 |
| CSNK1A1 | 80 |
| CSNK1A1L | 97 |
| CSNK1D | 82 |
| CSNK1E | 100 |
| CSNK1G1 | 97 |
| CSNK1G2 | 100 |
| CSNK1G3 | 100 |
| CSNK2A1 | 93 |
| CSNK2A2 | 70 |
| CTK | 96 |
| DAPK1 | 54 |
| DAPK2 | 40 |
| DAPK3 | 52 |
| DCAMKL1 | 74 |
| DCAMKL2 | 100 |
| DCAMKL3 | 77 |
| DDR1 | 100 |
| DDR2 | 93 |
| DLK | 89 |
| DMPK | 98 |
| DMPK2 | 84 |
| DRAK1 | 89 |
| DRAK2 | 86 |
| DYRK1A | 95 |
| DYRK1B | 66 |
| DYRK2 | 89 |
| EGFR | 93 |
| EGFR (E746-A750del) | 100 |
| EGFR (G719C) | 91 |
| EGFR (G719S) | 88 |
| EGFR (L747-E749del, A750P) | 81 |
| EGFR (L747-S752del, P753S) | 94 |
| EGFR (L747-T751del, Sins) | 84 |
| EGFR (L858R) | 83 |
| EGFR (L858R, T790M) | 100 |
| EGFR (L861Q) | 57 |
| EGFR (S752-I759del) | 97 |
| EGFR (T790M) | 97 |
| EIF2AK1 | 100 |
| EPHA1 | 100 |
| EPHA2 | 88 |
| EPHA3 | 88 |
| EPHA4 | 94 |
| EPHA5 | 98 |
| EPHA6 | 88 |
| EPHA7 | 98 |
| EPHA8 | 99 |
| EPHB1 | 100 |
| EPHB2 | 98 |
| EPHB3 | 89 |
| EPHB4 | 83 |
| EPHB6 | 100 |
| ERBB2 | 88 |
| ERBB3 | 84 |
| ERBB4 | 100 |
| ERK1 | 100 |
| ERK2 | 96 |
| ERK3 | 62 |
| ERK4 | 100 |
| ERK5 | 85 |
| ERK8 | 100 |
| ERN1 | 92 |
| FAK | 93 |
| FER | 95 |
| FES | 99 |

TABLE 7-continued

| Compound ID | Compound 18 |
|---|---|
| FGFR1 | 99 |
| FGFR2 | 87 |
| FGFR3 | 83 |
| FGFR3 (G697C) | 100 |
| FGFR4 | 98 |
| FGR | 81 |
| FLT1 | 97 |
| FLT3 | 100 |
| FLT3 (D835H) | 98 |
| FLT3 (D835Y) | 100 |
| FLT3 (ITD) | 94 |
| FLT3 (K663Q) | 100 |
| FLT3 (N841I) | 100 |
| FLT3 (R834Q) | 100 |
| FLT3-autoinhibited | 100 |
| FLT4 | 93 |
| FRK | 100 |
| FYN | 90 |
| GAK | 65 |
| GCN2 (Kin.Dom.2, S808G) | 91 |
| GRK1 | 85 |
| GRK4 | 90 |
| GRK7 | 99 |
| GSK3A | 100 |
| GSK3B | 84 |
| HASPIN | 76 |
| HCK | 99 |
| HIPK1 | 90 |
| HIPK2 | 100 |
| HIPK3 | 91 |
| HIPK4 | 85 |
| HPK1 | 100 |
| HUNK | 91 |
| ICK | 81 |
| IGF1R | 95 |
| IKK-alpha | 100 |
| IKK-beta | 98 |
| IKK-epsilon | 100 |
| INSR | 83 |
| INSRR | 100 |
| IRAK1 | 100 |
| IRAK3 | 98 |
| IRAK4 | 100 |
| ITK | 88 |
| JAK1 (JH1domain-catalytic) | 77 |
| JAK1 (JH2domain-pseudokinase) | 99 |
| JAK2 (JH1domain-catalytic) | 100 |
| JAK3 (JH1domain-catalytic) | 100 |
| JNK1 | 60 |
| JNK2 | 78 |
| JNK3 | 67 |
| KIT | 79 |
| KIT (A829P) | 100 |
| KIT (D816H) | 99 |
| KIT (D816V) | 76 |
| KIT (L576P) | 51 |
| KIT (V559D) | 82 |
| KIT (V559D, T670I) | 92 |
| KIT (V559D, V654A) | 94 |
| KIT-autoinhibited | 87 |
| LATS1 | 78 |
| LATS2 | 93 |
| LCK | 99 |
| LIMK1 | 100 |
| LIMK2 | 82 |
| LKB1 | 100 |
| LOK | 100 |
| LRRK2 | 11 |
| LRRK2 (G2019S) | 6.5 |
| LTK | 59 |
| LYN | 100 |
| LZK | 92 |
| MAK | 98 |
| MAP3K1 | 90 |
| MAP3K15 | 100 |
| MAP3K2 | 98 |
| MAP3K3 | 100 |
| MAP3K4 | 100 |
| MAP4K2 | 97 |
| MAP4K3 | 100 |
| MAP4K4 | 100 |
| MAP4K5 | 100 |
| MAPKAPK2 | 95 |
| MAPKAPK5 | 99 |
| MARK1 | 97 |
| MARK2 | 100 |
| MARK3 | 84 |
| MARK4 | 82 |
| MAST1 | 100 |
| MEK1 | 98 |
| MEK2 | 100 |
| MEK3 | 79 |
| MEK4 | 72 |
| MEK5 | 92 |
| MEK6 | 99 |
| MELK | 91 |
| MERTK | 66 |
| MET | 97 |
| MET (M1250T) | 80 |
| MET (Y1235D) | 100 |
| MINK | 94 |
| MKK7 | 100 |
| MKNK1 | 85 |
| MKNK2 | 91 |
| MLCK | 88 |
| MLK1 | 100 |
| MLK2 | 100 |
| MLK3 | 100 |
| MRCKA | 99 |
| MRCKB | 100 |
| MST1 | 100 |
| MST1R | 100 |
| MST2 | 80 |
| MST3 | 91 |
| MST4 | 77 |
| MTOR | 100 |
| MUSK | 100 |
| MYLK | 61 |
| MYLK2 | 82 |
| MYLK4 | 81 |
| MYO3A | 100 |
| MYO3B | 85 |
| NDR1 | 92 |
| NDR2 | 100 |
| NEK1 | 96 |
| NEK10 | 100 |
| NEK11 | 100 |
| NEK2 | 96 |
| NEK3 | 100 |
| NEK4 | 90 |
| NEK5 | 83 |
| NEK6 | 100 |
| NEK7 | 100 |
| NEK9 | 100 |
| NIK | 62 |
| NIM1 | 100 |
| NLK | 100 |
| OSR1 | 88 |
| p38-alpha | 96 |
| p38-beta | 82 |
| p38-delta | 100 |
| p38-gamma | 95 |
| PAK1 | 100 |
| PAK2 | 100 |
| PAK3 | 100 |
| PAK4 | 100 |
| PAK6 | 100 |
| PAK7 | 83 |
| PCTK1 | 93 |
| PCTK2 | 88 |
| PCTK3 | 100 |
| PDGFRA | 80 |
| PDGFRB | 78 |
| PDPK1 | 86 |
| PFCDPK1 (*P. falciparum*) | 96 |
| PFPK5 (*P. falciparum*) | 100 |

TABLE 7-continued

| Compound ID | Compound 18 |
|---|---|
| PFTAIRE2 | 72 |
| PFTK1 | 82 |
| PHKG1 | 88 |
| PHKG2 | 66 |
| PIK3C2B | 98 |
| PIK3C2G | 100 |
| PIK3CA | 87 |
| PIK3CA (C420R) | 95 |
| PIK3CA (E542K) | 100 |
| PIK3CA (E545A) | 99 |
| PIK3CA (E545K) | 100 |
| PIK3CA (H1047L) | 90 |
| PIK3CA (H1047Y) | 100 |
| PIK3CA (I800L) | 97 |
| PIK3CA (M1043I) | 91 |
| PIK3CA (Q546K) | 82 |
| PIK3CB | 86 |
| PIK3CD | 83 |
| PIK3CG | 100 |
| PIK4CB | 90 |
| PIM1 | 98 |
| PIM2 | 98 |
| PIM3 | 99 |
| PIP5K1A | 84 |
| PIP5K1C | 100 |
| PIP5K2B | 62 |
| PIP5K2C | 100 |
| PKAC-alpha | 98 |
| PKAC-beta | 100 |
| PKMYT1 | 100 |
| PKN1 | 100 |
| PKN2 | 100 |
| PKNB (*M. tuberculosis*) | 100 |
| PLK1 | 89 |
| PLK2 | 100 |
| PLK3 | 100 |
| PLK4 | 97 |
| PRKCD | 100 |
| PRKCE | 100 |
| PRKCH | 100 |
| PRKCI | 100 |
| PRKCQ | 93 |
| PRKD1 | 85 |
| PRKD2 | 98 |
| PRKD3 | 100 |
| PRKG1 | 72 |
| PRKG2 | 99 |
| PRKR | 96 |
| PRKX | 100 |
| PRP4 | 93 |
| PYK2 | 100 |
| QSK | 86 |
| RAF1 | 100 |
| RET | 96 |
| RET (M918T) | 96 |
| RET (V804L) | 92 |
| RET (V804M) | 100 |
| RIOK1 | 91 |
| RIOK2 | 100 |
| RIOK3 | 67 |
| RIPK1 | 76 |
| RIPK2 | 96 |
| RIPK4 | 82 |
| RIPK5 | 100 |
| ROCK1 | 88 |
| ROCK2 | 93 |
| ROS1 | 93 |
| RPS6KA4 (Kin.Dom.1-N-terminal) | 97 |
| RPS6KA4 (Kin.Dom.2-C-terminal) | 14 |
| RPS6KA5 (Kin.Dom.1-N-terminal) | 100 |
| RPS6KA5 (Kin.Dom.2-C-terminal) | 78 |
| RSK1 (Kin.Dom.1-N-terminal) | 69 |
| RSK1 (Kin.Dom.2-C-terminal) | 88 |
| RSK2 (Kin.Dom.1-N-terminal) | 85 |
| RSK2 (Kin.Dom.2-C-terminal) | 97 |
| RSK3 (Kin.Dom.1-N-terminal) | 100 |
| RSK3 (Kin.Dom.2-C-terminal) | 96 |
| RSK4 (Kin.Dom.1-N-terminal) | 93 |
| RSK4 (Kin.Dom.2-C-terminal) | 90 |
| S6K1 | 99 |
| SBK1 | 96 |
| SGK | 100 |
| SgK110 | 74 |
| SGK2 | 100 |
| SGK3 | 100 |
| SIK | 94 |
| SIK2 | 97 |
| SLK | 96 |
| SNARK | 100 |
| SNRK | 99 |
| SRC | 99 |
| SRMS | 98 |
| SRPK1 | 76 |
| SRPK2 | 100 |
| SRPK3 | 100 |
| STK16 | 100 |
| STK33 | 42 |
| STK35 | 100 |
| STK36 | 94 |
| STK39 | 81 |
| SYK | 80 |
| TAK1 | 91 |
| TAOK1 | 100 |
| TAOK2 | 85 |
| TAOK3 | 100 |
| TBK1 | 100 |
| TEC | 100 |
| TESK1 | 100 |
| TGFBR1 | 99 |
| TGFBR2 | 80 |
| TIE1 | 94 |
| TIE2 | 97 |
| TLK1 | 92 |
| TLK2 | 98 |
| TNIK | 100 |
| TNK1 | 100 |
| TNK2 | 100 |
| TNNI3K | 97 |
| TRKA | 99 |
| TRKB | 100 |
| TRKC | 88 |
| TRPM6 | 100 |
| TSSK1B | 100 |
| TTK | 13 |
| TXK | 100 |
| TYK2 (JH1domain-catalytic) | 99 |
| TYK2 (JH2domain-pseudokinase) | 100 |
| TYRO3 | 68 |
| ULK1 | 100 |
| ULK2 | 100 |
| ULK3 | 96 |
| VEGFR2 | 91 |
| VRK2 | 99 |
| WEE1 | 100 |
| WEE2 | 97 |
| WNK1 | 95 |
| WNK3 | 96 |
| YANK1 | 92 |
| YANK2 | 100 |
| YANK3 | 100 |
| YES | 92 |
| YSK1 | 89 |
| YSK4 | 81 |
| ZAK | 100 |
| ZAP70 | 97 |

Having now described some embodiments of the disclosure, it should be apparent to those skilled in the art that the foregoing is merely illustrative and not limiting, having been presented by way of example only. The disclosure can therefore be embodied in other specific forms without departing from the spirit or essential characteristics thereof.

Those skilled in the art should recognize or be able to ascertain, using no more than routine experimentation, equivalents to the specific embodiments of the disclosure. It is therefore to be understood that the embodiments described herein are presented by way of example only and that the scope of the disclosure is thus indicated by the appended claims and equivalents thereto, and that the disclosure may be practiced otherwise than as specifically described in the foregoing description.

As used herein, the singular forms "a," "an," and "the" include plural referents unless the context clearly dictates otherwise. Thus, for example, reference to "a compound" includes not only a compound but also a combination or mixture of two or more compounds, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

The entire disclosure of each of the patent documents and scientific articles referred to herein is incorporated by reference in its entirety for all purposes.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed:

1. A compound of formula I:

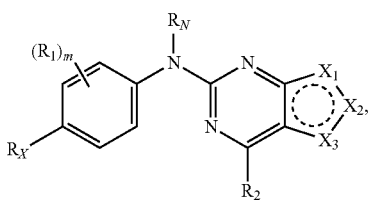

or a pharmaceutically acceptable salt thereof, wherein:
$R_X$ is

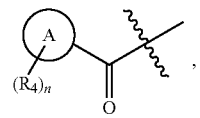

is

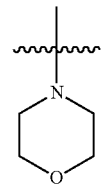 [SMILES: *N1CCOCC1]

each $R_4$ is independently unsubstituted or substituted $C_1$-$C_6$ alkyl;
n is 0, 1, 2, 3, 4, 5, or 6;

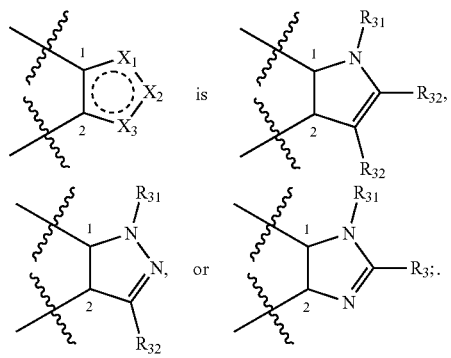

$R_{31}$ is H;
each $R_{32}$ is independently H, halogen, or $NR_{81}R_{82}$;
$R_{81}$ is H or unsubstituted or substituted $C_1$-$C_6$ alkyl;
$R_{82}$ is $C(O)R_{83}$;
$R_{83}$ is unsubstituted or substituted $C_1$-$C_6$ alkyl, unsubstituted or substituted $C_2$-$C_6$ alkenyl, or unsubstituted or substituted $C_2$-$C_6$ alkynyl;
$R_N$ is H;
each $R_1$ is independently unsubstituted or substituted $C_1$-$C_6$ alkyl, unsubstituted or substituted $C_1$-$C_6$ alkoxy, or halogen;
m is 1, 2, or 3;
$R_2$ is H, $C_1$-$C_6$ alkyl, halogen, $NR_{N1}R_{N2}$, or $OR_{N3}$;
$R_{N1}$ and $R_{N2}$ are each independently H, unsubstituted $C_1$-$C_6$ alkyl, unsubstituted or substituted $C_2$-$C_6$ alkenyl, $(CH_2)_{1-3}$—O—$C_1$-$C_6$ alkyl, or $(CH_2)_{0-3}$—$R_{91}$, or $R_{N1}$ and $R_{N2}$, together with the nitrogen atom to which they are bonded, form a 5- or 6-membered heterocycle optionally comprising 1 or 2 additional heteroatoms selected from N and O;
$R_{N3}$ is $(CH_2)_{0-3}$—$R_{92}$;
$R_{91}$ is unsubstituted or substituted $C_3$-$C_8$ cycloalkyl, unsubstituted or substituted 5- or 6-membered heterocycle comprising 1-3 heteroatoms selected from N, O, and S, or phenyl substituted with $S(O)_2R_{10}$, $NHC(O)R_{11}$, $C(O)R_{12}$, or $C(O)NHR_{13}$;
$R_{92}$ is substituted $C_3$-$C_8$ cycloalkyl, unsubstituted or substituted 5- or 6-membered heterocycle comprising 1-3 heteroatoms selected from N, O, and S, or phenyl substituted with $NO_2$, $S(O)_2R_{10}$, $NHC(O)R_{11}$, $C(O)R_{12}$, or $C(O)NHR_{13}$; and
$R_{10}$, $R_{11}$, $R_{12}$, and $R_{13}$ are each independently unsubstituted or substituted $C_1$-$C_6$ alkyl, unsubstituted or substituted $C_2$-$C_6$ alkenyl, NH—$C_1$-$C_6$ alkyl, unsubstituted or substituted 5- or 6-membered heterocycle comprising 1-3 heteroatoms selected from N, O, and S, or unsubstituted or substituted phenyl.

2. The compound of claim 1, wherein

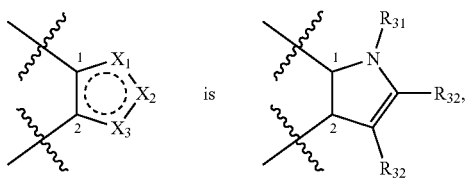

3. The compound of claim 1, wherein

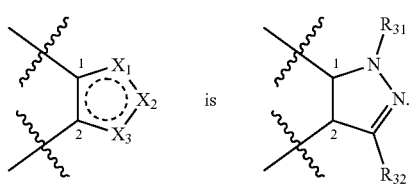

4. The compound of claim 1, wherein

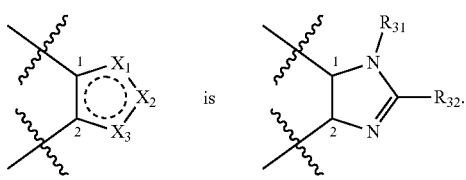

5. The compound of claim 1, wherein n is 0 or 1.

6. The compound of claim 1, wherein $R_{32}$ is halogen.

7. The compound of claim 6, wherein $R_{32}$ is chlorine or fluorine.

8. The compound of claim 1, wherein $R_1$ is $C_1$-$C_6$ alkoxy selected from methoxy, ethoxy, propoxy, i-propoxy, butoxy, i-butoxy, t-butoxy, pentoxy, and hexyloxy, each of which is optionally substituted.

9. The compound of claim 1, wherein $R_2$ is $NR_{N1}R_{N2}$.

10. The compound of claim 9, wherein one of $R_{N1}$ and $R_{N2}$ is H, and the other is unsubstituted or substituted $C_1$-$C_6$ alkyl, unsubstituted or substituted $C_2$-$C_6$ alkenyl, $(CH_2)_{1-3}$—O—$C_1$-$C_6$ alkyl, or $(CH_2)_{0-3}$—$R_{91}$.

11. The compound of claim 1, having formula Ib1:

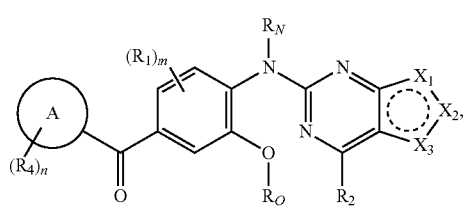

(Ib1)

or a pharmaceutically acceptable salt thereof, wherein $R_O$ is unsubstituted or substituted methyl and m is 1, 2, or 3.

12. The compound of claim 1, wherein $R_2$ is $OR_{N3}$.

13. A compound selected from:

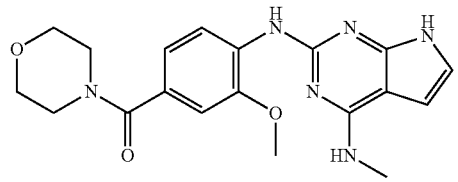

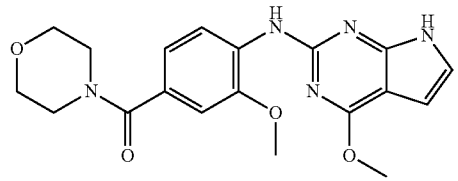

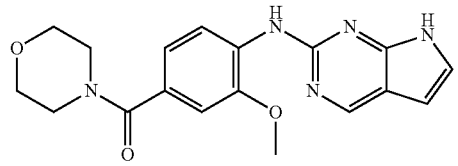

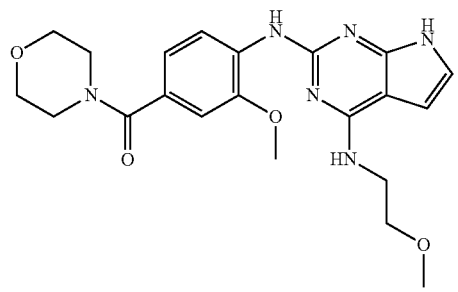

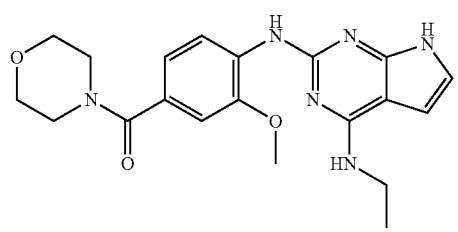

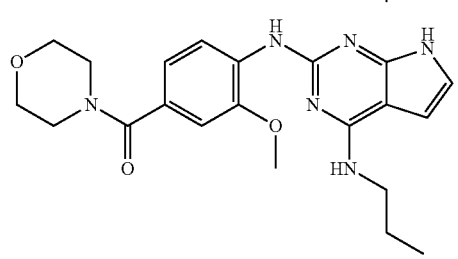

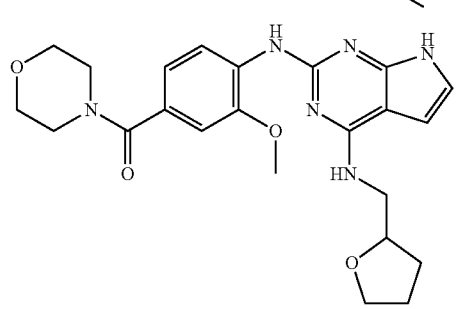

205
-continued
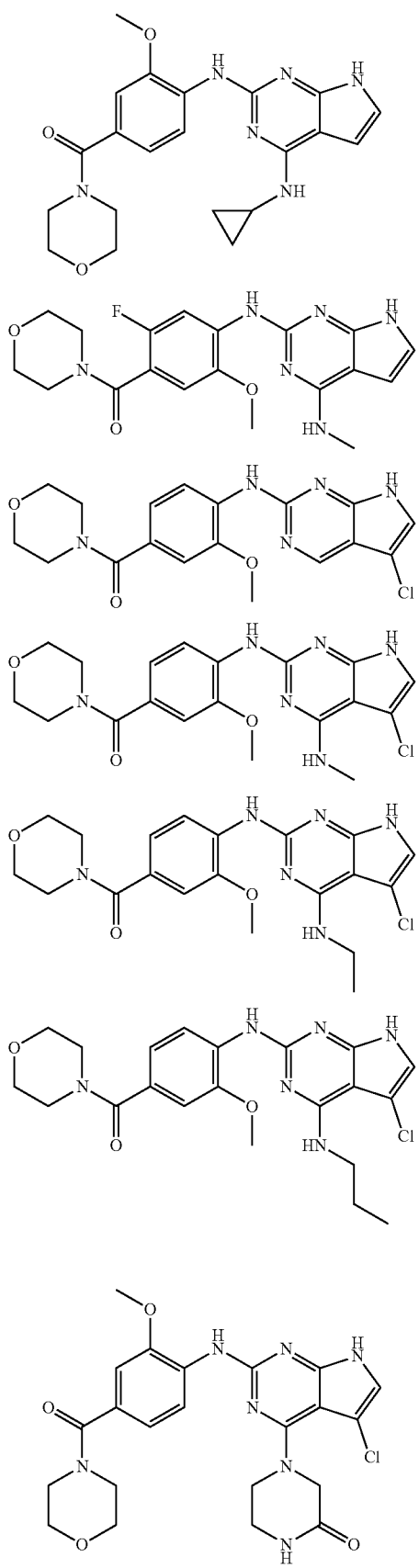
206
-continued
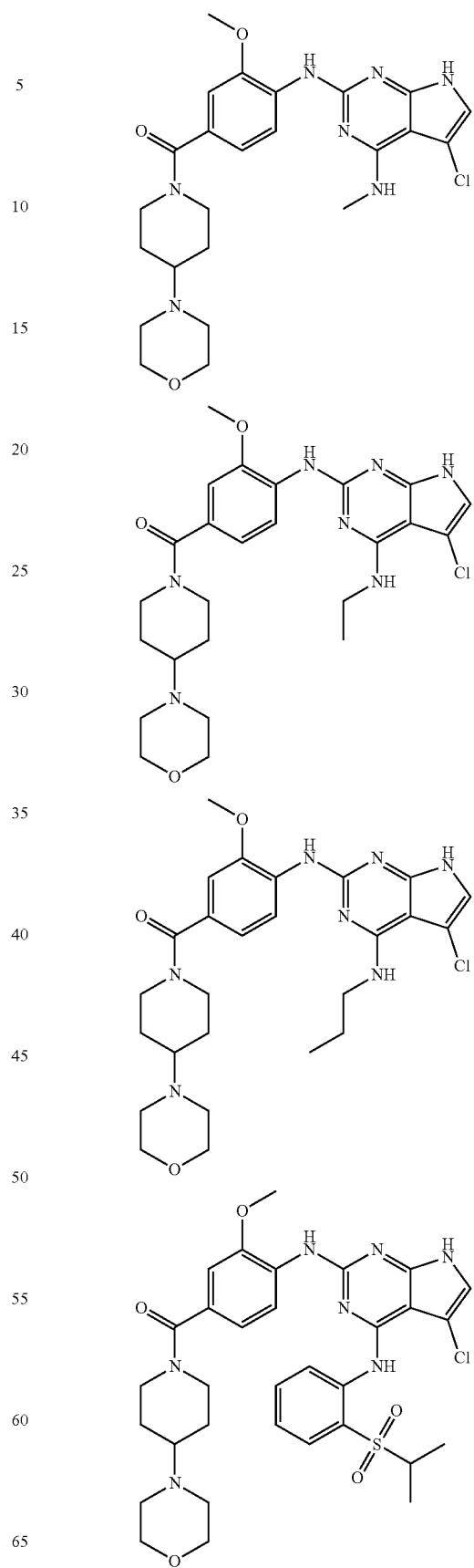

207
-continued
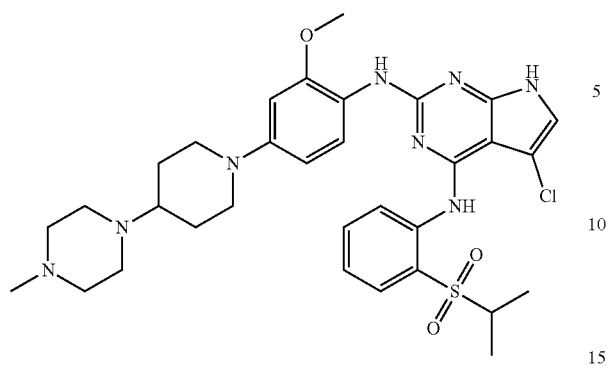
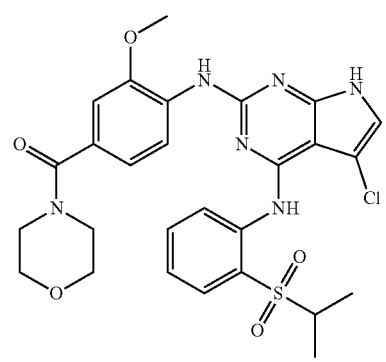
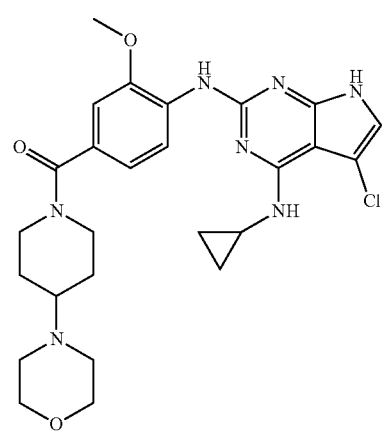
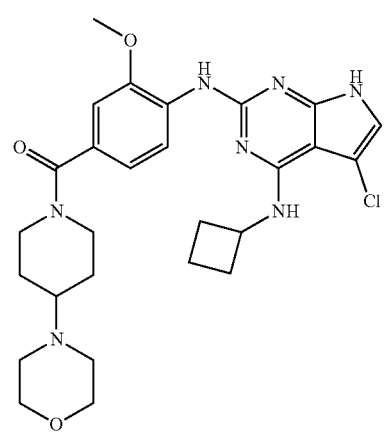
208
-continued
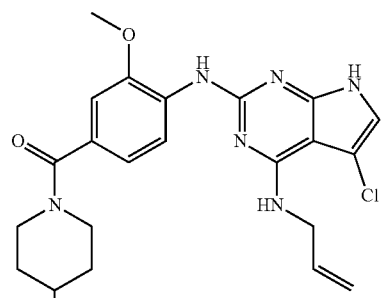
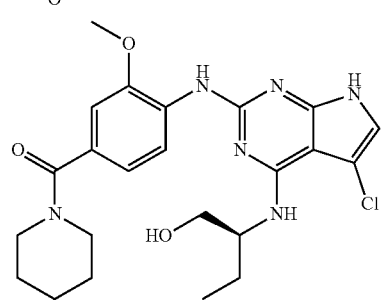
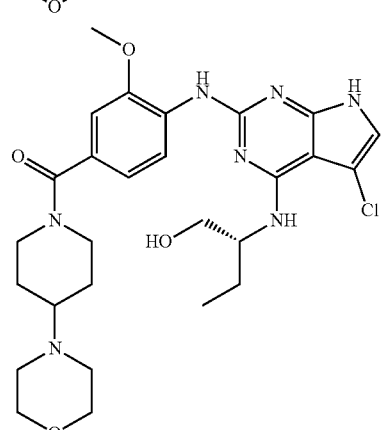
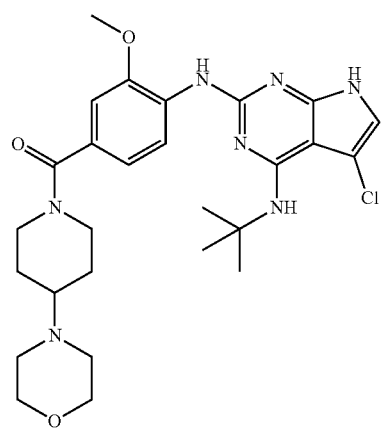

209
-continued
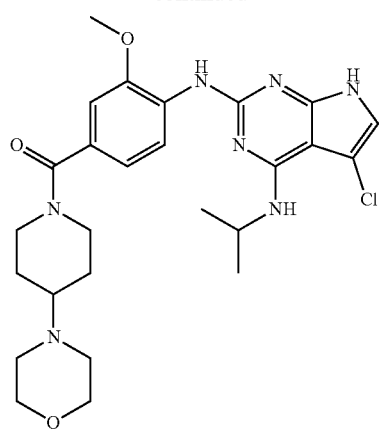
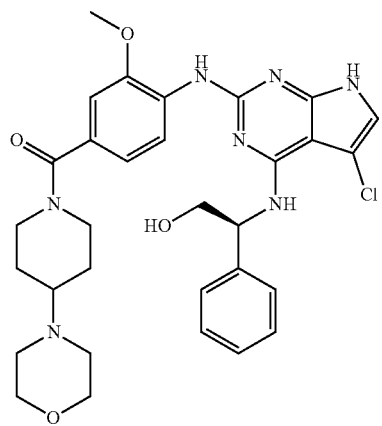
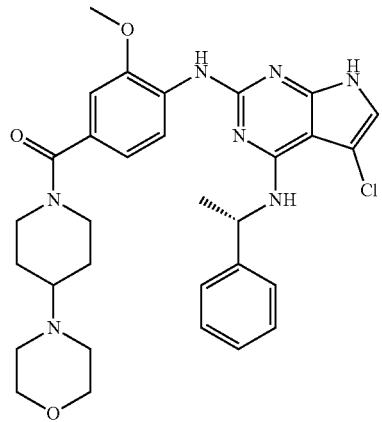
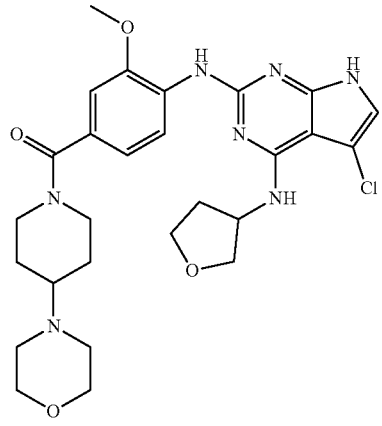
210
-continued
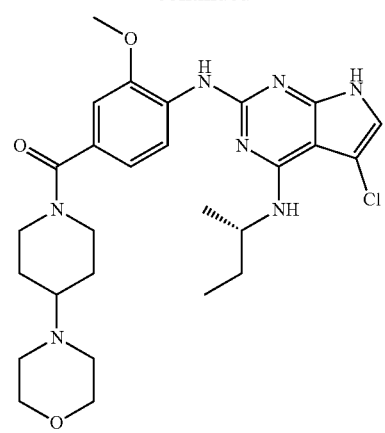
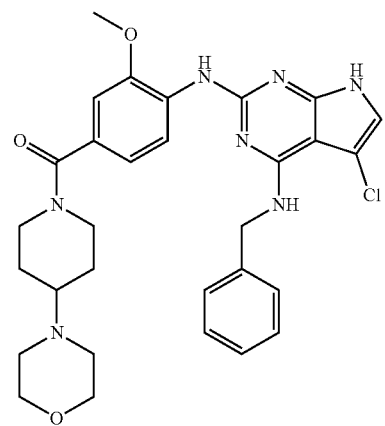
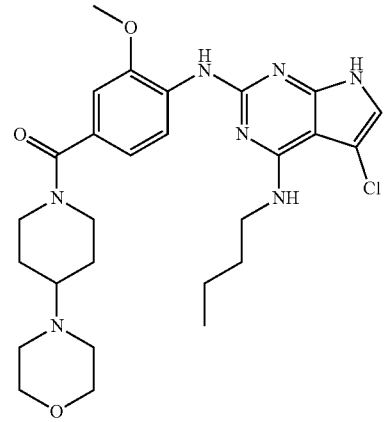
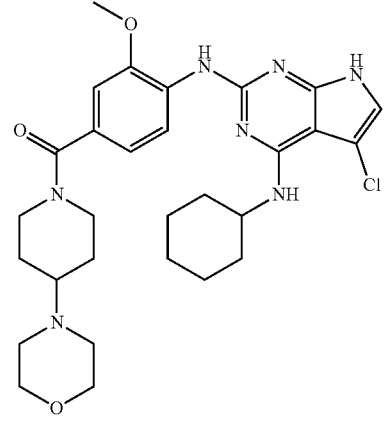

211
-continued
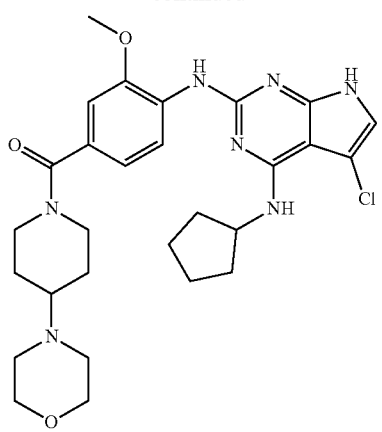
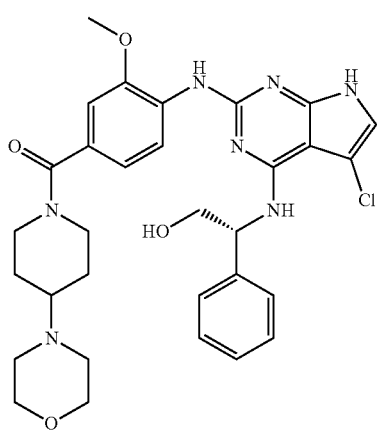
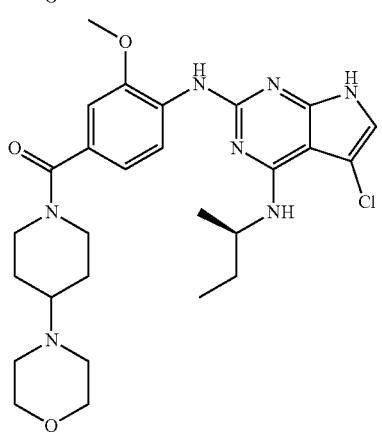
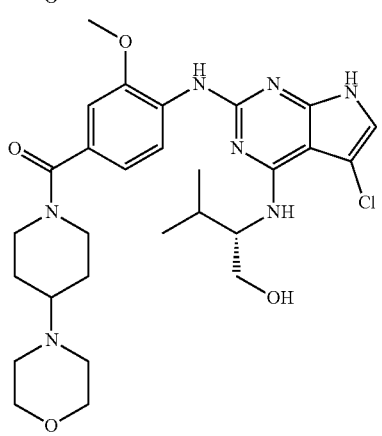
212
-continued
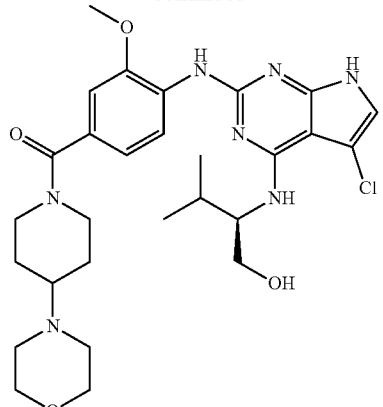
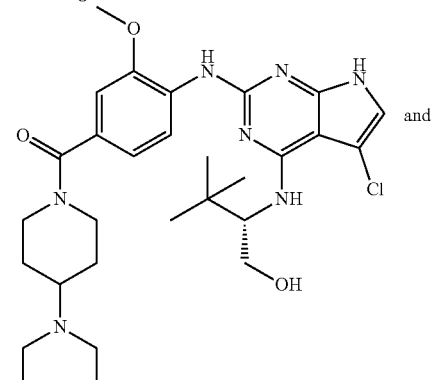
and
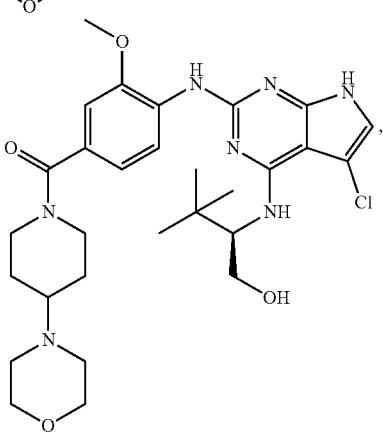
or a pharmaceutically acceptable salt thereof.
14. The compound of claim 13, wherein the compound is
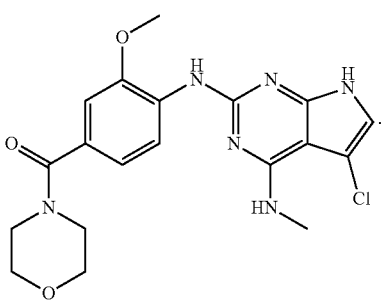 [SMILES: CNc1nc(Nc2ccc(C(=O)N3CCOCC3)cc2OC)nc2[nH]cc(Cl)c12]
or a pharmaceutically acceptable salt thereof.

15. A pharmaceutical composition comprising the compound of claim 1 or a pharmaceutically acceptable salt thereof, and a pharmaceutically acceptable carrier.

16. A method of treating Parkinson's disease in a subject, comprising administering to the subject an effective amount of the compound of claim 1 or a pharmaceutically acceptable salt thereof.

17. A compound selected from:

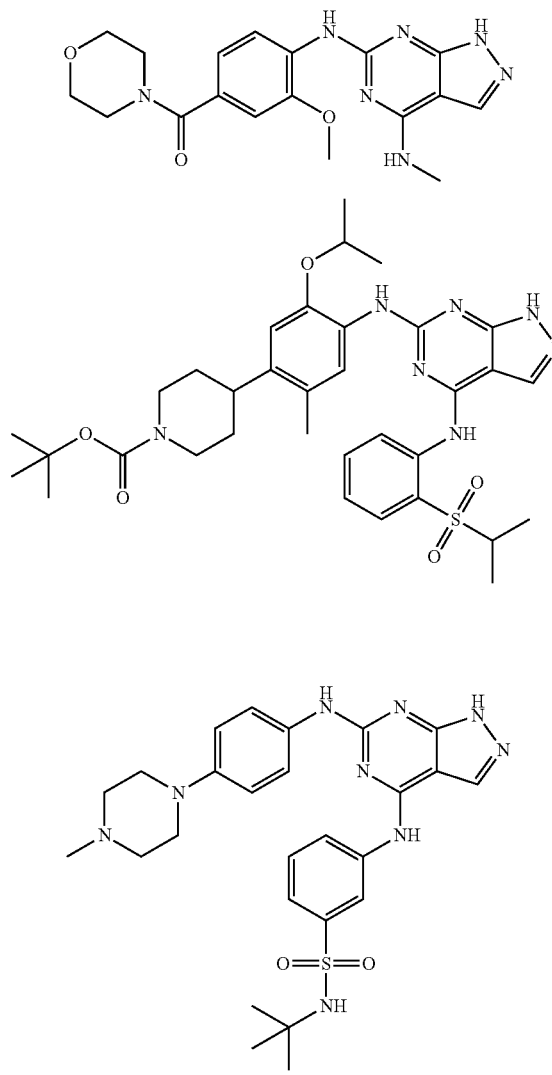

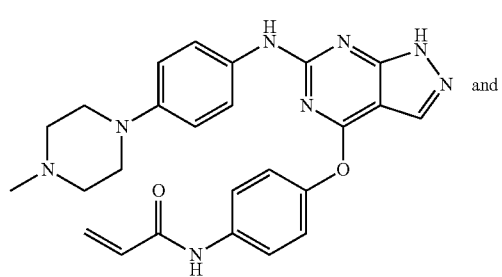

-continued

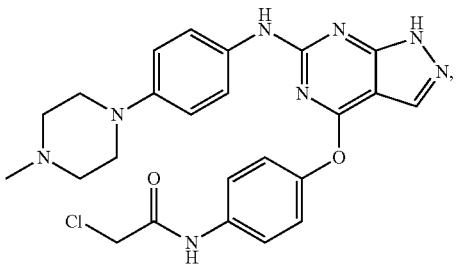

or a pharmaceutically acceptable salt thereof.

18. A compound selected from:

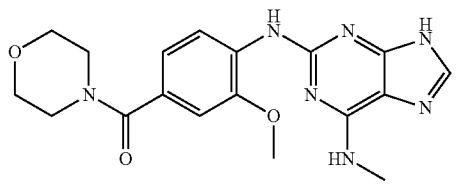

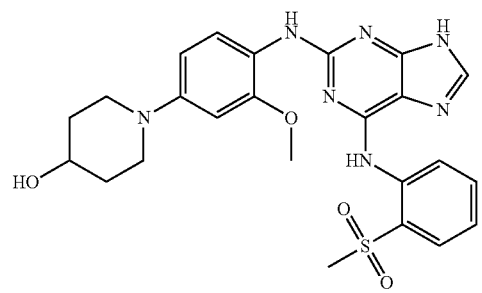

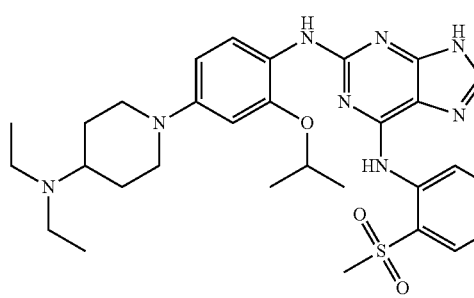

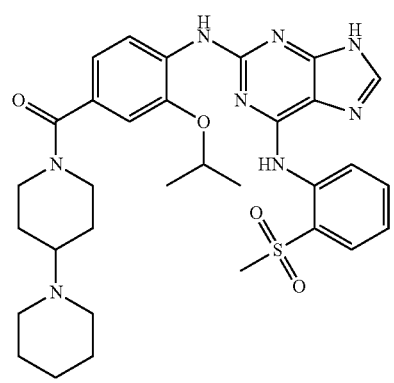

and

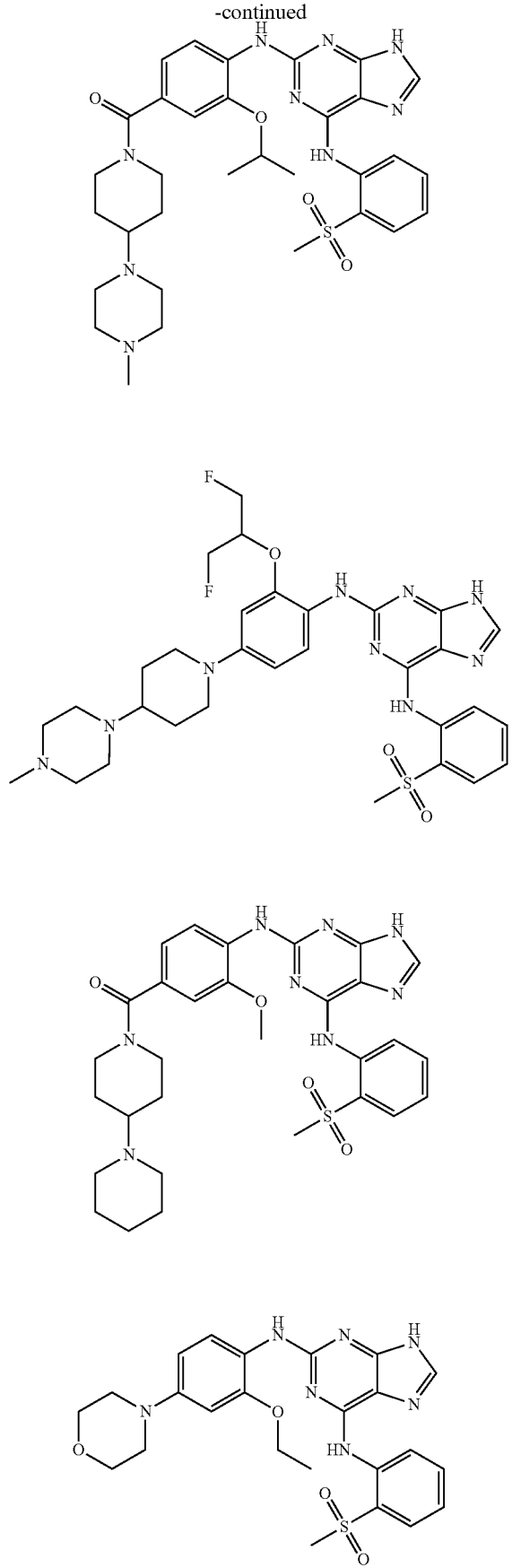

217
-continued
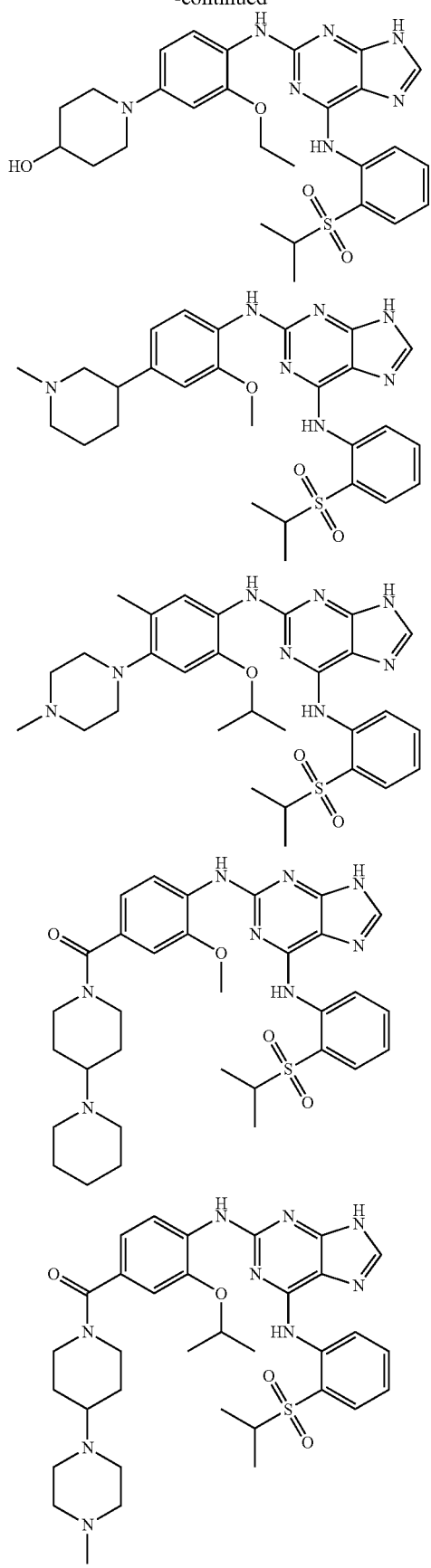
218
-continued
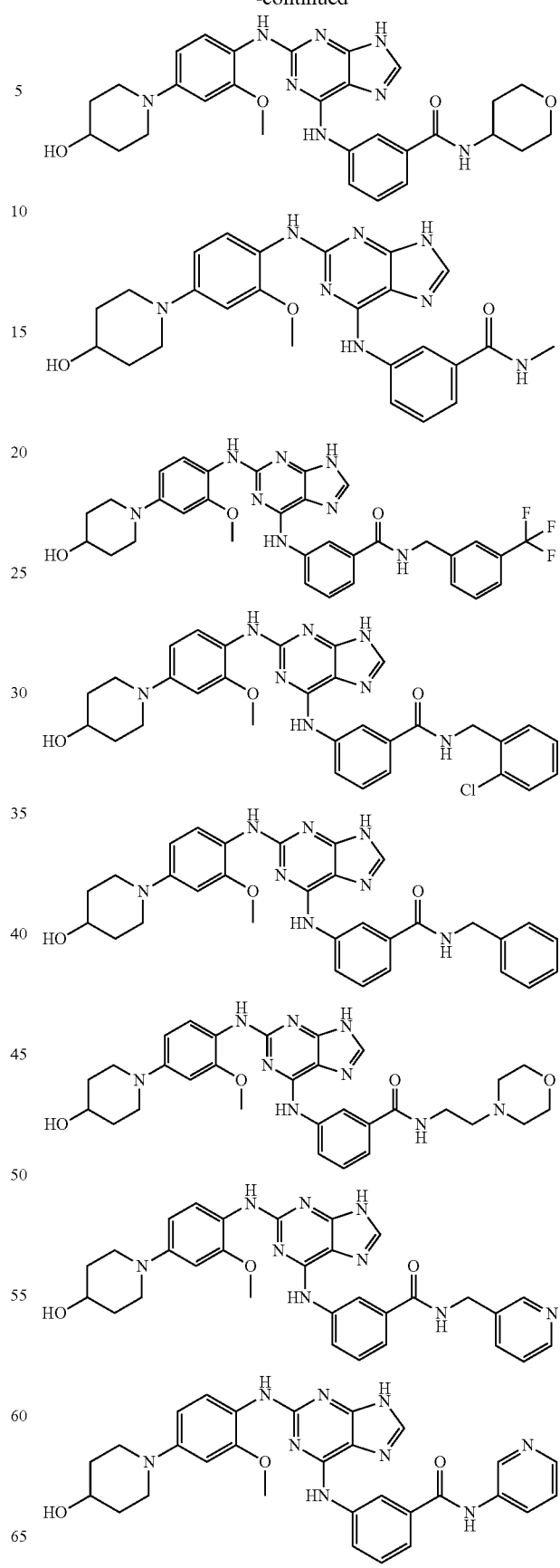

-continued
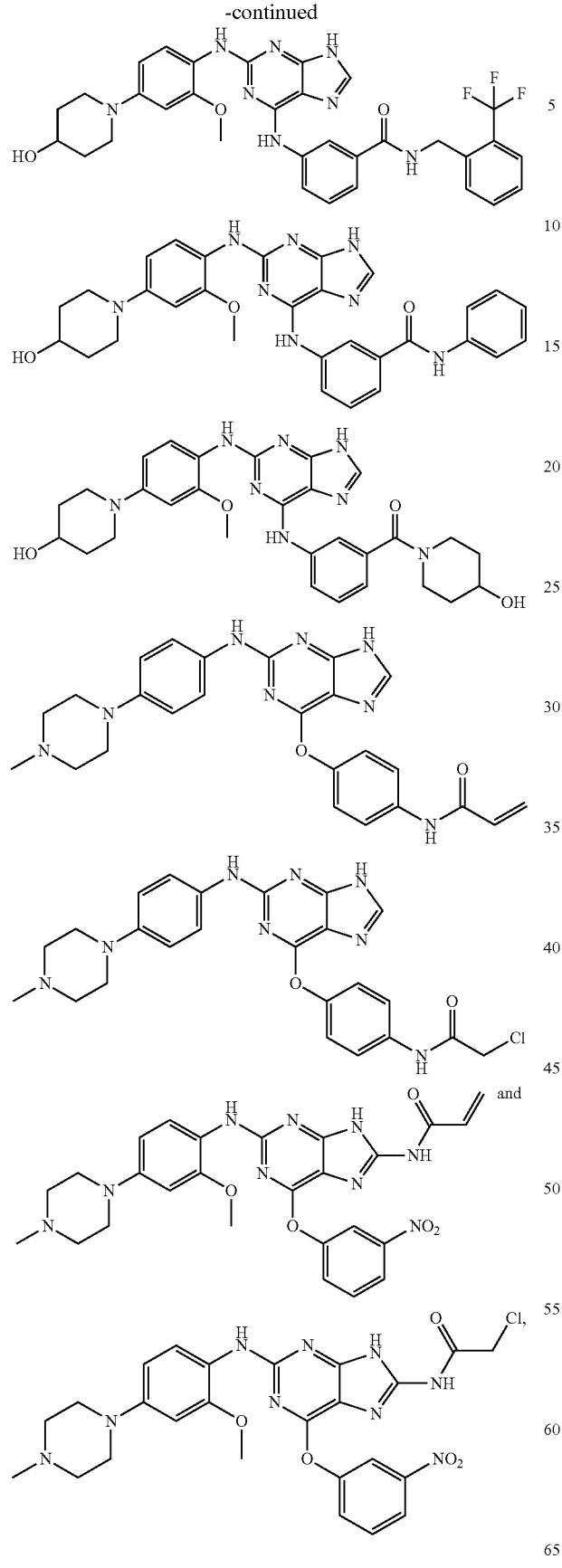
or a pharmaceutically acceptable salt thereof.
19. A compound selected from:
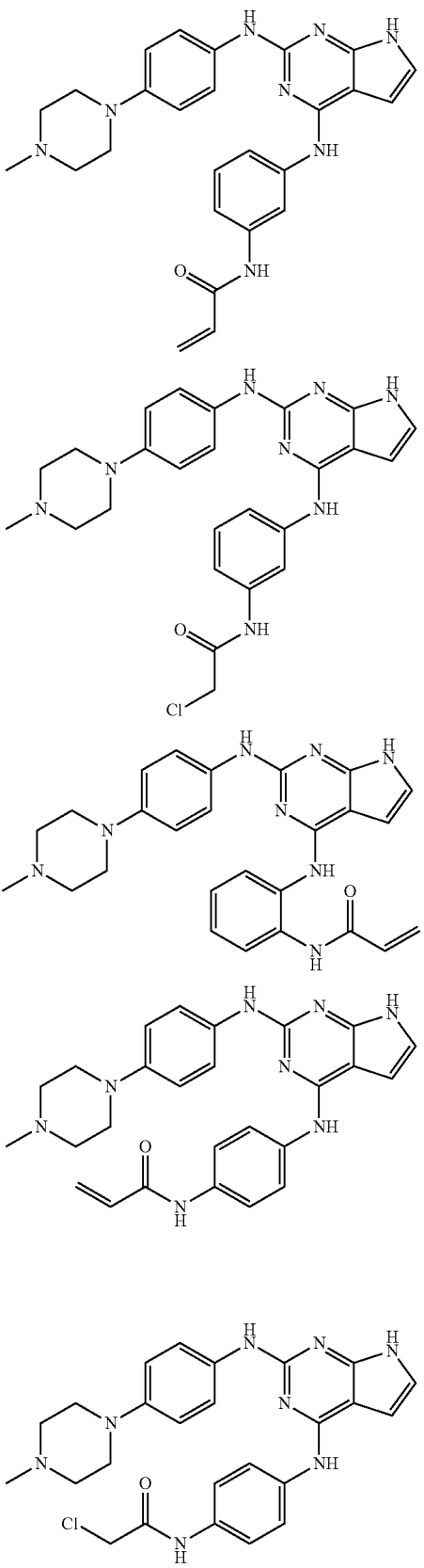

221
-continued
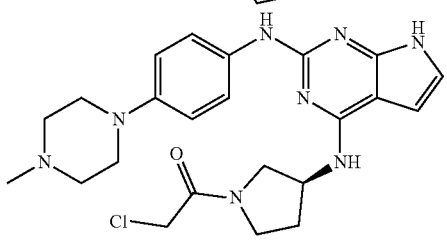
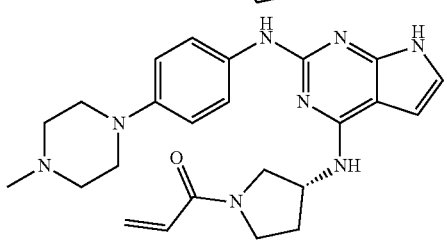
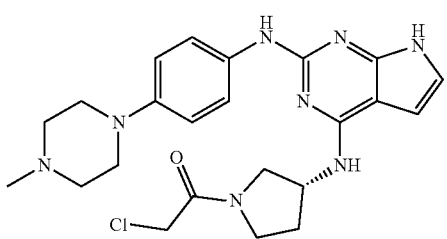
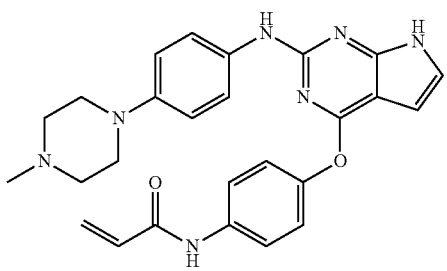
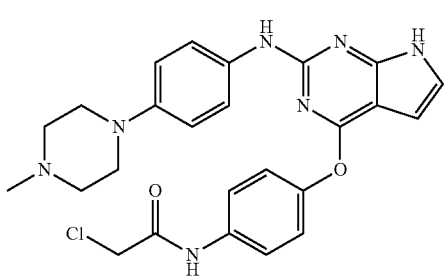
222
-continued
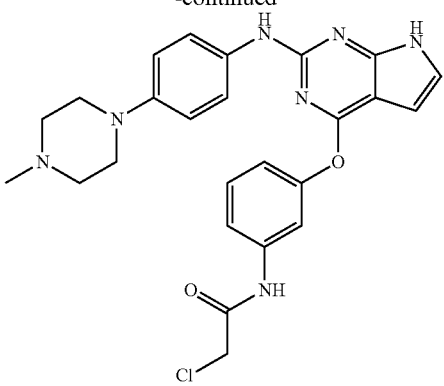
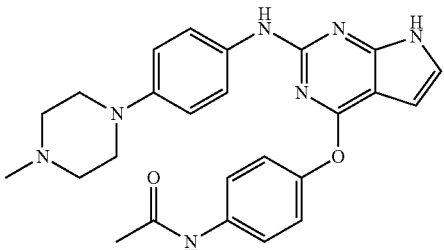
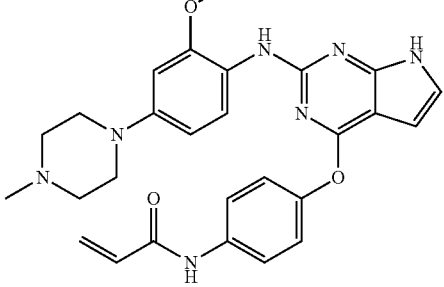
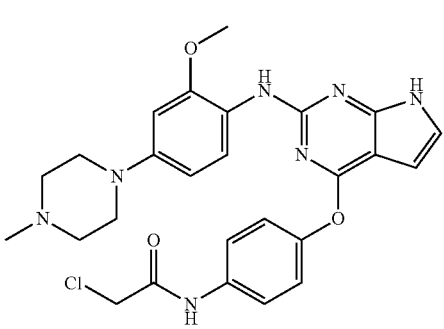
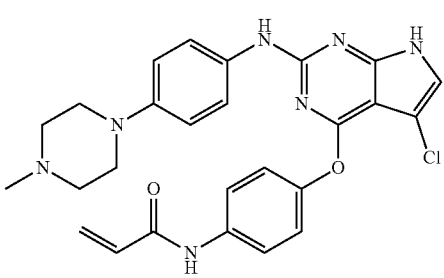

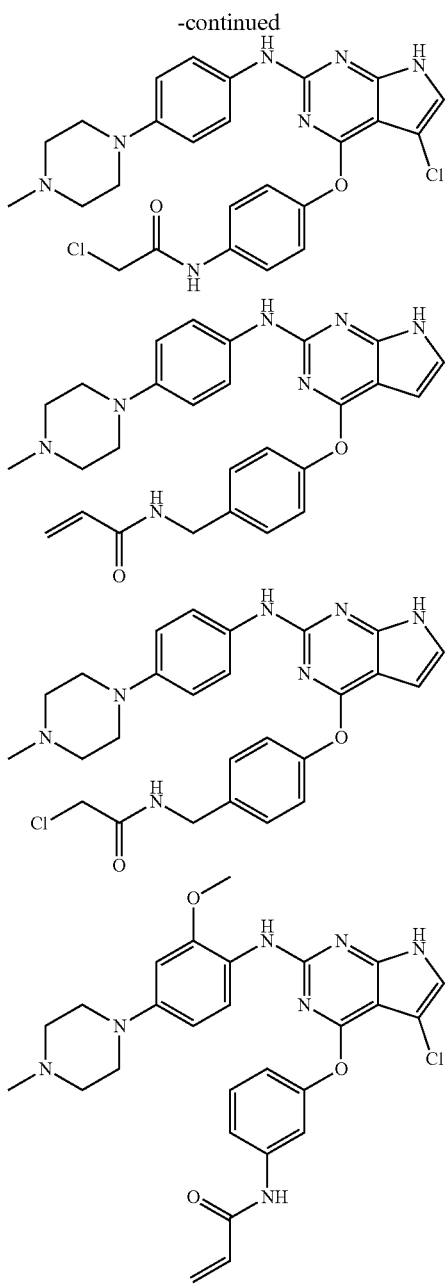

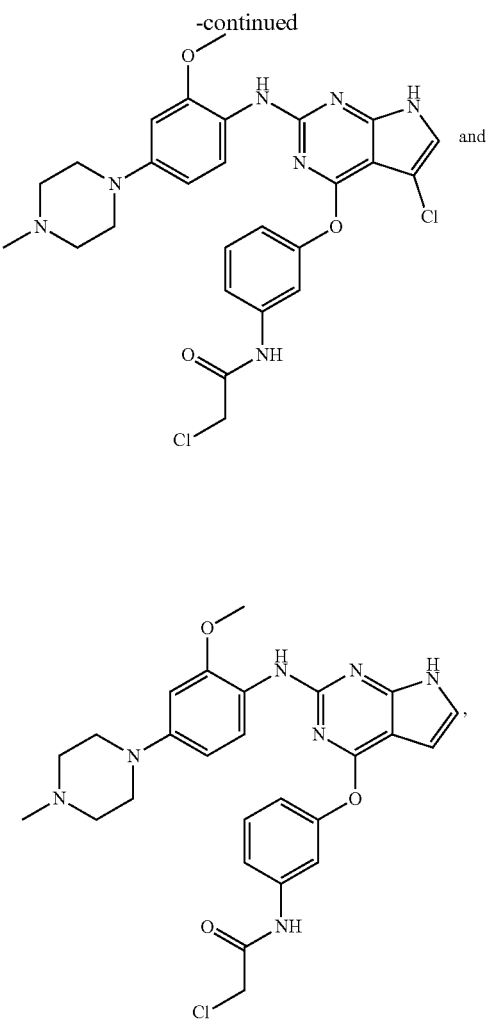

or a pharmaceutically acceptable salt thereof.

20. A pharmaceutical composition comprising the compound or a pharmaceutically acceptable salt thereof of claim 13, and a pharmaceutically acceptable carrier.

21. A method of treating Parkinson's disease in a subject, comprising administering to the subject an effective amount of the compound or a pharmaceutically acceptable salt thereof of claim 13.

* * * * *

UNITED STATES PATENT AND TRADEMARK OFFICE
CERTIFICATE OF CORRECTION

PATENT NO.         : 10,913,744 B2
APPLICATION NO.    : 15/547913
DATED              : February 9, 2021
INVENTOR(S)        : Nathanael S. Gray et al.

Page 1 of 1

It is certified that error appears in the above-identified patent and that said Letters Patent is hereby corrected as shown below:

In the Claims

In Column 202, Lines 24-30:
Delete the following structure:

" 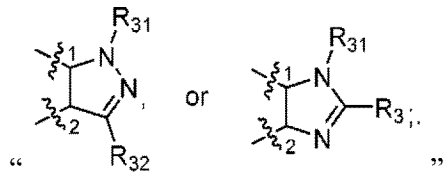 "

Replace with:

-- 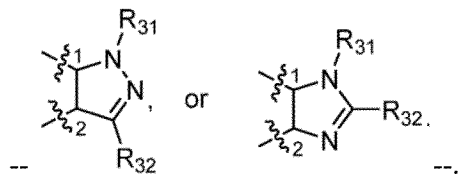 --.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*